United States Patent
Fiji et al.

(10) Patent No.: US 9,315,518 B2
(45) Date of Patent: Apr. 19, 2016

(54) IMIDAZOPYRIDIN-2-ONE DERIVATIVES

(75) Inventors: Hannah D. Fiji, Boyertown, PA (US);
Michael J. Kelly, III, Wayne, PA (US);
Jeffrey C. Kern, Gilbertsville, PA (US);
Mark E. Layton, Harleysville, PA (US);
Joseph E. Pero, Harleysville, PA (US);
Alexander J. Reif, Holland, PA (US);
Michael A. Rossi, Limerick, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/125,813

(22) PCT Filed: Jun. 14, 2012

(86) PCT No.: PCT/US2012/042387
§ 371 (c)(1),
(2), (4) Date: Mar. 12, 2014

(87) PCT Pub. No.: WO2012/174199
PCT Pub. Date: Dec. 20, 2012

(65) Prior Publication Data
US 2014/0350002 A1    Nov. 27, 2014

Related U.S. Application Data

(60) Provisional application No. 61/497,745, filed on Jun. 16, 2011.

(51) Int. Cl.
*C07D 513/04*    (2006.01)
*C07D 471/04*    (2006.01)
*C07D 519/00*    (2006.01)

(52) U.S. Cl.
CPC ............ *C07D 513/04* (2013.01); *C07D 471/04* (2013.01); *C07D 519/00* (2013.01)

(58) Field of Classification Search
CPC combination set(s) only.
See application file for complete search history.

(56) References Cited

U.S. PATENT DOCUMENTS

| | | | |
|---|---|---|---|
| 5,002,944 A * | 3/1991 | Spada et al. | 514/221 |
| 8,461,162 B2 | 6/2013 | Stanton et al. | |
| 8,518,911 B2 | 8/2013 | Katz et al. | |
| 8,592,425 B2 | 11/2013 | Altman et al. | |
| 8,765,784 B2 | 7/2014 | Arrington et al. | |
| 8,772,276 B2 | 7/2014 | Kuduk et al. | |
| 8,785,481 B2 | 7/2014 | Beshore et al. | |
| 8,785,482 B2 | 7/2014 | Beshore et al. | |
| 8,946,237 B2 | 2/2015 | Lim et al. | |
| 8,952,005 B2 | 2/2015 | Layton et al. | |
| 8,975,286 B2 | 3/2015 | Dudkin et al. | |
| 8,993,779 B2 | 3/2015 | Dudkin et al. | |
| 2013/0158002 A1 | 6/2013 | Layton et al. | |
| 2014/0088151 A1 | 3/2014 | Beshore et al. | |

FOREIGN PATENT DOCUMENTS

| | | |
|---|---|---|
| WO | WO2004/024936 | 3/2004 |
| WO | WO2011/034741 | 3/2011 |

OTHER PUBLICATIONS

Johnson, A. W. Invitation to Organic Chemistry 1999 Jones and Bartlett: Mississauga, Canada, p. 24.*
Duplantier "3-Benzyl-1,3-oxazolidin-2-ones as mGluR2positive allosteric modulators: Hit-to lead and lead optimization" Bioorganic & Medicinal Chemistry Letters 19 (2009) 2524-2529.*
International Search Report and Written Opinion, International Application No. PCT/US12/42387, Date of Mailing Aug. 27, 2012.

* cited by examiner

*Primary Examiner* — David K O Dell
(74) *Attorney, Agent, or Firm* — Keith D. MacMillan; John C. Todaro

(57) ABSTRACT

The present invention is directed to imidazopyridin-2-one derivatives which are potentiators of metabotropic glutamate receptors, particularly the $mGluR^2$ receptor, and which are useful in the treatment or prevention of neurological and psychiatric disorders associated with glutamate dysfunction and diseases in which metabotropic glutamate receptors are involved. The invention is also directed to pharmaceutical compositions comprising these compounds and the use of these compounds and compositions in the prevention or treatment of such diseases in which metabotropic glutamate receptors are involved.

9 Claims, No Drawings

IMIDAZOPYRIDIN-2-ONE DERIVATIVES

BACKGROUND OF THE INVENTION

The excitatory amino acid L-glutamate (sometimes referred to herein simply as glutamate) through its many receptors mediates most of the excitatory neurotransmission within the mammalian central nervous system (CNS). The excitatory amino acids, including glutamate, are of great physiological importance, playing a role in a variety of physiological processes, such as long-term potentiation (learning and memory), the development of synaptic plasticity, motor control, respiration, cardiovascular regulation, and sensory perception.

Glutamate acts via at least two distinct classes of receptors. One class is composed of the ionotropic glutamate (iGlu) receptors that act as ligand-gated ionic channels. Via activation of the iGlu receptors, glutamate is thought to regulate fast neuronal transmission within the synapse of two connecting neurons in the CNS. The second general type of receptor is the G-protein or second messenger-linked "metabotropic" glutamate (mGluR) receptor. Both types of receptors appear not only to mediate normal synaptic transmission along excitatory pathways, but also participate in the modification of synaptic connections during development and throughout life. Schoepp, Bockaert, and Sladeczek, Trends in Pharmacol. Sci., 11, 508 (1990); McDonald and Johnson, Brain Research Reviews, 15, 41 (1990).

The present invention relates to potentiators of mGlu receptors, in particular mGluR2 receptors. The mGluR receptors belong to the Type III G-protein coupled receptor (GPCR) superfamily. This superfamily of GPCR's including the calcium-sensing receptors, GABAB receptors and pheromone receptors, which are unique in that they are activated by binding of effectors to the amino-terminus portion of the receptor protein. The mGlu receptors are thought to mediate glutamate's demonstrated ability to modulate intracellular signal transduction pathways. Ozawa, Kamiya and Tsuzuski, Prog. Neurobio., 54, 581 (1998). They have been demonstrated to be localized both pre- and post-synaptically where they can regulate neurotransmitter release, either glutamate or other neurotransmitters, or modify the post-synaptic response of neurotransmitters, respectively.

At present, there are eight distinct mGlu receptors that have been positively identified, cloned, and their sequences reported. These are further subdivided based on their amino acid sequence homology, their ability to effect certain signal transduction mechanisms, and their known pharmacological properties. Ozawa, Kamiya and Tsuzuski, Prog. Neurobio., 54, 581 (1998). For instance, the Group I mGluR receptors, which include the mGlu1R and mGluR5, are known to activate phospholipase C (PLC) via G$\alpha$q-proteins thereby resulting in the increased hydrolysis of phosphoinositides and intracellular calcium mobilization. There are several compounds that are reported to activate the Group I mGlu receptors including DHPG, (R/S)-3,5-dihydroxyphenylglycine. Schoepp, Goldworthy, Johnson, Salhoff and Baker, J. Neurochem., 63, 769 (1994); Ito, et al., keurorep., 3, 1013 (1992). The Group II mGlu receptors consist of the two distinct receptors, mGluR2 and mGluR3 receptors. Both have been found to be negatively coupled to adenylate cyclase via activation of G$\alpha$i-protein. These receptors can be activated by a selective compound such as 1S,2S,5R,6S-2 aminobicyclo [3.1.0]hexane-2,6-dicarboxylate. Monn, et al., J. Med. Chem., 40, 528 (1997); Schoepp, et al., Neuropharmacol., 36, 1 (1997). This activation leads to inhibition of glutamate release in the synapse (Cartmell et al, J Neurochem 75, 889 (2000)). Similarly, the Group III mGlu receptors, including mGluR4, mGluR6, mGluR7 and mGluR8, are negatively coupled to adenylate cyclase via G$\alpha$i and are potently activated by L-AP4 (L-(+)-2-amino-4-phosphonobutyric acid). Schoepp, Neurochem. Int., 24, 439 (1994).

Nonselective mGluR2/mGluR3 receptor agonists (Monn, et al., J. Med. Chem., 43, 4893, (2000)) have shown efficacy in numerous animal models of anxiety and psychosis as well as human clinical trials in schizophrenia patients; Patil et al, Nature Medicine, 13, 1102 (2007). Recent reports indicate that mGluR2 but not the mGluR3 receptor mediates the actions of the dual mGluR2/mGluR3 agonist LY379268 in mouse models predictive of antipsychotic activity. Woolley et al, Psycopharmacology, 196, 431 (2008). Additionally, recent animal studies demonstrate that selective potentiation of the mGluR2 receptor has similar effects to such non-selective agonists (Galici et al, Journal of Pharmacology and Experimental Therapeutics, 315, 1181 (2005)) suggesting an alternative strategy concerning the discovery of selective, positive allosteric modulators (PAMs or allosteric potentiators) of mGluR2 (Johnson et al, J. Med. Chem. 46, 3189, (2003); Pinkerton et al., J. Med. Chem., 47, 4595 (2004). These potentiators act by enabling the receptor to produce an enhanced response to endogenous glutamate. Such allosteric potentiators do not bind at the glutamate binding site also known as the "orthosteric site", and may benefit by binding to a site other than the highly conserved orthosteric site. A potential advantage to this approach includes the opportunity to have a distinct pharmacological profile by enhancing the activity of the endogenous ligand upon its binding to the orthosteric site. The pharmacological distinctions include the potential for pharmacological specificity between related receptor types that share the same endogenous ligand. In addition, positive allosteric modulators of mGluR2 have been shown to potentiate the response of mGluR2 agonists such as LY379268 (Johnson et. Al. Biochemical Soc. Trans. 32, 881 (2004) and this represents an alternative strategy for treatment using mGluR2 selective PAMs.

It has become increasingly clear that there is a link between modulation of excitatory amino acid receptors, including the glutamatergic system, through changes in glutamate release or alteration in postsynaptic receptor activation, and a variety of neurological and psychiatric disorders. e.g. Monaghan, Bridges and Cotman, Ann. Rev. Pharmacol. Toxicol., 29, 365-402 (1989); Schoepp and Sacann, Neurobio. Aging, 15, 261-263 (1994); Meldrum and Garthwaite, Tr. Pharmacol. Sci., 11, 379-387 (1990). The medical consequences of such glutamate dysfunction make the abatement of these neurological processes an important therapeutic goal.

WO 2011/034741 A1, published 24 Mar. 2011, discloses imidazopyridin-2-one derivatives as mGluR2 positive allosteric modulators. Compounds of the present invention were found to mitigate the time-dependent inhibition (TDI) liability associated with compounds described in WO 2011/034741 A1.

SUMMARY OF THE INVENTION

The present invention is directed to imidazopyridin-2-one derivatives which are potentiators of metabotropic glutamate receptors, particularly the mGluR2 receptor, and which are useful in the treatment or prevention of neurological and psychiatric disorders associated with glutamate dysfunction and diseases in which metabotropic glutamate receptors are involved. The invention is also directed to pharmaceutical compositions comprising these compounds and the use of these compounds and compositions in the prevention or treatment of such diseases in which metabotropic glutamate receptors are involved.

DETAILED DESCRIPTION OF THE INVENTION

The invention encompasses a genus of compounds of Formula I

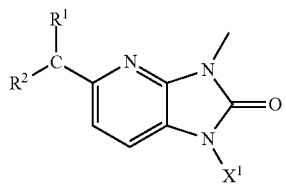

or a pharmaceutically acceptable salt thereof, wherein:

$X^1$ is selected from the group consisting of: $C_{1-8}$alkyl, $C_{2-8}$alkenyl, $C_{2-8}$alkynyl, $C_{3-6}$cycloalkyl and $C_{3-6}$cycloalkyl$C_{1-4}$alkyl, any of which may bear up to 5 halogen substituents;

$R^1$ represents H or $C_{1-4}$alkyl which is optionally substituted with OH, CN, $CF_3$, $C_{1-4}$alkoxy, amino, $C_{1-4}$alkylamino or di($C_{1-4}$alkyl)amino;

$R^2$ is selected from:

(i) $C_{1-8}$alkyl or $C_{2-8}$alkenyl, either of which optionally bears up to 3 substituents independently selected from halogen, OH, CN, $CF_3$, $OR^4$, $SR^5$, $SO_2R^5$, $SO_2N(R^4)_2$, $COR^4$, $CO_2R^4$, $CON(R^4)_2$, N3, $N(R^4)_2$, $NR^4COR^5$, $NR^4SO_2R^5$ and phenyl, said phenyl bearing 0 to 5 halogen substituents; and (ii) $C_{3-10}$cycloalkyl, $C_{3-10}$cycloalkyl$C_{1-4}$alkyl, Het, Het $C_{1-4}$alkyl, aryl or aryl$C_{1-4}$alkyl, any of which optionally bears up to 4 substituents independently selected from halogen, OH, oxo, CN, $CF_3$, $R^5$, $OR^4$, $SR^5$, $SO_2R^5$, $SO_2N(R^4)_2$, $COR^4$, $CO_2R^4$, $CON(R^4)_2$, $N(R^4)_2$, $NR^4COR^5$, $NR^4SO_2R^5$ and —P(O)—$(OR^4)_2$; where "aryl" refers to phenyl or 5- or 6-membered heteroaryl, either of which phenyl or heteroaryl is optionally fused to a 5- or 6-membered carbocycle or heterocycle, each "Het" independently refers to a nonaromatic or partially aromatic mono- or bicyclic heterocyclic system of up to 10 ring atoms and $C_{3-10}$cycloalkyl and the cyclic portion of $C_{3-10}$cycloalkyl$C_{1-4}$alkyl may be fused with phenyl or a 5- or 6-membered heteroaryl;

or $R^1$ and $R^2$ together may complete a non-aromatic monocyclic, bicyclic or tricyclic carbocyclic or heterocyclic ring system of up to 12 ring atoms which optionally bears up to 4 substituents independently selected from $R^3$;

$R^3$ is selected from the group consisting of: halogen, OH, oxo, CN, $CF_3$, $R^5$, $OR^4$, $SR^5$, $SO_2R^5$, $COCH_2SO_2R^5$, $SO_2N(R^4)_2$, $COR^5$, $CO_2R^4$, $CON(R^4)_2$, $N(R^4)_2$, $NR^4COR^5$, $NR^4CON(R^4)_2$, $NR^4CO_2R^4$, $NR^4SO_2R^5$, —$C_{1-4}$alkyl-$N(R^4)_2$, —$C_{1-4}$alkyl-$NR^4COR^5$ and —$C_{1-4}$alkyl-$NR^4CO_2R^4$;

each $R^4$ independently represents H, $C_{1-6}$alkyl, $C_{3-10}$cycloalkyl, $C_{3-10}$cycloalkyl$C_{1-4}$alkyl, $C_{3-10}$cycloalkenyl or $C_{3-10}$cycloalkenyl$C_{1-4}$alkyl, any of which except H optionally bear up to 3 halogen atoms or with OH, CN, $CF_3$, $OCF_3$, $C_{1-4}$alkoxy, $C_{1-4}$alkyl-C(O)—, amino, $C_{1-4}$alkylamino and di($C_{1-4}$-alkyl)amino, or $R^4$ represents phenyl, benzyl, phenylethyl, 5- or 6-membered monocyclic heteroaryl optionally bridged with —$(CH_2)_p$—, or a 9- or 10-membered bicyclic heteroaryl optionally bridged with —$(CH_2)_p$—, any of which optionally bear up to 3 substituents independently selected from halogen, OH, CN, $CF_3$, $OCF_3$, $C_{1-4}$alkyl, $C_{3-6}$cycloalkyl, phenyl, $C_{1-4}$alkoxy, amino, $C_{1-4}$alkylamino, di($C_{1-4}$alkyl)amino, a 5- or 6-membered monocyclic heteroaryl optionally bridge with methylene and optionally substituted with one or two methyl groups, and Het, optionally substituted with 1 to 3 substituents selected from oxo and methyl, or $R^4$ represents Het, optionally bridged with —$(CH_2)_p$— and said Het optionally bearing up to 3 substituents independently selected from halogen, OH, oxo, CN, $CF_3$, $OCF_3$, $C_{1-4}$alkyl, $C_{3-6}$cycloalkyl, phenyl, benzyl, a 5- or 6-membered monocyclic heteroaryl optionally bridged with methylene and substituted with one or two methyl groups, $C_{1-4}$alkoxy, $C_{1-4}$alkyl-O—C(O)—, $C_{1-4}$alkyl-C(O)—, acetyl, amino, $C_{1-4}$alkylamino, di($C_{1-4}$alkyl)amino and Het, optionally substituted with 1 to 3 substituents selected from oxo and methyl;

each p is independently 1, 2, 3 or 4; and $R^5$ has the same definition as $R^4$ except that $R^5$ is not H.

Within the genus, the invention encompasses a first sub-genus of compounds of Formula I, or a pharmaceutically acceptable salt thereof, wherein $X^1$ is selected from 2,2-dimethylpropyl, [2,2-difluorocyclopropyl]methyl and [2,2-difluoro-1-methylcyclopropyl]methyl.

Also within the genus, the invention encompasses a second sub-genus of compounds of Formula I, or a pharmaceutically acceptable salt thereof, wherein $R^1$ and $R^2$ together complete a non-aromatic mono-cyclic or bi-cyclic heterocyclic ring system of up to 12 ring atoms which optionally bears up to 4 substituents independently selected from $R^3$.

Within the second sub-genus, the invention encompasses a first class of compounds having Formula Ia

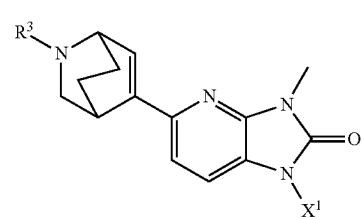

or a pharmaceutically acceptable salt thereof.

Within the first class, the invention encompasses a first sub-class of compounds having Formula Ia, or a pharmaceutically acceptable salt thereof, wherein $R^3$ is $COR^5$, $CO_2R^5$, $NR^4COR^5$, $NR^4CO_2R^5$, $SO_2R^5$ or $NR^4SO_2R^5$.

Within the first sub-class, the invention encompasses a first group of compounds having Formula Ia, or a pharmaceutically acceptable salt thereof, wherein $R^3$ is $COR^5$.

Within the first group, the invention encompasses a first sub-group of compounds having Formula Ia, or a pharmaceutically acceptable salt thereof, wherein $R^5$ is a 5- or 6-membered monocyclic heteroaryl, which optionally bears up to 3 substituents independently selected from halogen, OH, CN, $CF_3$, $C_{1-4}$alkyl, $C_{3-6}$cycloalkyl, phenyl, $C_{1-4}$alkoxy, amino, $C_{1-4}$alkylamino and di($C_{1-4}$alkyl)amino.

Within the first sub-group, the invention encompasses compounds of Formula Ia, or a pharmaceutically acceptable salt thereof, wherein $R^5$ is selected from the group consisting of: isoxazole, thiadiazole, pyridine, imidazole, pyrazole, oxazole, triazole, thiazole and isothiazole, any of which optionally bear up to 3 methyl substituents. In an embodiment, $R^5$ is isoxazole.

Also within the second sub-genus, the invention encompasses a second class of compounds having Formula Ib

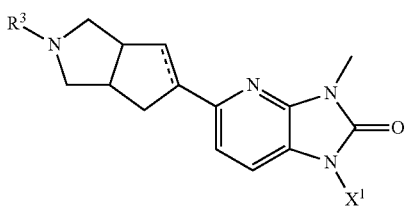

Ib or a pharmaceutically acceptable salt thereof, wherein ==== is an optional double bond.

Within the second class, the invention encompasses a second sub-class of compounds having Formula Ib, or a pharmaceutically acceptable salt thereof, wherein $R^3$ is $COR^5$, $CO_2R^5$, $NR^4COR^5$, $NR^4CO_2R^5$, $SO_2R^5$ or $NR^4SO_2R^5$.

Within the second sub-class, the invention encompasses a second group of compounds having Formula Ib, or a pharmaceutically acceptable salt thereof, wherein $R^3$ is $COR^5$.

Within the second group, the invention encompasses a second sub-group of compounds having Formula Ib, or a pharmaceutically acceptable salt thereof, wherein $R^5$ is a 5- or 6-membered monocyclic heteroaryl, which optionally bears up to 3 substituents independently selected from halogen, OH, CN, $CF_3$, $C_{1-4}$alkyl, $C_{3-6}$cycloalkyl, phenyl, $C_{1-4}$alkoxy, amino, $C_{1-4}$alkylamino and di($C_{1-4}$alkyl)amino.

Also within the second sub-genus, the invention encompasses a third class of compounds having of Formula Ic

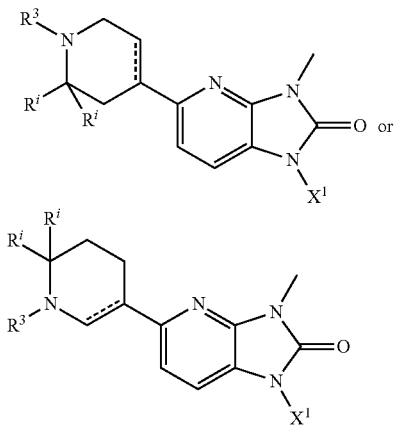

Ic or a pharmaceutically acceptable salt thereof, wherein ==== is an optional double bond and each $R^1$ is independently hydrogen or methyl.

Also within the genus, the invention encompasses a third sub-genus of compounds of Formula I, or a pharmaceutically acceptable salt thereof, wherein $R^1$ and $R^2$ together complete a non-aromatic mono-cyclic six-membered carbocyclic ring which optionally bears up to 4 substituents independently selected from $R^3$.

Within the third sub-genus, the invention encompasses compounds having Formula Id

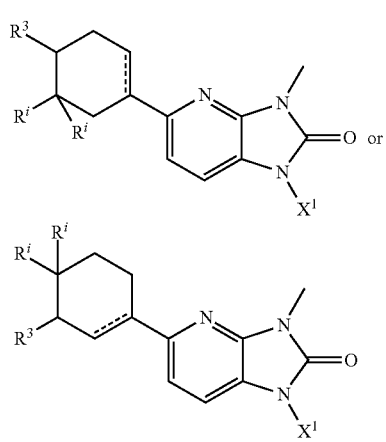

Id or a pharmaceutically acceptable salt thereof, wherein ==== is an optional double bond and each $R^1$ is hydrogen or methyl.

The invention also encompasses the examples that follow.

The invention also encompasses a pharmaceutical composition comprising a compound of Formula Ia in combination with a pharmaceutically acceptable carrier.

The invention also encompasses a method for treating a neurological or psychiatric disorder associated with glutamate dysfunction in a patient in need thereof comprising administering to the patient a therapeutically effective amount of a compound of Formula I. The invention also encompasses this method wherein the neurological or psychiatric disorder associated with glutamate dysfunction is schizophrenia.

"Alkyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono-, bi- or tri-cyclic structures, optionally combined with linear or branched structures, having the indicated number of carbon atoms. Examples of cycloalkyl groups include cyclopropyl, methylcyclopropyl, cyclopentyl, cycloheptyl, adamantyl, 2-ethyl-1-bicyclo[4.4.0]decyl, and the like.

"Cycloalkenyl" means cycloalkyl as defined above having at least one double bond, excluding aromatics.

"Alkoxy" means alkoxy groups of a straight or branched having the indicated number of carbon atoms. $C_{1-6}$alkoxy, for example, includes methoxy, ethoxy, propoxy, isopropoxy, and the like.

Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl, and the like.

"Halogen" and "halo" includes fluorine, chlorine, bromine and iodine.

With respect to "$C_{3-6}$cycloalkyl$C_{1-4}$alkyl", said $C_{3-6}$cycloalkyl may be substituted on any substitutable position on the $C_{1-4}$alkyl group and includes for example (1-methylcyclopropyl)methyl. Where appropriate, substitution on a ring can be at the 1-position, e.g., 1-hydroxycyclobutylcarbonyl.

Unless indicated otherwise, the term "bicyclic" and "tricyclic" includes bridged or spiro-cyclics as well as fused ring systems.

A nitrogen atom forming part of a heteroaryl ring may be in the form of the N-oxide. A sulfur atom forming part of a nonaromatic heterocycle may be in the form of the S-oxide or S,S-dioxide.

A heteroaryl group may be attached to the remainder of the molecule via a ring carbon or a ring nitrogen, provided that this is consistent with preservation of aromaticity.

In Formula I, $R^1$ and $R^2$ together with the nitrogen atom to which they are attached may complete a non-aromatic monocyclic, bicyclic, or tricyclic carbocyclic or heterocyclic system of up to 12 ring atoms. The heterocyclic ring system may contain one or more heteroatoms in addition to nitrogen selected from N, O and S and the remainder are C. In the case of a bicyclic system, said heteroatoms may be confined to one of the rings or distributed over both of the rings. In the case of a monocyclic system, the ring typically comprises 5 or 6 ring atoms.

Examples of spiro-linked heterocyclic ring systems include 2,9-diazaspiro[5.5]undecane and the like.

Examples of bicyclic rings include 3,8-diazabicyclo[3.2.1]octane, 2,3-diazabicyclo[2.2.2]octane, 2,5-diazabicyclo[2.2.1]heptane, 1,2,3,4-tetrahydroquinoline and 5,6,7,8-tetrahydro[1,2,4]triazolo[4,3-a]pyrazine.

It will be apparent to those skilled in the art that a hydroxy substituent on an unsaturated ring may be capable of tautomerising to a ketone. In such circumstances, both tautomers are to be considered equivalent. Thus, for example, 2-hydroxypyridine is considered equivalent to 2-oxo-1,2-dihydropyridine.

The compounds of the present invention are potentiators of metabotropic glutamate (mGluR) receptor function, in particular they are potentiators of mGluR2 receptors. That is, the compounds of the present invention do not appear to bind at the glutamate recognition site on the mGluR receptor, but in the presence of glutamate or a glutamate agonist, the compounds of the present invention increase mGluR receptor response. The present potentiators are expected to have their effect at mGluR receptors by virtue of their ability to increase the response of such receptors to glutamate or glutamate agonists, enhancing the function of the receptors. It is recognized that the compounds of the present invention would be expected to increase the effectiveness of glutamate and glutamate agonists of the mGluR2 receptor. Thus, the potentiators of the present invention are expected to be useful in the treatment of various neurological and psychiatric disorders associated with glutamate dysfunction described to be treated herein and others that can be treated by such potentiators as are appreciated by those skilled in the art.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. It will be understood that, as used herein, references to the compounds of Formula I are meant to also include pharmaceutically acceptable salts thereof.

Exemplifying the invention are the examples described herein. The subject compounds are useful in a method of potentiating metabotropic glutamate receptor activity in a patient such as a mammal in need of such inhibition comprising the administration of an effective amount of the compound. The present invention is directed to the use of the subject compounds disclosed herein as potentiators of metabotropic glutamate receptor activity. In addition to primates, especially humans, a variety of other mammals can be treated according to the method of the present invention.

The present invention is further directed to a method for the manufacture of a medicament for potentiating metabotropic glutamate receptor activity in humans and animals comprising combining a compound of the present invention with a pharmaceutical carrier or diluent.

The subject treated in the present methods is generally a mammal, preferably a human being, male or female, in whom potentiation of metabotropic glutamate receptor activity is desired. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as inhibitors of metabotropic glutamate receptor activity, in particular mGluR2 activity, may be demonstrated by methodology known in the art. Inhibition constants are determined as follows. The compounds of the present invention may be tested in a fluorescence laser imaging plate reader (FLIPR) based assay. This assay is a common functional assay to monitor $Ca^{2+}$ mobilization in whole cells expressing recombinant receptor coupled with a promiscuous G-protein. CHO dhfr-cells stably expressing recombinant human mGluR2 and Gα16 loaded with Fluo-4 AM (Invitrogen, Carlsbad Calif.) are treated with dose responses of compounds and the $Ca^{2+}$ response is monitored on a FLIPR384 (Molecular Devices, Sunnydale Calif.) for agonist activity. The potentiation response is monitored after a subsequent addition of an EC20 concentration of glutamate (900 nM). The maximum calcium response at each concentration of compound for agonist or potentiation are plotted as dose responses and the curves are fitted with a four parameters logistic equation giving EC50 and Hill coefficient using the iterative non linear curve fitting software program.

The compounds of the present invention may also be tested in a [$^{35}$S]-GTPγS assay. The stimulation of [$^{35}$S]-GTPγS binding is a common functional assay to monitor Gαi-coupled receptor in native and recombinant receptor membrane preparation. Membrane from cells stably expressing hmGlu2 CHO-K1 (50 μg) are incubated in a 96 well plate for 1 hour in the presence of GTPγS$^{35}$ (0.05 nM), GDP (5 μM) and compounds. The reaction is stopped by rapid filtration over Unifilter GF/B plate (Packard, Bioscience, Meriden Conn.) using a 96-well cell harvester (Brandel Gaithersburg, Md.). The filter plates are counted using Topcount counter (Packard, Bioscience, Meriden Conn., USA). When compounds are evaluated as potentiators they are tested in the presence of glutamate (1 μM). The activation (agonist) or the potentiation of glutamate (potentiator) curves are fitted with a four parameters logistic equation giving $EC_{50}$ and Hill coefficient using the iterative non linear curve fitting software GraphPad (San Diego Calif., USA).

Compounds of the invention were tested and demonstrated activity in potentiating the mGluR2 receptor in the FLIPR assay, generally with an $EC_{50}$ of less than about 10 μM. Compounds within the present invention had activity in potentiating the mGluR2 receptor in the FLIPR and GTPγS assays with an $EC_{50}$ of less than about 1 μM. Each of the identified compounds resulted in a minimum 1.8-fold potentiation of glutamate response in the presence of an EC20 concentration of glutamate (900 nM). Such results are indicative of the intrinsic activity of the compounds in use as potentiators of mGluR2 receptor activity.

Representative FLIPR and GTPγS EC$_{50}$ Values

| Ex. No. | hFLIPR pot. EC$_{50}$ (nM) | rGTPγS pot. EC$_{50}$ (nM) |
| --- | --- | --- |
| 2-7 | 16.02 | 9.08 |
| 2-8 | 28.14 | 69.3 |
| 2-9 | 100.1 | 299.1 |
| 2-16 | 64.1 | 214.7 |
| 2-22 | 56.06 | 114.7 |
| 2-34 | 22.79 | 17.86 |
| 5-2 | 322 | ND |
| 6-4 | 28.96 | 26.62 |
| 8-6 | 512.7 | ND |
| 8-9 | 269.9 | 2820 |
| 8-14 | 134.2 | 51.38 |
| 8-38 | 17.91 | 54.7 |
| 11-5 | 390.7 | ND |
| 14-6 | 123.3 | 248.3 |
| 17-15 | 594.1 | ND |
| 17-20 | 332.7 | ND |
| 18-10 | 2189 | ND |
| 18-42 | 985.5 | ND |
| 18-200 | 43.24 | 44.01 |
| 19-4 | 951.1 | ND |
| 19-62 | 116.3 | ND |
| 24-7 | 48.5 | 88.63 |
| 24-20 | 177.4 | ND |
| 25-5 | 359.2 | ND |
| 34-3 | 14.38 | 40.64 |
| 38-5 | 1178 | ND |

Metabotropic glutamate receptors including the mGluR2 receptor have been implicated in a wide range of biological functions. This has suggested a potential role for these receptors in a variety of disease processes in humans or other species.

The compounds of the present invention may have utility in treating, preventing, ameliorating, controlling or reducing the risk of a variety of neurological and psychiatric disorders associated with glutamate dysfunction, including one or more of the following conditions or diseases: acute neurological and psychiatric disorders such as cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, substance tolerance, substance withdrawal (including, substances such as opiates, nicotine, tobacco products, alcohol, benzodiazepines, cocaine, sedatives, hypnotics, etc.), psychosis, schizophrenia, anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic pain states, severe pain, intractable pain, neuropathic pain, and post-traumatic pain), tardive dyskinesia, sleep disorders (including narcolepsy), autism, autism spectrum disorders, attention deficit/hyperactivity disorder, and conduct disorder.

In an embodiment the present invention provides a method for treating migraine, comprising: administering to a patient in need thereof an effective amount of a compound of Formula I. In another embodiment the present invention provides a method for preventing or treating anxiety, comprising: administering to a patient in need thereof an effective amount of a compound of Formula I. Particular anxiety disorders of the invention are generalized anxiety disorder, panic disorder, and obsessive compulsive disorder. In another embodiment the present invention provides a method for treating schizophrenia, comprising: administering to a patient in need thereof an effective amount of a compound of Formula I. In yet another embodiment the present invention provides a method for treating epilepsy, comprising: administering to a patient in need thereof an effective amount of a compound of Formula I.

In an embodiment, the present invention provides a method for the treatment of schizophrenia comprising: administering to a patient in need thereof an effective amount of a compound of Formula I or a pharmaceutical composition thereof. In one of the available sources of diagnostic tools, The Merck Manual (2006-2007), schizophrenia is characterized by psychosis (loss of contact with reality), hallucinations (false perceptions), delusions (false beliefs), disorganized speech and behavior, flattened affect (restricted range of emotions), cognitive deficits (impaired reasoning and problem solving), and occupational and social dysfunction. The skilled artisan will recognize that there are alternative nomenclatures, nosologies, and classification systems for neurological and psychiatric disorders, including migraine, and that these systems evolve with medical scientific progress Thus, in an embodiment the present invention provides a method for treating migraine, comprising: administering to a patient in need thereof an effective amount of a compound of formula I or a pharmaceutical composition thereof. In one of the available sources of diagnostic tools, Dorland's Medical Dictionary (23' d Ed., 1982, W.B. Saunders Company, Philadelphia, Pa.), migraine is defined as a symptom complex of periodic headaches, usually temporal and unilateral, often with irritability, nausea, vomiting, constipation or diarrhea, and photophobia. As used herein the term "migraine" includes these periodic headaches, both temporal and unilateral, the associated irritability, nausea, vomiting, constipation or diarrhea, photophobia, and other associated symptoms. The skilled artisan will recognize that there are alternative nomenclatures, nosologies, and classification systems for neurological and psychiatric disorders, including migraine, and that these systems evolve with medical scientific progress.

In another embodiment the present invention provides a method for treating anxiety, comprising: administering to a patient in need thereof an effective amount of a compound of Formula I or a pharmaceutical composition thereof. At present, the fourth edition of the Diagnostic and Statistical Manual of Mental Disorders (DSM-IV) (1994, American Psychiatric Association, Washington, D.C.), provides a diagnostic tool including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified. As used herein the term "anxiety" includes treatment of those anxiety disorders and related disorder as described in the DSM-IV. The skilled artisan will recognize that there are alternative nomenclatures, nosologies, and classification systems for neurological and psychiatric disorders, and particular anxiety, and that these systems evolve with medical scientific progress. Thus, the term "anxiety" is intended to include like disorders that are described in other diagnostic sources.

In another embodiment the present invention provides a method for treating depression, comprising: administering to a patient in need thereof an effective amount of a compound of Formula I or a pharmaceutical composition thereof. At present, the fourth edition of the Diagnostic and Statistical Manual of Mental Disorders (DSM-IV) (1994, American Psychiatric Association, Washington, D.C.), provides a diagnostic tool including depression and related disorders. Depressive disorders include, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias; seasonal affective disorder; or bipolar disorders or manic depression, for example, bipolar I disorder, bipolar II disorder and cyclothymic disorder. As used herein the term "depression" includes treatment of those depression disorders and related disorder as described in the DSM-IV.

In another embodiment the present invention provides a method for treating epilepsy, comprising: administering to a patient in need thereof an effective amount of a compound of Formula I or a pharmaceutical composition thereof. At present, there are several types and subtypes of seizures associated with epilepsy, including idiopathic, symptomatic, and cryptogenic. These epileptic seizures can be focal (partial) or generalized. They can also be simple or complex. Epilepsy is described in the art, such as Epilepsy: A comprehensive textbook. Ed. by Jerome Engel, Jr. and Timothy A. Pedley. (Lippincott-Raven, Philadelphia, 1997). At present, the International Classification of Diseases, Ninth Revision, (ICD-9) provides a diagnostic tool including epilepsy and related disorders. These include: generalized nonconvulsive epilepsy, generalized convulsive epilepsy, petit mal status epilepticus, grand mal status epilepticus, partial epilepsy with impairment of consciousness, partial epilepsy without impairment of consciousness, infantile spasms, epilepsy partialis continua, other forms of epilepsy, epilepsy, unspecified, NOS. As used herein the term "epilepsy" includes these all types and subtypes. The skilled artisan will recognize that there are alternative nomenclatures, nosologies, and classification systems for neurological and psychiatric disorders, including epilepsy, and that these systems evolve with medical scientific progress.

The subject compounds may be further useful in a method for the prevention, treatment, control, amelioration, or reduction of risk of the diseases, disorders and conditions noted herein.

The subject compounds may be further useful in a method for the prevention, treatment, control, amelioration, or reduction of risk of the aforementioned diseases, disorders and conditions in combination with other agents, including an mGluR agonist.

The term "potentiated amount" refers to an amount of an mGluR agonist, that is, the dosage of agonist which is effective in treating the neurological and psychiatric disorders described herein when administered in combination with an effective amount of a compound of the present invention. A potentiated amount is expected to be less than the amount that is required to provided the same effect when the mGluR agonist is administered without an effective amount of a compound of the present invention.

A potentiated amount can be readily determined by the attending diagnostician, as one skilled in the art, by the use of conventional techniques and by observing results obtained under analogous circumstances. In determining a potentiated amount, the dose of an mGluR agonist to be administered in combination with a compound of formula I, a number of factors are considered by the attending diagnostician, including, but not limited to: the mGluR agonist selected to be administered, including its potency and selectivity; the compound of formula I to be coadministered; the species of mammal; its size, age, and general health; the specific disorder involved; the degree of involvement or the severity of the disorder; the response of the individual patient; the modes of administration; the bioavailability characteristics of the preparations administered; the dose regimens selected; the use of other concomitant medication; and other relevant circumstances.

A potentiated amount of an mGluR agonist to be administered in combination with an effective amount of a compound of Formula I is expected to vary from about 0.1 milligram per kilogram of body weight per day (mg/kg/day) to about 100 mg/kg/day and is expected to be less than the amount that is required to provided the same effect when administered without an effective amount of a compound of formula I. Preferred amounts of a co-administered mGlu agonist are able to be determined by one skilled in the art.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form may be utilized containing such other drugs and the compound of Formula I. However, the combination therapy may also includes therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention may be utilized. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives.

Pharmaceutical compositions of the present compounds may be in the form of a sterile injectable aqueous or oleaginous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require potentiation of metabotropic glutamate receptor activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

When treating, preventing, controlling, ameliorating, or reducing the risk of neurological and psychiatric disorders associated with glutamate dysfunction or other diseases for which compounds of the present invention are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligram to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein. The compounds of the present invention can be prepared in a variety of fashions.

All patents, publications and pending patent applications identified are hereby incorporated by reference.

Abbreviations used in the description of the chemistry and in the Examples that follow are: Ac2O (acetic anhydride); AcOH (acetic acid); AEBSF (p-aminoethylbenzenesulfonyl fluoride); Boc (di-tert-butyl carbamate); (Boc)$_2$O (di-tert-butyl dicarbonate); BSA (bovine serum albumin); BuLi (n-Butyl lithium); CDCl3 (chloroform-d); CuI (copper iodide); CuSO4 (copper sulfate); DBU (1,8-diazabicyclo[5.4.0]undec-7-ene); DCE (dichloroethane); DCM (dichloromethane); DEAD (diethyl azodicarboxylate); DIBAL-H (diisobutyl aluminum hydride); DIPEA (diisopropylethylamine); DMBA (1,3-dimethylbarbituric acid); DMF (N,N-dimethylformamide); DMP (Dess-Martin periodinane); DMSO (dimethyl sulfoxide); DPPA (diphenylphosphoryl azide); DTT (dithiothreitol); EDTA (ethylene-diamine-tetra-acetic acid); EGTA (ethylene-glycol-tetra-acetic acid); Et2O (diethylether); EtOAc (ethyl acetate); EtOH (ethanol); HATU (2-(1H-7-azabenzotriazol-1-yl)-1,1,3,3-tetramethyl uronium hexafluorophosphate methanaminium); HOAc (acetic acid); HOBT (hydroxybenzotriazole); HPLC (high-performance liquid chromatography); HRMS (high resolution mass spectrum); LAH (lithium aluminum hydride); LCMS (liquid chromatograph-mass spectrometer); LHMDS (lithium bis(trimethylsilyl)amide); LRMS (low resolution mass spectrum); mCPBA (3-chloroperoxybenzoic acid); MeOH (methanol); MP-B(CN)H3 (Macroporous cyanoborohydride); NaHCO3 (sodium bicarbonate); Na2SO4 (sodium sulfate); Na(OAc)$_3$BH (sodium triacetoxyborohydride); NH4OAc (ammonium acetate); NBS (N-bromosuccinamide); NFSi (N-fluorobenzenesulfonimide); NMP (1-methyl-2-pyrrolidinone); NMR (nuclear magnetic resonance); PBS (phosphate buffered saline); PCR (polymerase chain reaction); Pd(dppf) ([1,1'-bis(diphenylphosphino)ferrocene] palladium); Pd(Ph3)$_4$ (palladium(0) tetrakis-triphenylphosphine); POCl3 (phosphorous oxychloride); PS-DIEA (polystyrene diisopropylethylamine); PS-PPh3 (polystyrenetriphenyl phosphine); PTSA (para-toluene sulfonic acid); Pyr (pyridine); RT (room temperature); Selectfluor (1-chloromethyl-4-fluoro-1,4-diazoniabicyclo[2.2.2]octane bis(tetrafluoroborate); TBAF (tetrabutylammonium fluoride); T-BuOH (tert-butanol); TEA (triethylamine); THF (tetrahydrofuran); TLC (thin layer chromatography); Tf (trifluoromethanesulfonyl); TFA (trifluoroacteic acid); and TMSCH2N2 (trimethylsilyldiazomethane).

The compounds of this invention may be prepared by employing reactions as shown in the following Reaction Schemes and Examples, in addition to other standard manipulations that are known in the literature or exemplified in the experimental procedures. The illustrative Reaction Schemes below, therefore, are not limited by the compounds listed or by any particular substituents employed for illustrative purposes. Substituent numbering as shown in the Reaction Schemes do not necessarily correlate to that used in the claims and often, for clarity, a single substituent is shown attached to the compound where multiple substituents are optionally allowed under the definitions of Formula I hereinabove.

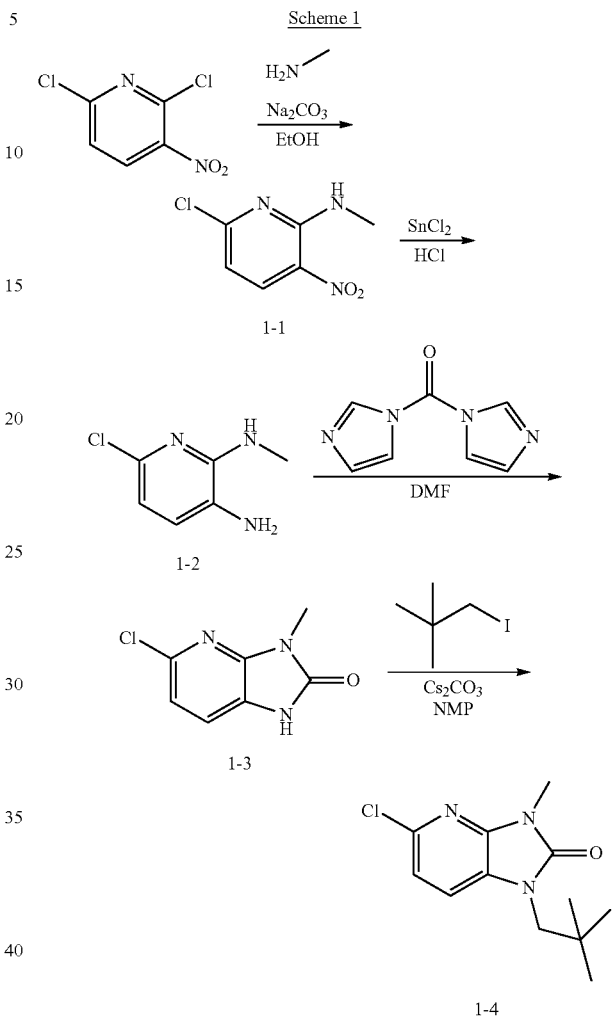

5-Chloro-1-(2,2-dimethylpropyl)-3-methyl-1,3-dihydro-2H-imidazo[4,5-b]pyridin-2-one (1-4)

6-Chloro-N-methyl-3-nitropyridin-2-amine (1-1)

2,6-Dichloro-3-nitropyridine (2.0 g, 10.4 mmol) and sodium carbonate 2.75 g, 25.9 mmol) were added to a round bottom flask under nitrogen, and suspended in ethanol (100 mL). Methylamine in methanol (7.8 mL, 15.6 mmol, 2M) was then added and stirred at room temperature for 3 hours. The yellow solution was concentrated, and then re-dissolved in ethyl acetate followed by washing with sodium bicarbonate and brine. The organic phase was dried over sodium sulfate, filtered, and concentrated. The yellow solid was then re-dissolved in ethanol and recrystallized to give 6-chloro-N-methyl-3-nitropyridin-2-amine (1-1) as a yellow solid. MS m/z (M+H): calculated=188.0228, calculated=188.0221.

6-Chloro-$N^2$-methylpyridine-2,3-diamine (1-2)

6-Chloro-N-methyl-3-nitropyridin-2-amine (1-1, 10.5 g, 56 mmol) and tin(II) chloride dehydrate (50.5 g, 224 mmol)

were suspended in concentrated HCl (80 mL) and refluxed overnight. The solution was cooled to room temperature and then added very slowly to a NaOH/ethyl acetate solution at −78° C., until the solution had a slightly basic pH. The suspension was washed with sodium bicarbonate, brine, dried over sodium sulfate, filtered, and concentrated to produce 6-chloro-$N^2$-methylpyridine-2,3-diamine (1-2) as a black solid. HRMS (M+H)$^+$: observed=158.0487, calculated=158.0480.

5-Chloro-3-methyl-1,3-dihydro-2H-imidazo[4,5-b]pyridin-2-one (1-3)

6-Chloro-$N^2$-methylpyridine-2,3-diamine (1-2, 35 g, 222 mmol) and 1,1'-carbonyldiimidazole (63 g, 389 mmol) were added to a round bottom flask and suspended in DMF (150 mL). The solution was heated to 80° C. in an oil bath overnight. The reaction was then suspended in ethyl acetate and sodium bicarbonate. The suspension was washed with sodium bicarbonate, brine(×5), dried over sodium sulfate, filtered, and concentrated to produce 5-chloro-3-methyl-1,3-dihydro-2H-imidazo[4,5-b]pyridin-2-one (1-3) as a white solid. HRMS (M+H)$^+$: observed=184.0279, calculated=184.0272.

5-Chloro-1-(2,2-dimethylpropyl)-3-methyl-1,3-dihydro-2H-imidazo[4,5-b]-pyridin-2-one (1-4)

5-Chloro-3-methyl-1,3-dihydro-2H-imidazo[4,5-b]pyridin-2-one (1-3, 2.97 g, 16.2 mmol) and cesium carbonate (15.8 g, 48.6 mmol) were added to a round bottom flask and suspended in NMP (25 mL) under nitrogen. Neopentyl iodide (6.4 g, 32.4 mmol) was added to the suspension and then refluxed at 90° C. overnight. The reaction was then cooled to room temperature and suspended in ethyl acetate and sodium bicarbonate. The suspension was washed with sodium bicarbonate, brine(×5), dried over sodium sulfate, filtered, and concentrated. The mixture was purified using normal phase chromatography(0-60% ethyl acetate/hexanes), and the desired fractions were collected to produce 5-chloro-1-(cyclopropylmethyl)-3-methyl-1,3-dihydro-2H-imidazo[4,5-b]pyridin-2-one (1-4) as a tan solid. HRMS (M+H)$^+$: observed=253.7341, calculated=253.7340.

Scheme 2

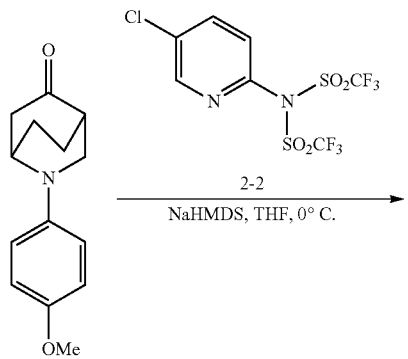

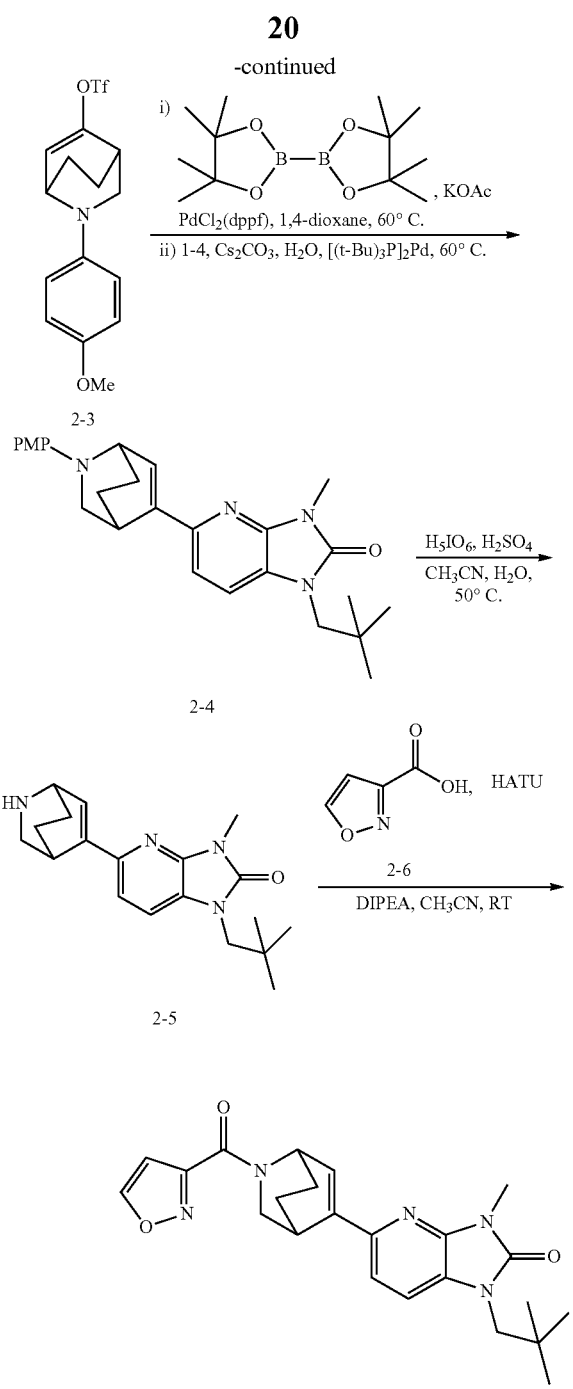

1-(2,2-Dimethylpropyl)-5-[2-(isoxazol-3-ylcarbonyl)-2-azabicyclo-[2.2.2]oct-5-en-5-yl]-3-methyl-1,3-dihydro-2H-imidazo[4,5-b]pyridin-2-one (2-7)

2-(4-Methoxyphenyl)-2-azabicyclo[2.2.2]oct-5-en-5-yl trifluoromethanesulfonate (2-3)

2-(4-Methoxyphenyl)-2-azabicyclo[2.2.2]octan-5-one, Sunden, H.; Ibrahem, I.; Eriksson, L.; Cordova, A. *Angew.*

*Chem. Int. Ed.* 2005, 117, 4955-4958 (2-1, 4 g, 17.3 mmol, 1.0 equiv), was added to anhydrous THF (87 mL) and cooled to 0° C. To this solution was added NaHMDS (10.4 mL, 20.8 mmol, 1.2 equiv, 2M solution in THF) followed by N-(5-chloro-2-pyridyl)triflimide (2-2, 9.5 g, 24.2 mmol, 1.4 equiv) in two equal portions. After 60 min at 0° C., TLC analysis showed consumption of starting material. The reaction was quenched with brine (80 mL) and diluted with ethyl acetate (150 mL) and water (150 mL). The layers were separated and the aqueous layer was extracted with ethyl acetate (3×100 mL). The combined organics were dried over $Na_2SO_4$, filtered and concentrated in vacuo to give a red oil. Purification by normal-phase chromatography (0-40% EtOAc:Hex) afforded 2-3 as a pale yellow solid, which was immediately carried forward.

1-(2,2-Dimethylpropyl)-5-[2-(4-methoxyphenyl)-2-azabicyclo[2.2.2]oct-5-en-5-yl]-3-methyl-1,3-dihydro-2H-imidazo[4,5-b]pyridin-2-one (2-4)

2-(4-Methoxyphenyl)-2-azabicyclo[2.2.2]oct-5-en-5-yl trifluoromethanesulfonate (2-3, 6.2 g, 17.1 mmol, 1.0 equiv), bis(pinocolato)diboron (4.8 g, 18.8 mmol, 1.1 equiv), potassium acetate (5.0 g, 51.2 mmol, 3.0 equiv) and $PdCl_2(dppf)$ (0.87 g, 1.2 mmol, 0.07 equiv) were added to anhydrous 1,4-dioxane (22 mL) and heated to 60° C. After 18 h, the reaction contents were cooled to RT, followed by the subsequent addition of water (4.3 mL), 5-chloro-1-(2,2-dimethylpropyl)-3-methyl-1,3-dihydro-2H-imidazo[4,5-b]-pyridin-2-one (1-4, 4.3 g, 17.1 mmol, 1.0 equiv), $Cs_2CO_3$ (11.2 g, 34.3 mmol, 2.01 equiv) and bis(tri-tert-butylphosphine)palladium (0) (1.1 g, 2.22 mmol, 0.13 equiv). The resulting mixture was heated to 60° C. for 4.5 h. Following this duration, LCMS showed consumption of starting material. The contents were then cooled to room temperature, diluted with ethyl acetate (100 mL), filtered through Celite and rinsed with ethyl acetate (3×70 mL) and water (1×30 mL). The filtrate layers were separated and the combined organics were washed with saturated $NaHCO_3$ (120 mL). The combined aqueous layers were then back-extracted with ethyl acetate (2×50 mL). The combined organics were dried over $Na_2SO_4$, filtered and concentrated in vacuo to give a dark red oil. Purification by normal-phase chromatography (0-50% EtOAc:Hex) afforded 2-4 as an off-white solid. MS m/z (M+H): calculated=433.2598; observed=433.2591.

5-(2-Azabicyclo[2.2.2]oct-5-en-5-yl)-1-(2,2-dimethylpropyl)-3-methyl-1,3-dihydro-2H-imidazo[4,5-b]pyridin-2-one (2-5)

1-(2,2-Dimethylpropyl)-5-[2-(4-methoxyphenyl)-2-azabicyclo[2.2.2]oct-5-en-5-yl]-3-methyl-1,3-dihydro-2H-imidazo[4,5-b]pyridin-2-one (2-4, 339 mg, 0.78 mmol, 1.0 equiv) was added to $CH_3CN$ (7 mL) and water (7 mL) To this suspension was added aqueous $H_2SO_4$ (0.78 mL, 0.78 mmol, 1.0 equiv, 1.0 M) followed by periodic acid in one portion (179 mg, 0.78 mmol, 1.0 equiv). The reaction contents were heated to 50° C. for 18 h. Following this duration, LCMS showed consumption of starting material. The mixture was subsequently filtered through Celite, rinsed with $CH_3CN$ and purified by reverse-phase HPLC (15-70% $CH_3CN$:0.1% TFA in $H_2O$) to give 2-5 as an off-white solid. MS m/z (M+H): calculated=327.2179; observed=327.2187.

1-(2,2-Dimethylpropyl)-5-[2-(isoxazol-3-ylcarbonyl)-2-azabicyclo[2.2.2]-oct-5-en-5-yl]-3-methyl-1,3-dihydro-2H-imidazo[4,5-b]pyridin-2-one (2-7)

5-(2-Azabicyclo[2.2.2]oct-5-en-5-yl)-1-(2,2-dimethylpropyl)-3-methyl-1,3-dihydro-2H-imidazo[4,5-b]pyridin-2-one (2-5, 291 mg, 0.90 mmol, 1.0 equiv), isoxazole-3-carboxylic acid (2-6, 151 mg, 1.4 mmol, 1.5 equiv), DIPEA (0.47 mL, 2.7 mmol, 3.0 equiv) and HATU (510 mg, 1.4 mmol, 1.5 equiv) were added to anhydrous 1,4-dioxane (9 mL). After stirring for 10 min at room temperature, LCMS showed consumption of starting material. Purification by reverse-phase HPLC (20-100% $CH_3CN$:0.1% TFA in $H_2O$) provided 2-7 as a white solid. MS m/z (M+H): calculated=422.2187; observed=422.2189. $^1$H NMR δ (ppm)($CHCl_3$-d): 8.40 (1H, dd, J=27.77, 1.66 Hz), 7.22-7.17 (1H, m), 7.12 (1H, dd, J=8.11, 1.50 Hz), 6.97 (1H, m), 6.70 (1H, dd, J=11.92, 1.66 Hz), 5.55-5.52 (0.4H, m), 5.42-5.38 (0.6H, m), 3.95 (0.4H, m), 3.88 (1H, m), 3.62 (2.6H, m), 3.53 (0.4H, m), 3.47 (3H, d, J=3.86 Hz), 3.36 (0.6H, d, J=12.39 Hz), 2.21-2.11 (1H, m), 1.91-1.80 (1H, m), 1.61-1.52 (2H, m) 0.99 (9H, d, J=1.91 Hz). (Mixture of rotamers at RT).

The following compounds were prepared from 2-5 by a reaction sequence analogous to that illustrated in Scheme 2:

TABLE 1

| # | Structure | Name | HRMS/LRMS |
|---|---|---|---|
| 2-8 | 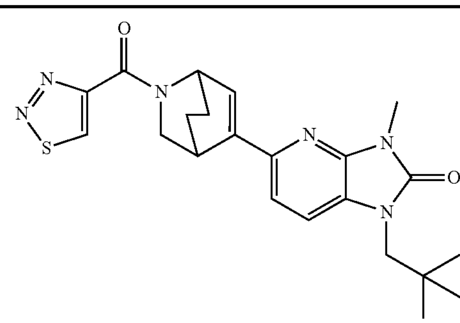 | 1-(2,2-dimethylpropyl)-3-methyl-5-[2-(1,2,3-thiadiazol-4-ylcarbonyl)-2-azabicyclo[2.2.2]oct-5-en-5-yl]-1,3-dihydro-2H-imidazo[4,5-b]pyridin-2-one | C22H26N6O2S [M + H] calc 439.1912 obs 439.1911 |

TABLE 1-continued

| # | Structure | Name | HRMS/LRMS |
|---|---|---|---|
| 2-9 | 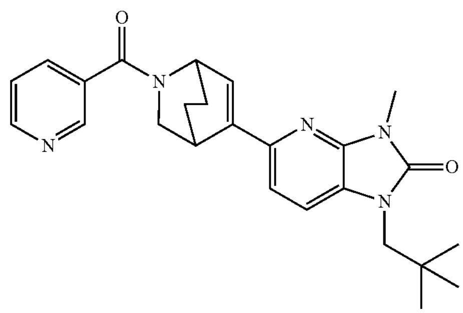 [SMILES: Cn1c(=O)n(CC(C)(C)C)c2ccc(C3=CC4CCC3CN4C(=O)c3cccnc3)nc21] | 1-(2,2-dimethylpropyl)-3-methyl-5-[2-(pyridin-3-ylcarbonyl)-2-azabicyclo[2.2.2]oct-5-en-5-yl]-1,3-dihydro-2H-imidazo[4,5-b]pyridin-2-one | C25H29N5O2 [M + H] calc 432.2396 obs 432.2395 |
| 2-10 | 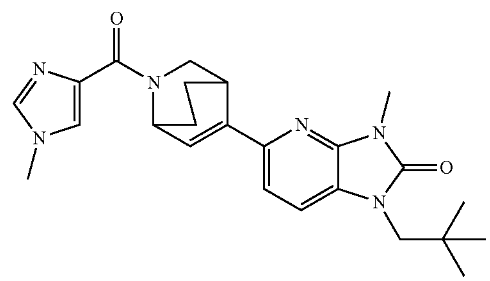 | 1-(2,2-dimethylpropyl)-3-methyl-5-{2-[(1-methyl-1H-imidazol-4-yl)carbonyl]-2-azabicyclo[2.2.2]oct-5-en-5-yl}-1,3-dihydro-2H-imidazo[4,5-b]pyridin-2-one | C24H30N6O2 [M + H] calc 435.2504 obs 435.2513 |
| 2-11 | 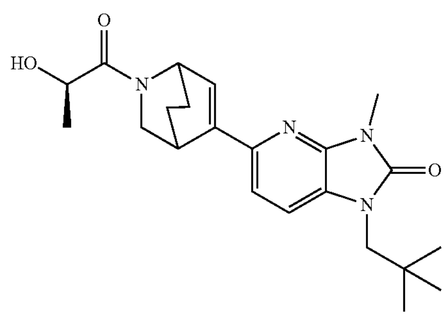 [SMILES: C[C@@H](O)C(=O)N1CC2CCC1C=C2c1ccc2c(n1)n(C)c(=O)n2CC(C)(C)C] | 1-(2,2-dimethylpropyl)-5-{2-[(2R)-2-hydroxypropanoyl]-2-azabicyclo[2.2.2]oct-5-en-5-yl}-3-methyl-1,3-dihydro-2H-imidazo[4,5-b]pyridin-2-one | C22H30N4O3 [M + H] calc 399.2392 obs 399.2398 |
| 2-12 | 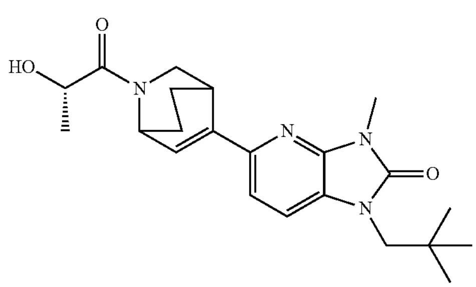 [SMILES: C[C@H](O)C(=O)N1CC2CCC1C=C2c1ccc2c(n1)n(C)c(=O)n2CC(C)(C)C] | 1-(2,2-dimethylpropyl)-5-{2-[(2S)-2-hydroxypropanoyl]-2-azabicyclo[2.2.2]oct-5-en-5-yl}-3-methyl-1,3-dihydro-2H-imidazo[4,5-b]pyridin-2-one | C22H30N4O3 [M + H] calc 399.2392 obs 399.2398 |
| 2-13 | 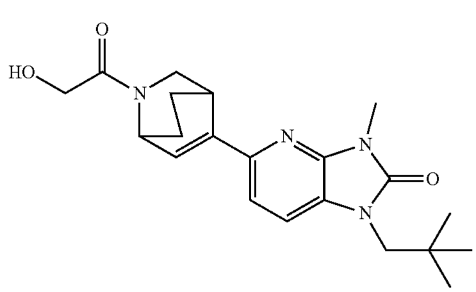 | 1-(2,2-dimethylpropyl)-5-[2-(hydroxyacetyl)-2-azabicyclo[2.2.2]oct-5-en-5-yl]-3-methyl-1,3-dihydro-2H-imidazo[4,5-b]pyridin-2-one | C21H28N4O3 [M + H] calc 385.2236 obs 385.2243 |

TABLE 1-continued

| # | Structure | Name | HRMS/LRMS |
|---|---|---|---|
| 2-14 | 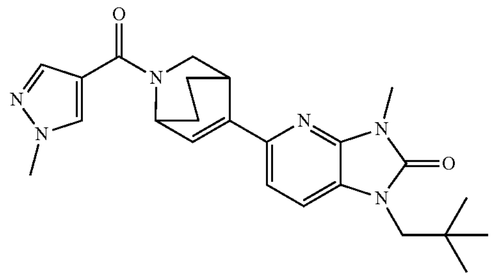 [SMILES: Cn1cc(C(=O)N2CC3CCC2C=C3c2ccc3c(n2)n(C)c(=O)n3CC(C)(C)C)cn1] | 1-(2,2-dimethylpropyl)-3-methyl-5-{2-[(1-methyl-1H-pyrazol-4-yl)carbonyl]-2-azabicyclo[2.2.2]oct-5-en-5-yl}-1,3-dihydro-2H-imidazo[4,5-b]pyridin-2-one | C24H30N6O2 [M + H] calc 435.2504 obs 435.2513 |
| 2-15 | 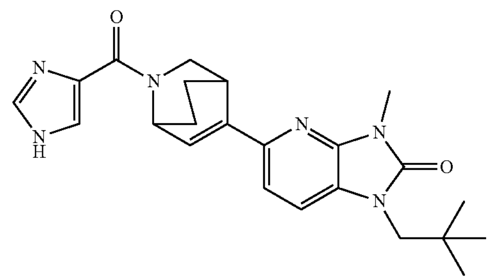 [SMILES: Cn1c(=O)n(CC(C)(C)C)c2ccc(C3=CC4CCC3CN4C(=O)c3c[nH]cn3)nc21] | 1-(2,2-dimethylpropyl)-5-[2-(1H-imidazol-4-ylcarbonyl)-2-azabicyclo[2.2.2]oct-5-en-5-yl]-3-methyl-1,3-dihydro-2H-imidazo[4,5-b]pyridin-2-one | C23H28N6O2 [M + H] calc 421.2348 obs 421.2358 |
| 2-16 | 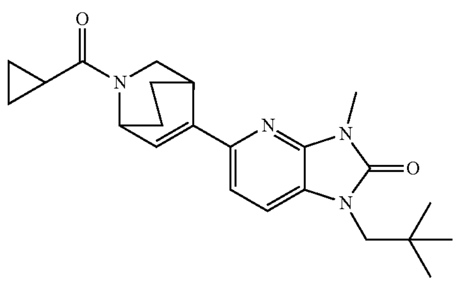 [SMILES: Cn1c(=O)n(CC(C)(C)C)c2ccc(C3=CC4CCC3CN4C(=O)C3CC3)nc21] | 5-[2-(cyclopropylcarbonyl)-2-azabicyclo[2.2.2]oct-5-en-5-yl]-1-(2,2-dimethylpropyl)-3-methyl-1,3-dihydro-2H-imidazo[4,5-b]pyridin-2-one | C23H30N4O2 [M + H] calc 395.2443 obs 395.2448 |
| 2-17 | 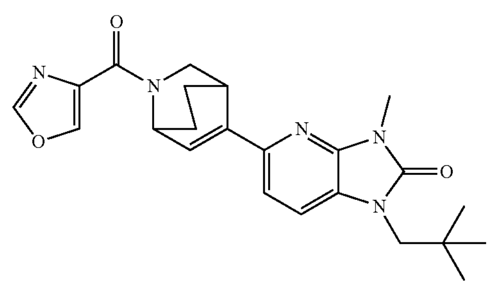 [SMILES: Cn1c(=O)n(CC(C)(C)C)c2ccc(C3=CC4CCC3CN4C(=O)c3cocn3)nc21] | 1-(2,2-dimethylpropyl)-3-methyl-5-[2-(1,3-oxazol-4-ylcarbonyl)-2-azabicyclo[2.2.2]oct-5-en-5-yl]-1,3-dihydro-2H-imidazo[4,5-b]pyridin-2-one | C23H27N5O3 [M + H] calc 422.2188 obs 422.2193 |
| 2-18 | 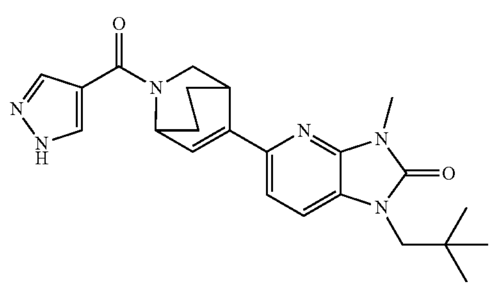 [SMILES: Cn1c(=O)n(CC(C)(C)C)c2ccc(C3=CC4CCC3CN4C(=O)c3cn[nH]c3)nc21] | 1-(2,2-dimethylpropyl)-3-methyl-5-[2-(1H-pyrazol-4-ylcarbonyl)-2-azabicyclo[2.2.2]oct-5-en-5-yl]-1,3-dihydro-2H-imidazo[4,5-b]pyridin-2-one | C23H28N6O2 [M + H] calc 421.2348 obs 421.2361 |

TABLE 1-continued

| # | Structure | Name | HRMS/LRMS |
|---|---|---|---|
| 2-19 | 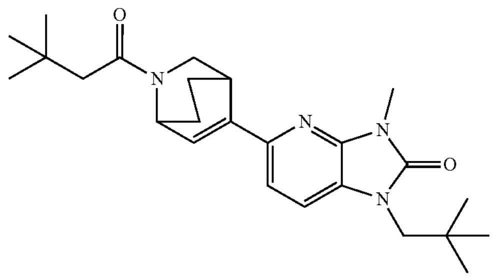 [SMILES: Cn1c(=O)n(CC(C)(C)C)c2ccc(C3=CC4CCC3CN4C(=O)CC(C)(C)C)nc21] | 5-[2-(3,3-dimethylbutanoyl)-2-azabicyclo[2.2.2]oct-5-en-5-yl]-1-(2,2-dimethylpropyl)-3-methyl-1,3-dihydro-2H-imidazo[4,5-b]pyridin-2-one | C25H36N4O2 [M + H] calc 425.2912 obs 425.2920 |
| 2-20 | 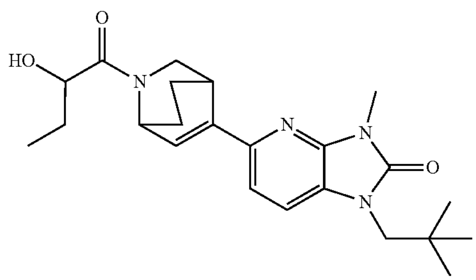 [SMILES: CCC(O)C(=O)N1CC2CCC1C=C2c1ccc2c(n1)n(C)c(=O)n2CC(C)(C)C] | 1-(2,2-dimethylpropyl)-5-[2-(2-hydroxybutanoyl)-2-azabicyclo[2.2.2]oct-5-en-5-yl]-3-methyl-1,3-dihydro-2H-imidazo[4,5-b]pyridin-2-one | C23H32N4O3 [M + H] calc 413.2548 obs 413.2557 |
| 2-21 | 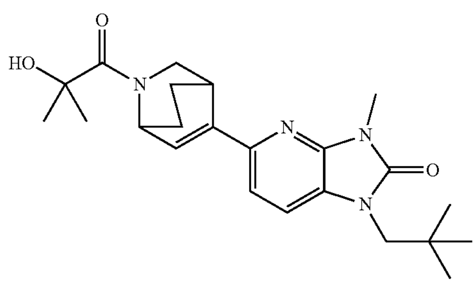 [SMILES: Cn1c(=O)n(CC(C)(C)C)c2ccc(C3=CC4CCC3CN4C(=O)C(C)(C)O)nc21] | 1-(2,2-dimethylpropyl)-5-[2-(2-hydroxy-2-methylpropanoyl)-2-azabicyclo[2.2.2]oct-5-en-5-yl]-3-methyl-1,3-dihydro-2H-imidazo[4,5-b]pyridin-2-one | C23H32N4O3 [M + H] calc 413.2548 obs 413.2556 |
| 2-22 | 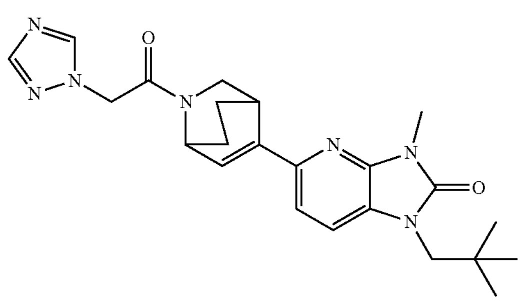 [SMILES: Cn1c(=O)n(CC(C)(C)C)c2ccc(C3=CC4CCC3CN4C(=O)Cn3cncn3)nc21] | 1-(2,2-dimethylpropyl)-3-methyl-5-[2-(1H-1,2,4-triazol-1-ylacetyl)-2-azabicyclo[2.2.2]oct-5-en-5-yl]-1,3-dihydro-2H-imidazo[4,5-b]pyridin-2-one | C23H29N7O2 [M + H] calc 436.2457 obs 436.2469 |
| 2-23 | 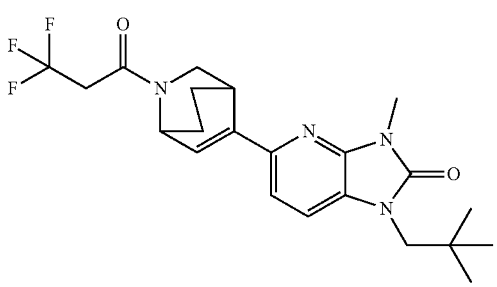 [SMILES: Cn1c(=O)n(CC(C)(C)C)c2ccc(C3=CC4CCC3CN4C(=O)CC(F)(F)F)nc21] | 1-(2,2-dimethylpropyl)-3-methyl-5-[2-(3,3,3-trifluoropropanoyl)-2-azabicyclo[2.2.2]oct-5-en-5-yl]-1,3-dihydro-2H-imidazo[4,5-b]pyridin-2-one | C22H27F3N4O2 [M + H] calc 437.2161 obs 437.2170 |

TABLE 1-continued

| # | Structure | Name | HRMS/LRMS |
|---|---|---|---|
| 2-24 | 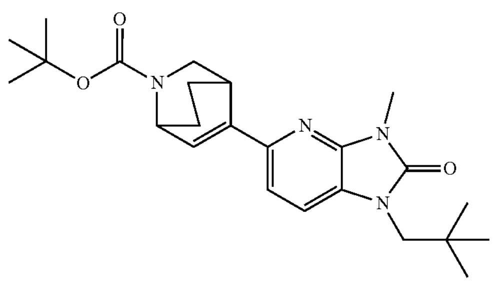 | tert-butyl 5-[1-(2,2-dimethylpropyl)-3-methyl-2-oxo-2,3-dihydro-1H-imidazo[4,5-b]pyridin-5-yl]-2-azabicyclo[2.2.2]oct-5-ene-2-carboxylate | C24H34N4O3 [M + H] calc 427.2704 obs 427.2711 |
| 2-25 | 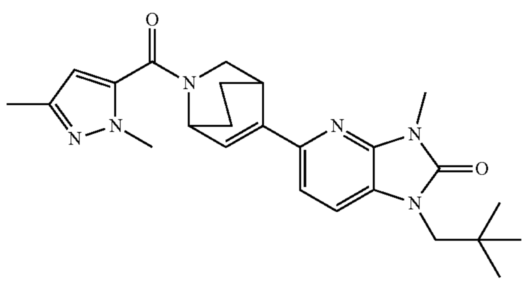 [SMILES: Cc1cc(C(=O)N2CC3CCC2C=C3c2ccc3c(n2)n(C)c(=O)n3CC(C)(C)C)n(C)n1] | 1-(2,2-dimethylpropyl)-5-{2-[(1,3-dimethyl-1H-pyrazol-5-yl)carbonyl]-2-azabicyclo[2.2.2]oct-5-en-5-yl}-3-methyl-1,3-dihydro-2H-imidazo[4,5-b]pyridin-2-one | C25H32N6O2 [M + H] calc 449.2661 obs 449.2667 |
| 2-26 | 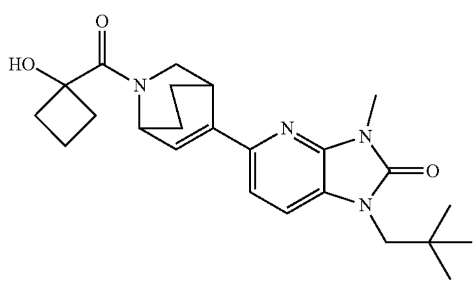 [SMILES: Cn1c(=O)n(CC(C)(C)C)c2ccc(C3=CC4CCC3CN4C(=O)C3(O)CCC3)nc21] | 1-(2,2-dimethylpropyl)-5-{2-[(1-hydroxycyclobutyl)carbonyl]-2-azabicyclo[2.2.2]oct-5-en-5-yl}-3-methyl-1,3-dihydro-2H-imidazo[4,5-b]pyridin-2-one | C24H32N4O3 [M + H] calc 425.2548 obs 425.2559 |
| 2-27 | 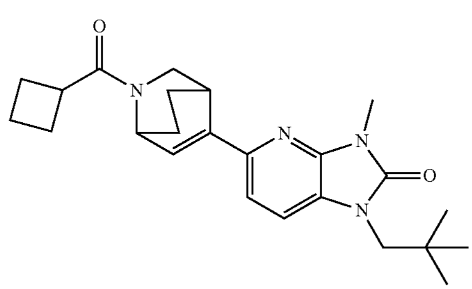 [SMILES: Cn1c(=O)n(CC(C)(C)C)c2ccc(C3=CC4CCC3CN4C(=O)C3CCC3)nc21] | 5-[2-(cyclobutylcarbonyl)-2-azabicyclo[2.2.2]oct-5-en-5-yl]-1-(2,2-dimethylpropyl)-3-methyl-1,3-dihydro-2H-imidazo[4,5-b]pyridin-2-one | C24H32N4O2 [M + H] calc 409.2599 obs 409.2606 |
| 2-28 | 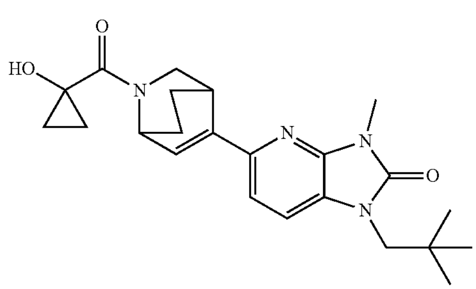 [SMILES: Cn1c(=O)n(CC(C)(C)C)c2ccc(C3=CC4CCC3CN4C(=O)C3(O)CC3)nc21] | 1-(2,2-dimethylpropyl)-5-{2-[(1-hydroxycyclopropyl)carbonyl]-2-azabicyclo[2.2.2]oct-5-en-5-yl}-3-methyl-1,3-dihydro-2H-imidazo[4,5-b]pyridin-2-one | C23H30N4O3 [M + H] calc 411.2392 obs 411.2398 |

TABLE 1-continued

| # | Structure | Name | HRMS/LRMS |
|---|---|---|---|
| 2-29 | 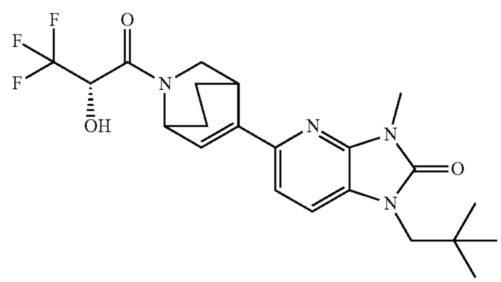 [SMILES: Cn1c(=O)n(CC(C)(C)C)c2ccc(C3=CC4CCC3CN4C(=O)[C@H](O)C(F)(F)F)nc21] | 1-(2,2-dimethylpropyl)-3-methyl-5-{2-[(2S)-3,3,3-trifluoro-2-hydroxypropanoyl]-2-azabicyclo[2.2.2]oct-5-en-5-yl}-1,3-dihydro-2H-imidazo[4,5-b]pyridin-2-one | C22H27F3N4O3 [M + H] calc 453.211 obs 453.2115 |
| 2-30 | 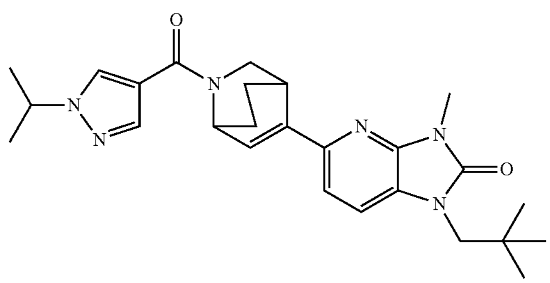 [SMILES: CC(C)n1cc(C(=O)N2CC3CCC2C=C3c2ccc3c(n2)n(C)c(=O)n3CC(C)(C)C)cn1] | 1-(2,2-dimethylpropyl)-3-methyl-5-(2-{[1-(1-methylethyl)-1H-pyrazol-4-yl]carbonyl}-2-azabicyclo[2.2.2]oct-5-en-5-yl)-1,3-dihydro-2H-imidazo[4,5-b]pyridin-2-one | C26H34N6O2 [M + H] calc 463.2817 obs 463.2829 |
| 2-31 | 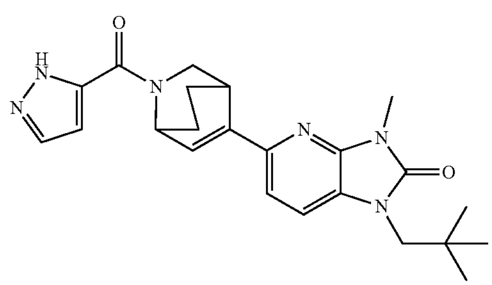 [SMILES: Cn1c(=O)n(CC(C)(C)C)c2ccc(C3=CC4CCC3CN4C(=O)c3ccn[nH]3)nc21] | 1-(2,2-dimethylpropyl)-3-methyl-5-[2-(1H-pyrazol-5-ylcarbonyl)-2-azabicyclo[2.2.2]oct-5-en-5-yl]-1,3-dihydro-2H-imidazo[4,5-b]pyridin-2-one | C23H28N6O2 [M + H] calc 421.2348 obs 421.2354 |
| 2-32 | 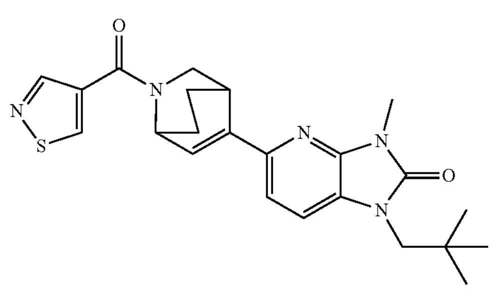 | 1-(2,2-dimethylpropyl)-5-[2-(isothiazol-4-ylcarbonyl)-2-azabicyclo[2.2.2]oct-5-en-5-yl]-3-methyl-1,3-dihydro-2H-imidazo[4,5-b]pyridin-2-one | C23H27N5O2S [M + H] calc 438.196 obs 438.1969 |
| 2-33 | 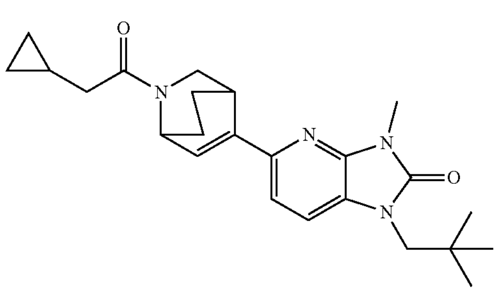 [SMILES: Cn1c(=O)n(CC(C)(C)C)c2ccc(C3=CC4CCC3CN4C(=O)CC3CC3)nc21] | 5-[2-(cyclopropylacetyl)-2-azabicyclo[2.2.2]oct-5-en-5-yl]-1-(2,2-dimethylpropyl)-3-methyl-1,3-dihydro-2H-imidazo[4,5-b]pyridin-2-one | C24H32N4O2 [M + H] calc 409.2599 obs 409.2608 |

TABLE 1-continued

| # | Structure | Name | HRMS/LRMS |
|---|---|---|---|
| 2-34 | 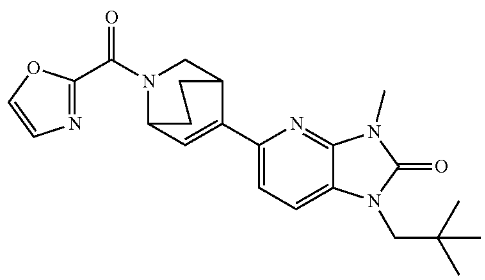 [SMILES: Cn1c(=O)n(CC(C)(C)C)c2ccc(C3=CC4CCC3CN4C(=O)c3ncco3)nc21] | 1-(2,2-dimethylpropyl)-3-methyl-5-[2-(1,3-oxazol-2-ylcarbonyl)-2-azabicyclo[2.2.2]oct-5-en-5-yl]-1,3-dihydro-2H-imidazo[4,5-b]pyridin-2-one | C23H27N5O3 [M + H] calc 422.2188 obs 422.2 (LRMS) |
| 2-35 | 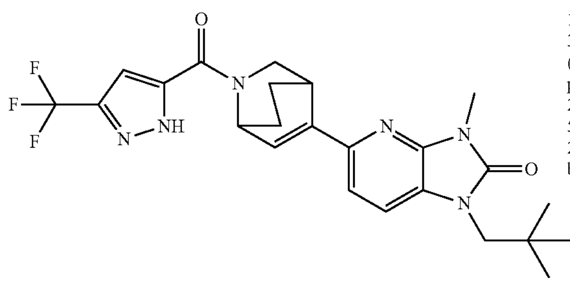 [SMILES: Cn1c(=O)n(CC(C)(C)C)c2ccc(C3=CC4CCC3CN4C(=O)c3cc(C(F)(F)F)n[nH]3)nc21] | 1-(2,2-dimethylpropyl)-3-methyl-5-(2-{[3-(trifluoromethyl)-1H-pyrazol-5-yl]carbonyl}-2-azabicyclo[2.2.2]oct-5-en-5-yl)-1,3-dihydro-2H-imidazo[4,5-b]pyridin-2-one | C24H27F3N6O2 [M + H] calc 489.2222 obs 489.2232 |
| 2-36 | 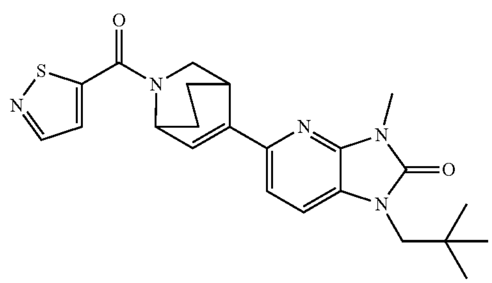 [SMILES: Cn1c(=O)n(CC(C)(C)C)c2ccc(C3=CC4CCC3CN4C(=O)c3ccns3)nc21] | 1-(2,2-dimethylpropyl)-5-[2-(isothiazol-5-ylcarbonyl)-2-azabicyclo[2.2.2]oct-5-en-5-yl]-3-methyl-1,3-dihydro-2H-imidazo[4,5-b]pyridin-2-one | C23H27N5O2S [M + H] calc 438.196 obs 438.1966 |
| 2-37 | 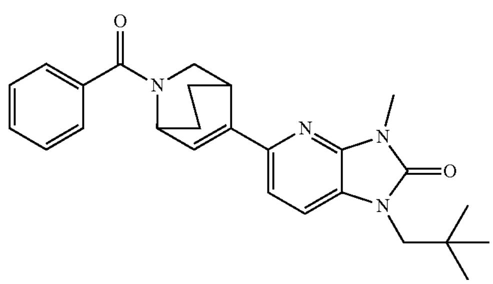 [SMILES: Cn1c(=O)n(CC(C)(C)C)c2ccc(C3=CC4CCC3CN4C(=O)c3ccccc3)nc21] | 1-(2,2-dimethylpropyl)-3-methyl-5-[2-(phenylcarbonyl)-2-azabicyclo[2.2.2]oct-5-en-5-yl]-1,3-dihydro-2H-imidazo[4,5-b]pyridin-2-one | C26H30N4O2 [M + H] calc 431.2443 obs 431.2449 |

Scheme 3

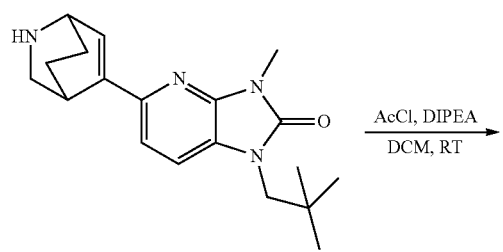

2-5

AcCl, DIPEA
DCM, RT

-continued

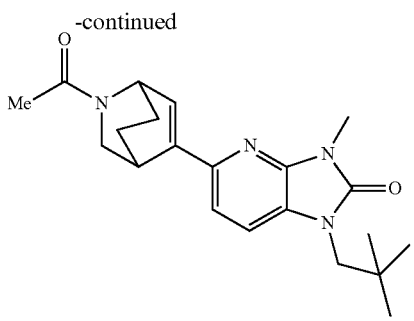

3-1

5-(2-Acetyl-2-azabicyclo[2.2.2]oct-5-en-5-yl)-1-(2,2-dimethylpropyl)-3-methyl-1,3-dihydro-2H-imidazo[4,5-b]pyridin-2-one (3-1)

5-(2-Azabicyclo[2.2.2]oct-5-en-5-yl)-1-(2,2-dimethylpropyl)-3-methyl-1,3-dihydro-2H-imidazo[4,5-b]pyridin-2-one (2-5, 25 mg, 0.08 mmol, 1.0 equiv) was added to anhydrous DCM (0.80 mL). To this solution was added DIPEA (40 μL, 0.23 mmol, 3.0 equiv) and acetyl chloride (11 μL, 0.15 mmol, 2.0 equiv) and the resulting mixture was allowed to stir at room temperature for 10 min. Following this duration, LCMS showed consumption of starting material. Saturated NaHCO$_3$ (3 mL) and ethyl acetate (3 mL) were then added and the layers were separated. The aqueous layer was back-extracted with ethyl acetate (3×3 mL) and the combined organics were dried over Na$_2$SO$_4$, filtered and concentrated in vacuo to give a yellow oil. Purification by reverse-phase HPLC (10-100% CH$_3$CN:0.1% TFA in H$_2$O) afforded 3-1 as a white solid. MS m/z (M+H): calculated=369.2285; observed=369.2284.

Scheme 4

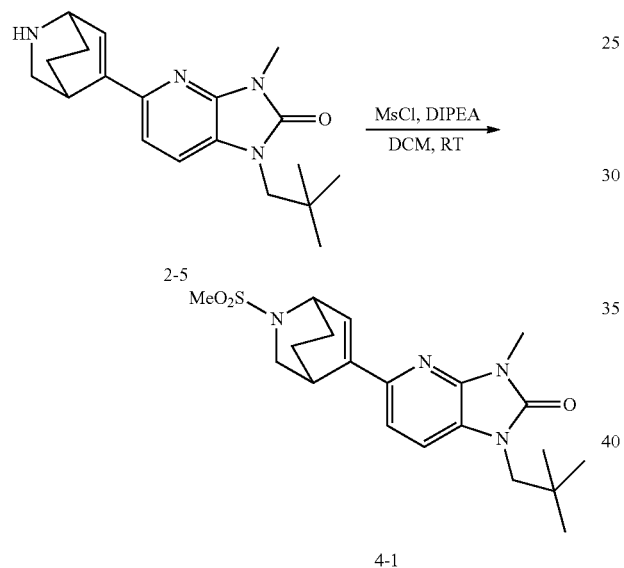

1-(2,2-Dimethylpropyl)-3-methyl-5-[2-(methylsulfonyl)-2-azabicyclo-[2.2.2]oct-5-en-5-yl]-1,3-dihydro-2H-imidazo[4,5-b]pyridin-2-one (4-1)

5-(2-Azabicyclo[2.2.2]oct-5-en-5-yl)-1-(2,2-dimethylpropyl)-3-methyl-1,3-dihydro-2H-imidazo[4,5-b]pyridin-2-one (2-5, 25 mg, 0.08 mmol, 1.0 equiv) was added to anhydrous DCM (0.80 mL). To this solution was added DIPEA (40 μL, 0.23 mmol, 3.0 equiv) and methanesulfonyl chloride (12 μL, 0.15 mmol, 2.0 equiv) and the resulting mixture was allowed to stir at room temperature for 10 min. Following this duration, LCMS showed consumption of starting material. Saturated NaHCO$_3$ (3 mL) and ethyl acetate (3 mL) were then added and the layers were separated. The aqueous layer was back-extracted with ethyl acetate (3×3 mL) and the combined organics were dried over Na$_2$SO$_4$, filtered and concentrated in vacuo to give a yellow oil. Purification by reverse-phase HPLC (10-100% CH$_3$CN:0.1% TFA in H$_2$O) afforded 4-1 as a white solid. MS m/z (M+H): calculated=405.1955; observed=405.1952.

Scheme 5

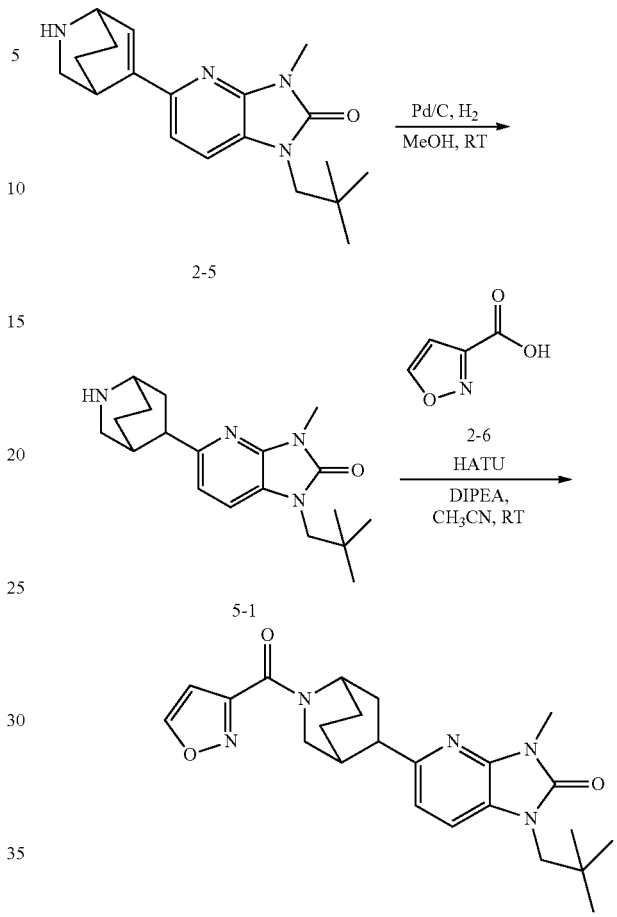

1-(2,2-Dimethylpropyl)-5-[2-(isoxazol-3-ylcarbonyl)-2-azabicyclo[2.2.2]-oct-5-yl]-3-methyl-1,3-dihydro-2H-imidazo[4,5-b]pyridin-2-one (5-2)

5-(2-Azabicyclo[2.2.2]oct-5-yl)-1-(2,2-dimethylprop)-3-methyl-1,3-dihydro-2H-imidazo[4,5-b]pyridin-2-one (5-1)

5-(2-Azabicyclo[2.2.2]oct-5-en-5-yl)-1-(2,2-dimethylpropyl)-3-methyl-1,3-dihydro-2H-imidazo[4,5-b]pyridin-2-one (2-5, 30 mg, 0.09 mmol, 1.0 equiv) was added to anhydrous MeOH (0.91 mL). To this solution was added 10% palladium(0) on carbon (9.8 mg, 9.2 μmol, 0.10 equiv) in one portion. The reaction vessel was then evacuated and back-filled with hydrogen (balloon). This process was repeated an additional two times. The resulting mixture was subsequently allowed to stir under an atmosphere of H$_2$ for 1 h at room temperature, after which LCMS showed complete consumption of starting material. The suspension was then filtered through Celite, rinsed with DCM (10 mL) and concentrated to give 5-1 as an orange semi-solid. The crude material was taken forward without further purification.

1-(2,2-Dimethylpropyl)-5-[2-(isoxazol-3-ylcarbonyl)-2-azabicyclo[2.2.2]-oct-5-yl]-3-methyl-1,3-dihydro-2H-imidazo[4,5-b]pyridin-2-one (5-2)

5-(2-Azabicyclo[2.2.2]oct-5-yl)-1-(2,2-dimethylpropyl)-3-methyl-1,3-dihydro-2H-imidazo[4,5-b]pyridin-2-one (5-1, 30.2 mg, 0.09 mmol, 1.0 equiv), isoxazole-3-carboxylic acid (2-6, 15.6 mg, 0.14 mmol, 1.5 equiv), DIPEA (48 µL, 0.28 mmol, 3.0 equiv) and HATU (52.4 mg, 0.14 mmol, 1.5 equiv) were added to anhydrous 1,4-dioxane (0.92 mL). After stirring for 10 min at room temperature, LCMS showed consumption of starting material. Purification by reverse-phase HPLC (20-100% $CH_3CN$:0.1% TFA in $H_2O$) provided 5-2 as a white solid. MS m/z (M+H): calculated=424.2343; observed=424.2345.

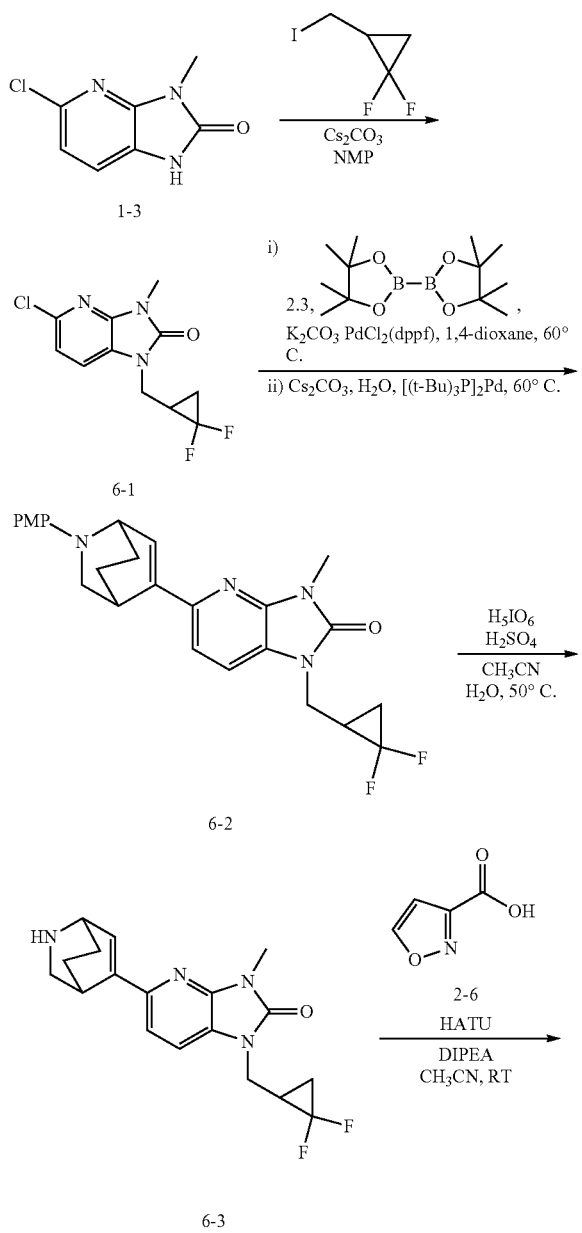

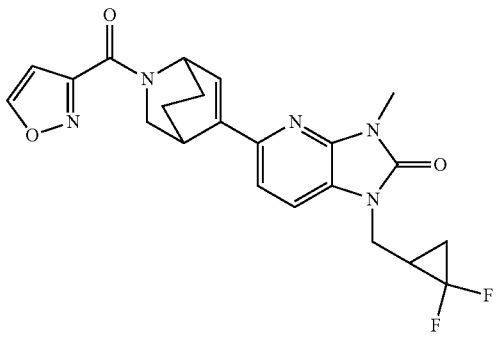

1-[(2,2-Difluorocyclopropyl)methyl]-5-[2-(isoxazol-3-ylcarbonyl)-2-azabicyclo 2.2.2]oct-5-en-5-1-3-methyl-1,3-dihydro-2H-imidazo[4,5-b]pyridin-2-one (6-4)

5-Chloro-1-[(2,2-difluorocyclopropyl)methyl]-3-methyl-1,3-dihydro-2H-imidazo[4,5-b]pyridin-2-one (6-1)

5-Chloro-3-methyl-1,3-dihydro-2H-imidazo[4,5-b]pyridin-2-one (1-3, 516 mg, 2.81 mmol) and cesium carbonate (4.97 g, 15.26 mmol) were added to a round bottom flask and suspended in NMP (4.6 mL) under nitrogen. 1,1-Difluoro-2-(iodomethyl)cyclopropane (481 µL, 5.06 mmol) was added to the suspension and then heated to 100° C. in microwave reactor for 10 min. Following this duration, the reaction was cooled to room temperature and suspended in ethyl acetate and sodium bicarbonate. The suspension was washed with sodium bicarbonate, brine(×5), dried over sodium sulfate, filtered, and concentrated. The mixture was purified using reverse-phase chromatography (5-95% 0.1% TFA in $H_2O$: acetonitrile) to give 5-chloro-1-[(2,2-difluorocyclopropyl)methyl]-3-methyl-1,3-dihydro-2H-imidazo[4,5-b]pyridin-2-one (6-1) as an off-white solid. MS m/z (M+H): calculated=274.0553; observed=274.0551.

1-[(2,2-Difluorocyclopropyl)methyl]-5-[2-4-methoxyphenyl]-2-azabicyclo-[2.2.2]oct-5-en-5-yl]-3-methyl-1,3-dihydro-2H-imidazo[4,5-b]pyridin-2-one (6-2)

2-(4-Methoxyphenyl)-2-azabicyclo[2.2.2]oct-5-en-5-yl trifluoromethanesulfonate (2-3, 149 mg, 0.41 mmol, 1.0 equiv), bis(pinocolato)diboron (114 mg, 0.45 mmol, 1.1 equiv), potassium acetate (121 mg, 1.23 mmol, 3.0 equiv) and $PdCl_2$(dppf) (21 mg, 0.03 mmol, 0.07 equiv) were added to anhydrous 1,4-dioxane (521 µL) and heated to 60° C. After 18 h, the reaction contents were cooled to RT, followed by the subsequent addition of water (104 µL), 5-Chloro-1-[(2,2-difluorocyclopropyl)methyl]-3-methyl-1,3-dihydro-2H-imidazo[4,5-b]pyridin-2-one (6-1, 112 mg, 0.41 mmol, 1.0 equiv), $Cs_2CO_3$ (268 mg, 0.82 mmol, 2.01 equiv) and Bis(tritert-butylphosphine)palladium(0) (27.2 mg, 0.13 mmol, 0.13 equiv). The resulting mixture was heated to 60° C. for 4.5 h. Following this duration, LCMS showed consumption of starting material. The contents were then cooled to room temperature, diluted with ethyl acetate (5 mL), filtered through Celite and rinsed with ethyl acetate (3×5 mL) and water (1×5 mL). The filtrate layers were separated and the combined organics were washed with saturated NaHCO$_3$ (15 mL). The combined aqueous layers were then back-extracted with ethyl acetate (2×5 mL). The combined organics were dried over Na$_2$SO$_4$, filtered and concentrated in vacuo to give a dark red oil. Purification by reverse-phase HPLC (20-90% 0.1% TFA in H$_2$O:CH$_3$CN) afforded 6-2 as an off-white solid MS m/z (M+H): calculated=452.5; observed=453.2.

5-(2-Azabicyclo[2.2.2]oct-5-en-5-yl)-1-[(2,2-difluorocyclopropyl)-methyl]-3-methyl-1,3-dihydro-2H-imidazo[4,5-b]pyridin-2-one (6-3)

1-[(2,2-Difluorocyclopropyl)methyl]-5-[2-(4-methoxyphenyl)-2-azabicyclo-[2.2.2]oct-5-en-5-yl]-3-methyl-1,3-dihydro-2H-imidazo[4,5-b]pyridin-2-one (6-2, 52 mg, 0.12 mmol, 1.0 equiv) was added to CH$_3$CN (1 mL) and water (1 mL). To this suspension was added aqueous H$_2$SO$_4$ (115 µL, 0.12 mmol, 1.0 equiv, 1.0 M) followed by periodic acid in one portion (26 mg, 0.12 mmol, 1.0 equiv). The reaction contents were heated to 50° C. for 18 h. Following this duration, LCMS showed consumption of starting material. The mixture was subsequently filtered through Celite, rinsed with CH$_3$CN and purified by reverse-phase HPLC (10-90% CH$_3$CN:H$_2$O) to give 6-3 as an off-white solid. MS m/z (M+H): calculated=346.4; observed=347.1.

1-[(2,2-Difluorocyclopropyl)methyl]-5-[2-(isoxazol-3-ylcarbonyl)-2-azabicyclo-[2.2.2]oct-5-en-5-yl]-3-methyl-1,3-dihydro-2H-imidazo[4,5-b]pyridin-2-one (6-4)

5-(2-Azabicyclo[2.2.2]oct-5-en-5-yl)-1-[(2,2-difluorocyclopropyl)-methyl]-3-methyl-1,3-dihydro-2H-imidazo[4,5-b]pyridin-2-one (6-3, 40 mg, 0.12 mmol, 1.0 equiv), isoxazole-3-carboxylic acid (2-6, 21 mg, 0.18 mmol, 1.5 equiv), DIPEA (64 µL, 0.36 mmol, 3.0 equiv) and HATU (69 mg, 0.18 mmol, 1.5 equiv) were added to anhydrous 1,4-dioxane (12 mL). After stirring for 10 min at room temperature, LCMS showed consumption of starting material. Purification by reverse-phase HPLC (20-100% CH$_3$CN:0.1% TFA in H$_2$O) provided 2-7 as a white solid. MS m/z (M+H): calculated=442.1685; observed=442.1682. $^1$H NMR δ (ppm) (CHCl$_3$-d): 8.41 (1H, dd, J=27.39, 1.68 Hz), 7.26-7.21 (1H, m), 7.18 (1H, dd, J=8.10, 1.54 Hz), 6.99 (1H, ddd, J=22.62, 6.35, 2.02 Hz), 6.70 (1H, dd, J=12.85, 1.68 Hz), 5.56-5.52 (0.4H, m), 5.41 (0.6H, m), 4.24-4.16 (1H, m), 3.95 (0.4H, dd, J=11.04, 2.28 Hz), 3.90-3.84 (1H, m), 3.75 (1H, dd, J=15.06, 7.88 Hz), 3.62 (0.6H, dd, J=12.35, 2.29 Hz), 3.58-3.52 (0.4H, m), 3.48 (3H, d, J=3.78 Hz), 3.36 (0.6H, d, J=12.38 Hz), 2.22-2.11 (1H, m), 2.05-1.9 (1H, m), 1.91-1.80 (1H, m), 1.61-1.46 (3H, m), 1.29-1.24 (1H, m). (Mixture of rotamers at RT)

The following compound was prepared from 6-3 by a reaction sequence analogous to that illustrated in Scheme 6:

TABLE 2

| # | Structure | Name | HRMS/LRMS |
|---|-----------|------|-----------|
| 6-5 | 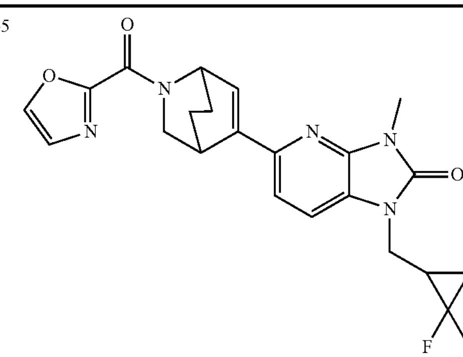 | 1-[(2,2-difluorocyclopropyl)methyl]-3-methyl-5-[2-(1,3-oxazol-2-ylcarbonyl)-2-azabicyclo[2.2.2]oct-5-en-5-yl]-1,3-dihydro-2H-imidazo[4,5-b]pyridin-2-one | C22H21F2N5O3 [M + H] calc 442.1688 obs 442.1701 |

Scheme 7

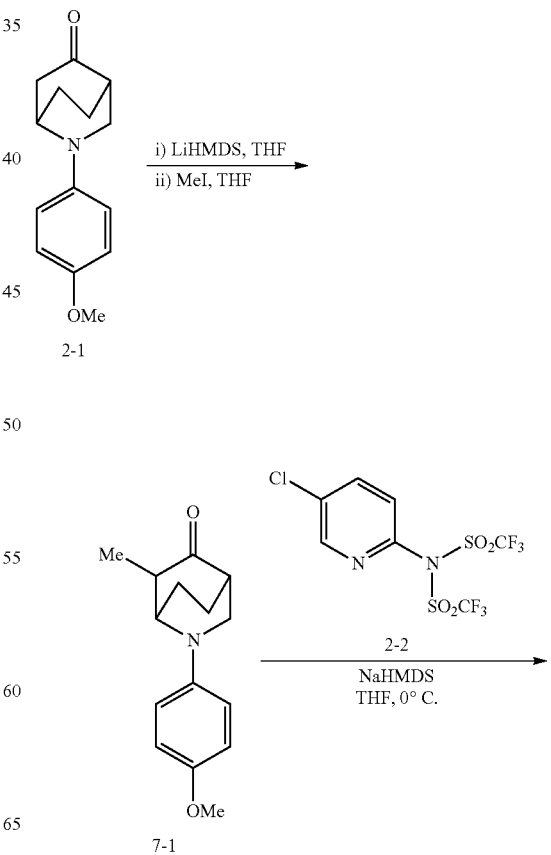

7-1

-continued

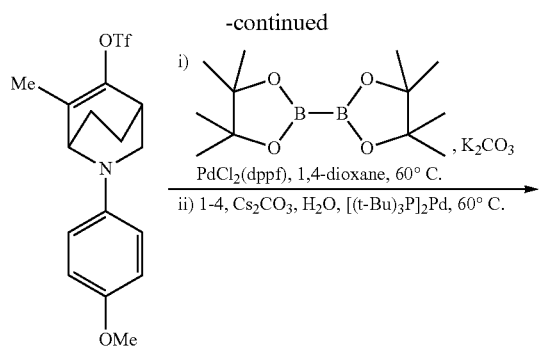

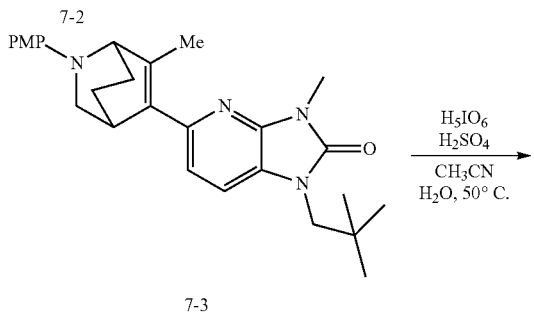

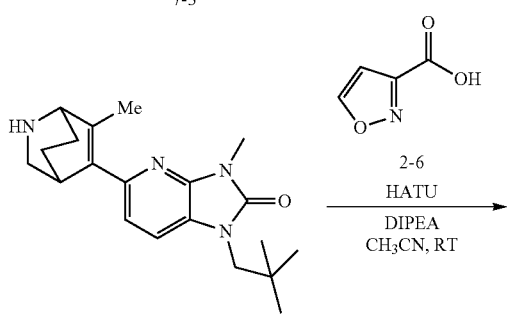

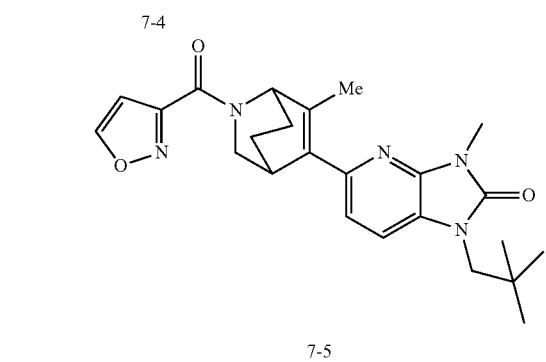

1-(2,2-Dimethylpropyl)-5-[2-(isoxazol-3-ylcarbonyl)-6-methyl-2-azabicyclo[2.2.2]oct-5-en-5-yl]-3-methyl-1,3-dihydro-2H-imidazo[4,5-b]pyridin-2-one (7-5)

2-(4-Methoxyphenyl)-6-methyl-2-azabicyclo[2.2.2]octan-5-one (7-1)

LHMDS (2.2 mL, 2.16 mmol, 1.0 equiv, 1.0 M in THF) was added to an oven-dried flask under $N_2$ and cooled to −78° C. A solution of 2-(4-methoxyphenyl)-2-azabicyclo-[2.2.2]octan-5-one (2-1, 500 mg, 2.16 mmol, 1.0 equiv) in anhydrous tetrahydrofuran (8.6 mL) was added dropwise via cannula, and the resulting mixture was allowed to stir for 20 min at −78° C. Following this duration, the enolate mixture was added via cannula to a solution of iodomethane (0.68 mL, 10.8 mmol, 5.0 equiv) in anhydrous tetrahydrofuran (2.2 mL). After 1 h, the reaction contents were removed from the −78° C. bath and allowed to gradually warm to RT. After 18 h, LCMS showed complete consumption of starting material. The reaction was quenched with saturated $NH_4Cl$ (15 mL), added to ethyl acetate (20 mL) and diluted with water (5 mL). The layers were separated and the aqueous layer was back-extracted with ethyl acetate (3×10 mL). The combined organics were dried over $Na_2SO_4$, filtered and concentrated in vacuo to give an orange solid. Purification by normal-phase HPLC (0-40% $CH_3CN$:0.1% TFA in $H_2O$) provided 7-1 as a pale yellow solid (inconsequential 1:1 mixture of diastereomers).

2-(4-Methoxyphenyl)-6-methyl-2-azabicyclo[2.2.2]oct-5-en-5-yl trifluoromethanesulfonate (7-2)

2-(4-Methoxyphenyl)-6-methyl-2-azabicyclo[2.2.2]octan-5-one (7-1, 399 mg, 1.63 mmol, 1.0 equiv) was added to anhydrous THF (8.1 mL) and cooled to 0° C. To this solution was added NaHMDS (1.0 mL, 2.0 mmol, 1.2 equiv, 2M solution in THF) followed by Comin's reagent (2-2, 894 mg, 2.3 mmol, 1.4 equiv) in two equal portions. After 60 min at 0° C., TLC analysis showed consumption of starting material. The reaction was quenched with brine (8 mL) and diluted with ethyl acetate (15 mL) and water (15 mL). The layers were separated and the aqueous layer was extracted with ethyl acetate (3×10 mL). The combined organics were dried over $Na_2SO_4$, filtered and concentrated in vacuo to give a red oil. Purification by normal-phase chromatography (0-40% EtOAc:Hex) afforded 7-2 as a pale yellow solid, which was immediately carried forward.

1-(2,2-Dimethylpropyl)-5-[2-(4-methoxyphenyl)-6-methyl-2-azabicyclo-[2.2.2]oct-5-en-5-yl]-3-methyl-1,3-dihydro-2H-imidazo[4,5-b]pyridin-2-one (7-3)

2-(4-Methoxyphenyl)-6-methyl-2-azabicyclo[2.2.2]oct-5-en-5-yl trifluoromethanesulfonate (7-2, 429 mg, 1.14 mmol, 1.0 equiv), bis(pinocolato)diboron (317 mg, 1.25 mmol, 1.1 equiv), potassium acetate (334 mg, 3.41 mmol, 3.0 equiv) and $PdCl_2$(dppf) (58.2 mg, 0.079 mmol, 0.07 equiv) were added to anhydrous 1,4-dioxane (1.4 mL) and heated to 60° C. After 18 h, the reaction contents were cooled to RT, followed by the subsequent addition of water (289 µL), 5-chloro-1-(2,2-dimethylpropyl)-3-methyl-1,3-dihydro-2H-imidazo[4,5-b]-pyridin-2-one (1-4, 288 mg, 1.14 mmol, 1.0 equiv), $Cs_2CO_3$ (744 mg, 2.28 mmol, 2.01 equiv) and Bis(tri-tert-butylphosphine)palladium(0) (75 mg, 0.148 mmol, 0.13 equiv). The resulting mixture was heated to 60° C. for 4.5 h. Following this duration, LCMS showed consumption of starting material. The contents were then cooled to room temperature, diluted with ethyl acetate (10 mL), filtered through Celite and rinsed with ethyl acetate (3×7 mL) and water (1×3 mL).

The filtrate layers were separated and the combined organics were washed with saturated $NaHCO_3$ (12 mL). The combined aqueous layers were then back-extracted with ethyl acetate (2×5 mL). The combined organics were dried over $Na_2SO_4$, filtered and concentrated in vacuo to give a dark red oil. Purification by reverse-phase chromatography (20-100% $CH_3CN$:0.1% TFA in $H_2O$) afforded 7-3 as a tan solid. MS m/z (M+H): calculated=447.2755; observed=447.2769.

1-(2,2-Dimethylpropyl)-3-methyl-5-(6-methyl-2-azabicyclo[2.2.2]oct-5-en-5-yl)-1,3-dihydro-2H-imidazo[4,5-b]pyridin-2-one (7-4)

1-(2,2-Dimethylpropyl)-5-[2-(4-methoxyphenyl)-6-methyl-2-azabicyclo-[2.2.2]oct-5-en-5-yl]-3-methyl-1,3-dihydro-2H-imidazo[4,5-b]pyridin-2-one (7-3, 40.3 mg, 0.09 mmol, 1.0 equiv) was added to CH$_3$CN (820 µL) and water (820 µL). To this suspension was added aqueous H$_2$SO$_4$ (90 µL, 0.09 mmol, 1.0 equiv, 1.0 M) followed by periodic acid in one portion (21 mg, 0.09 mmol, 1.0 equiv). The reaction contents were heated to 50° C. for 18 h. Following this duration, LCMS showed consumption of starting material. The mixture was subsequently filtered through Celite, rinsed with CH$_3$CN and purified by reverse-phase HPLC (15-90% CH$_3$CN:0.1% TFA in H$_2$O) to give 7-4 as a tan solid.

1-(2,2-Dimethylpropyl)-5-[2-(isoxazol-3-ylcarbonyl)-6-methyl-2-azabicyclo-[2.2.2]oct-5-en-5-yl]-3-methyl-1,3-dihydro-2H-imidazo[4,5-b]pyridin-2-one (7-5)

1-(2,2-Dimethylpropyl)-3-methyl-5-(6-methyl-2-azabicyclo[2.2.2]oct-5-en-5-yl)-1,3-dihydro-2H-imidazo[4,5-b]pyridin-2-one (7-4, 8.6 mg, 0.03 mmol, 1.0 equiv), isoxazole-3-carboxylic acid (2-6, 4.3 mg, 0.04 mmol, 1.5 equiv), DIPEA (13 µL, 0.08 mmol, 3.0 equiv) and HATU (14.4 mg, 0.04 mmol, 1.5 equiv) were added to anhydrous acetonitrile (253 µL). After stirring for 10 min at room temperature, LCMS showed consumption of starting material. Purification by reverse-phase HPLC (10-100% CH$_3$CN:0.1% TFA in H$_2$O) provided 7-5 as a white solid. MS m/z (M+H): calculated=436.2343; observed=436.2351.

Scheme 8

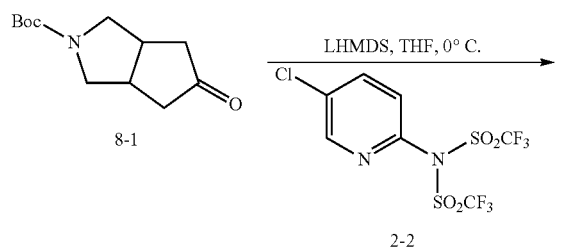

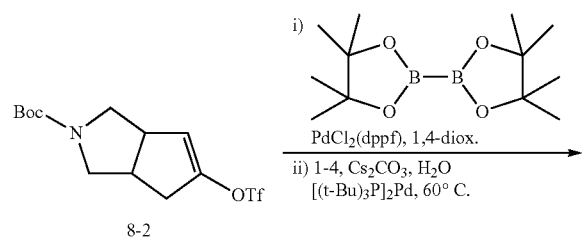

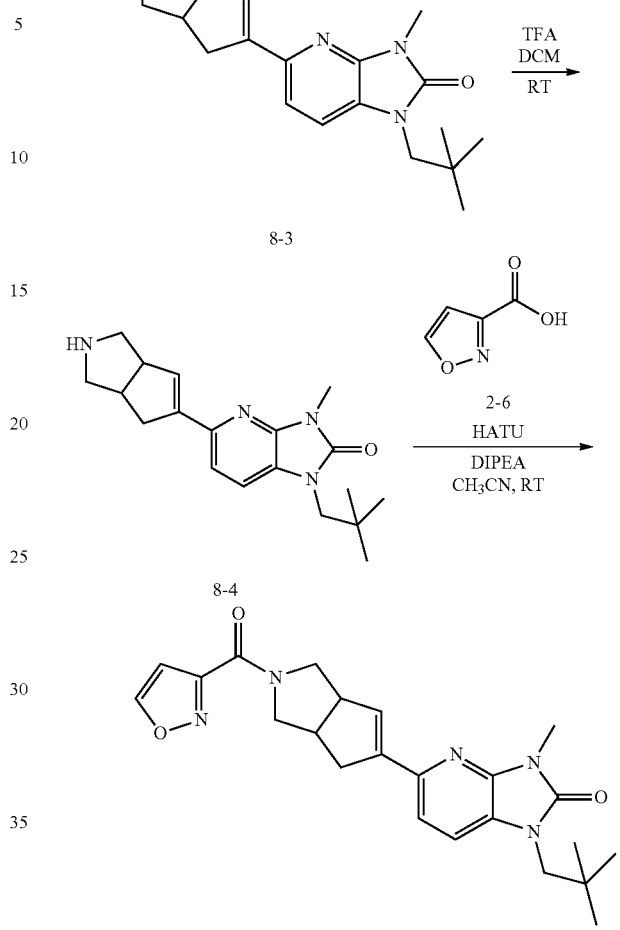

1-(2,2-Dimethylpropyl)-5-[2-(isoxazol-3-ylcarbonyl)-1,2,3,3a,4,6a-hexahydrocyclopenta-[c]pyrrol-5-yl]-3-methyl-1,3-dihydro-2H-imidazo[4,5-b]pyridin-2-one (8-5)

tert-Butyl 5-{[(trifluoromethyl)sulfonyl]oxy}-3,3a,4,6a-tetrahydrocyclo-penta-[c]pyrrole-2(1H)-carboxylate (8-2)

tert-butyl 5-oxohexahydrocyclopenta[c]pyrrole-2(1H)-carboxylate (8-1, 2 g 8.8 mmol, 1.0 equiv) was added to anhydrous THF (44 mL) and cooled to 0° C. To this solution was added LHMDS (9.7 mL, 9.7 mmol, 1.1 equiv, 1M solution in THF) followed by Comin's reagent (2-2, 3.5 g, 8.8 mmol, 1.0 equiv) in two equal portions. After 60 min at 0° C., TLC analysis showed consumption of starting material. The reaction was quenched with brine (40 mL) and diluted with ethyl acetate (75 mL) and water (75 mL). The layers were separated and the aqueous layer was extracted with ethyl acetate (3×50 mL). The combined organics were dried over Na$_2$SO$_4$, filtered and concentrated in vacuo to give a orange oil. Purification by normal-phase chromatography (0-30% EtOAc:Hex) afforded 8-2 as a pale yellow oil, which was immediately carried forward.

tert-Butyl 5-[1-(2,2-dimethylpropyl)-3-methyl-2-oxo-2,3-dihydro-1H-imidazo-[4,5-b]pyridin-5-yl]-3,3a,4,6a-tetrahydrocyclopenta[c]pyrrole-2(1H)-carboxylate (8-3)

tert-Butyl 5-{[(trifluoromethyl)sulfonyl]oxy}-3,3a,4,6a-tetrahydrocyclopenta-[c]pyrrole-2(1H)-carboxylate (8-2, 2 g, 5.5 mmol, 1.0 equiv), bis(pinocolato)diboron (1.5 g, 6.1 mmol, 1.1 equiv), potassium acetate (1.6 g, 16.8 mmol, 3.0 equiv) and PdCl$_2$(dppf) (0.288 g, 0.392 mmol, 0.07 equiv) were added to anhydrous 1,4-dioxane (7 mL) and heated to 60° C. After 18 h, the reaction contents were cooled to RT, followed by the subsequent addition of water (1.4 mL), 5-chloro-1-(2,2-dimethylpropyl)-3-methyl-1,3-dihydro-2H-imidazo[4,5-b]-pyridin-2-one (1-4, 1.4 g, 5.5 mmol, 1.0 equiv), Cs$_2$CO$_3$ (3.6 g, 11.1 mmol, 2.00 equiv) and Bis(tri-tert-butylphosphine)palladium(0) (0.372 g, 0.728 mmol, 0.13 equiv). The resulting mixture was heated to 60° C. for 4.5 h. Following this duration, LCMS showed consumption of starting material. The contents were then cooled to room temperature, diluted with ethyl acetate (50 mL), filtered through Celite and rinsed with ethyl acetate (3×50 mL) and water (1×30 mL). The filtrate layers were separated and the combined organics were washed with saturated NaHCO$_3$ (100 mL). The combined aqueous layers were then back-extracted with ethyl acetate (2×50 mL). The combined organics were dried over Na$_2$SO$_4$, filtered and concentrated in vacuo to give a dark red oil. Purification by normal-phase chromatography (0-50% EtOAc:Hex) afforded 8-3 as an off-white solid. MS m/z (M+H): calculated=427.55; observed=427.2.

1-(2,2-Dimethylpropyl)-5-(1,2,3,3a,4,6a-hexahydro-cyclopenta[c]pyrrol-5-yl)-3-methyl-1,3-dihydro-2H-imidazo[4,5-b]pyridin-2-one (8-4)

tert-Butyl 5-[1-(2,2-dimethylpropyl)-3-methyl-2-oxo-2,3-dihydro-1H-imidazo-[4,5-b]pyridin-5-yl]-3,3a,4,6a-tetrahydrocyclopenta[c]pyrrole-2(1H)-carboxylate (8-3, 1 g, 2.3 mmol) was added to a mixture of dichloromethane (18.7 mL) and trifluoroacetic acid (4.6 mL) at room temperature. After stirring for 18 h, the solvent was removed in vacuo. The resulting residue was then diluted with ethyl acetate (100 mL) and washed sequentially with saturated sodium bicarbonate (2×50 mL), water (1×50 mL) and brine (1×50 mL). The organics were dried over magnesium sulfate, filtered, and concentrated in vacuo to give 1-(2,2-Dimethylpropyl)-5-(1,2,3,3a,4,6a-hexahydrocyclopenta[c]pyrrol-5-yl)-3-methyl-1,3-dihydro-2H-imidazo[4,5-b]pyridin-2-one (8-4) as a white solid. This material was carried on without further purification.

1-(2,2-Dimethylpropyl)-5-[2-(isoxazol-3-ylcarbonyl)-1,2,3,3a,4,6a-hexahydro-cyclopenta-[c]pyrrol-5-yl]-3-methyl-1,3-dihydro-2H-imidazo[4,5-b]pyridin-2-one (8-5)

1-(2,2-Dimethylpropyl)-5-(1,2,3,3a,4,6a-hexahydrocyclopenta[c]pyrrol-5-yl)-3-methyl-1,3-dihydro-2H-imidazo[4,5-b]pyridin-2-one (8-4, 100 mg, 0.30 mmol, 1.0 equiv), isoxazole-3-carboxylic acid (2-6, 52 mg, 0.46 mmol, 1.5 equiv), DIPEA (0.16 mL, 0.91 mmol, 3.0 equiv) and HATU (175 mg, 0.46 mmol, 1.5 equiv) were added to anhydrous acetonitrile (3 mL). After stirring for 10 min at room temperature, LCMS showed consumption of starting material. Purification by reverse-phase HPLC (20-100% CH$_3$CN:0.1% TFA in H$_2$O) provided 8-5 as a white solid. MS m/z (M+H): calculated=422.2188; observed=422.2201. $^1$H NMR δ (ppm) (CHCl$_3$-d): 8.42 (1H, dd, J=7.77, 1.64 Hz), 7.12 (1H, dd, J=8.03, 1.54 Hz), 7.01 (1H, dd, J=8.02, 4.63 Hz), 6.76 (1H, d, J=1.64 Hz), 6.43 (1H, d, J=13.40 Hz), 4.32 (1H, dd, J=12.00, 8.94 Hz), 4.19 (1H, dd, J=12.14, 2.21 Hz), 4.15-4.08 (1H, m), 4.08 (1H, t, J=8.61 Hz), 4.01-3.85 (1H, m), 3.64 (2H, s), 3.49 (3H, d, J=2.90 Hz), 3.22-3.05 (1H, m), 3.06-2.98 (1H, m), 2.85-2.70 (1H, m), 1.02 (9H, s).

The following compounds were prepared from 8-4 by a reaction sequence analogous to that illustrated in Scheme 8:

TABLE 3

| # | Structure | Name | HRMS/LRMS |
|---|---|---|---|
| 8-6 | (structure shown) | tert-butyl 3-({5-[1-(2,2-dimethylpropyl)-3-methyl-2-oxo-2,3-dihydro-1H-imidazo[4,5-b]pyridin-5-yl]-3,3a,4,6a-tetrahydrocyclopenta[c]pyrrol-2(1H)-yl}carbonyl)-3-hydroxypyrrolidine-1-carboxylate | C29H41N5O5 [M + H] calc 540.318 obs 540.3201 |

TABLE 3-continued

| # | Structure | Name | HRMS/LRMS |
|---|---|---|---|
| 8-7 | 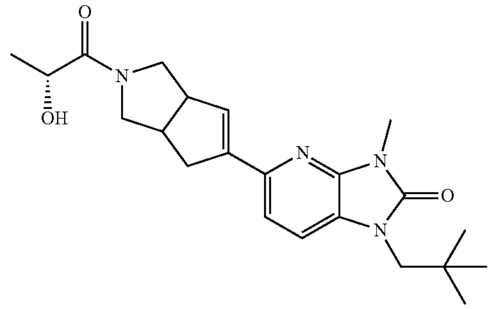 [SMILES: C[C@@H](O)C(=O)N1CC2C=C(c3ccc4c(n3)n(C)c(=O)n4CC(C)(C)C)CC2C1] | 1-(2,2-dimethylpropyl)-5-{2-[(2R)-2-hydroxypropanoyl]-1,2,3,3a,4,6a-hexahydrocyclopenta[c]pyrrol-5-yl}-3-methyl-1,3-dihydro-2H-imidazo[4,5-b]pyridin-2-one | C22H30N4O3 [M + H] calc 399.2392 obs 399.2388 |
| 8-8 | 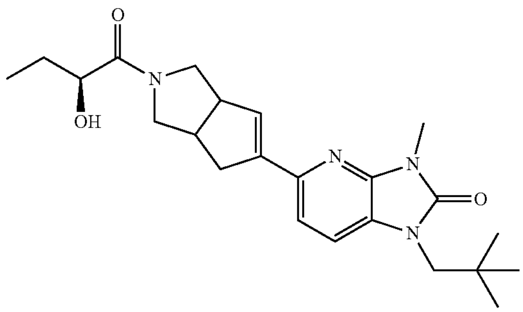 [SMILES: CC[C@H](O)C(=O)N1CC2C=C(c3ccc4c(n3)n(C)c(=O)n4CC(C)(C)C)CC2C1] | 1-(2,2-dimethylpropyl)-5-{2-[(2S)-2-hydroxybutanoyl]-1,2,3,3a,4,6a-hexahydrocyclopenta[c]pyrrol-5-yl}-3-methyl-1,3-dihydro-2H-imidazo[4,5-b]pyridin-2-one | C23H32N4O3 [M + H] calc 413.2548 obs 413.2560 |
| 8-9 | 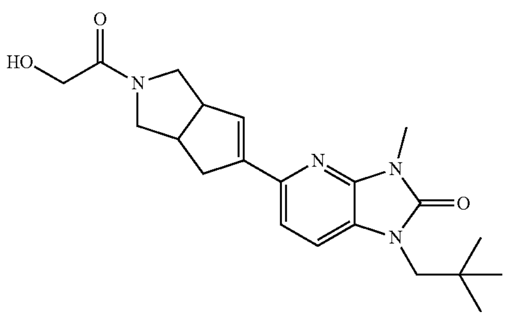 [SMILES: Cn1c(=O)n(CC(C)(C)C)c2ccc(C3=CC4CN(C(=O)CO)CC4C3)nc21] | 1-(2,2-dimethylpropyl)-5-[2-(hydroxyacetyl)-1,2,3,3a,4,6a-hexahydrocyclopenta[c]pyrrol-5-yl]-3-methyl-1,3-dihydro-2H-imidazo[4,5-b]pyridin-2-one | C21H28N4O3 [M + H] calc 385.2236 obs 385.1 |
| 8-10 | 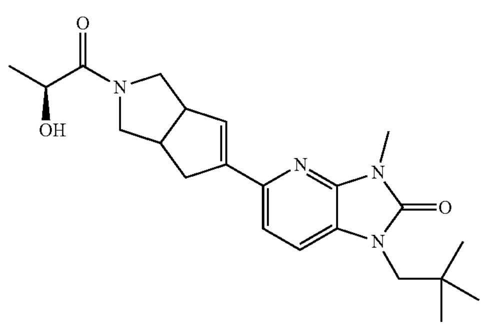 [SMILES: C[C@H](O)C(=O)N1CC2C=C(c3ccc4c(n3)n(C)c(=O)n4CC(C)(C)C)CC2C1] | 1-(2,2-dimethylpropyl)-5-{2-[(2S)-2-hydroxypropanoyl]-1,2,3,3a,4,6a-hexahydrocyclopenta[c]pyrrol-5-yl}-3-methyl-1,3-dihydro-2H-imidazo[4,5-b]pyridin-2-one | C22H30N4O3 [M + H] calc 399.2392 obs 399.2413 |
| 8-11 | 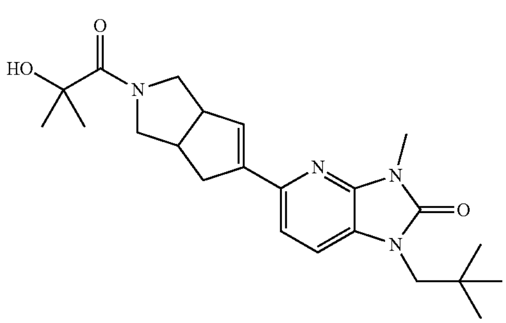 [SMILES: Cn1c(=O)n(CC(C)(C)C)c2ccc(C3=CC4CN(C(=O)C(C)(C)O)CC4C3)nc21] | 1-(2,2-dimethylpropyl)-5-[2-(2-hydroxy-2-methylpropanoyl)-1,2,3,3a,4,6a-hexahydrocyclopenta[c]pyrrol-5-yl]-3-methyl-1,3-dihydro-2H-imidazo[4,5-b]pyridin-2-one | C23H32N4O3 [M + H] calc 413.2548 obs 413.2563 |

TABLE 3-continued

| # | Structure | Name | HRMS/LRMS |
|---|---|---|---|
| 8-12 | 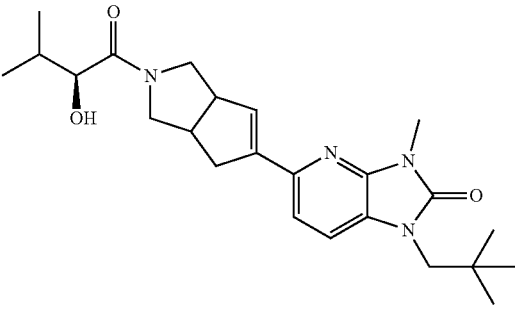 [SMILES: CC(C)[C@H](O)C(=O)N1CC2C=C(c3ccc4c(n3)n(C)c(=O)n4CC(C)(C)C)CC2C1] | 1-(2,2-dimethylpropyl)-5-{2-[(2S)-2-hydroxy-3-methylbutanoyl]-1,2,3,3a,4,6a-hexahydrocyclopenta[c]pyrrol-5-yl}-3-methyl-1,3-dihydro-2H-imidazo[4,5-b]pyridin-2-one | C24H34N4O3 [M + H] calc 427.2704 obs 427.2729 |
| 8-13 | 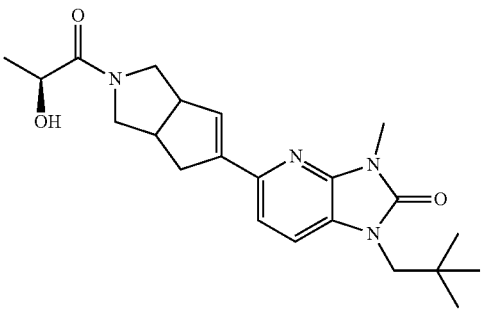 [SMILES: C[C@H](O)C(=O)N1CC2C=C(c3ccc4c(n3)n(C)c(=O)n4CC(C)(C)C)CC2C1] | 1-(2,2-dimethylpropyl)-5-{2-[(2S)-2-hydroxypropanoyl]-1,2,3,3a,4,6a-hexahydrocyclopenta[c]pyrrol-5-yl}-3-methyl-1,3-dihydro-2H-imidazo[4,5-b]pyridin-2-one | C22H30N4O3 [M + H] calc 399.2392 obs 399.2409 |
| 8-14 | 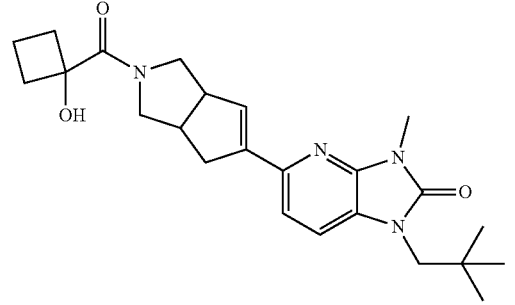 [SMILES: Cn1c(=O)n(CC(C)(C)C)c2ccc(C3=CC4CN(C(=O)C5(O)CCC5)CC4C3)nc21] | 1-(2,2-dimethylpropyl)-5-{2-[(1-hydroxycyclobutyl)carbonyl]-1,2,3,3a,4,6a-hexahydrocyclopenta[c]pyrrol-5-yl}-3-methyl-1,3-dihydro-2H-imidazo[4,5-b]pyridin-2-one | C24H32N4O3 [M + H] calc 425.2548 obs 425.2552 |
| 8-15 | 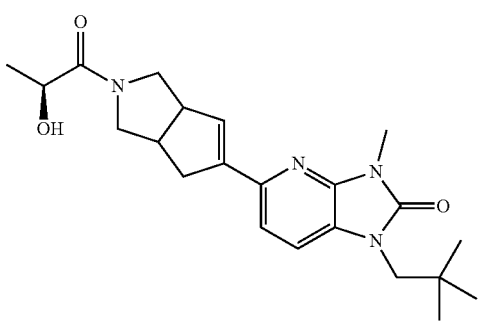 [SMILES: C[C@H](O)C(=O)N1CC2C=C(c3ccc4c(n3)n(C)c(=O)n4CC(C)(C)C)CC2C1] | 1-(2,2-dimethylpropyl)-5-{2-[(2S)-2-hydroxypropanoyl]-1,2,3,3a,4,6a-hexahydrocyclopenta[c]pyrrol-5-yl}-3-methyl-1,3-dihydro-2H-imidazo[4,5-b]pyridin-2-one | C22H30N4O3 [M + H] calc 399.2392 obs 399.2408 |
| 8-16 | 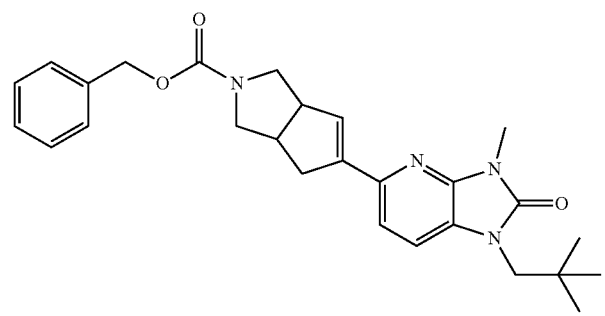 [SMILES: Cn1c(=O)n(CC(C)(C)C)c2ccc(C3=CC4CN(C(=O)OCc5ccccc5)CC4C3)nc21] | benzyl 5-[1-(2,2-dimethylpropyl)-3-methyl-2-oxo-2,3-dihydro-1H-imidazo[4,5-b]pyridin-5-yl]-3,3a,4,6a-tetrahydrocyclopenta[c]pyrrole-2(1H)-carboxylate | C27H32N4O3 [M + H] calc 461.2548 obs 461.2563 |

TABLE 3-continued

| # | Structure | Name | HRMS/LRMS |
|---|-----------|------|-----------|
| 8-17 | 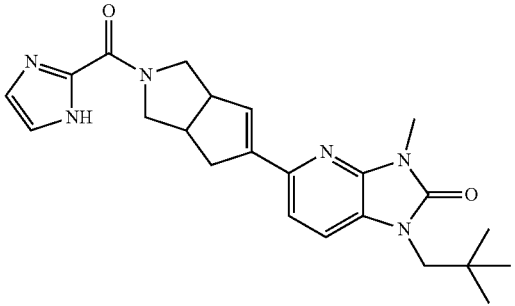 [SMILES: Cn1c(=O)n(CC(C)(C)C)c2ccc(C3=CC4CN(C(=O)c5ncc[nH]5)CC4C3)nc21] | 1-(2,2-dimethylpropyl)-5-[2-(1H-imidazol-2-ylcarbonyl)-1,2,3,3a,4,6a-hexahydrocyclopenta[c]pyrrol-5-yl]-3-methyl-1,3-dihydro-2H-imidazo[4,5-b]pyridin-2-one | C23H28N6O2 [M + H] calc 421.2349 obs 421.2362 |
| 8-18 | 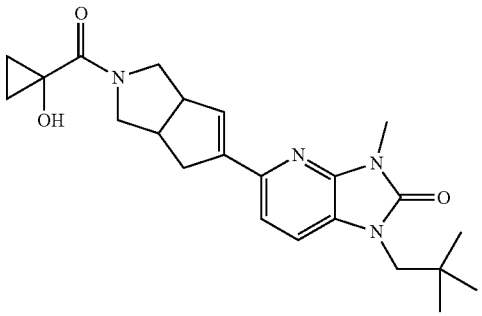 [SMILES: Cn1c(=O)n(CC(C)(C)C)c2ccc(C3=CC4CN(C(=O)C5(O)CC5)CC4C3)nc21] | 1-(2,2-dimethylpropyl)-5-{2-[(1-hydroxycyclopropyl)carbonyl]-1,2,3,3a,4,6a-hexahydrocyclopenta[c]pyrrol-5-yl}-3-methyl-1,3-dihydro-2H-imidazo[4,5-b]pyridin-2-one | C23H30N4O3 [M + H] calc 411.2392 obs 411.2405 |
| 8-19 | 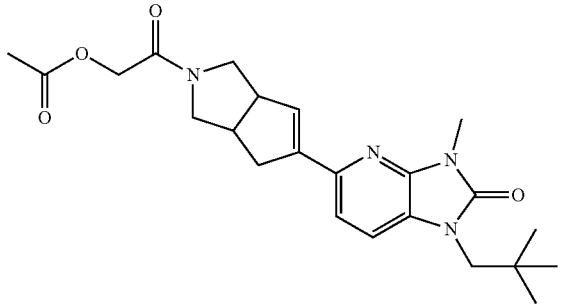 [SMILES: CC(=O)OCC(=O)N1CC2C=C(c3ccc4c(n3)n(C)c(=O)n4CC(C)(C)C)CC2C1] | 2-{5-[1-(2,2-dimethylpropyl)-3-methyl-2-oxo-2,3-dihydro-1H-imidazo[4,5-b]pyridin-5-yl]-3,3a,4,6a-tetrahydrocyclopenta[c]pyrrol-2(1H)-yl}-2-oxoethyl acetate | C23H30N4O4 [M + H] calc 427.2341 obs 427.2364 |
| 8-20 | 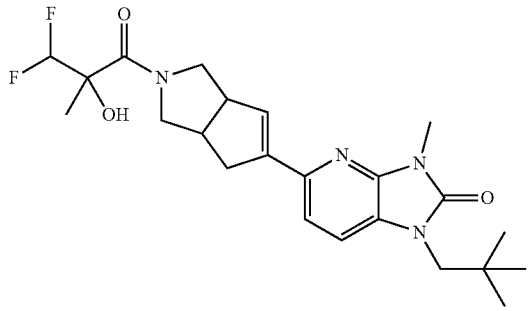 [SMILES: Cn1c(=O)n(CC(C)(C)C)c2ccc(C3=CC4CN(C(=O)C(C)(O)C(F)F)CC4C3)nc21] | 5-[2-(3,3-difluoro-2-hydroxy-2-methylpropanoyl)-1,2,3,3a,4,6a-hexahydrocyclopenta[c]pyrrol-5-yl]-1-(2,2-dimethylpropyl)-3-methyl-1,3-dihydro-2H-imidazo[4,5-b]pyridin-2-one | C23H30F2N4O3 [M + H] calc 449.2360 obs 449.2358 |
| 8-21 | 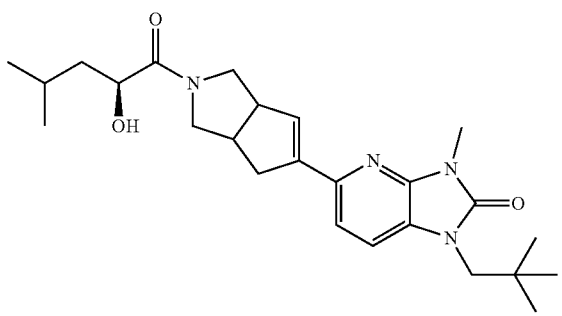 [SMILES: CC(C)C[C@H](O)C(=O)N1CC2C=C(c3ccc4c(n3)n(C)c(=O)n4CC(C)(C)C)CC2C1] | 1-(2,2-dimethylpropyl)-5-{2-[(2S)-2-hydroxy-4-methylpentanoyl]-1,2,3,3a,4,6a-hexahydrocyclopenta[c]pyrrol-5-yl}-3-methyl-1,3-dihydro-2H-imidazo[4,5-b]pyridin-2-one | C25H36N4O3 [M + H] calc 441.2861 obs 441.2878 |

TABLE 3-continued

| # | Structure | Name | HRMS/LRMS |
|---|-----------|------|-----------|
| 8-22 | 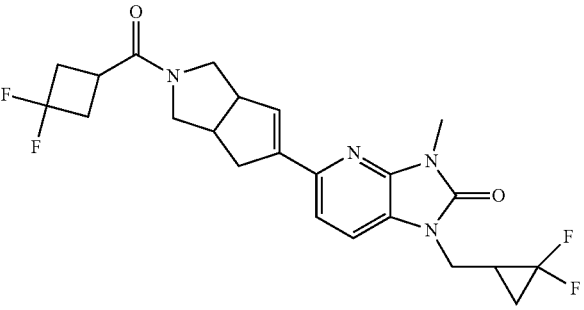 [SMILES: Cn1c(=O)n(CC2CC2(F)F)c2ccc(C3=CC4CN(C(=O)C5CC(F)(F)C5)CC4C3)nc21] | 5-{2-[(3,3-difluorocyclobutyl)carbonyl]-1,2,3,3,4,6a-hexahydrocyclopenta[c]pyrrol-5-yl}-1-[(2,2-difluorocyclopropyl)methyl]-3-methyl-1,3-dihydro-2H-imidazo[4,5-b]pyridin-2-one | C23H24F4N4O2 [M + H] calc 465.1911 obs 465.1915 |
| 8-23 | 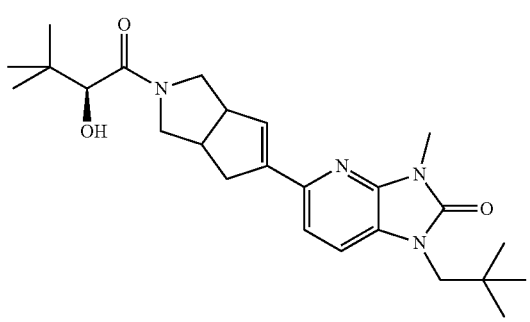 [SMILES: Cn1c(=O)n(CC(C)(C)C)c2ccc(C3=CC4CN(C(=O)[C@@H](O)C(C)(C)C)CC4C3)nc21] | 1-(2,2-dimethylpropyl)-5-{2-[(2S)-2-hydroxy-3,3-dimethylbutanoyl]-1,2,3,3a,4,6a-hexahydrocyclopenta[c]pyrrol-5-yl}-3-methyl-1,3-dihydro-2H-imidazo[4,5-b]pyridin-2-one | C25H36N4O3 [M + H] calc 441.2861 obs 441.2880 |
| 8-24 | 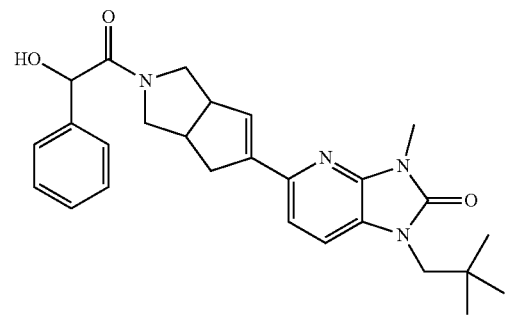 [SMILES: Cn1c(=O)n(CC(C)(C)C)c2ccc(C3=CC4CN(C(=O)C(O)c5ccccc5)CC4C3)nc21] | 1-(2,2-dimethylpropyl)-5-{2-(hydroxy(phenyl)acetyl]-1,2,3,3a,4,6a-hexahydrocyclopenta[c]pyrrol-5-yl}-3-methyl-1,3-dihydro-2H-imidazo[4,5-b]pyridin-2-one | C27H32N4O3 [M + H] calc 461.2548 obs 461.2560 |
| 8-25 | 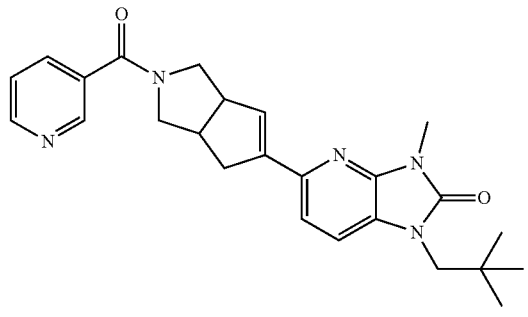 [SMILES: Cn1c(=O)n(CC(C)(C)C)c2ccc(C3=CC4CN(C(=O)c5cccnc5)CC4C3)nc21] | 1-(2,2-dimethylpropyl)-3-methyl-5-[2-(pyridin-3-ylcarbonyl)-1,2,3,3a,4,6a-hexahydrocyclopenta[c]pyrrol-5-yl]-1,3-dihydro-2H-imidazo[4,5-b]pyridin-2-one | C25H29N5O2 [M + H] calc 432.2396 obs 432.2412 |
| 8-26 | 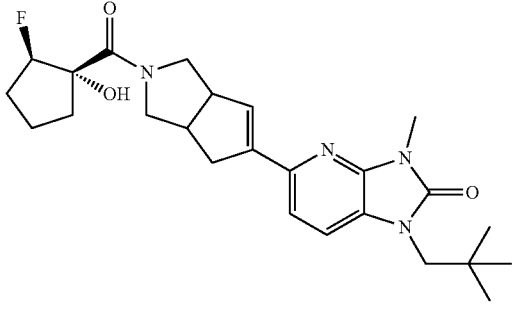 [SMILES: Cn1c(=O)n(CC(C)(C)C)c2ccc(C3=CC4CN(C(=O)[C@@]5(O)CCC[C@H]5F)CC4C3)nc21] | 1-(2,2-dimethylpropyl)-5-(2-{[(1S,2R)-2-fluoro-1-hydroxycyclopentyl]carbonyl}-1,2,3,3a,4,6a-hexahydrocyclopenta[c]pyrrol-5-yl)-3-methyl-1,3-dihydro-2H-imidazo[4,5-b]pyridin-2-one | C25H33FN4O3 [M + H] calc 457.261 obs 457.2624 |

TABLE 3-continued

| # | Structure | Name | HRMS/LRMS |
|---|---|---|---|
| 8-27 | 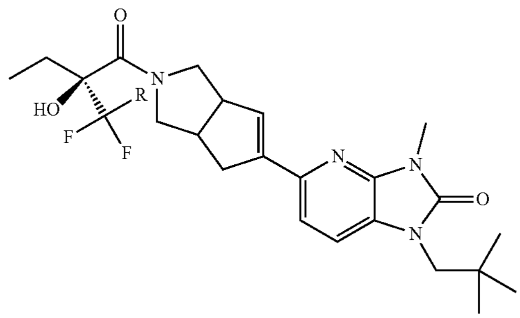 | 1-(2,2-dimethylpropyl)-5-{2-[(2S)-2-hydroxy-2-(trifluoromethyl)butanoyl]-1,2,3,3a,4,6a-hexahydrocyclopenta[c]pyrrol-5-yl}-3-methyl-1,3-dihydro-2H-imidazo[4,5-b]pyridin-2-one | C24H31F3N4O3 [M + H] calc 481.2422 obs 481.2442 |
| 8-28 | 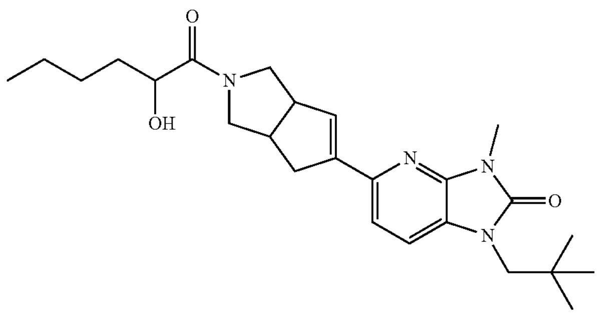 [SMILES: CCCCC(O)C(=O)N1CC2C=C(c3ccc4c(n3)n(C)c(=O)n4CC(C)(C)C)CC2C1] | 1-(2,2-dimethylpropyl)-5-[2-(2-hydroxyhexanoyl)-1,2,3,3a,4,6a-hexahydrocyclopenta[c]pyrrol-5-yl]-3-methyl-1,3-dihydro-2H-imidazo[4,5-b]pyridin-2-one | C25H36N4O3 [M + H] calc 441.2861 obs 441.2878 |
| 8-29 | 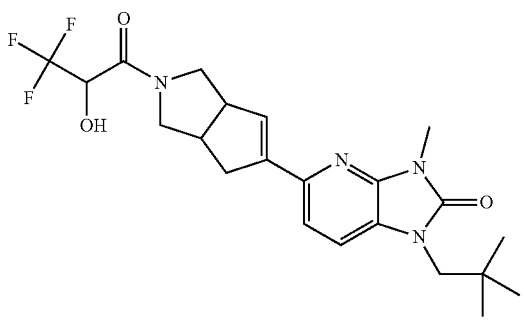 [SMILES: Cn1c(=O)n(CC(C)(C)C)c2ccc(C3=CC4CN(C(=O)C(O)C(F)(F)F)CC4C3)nc21] | 1-(2,2-dimethylpropyl)-3-methyl-5-[2-(3,3,3-trifluoro-2-hydroxypropanoyl)-1,2,3,3a,4,6a-hexahydrocyclopenta[c]pyrrol-5-yl]-1,3-dihydro-2H-imidazo[4,5-b]pyridin-2-one | C22H27F3N4O3 [M + H] calc 453.2110 obs 453.2129 |
| 8-30 | 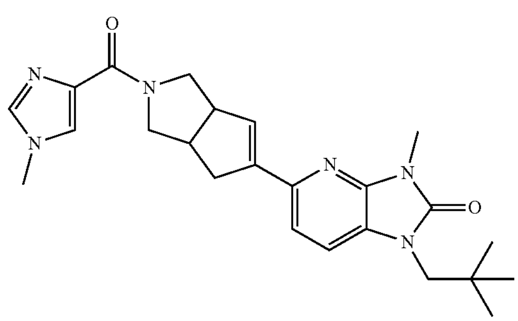 [SMILES: Cn1cnc(C(=O)N2CC3C=C(c4ccc5c(n4)n(C)c(=O)n5CC(C)(C)C)CC3C2)c1] | 1-(2,2-dimethylpropyl)-3-methyl-5-{2-[(1-methyl-1H-imidazol-4-yl)carbonyl]-1,2,3,3,4,6a-hexahydrocyclopenta[c]pyrrol-5-yl}-1,3-dihydro-2H-imidazo[4,5-b]pyridin-2-one | C24H30N6O2 [M + H] calc 435.2505 obs 435.2509 |
| 8-31 | 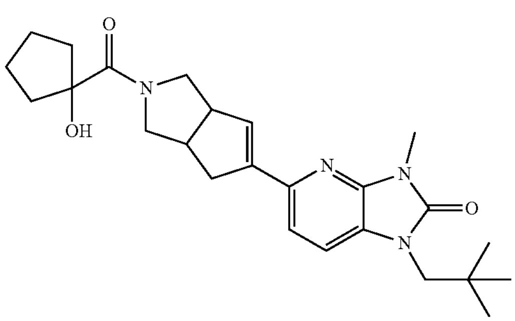 [SMILES: Cn1c(=O)n(CC(C)(C)C)c2ccc(C3=CC4CN(C(=O)C5(O)CCCC5)CC4C3)nc21] | 1-(2,2-dimethylpropyl)-5-{2-[(1-hydroxycyclopentyl)carbonyl]-1,2,3,3a,4,6a-hexahydrocyclopenta[c]pyrrol-5-yl}-3-methyl-1,3-dihydro-2H-imidazo[4,5-b]pyridin-2-one | C25H34N4O3 [M + H] calc 439.2704 obs 439.2707 |

TABLE 3-continued

| # | Structure | Name | HRMS/LRMS |
|---|---|---|---|
| 8-32 | 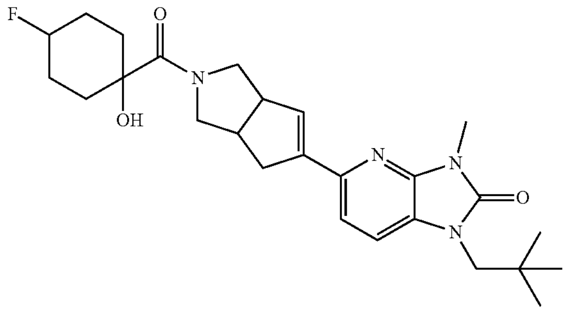 [SMILES: Cn1c(=O)n(CC(C)(C)C)c2ccc(C3=CC4CN(C(=O)C5(O)CCC(F)CC5)CC4C3)nc21] | 1-(2,2-dimethylpropyl)-5-{2-[(4-fluoro-1-hydroxycyclohexyl)carbonyl]-1,2,3,3a,4,6a-hexahydrocyclopenta[c]pyrrol-5-yl}-3-methyl-1,3-dihydro-2H-imidazo[4,5-b]pyridin-2-one | C26H35FN4O3 [M + H] calc 471.2767 obs 471.2779 |
| 8-33 | 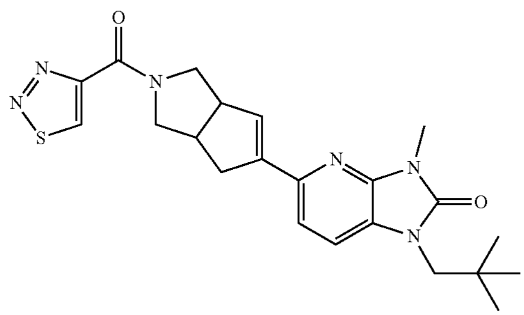 [SMILES: Cn1c(=O)n(CC(C)(C)C)c2ccc(C3=CC4CN(C(=O)c5csnn5)CC4C3)nc21] | 1-(2,2-dimethylpropyl)-3-methyl-5-[2-(1,2,3-thiadiazol-4-ylcarbonyl)-1,2,3,3a,4,6a-hexahydrocyclopenta[c]pyrrol-5-yl]-1,3-dihydro-2H-imidazo[4,5-b]pyridin-2-one | C22H26N6O2S [M + H] calc 439.1913 obs 442.1711 |
| 8-34 | 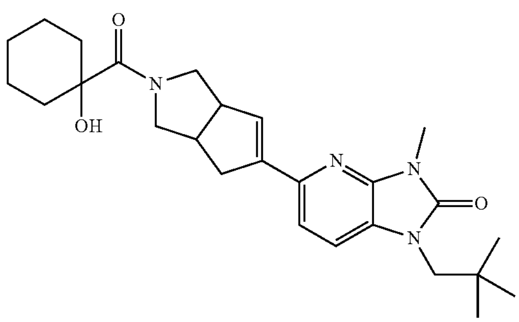 [SMILES: Cn1c(=O)n(CC(C)(C)C)c2ccc(C3=CC4CN(C(=O)C5(O)CCCCC5)CC4C3)nc21] | 1-(2,2-dimethylpropyl)-5-{2-[(1-hydroxycyclohexyl)carbonyl]-1,2,3,3a,4,6a-hexahydrocyclopenta[c]pyrrol-5-yl}-3-methyl-1,3-dihydro-2H-imidazo[4,5-b]pyridin-2-one | C26H36N4O3 [M + H] calc 453.2861 obs 453.2883 |
| 8-35 | 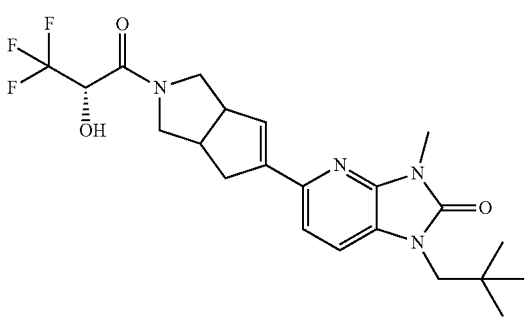 [SMILES: Cn1c(=O)n(CC(C)(C)C)c2ccc(C3=CC4CN(C(=O)[C@H](O)C(F)(F)F)CC4C3)nc21] | 1-(2,2-dimethylpropyl)-3-methyl-5-{2-[(2R)-3,3,3-trifluoro-2-hydroxypropanoyl]-1,2,3,3a,4,6a-hexahydrocyclopenta[c]pyrrol-5-yl}-1,3-dihydro-2H-imidazo[4,5-b]pyridin-2-one | C22H27F3N4O3 [M + H] calc 453.2110 obs 453.2126 |
| 8-36 | 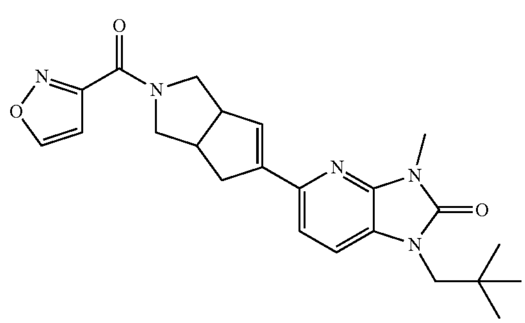 [SMILES: Cn1c(=O)n(CC(C)(C)C)c2ccc(C3=CC4CN(C(=O)c5ccon5)CC4C3)nc21] | 1-(2,2-dimethylpropyl)-5-[2-(isoxazol-3-ylcarbonyl)-1,2,3,3,4,6a-hexahydrocyclopenta[c]pyrrol-5-yl]-3-methyl-1,3-dihydro-2H-imidazo[4,5-b]pyridin-2-one | C23H27N5O3 [M + H] calc 422.2189 obs 422.2201 |

TABLE 3-continued

| # | Structure | Name | HRMS/LRMS |
|---|---|---|---|
| 8-37 | 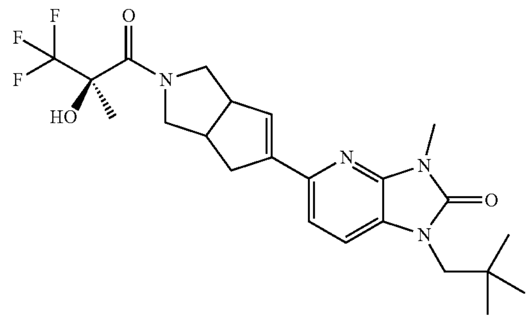 [SMILES: Cn1c(=O)n(CC(C)(C)C)c2ccc(C3=CC4CN(C(=O)[C@@](C)(O)C(F)(F)F)CC4C3)nc21] | 1-(2,2-dimethylpropyl)-3-methyl-5-{2-[(2R)-3,3,3-trifluoro-2-hydroxy-2-methylpropanoyl]-1,2,3,3a,4,6a-hexahydrocyclopenta[c]pyrrol-5-yl}-1,3-dihydro-2H-imidazo[4,5-b]pyridin-2-one | C23H29F3N4O3 [M + H] calc 467.2266 obs 467.2278 |
| 8-38 | 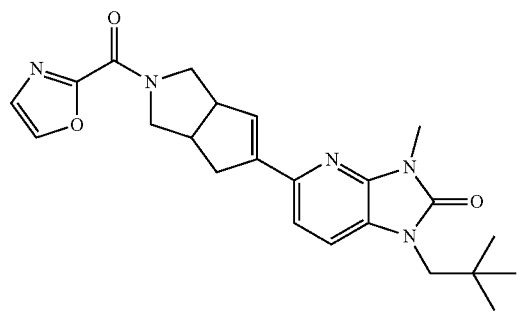 [SMILES: Cn1c(=O)n(CC(C)(C)C)c2ccc(C3=CC4CN(C(=O)c5ncco5)CC4C3)nc21] | 1-(2,2-dimethylpropyl)-3-methyl-5-[2-(1,3-oxazol-2-ylcarbonyl)-1,2,3,3a,4,6a-hexahydrocyclopenta[c]pyrrol-5-yl]-1,3-dihydro-2H-imidazo[4,5-b]pyridin-2-one | C23H27N5O3 [M + H] calc 422.2189 obs 422.2201 |
| 8-39 | 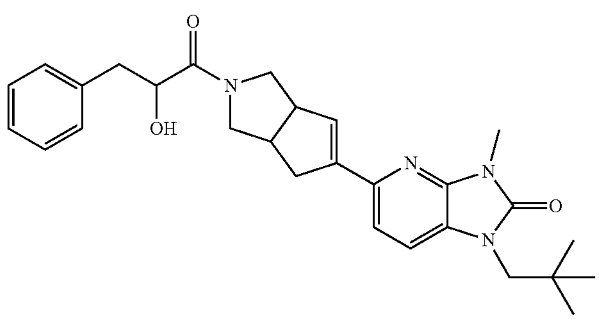 [SMILES: Cn1c(=O)n(CC(C)(C)C)c2ccc(C3=CC4CN(C(=O)C(O)Cc5ccccc5)CC4C3)nc21] | 1-(2,2-dimethylpropyl)-5-[2-(2-hydroxy-3-phenylpropanoyl)-1,2,3,3a,4,6a-hexahydrocyclopenta[c]pyrrol-5-yl]-3-methyl-1,3-dihydro-2H-imidazo[4,5-b]pyridin-2-one | C28H34N4O3 [M + H] calc 475.2704 obs 475.2720 |

Scheme 9

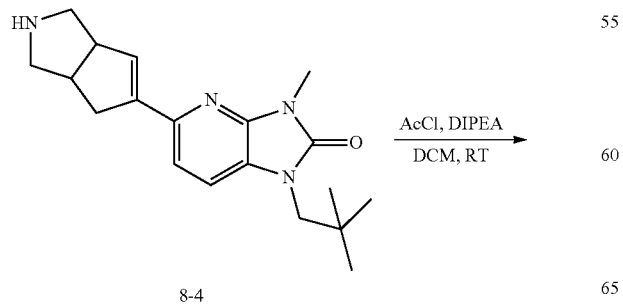

AcCl, DIPEA
DCM, RT 8-4

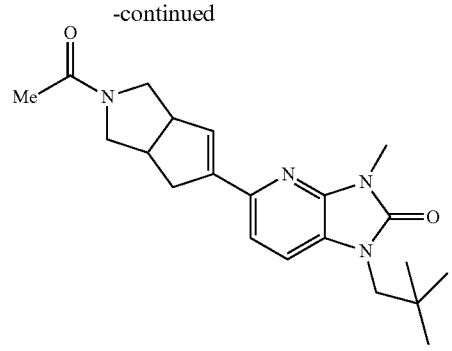

-continued 9-1

5-(2-Acetyl-1,2,3,3a,4,6a-hexahydrocyclopenta[c]pyrrol-5-yl)-1-(2,2-dimethylpropyl)-3-methyl-1,3-dihydro-2H-imidazo[4,5-b]pyridin-2-one (9-1)

1-(2,2-Dimethylpropyl)-5-(1,2,3,3a,4,6a-hexahydrocyclopenta[c]pyrrol-5-yl)-3-methyl-1,3-dihydro-2H-imidazo[4,5-b]pyridin-2-one (8-4, 100 mg, 0.30 mmol, 1.0 equiv), and DIPEA (0.16 mL, 0.91 mmol, 3.0 equiv) were added to anhydrous methylene chloride (3 mL) Stirred for 5 min and acetyl chloride (26.5 mg, 0.33 mmol, 1.1 equiv) was added. After stirring for 10 min at room temperature, LCMS showed consumption of starting material. Purification by reverse-phase HPLC (20-100% CH$_3$CN:0.1% TFA in H$_2$O) provided 9-1 as a pale yellow oil. MS m/z (M+H): calculated=369.2287; observed=369.2298.

Scheme 10

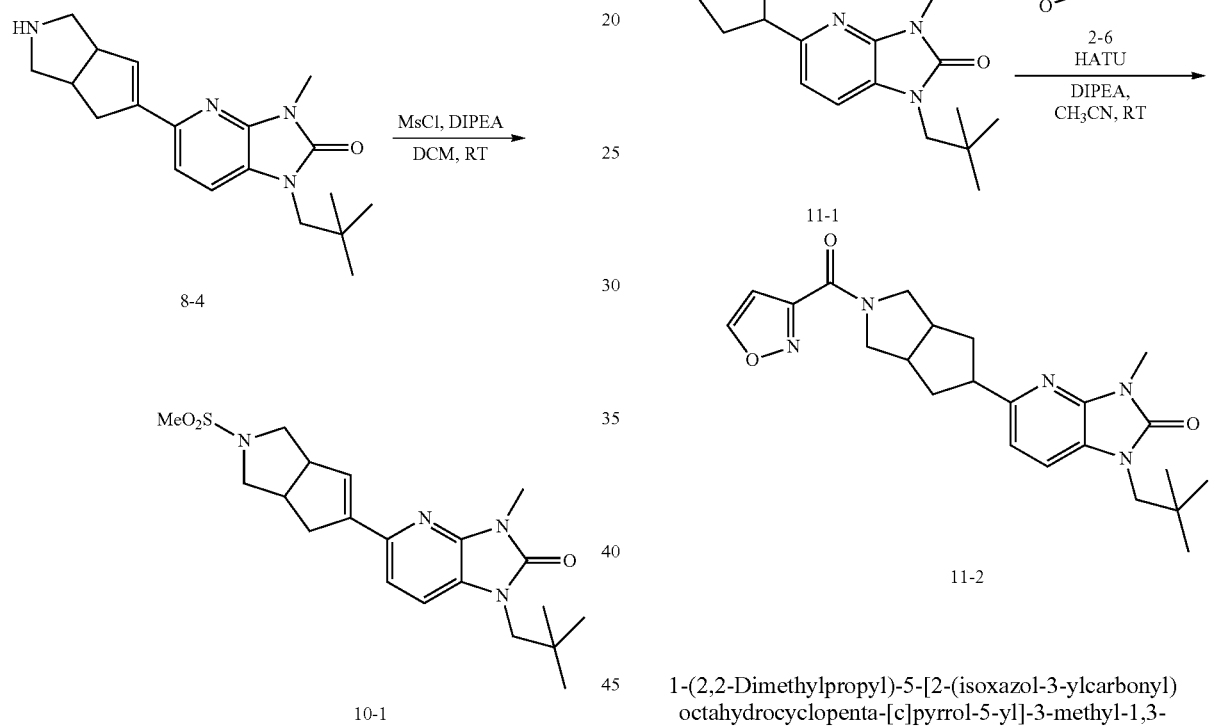

1-(2,2-Dimethylpropyl)-3-methyl-5-[2-(methylsulfonyl)-1,2,3,3a,4,6a-hexahydrocyclopenta[c]pyrrol-5-yl]-1,3-dihydro-2H-imidazo[4,5-b]pyridin-2-one (10-1)

1-(2,2-Dimethylpropyl)-5-(1,2,3,3a,4,6a-hexahydrocyclopenta[c]pyrrol-5-yl)-3-methyl-1,3-dihydro-2H-imidazo[4,5-b]pyridin-2-one (84, 100 mg, 0.30 mmol, 1.0 equiv), and DIPEA (0.16 mL, 0.91 mmol, 3.0 equiv) were added to anhydrous methylene chloride (3 mL). Stirred for 5 min and methanesulfonyl chloride (26.3 µL, 0.33 mmol, 1.1 equiv) was added. After stirring for 10 min at room temperature, LCMS showed consumption of starting material. Purification by reverse-phase HPLC (20-100% CH$_3$CN:0.1% TFA in H$_2$O) provided 10-1 as a pale yellow oil. MS m/z (M+H): calculated=405.1957; observed=405.1969.

Scheme 11

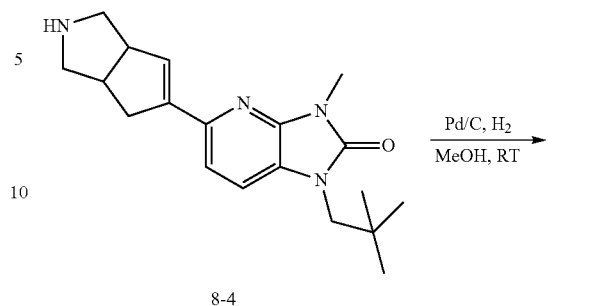

1-(2,2-Dimethylpropyl)-5-[2-(isoxazol-3-ylcarbonyl)octahydrocyclopenta-[c]pyrrol-5-yl]-3-methyl-1,3-dihydro-2H-imidazo[4,5-b]pyridin-2-one (11-2)

1-(2,2-Dimethylpropyl)-5-(1,2,3,3a,4,6a-hexahydrocyclopenta[c]pyrrol-5-yl)-3-methyl-1,3-dihydro-2H-imidazo[4,5-b]pyridin-2-one (11-1)

1-(2,2-Dimethylpropyl)-5-(1,2,3,3a,4,6a-hexahydrocyclopenta[c]pyrrol-5-yl)-3-methyl-1,3-dihydro-2H-imidazo[4,5-b]pyridin-2-one (8-4, 100 mg, 0.30 mmol, 1.0 equiv), was added to anhydrous MeOH (2.0 mL). To this solution was added 10% palladium(0) on carbon (32.6 mg, 31.0 µmol, 0.10 equiv) in one portion. The reaction vessel was then evacuated and back-filled with hydrogen (balloon). This process was repeated an additional two times. The resulting mixture was subsequently allowed to stir under an atmosphere of H$_2$ for 1 h at room temperature, after which LCMS showed complete consumption of starting material. The suspension was then filtered through Celite, rinsed with DCM (10 mL) and concentrated to give 11-1 as an oil. The crude material was taken forward without further purification.

1-(2,2-Dimethylpropyl)-5-[2-(isoxazol-3-ylcarbonyl) octahydrocyclopenta-[c]pyrrol-5-yl]-3-methyl-1,3-dihydro-2H-imidazo[4,5-b]pyridin-2-one (11-2)

1-(2,2-Dimethylpropyl)-5-(1,2,3,3a,4,6a-hexahydrocyclopenta[c]pyrrol-5-yl)-3-methyl-1,3-dihydro-2H-imidazo[4,5-b]pyridin-2-one (11-1, 50 mg, 0.15 mmol, 1.0 equiv), isoxazole-3-carboxylic acid (2-6, 25.8 mg, 0.22 mmol, 1.5 equiv), DIPEA (0.080 mL, 0.45 mmol, 3.0 equiv) and HATU (87 mg, 0.22 mmol, 1.5 equiv) were added to anhydrous acetonitrile (2 mL). After stirring for 10 min at room temperature, LCMS showed consumption of starting material. Purification by reverse-phase HPLC (20-100% $CH_3CN$:0.1% TFA in $H_2O$) provided 11-2 as a white solid. MS m/z (M+H): calculated=424.2345; observed=424.2353.

The following compounds were prepared from 11-1 by a reaction sequence analogous to that illustrated in Scheme 11:

TABLE 4

| # | Structure | Name | HRMS/LRMS |
|---|---|---|---|
| 11-3 | 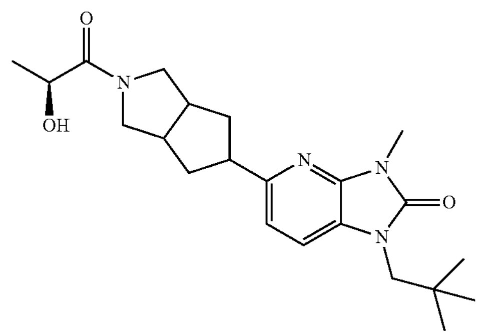 [SMILES: C[C@H](O)C(=O)N1CC2CC(c3ccc4c(n3)n(C)c(=O)n4CC(C)(C)C)CC2C1] | 1-(2,2-dimethylpropyl)-5-{2-[(2S)-2-hydroxypropanoyl]octahydrocyclopenta[c]pyrrol-5-yl}-3-methyl-1,3-dihydro-2H-imidazo[4,5-b]pyridin-2-one | C22H32N4O3 [M + H] calc 401.2548 obs 401.2545 |
| 11-4 | 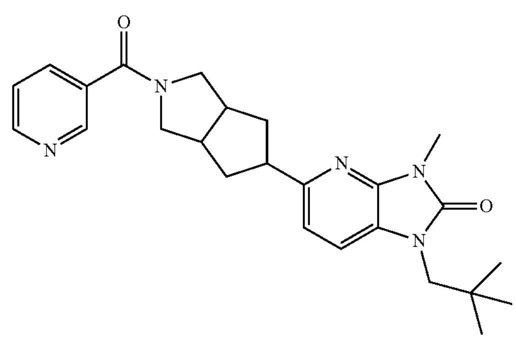 [SMILES: Cn1c(=O)n(CC(C)(C)C)c2ccc(C3CC4CN(C(=O)c5cccnc5)CC4C3)nc21] | 1-(2,2-dimethylpropyl)-3-methyl-5-[2-(pyridin-3-ylcarbonyl)octahydrocyclopenta[c]pyrrol-5-yl]-1,3-dihydro-2H-imidazo[4,5-b]pyridin-2-one | C25H31N5O2 [M + H] calc 434.2552 obs 434.2560 |
| 11-5 | 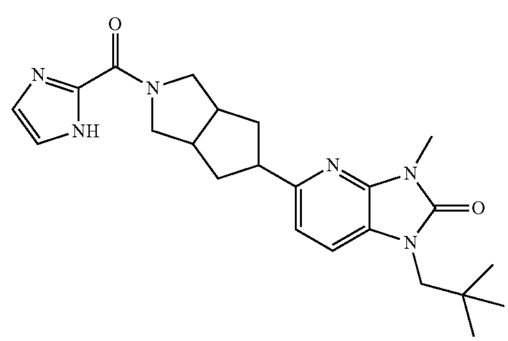 [SMILES: Cn1c(=O)n(CC(C)(C)C)c2ccc(C3CC4CN(C(=O)c5ncc[nH]5)CC4C3)nc21] | 1-(2,2-dimethylpropyl)-5-[2-(1H-imidazol-2-ylcarbonyl)octahydrocyclopenta[c]pyrrol-5-yl]-3-methyl-1,3-dihydro-2H-imidazo[4,5-b]pyridin-2-one | C23H30N6O2 [M + H] calc 423.2505 obs 423.2504 |
| 11-6 | 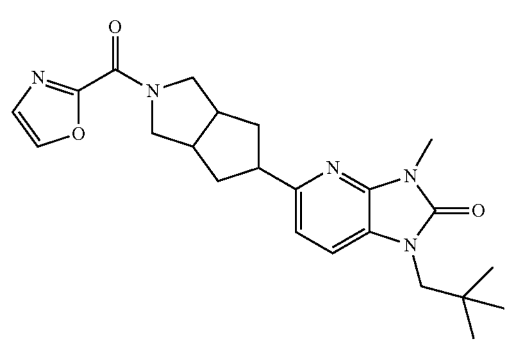 [SMILES: Cn1c(=O)n(CC(C)(C)C)c2ccc(C3CC4CN(C(=O)c5ncco5)CC4C3)nc21] | 1-(2,2-dimethylpropyl)-3-methyl-5-[2-(1,3-oxazol-2-ylcarbonyl)octahydrocyclopenta[c]pyrrol-5-yl]-1,3-dihydro-2H-imidazo[4,5-b]pyridin-2-one | C23H29N5O3 [M + H] calc 424.2345 obs 424.2353 |

TABLE 4-continued

| # | Structure | Name | HRMS/LRMS |
|---|---|---|---|
| 11-7 | 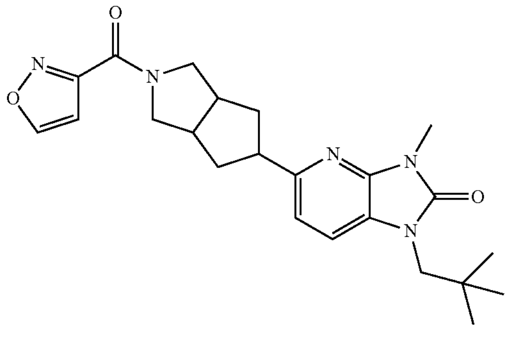 [SMILES: Cn1c(=O)n(CC(C)(C)C)c2ccc(C3CC4CN(C(=O)c5ccon5)CC4C3)nc21] | 1-(2,2-dimethylpropyl)-5-[2-(isoxazol-3-ylcarbonyl)octahydrocyclopenta[c]pyrrol-5-yl]-3-methyl-1,3-dihydro-2H-imidazo[4,5-b]pyridin-2-one | C23H29N5O3 [M + H] calc 424.2345 obs 424.2355 |
| 11-8 | 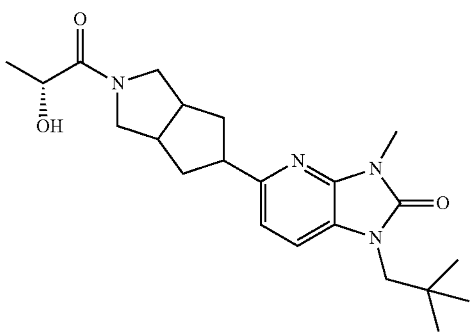 [SMILES: C[C@@H](O)C(=O)N1CC2CC(c3ccc4c(n3)n(C)c(=O)n4CC(C)(C)C)CC2C1] | 1-(2,2-dimethylpropyl)-5-{2-[(2R)-2-hydroxypropanoyl]octahydrocyclopenta[c]pyrrol-5-yl}-3-methyl-1,3-dihydro-2H-imidazo[4,5-b]pyridin-2-one | C22H32N4O3 [M + H] calc 401.2548 obs 401.2546 |

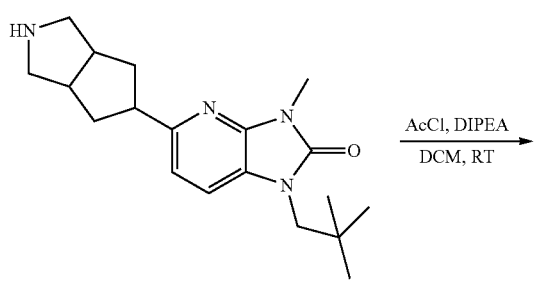

Scheme 12

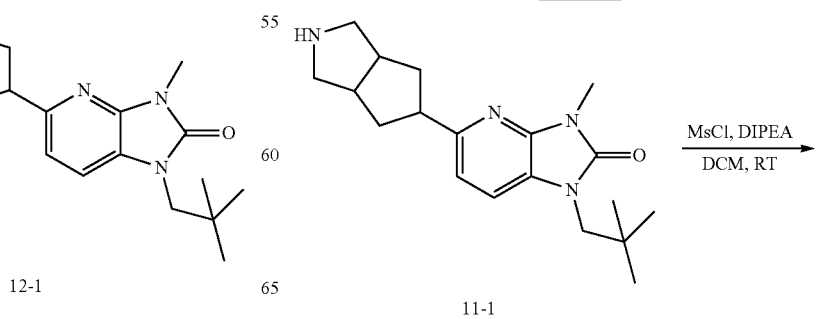

5-(2-Acetyloctahydrocyclopenta[c]pyrrol-5-yl)-1-(2,2-dimethylpropyl)-3-methyl-1,3-dihydro-2H-imidazo[4,5-b]pyridin-2-one (12-1)

1-(2,2-Dimethylpropyl)-5-(1,2,3,3a,4,6a-hexahydrocyclopenta[c]pyrrol-5-yl)-3-methyl-1,3-dihydro-2H-imidazo[4,5-b]pyridin-2-one (11-1, 50 mg, 0.15 mmol, 1.0 equiv), and DIPEA (0.080 mL, 0.45 mmol, 3.0 equiv) were added to anhydrous methylene chloride (2 mL). Stirred for 5 min and acetyl chloride (11.9 µL, 0.16 mmol, 1.1 equiv) was added. After stirring for 10 min at room temperature, LCMS showed consumption of starting material. Purification by reverse-phase HPLC (20-100% CH₃CN:0.1% TFA in H₂O) provided 12-1 as a pale yellow oil. MS m/z (M+H): calculated=371.2443; observed=371.2440.

Scheme 13

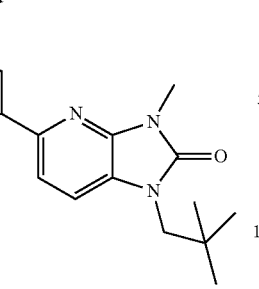

13-1

1-(2,2-Dimethylpropyl)-3-methyl-5-[2-(methylsulfonyl)octahydrocyclo-penta-[c]pyrrol-5-yl]-1,3-dihydro-2H-imidazo[4,5-b]pyridin-2-one (13-1)

1-(2,2-Dimethylpropyl)-5-(1,2,3,3a,4,6a-hexahydrocyclopenta[c]pyrrol-5-yl)-3-methyl-1,3-dihydro-2H-imidazo[4,5-b]pyridin-2-one (11-1, 50 mg, 0.15 mmol, 1.0 equiv), and DIPEA (0.080 mL, 0.45 mmol, 3.0 equiv) were added to anhydrous methylene chloride (2 mL). Stirred for 5 min and methanesulfonyl chloride (13.0 μL, 0.16 mmol, 1.1 equiv) was added. After stirring for 10 min at room temperature, LCMS showed consumption of starting material. Purification by reverse-phase HPLC (20-100% CH₃CN:0.1% TFA in H₂O) provided 13-1 as a pale yellow oil. MS m/z (M+H): calculated=407.2113; observed=407.2115.

Scheme 14

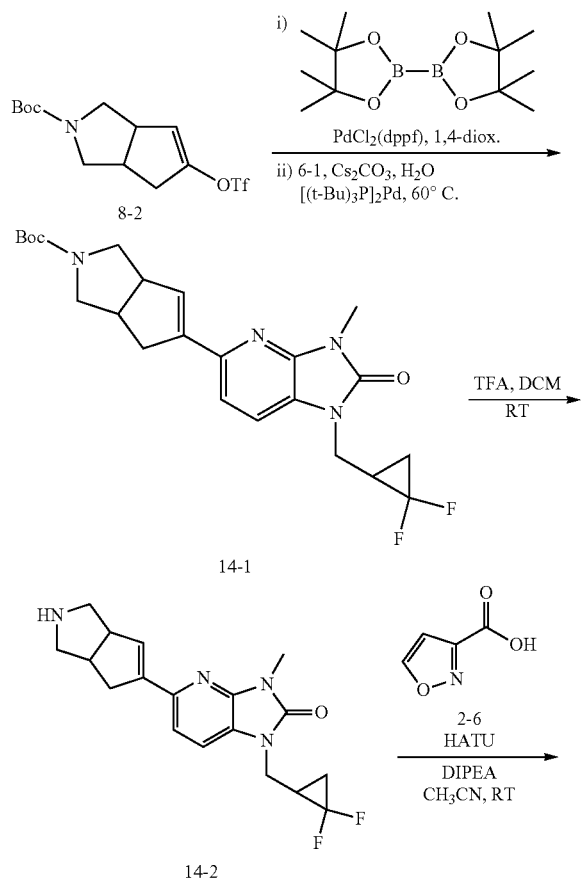

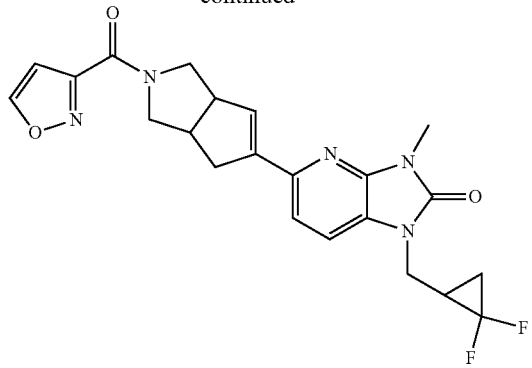

14-3

1-[(2,2-Difluorocyclopropyl)methyl]-5-[2-(isoxazol-3-ylcarbonyl)-1,2,3,3a,4,6a-hexahydrocyclopenta[c]pyrrol-5-yl]-3-methyl-1,3-dihydro-2H-imidazo[4,5-b]pyridin-2-one (14-3)

tert-Butyl 5-{1-[(2,2-difluorocyclopropyl)methyl]-3-methyl-2-oxo-2,3-dihydro-1H-imidazo[4,5-b]pyridin-5-yl}-3,3a,4,6a-tetrahydrocyclopenta[c]pyrrole-2 (1H)-carboxylate (14-1)

tert-Butyl 5-{[(trifluoromethyl)sulfonyl]oxy}-3,3a,4,6a-tetrahydrocyclopenta-[c]pyrrole-2(1H)-carboxylate (8-2, 1 g, 2.7 mmol, 1.0 equiv), bis(pinocolato)diboron (0.75 g, 3.0 mmol, 1.1 equiv), potassium acetate (0.8 g, 8.4 mmol, 3.0 equiv) and PdCl₂(dppf) (0.144 g, 0.196 mmol, 0.07 equiv) were added to anhydrous 1,4-dioxane (4 mL) and heated to 60° C. After 18 h, the reaction contents were cooled to RT, followed by the subsequent addition of water (1.4 mL), 5-Chloro-1-[(2,2-difluorocyclopropyl)methyl]-3-methyl-1, 3-dihydro-2H-imidazo[4,5-b]pyridin-2-one (6-1, 766 mg, 2.8 mmol, 1.0 equiv), Cs₂CO₃ (1.8 g, 5.5 mmol, 2.00 equiv) and Bis(tri-tert-butylphosphine)palladium(0) (0.186 g, 0.364 mmol, 0.13 equiv). The resulting mixture was heated to 60° C. for 4.5 h. Following this duration, LCMS showed consumption of starting material. The contents were then cooled to room temperature, diluted with ethyl acetate (50 mL), filtered through Celite and rinsed with ethyl acetate (3×50 mL) and water (1×30 mL). The filtrate layers were separated and the combined organics were washed with saturated NaHCO₃ (100 mL). The combined aqueous layers were then back-extracted with ethyl acetate (2×50 mL). The combined organics were dried over Na₂SO₄, filtered and concentrated in vacuo to give a dark orange oil. Purification by normal-phase chromatography (0-50% EtOAc:Hex) afforded 14-1 as an off-white solid. MS m/z (M+H): calculated=447.2; observed=447.2.

1-[(2,2-Difluorocyclopropyl)methyl]-5-(1,2,3,3a,4, 6a-hexahydrocyclopenta-[c]pyrrol-5-yl)-3-methyl-1, 3-dihydro-2H-imidazo[4,5-b]pyridin-2-one (14-2)

tert-Butyl 5-{1-[(2,2-difluorocyclopropyl)methyl]-3-methyl-2-oxo-2,3-dihydro-1H-imidazo[4,5-b]pyridin-5-yl}-3, 3a,4,6a-tetrahydrocyclopenta[c]pyrrole-2(1H)-carboxylate (14-1, 100 mg, 0.22 mmol) was added to a mixture of dichloromethane (2.0 mL) and trifluoroacetic acid (0.5 mL) at room temperature. After stirring for 18 h, the solvent was removed in vacuo. The resulting residue was then diluted with ethyl acetate (100 mL) and washed sequentially with saturated sodium bicarbonate (2×50 mL), water (1×50 mL) and brine (1×50 mL). The organics were dried over magnesium sulfate, filtered, and concentrated in vacuo to give 1-[(2,2-Difluorocyclopropyl)methyl]-5-(1,2,3,3a,4,6a-hexahydrocyclopenta-[c]pyrrol-5-yl)-3-methyl-1,3-dihydro-2H-imidazo[4,5-b]pyridin-2-one (14-2) as a white solid. This material was carried on without further purification.

1-[(2,2-Difluorocyclopropyl)methyl]-5-[2-(isoxazol-3-ylcarbonyl)-1,2,3,3a,4,6a-hexahydrocyclopenta[c]pyrrol-5-yl]-3-methyl-1,3-dihydro-2H-imidazo[4,5-b]pyridin-2-one (14-3)

1-[(2,2-Difluorocyclopropypmethyl]-5-(1,2,3,3a,4,6a-hexahydrocyclopenta-[c]pyrrol-5-yl)-3-methyl-1,3-dihydro-2H-imidazo[4,5-b]pyridin-2-one (14-2, 50 mg, 0.14 mmol, 1.0 equiv), isoxazole-3-carboxylic acid (2-6, 24.4 mg, 0.21 mmol, 1.5 equiv), DIPEA (0.076 mL, 0.43 mmol, 3.0 equiv) and HATU (82 mg, 0.21 mmol, 1.5 equiv) were added to anhydrous acetonitrile (3 mL). After stirring for 10 min at room temperature, LCMS showed consumption of starting material. Purification by reverse-phase HPLC (20-100% CH$_3$CN:0.1% TFA in H$_2$O) provided 14-3 as a white solid. MS m/z (M+H): calculated=442.1688; observed=442.1703.

$^1$H NMR δ (ppm)(CHCl$_3$-d): 8.42 (1H, d, J=7.54 Hz), 7.17 (1H, d, J=8.07 Hz), 7.09-7.03 (1H, m), 6.76 (1H, s), 6.44 (1H, d, J=15.05 Hz), 4.32 (1H, dd, J=11.94, 8.93 Hz), 4.25-4.19 (1H, m), 4.13-4.04 (1H, m), 4.00-3.85 (1H, m), 3.82-3.71 (1H, m), 3.70 (1H, s), 3.65 (1H, dd, J=11.78, 7.47 Hz), 3.50 (3H, d, J=3.05 Hz), 3.23-3.08 (1H, m), 3.10-2.96 (1H, m), 2.86-2.70 (1H, m), 2.06-1.98 (1H, m), 1.53 (1H, s), 1.33-1.27 (1H, m).

The following compounds were prepared from 14-2 by a reaction sequence analogous to that illustrated in Scheme 14:

TABLE 5

| # | Structure | Name | HRMS/LRMS |
|---|-----------|------|-----------|
| 14-4 | 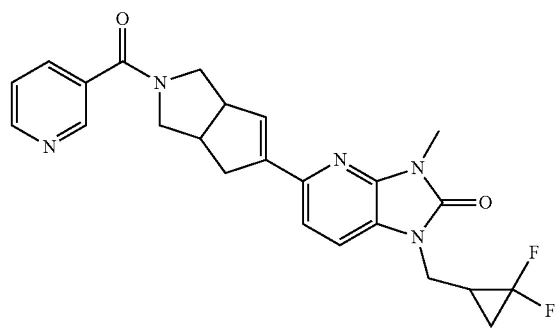 [SMILES: Cn1c(=O)n(CC2CC2(F)F)c2ccc(C3=CC4CN(C(=O)c5cccnc5)CC4C3)nc21] | 1-[(2,2-difluorocyclopropyl)methyl]-3-methyl-5-[2-(pyridin-3-ylcarbonyl)-1,2,3,3a,4,6a-hexahydrocyclopenta[c]pyrrol-5-yl]-1,3-dihydro-2H-imidazo[4,5-b]pyridin-2-one | C24H23F2N5O2 [M + H] calc 452.1895 obs 452.1917 |
| 14-5 | 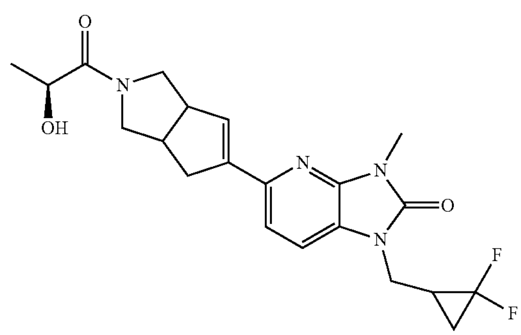 [SMILES: C[C@H](O)C(=O)N1CC2C=C(c3ccc4c(n3)n(C)c(=O)n4CC3CC3(F)F)CC2C1] | 1-[(2,2-difluorocyclopropyl)methyl]-5-{2-[(2S)-2-hydroxypropanoyl]-1,2,3,3a,4,6a-hexahydrocyclopenta[c]pyrrol-5-yl}-3-methyl-1,3-dihydro-2H-imidazo[4,5-b]pyridin-2-one | C21H24F2N4O3 [M + H] calc 419.1891 obs 402.1305 |
| 14-6 | 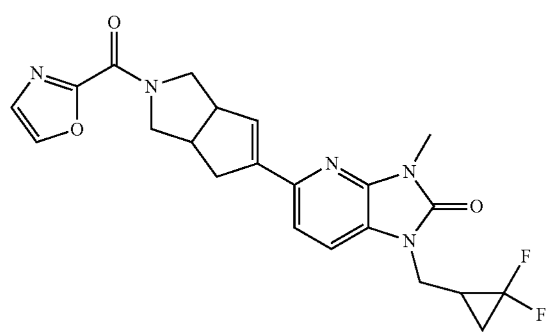 [SMILES: Cn1c(=O)n(CC2CC2(F)F)c2ccc(C3=CC4CN(C(=O)c5ncco5)CC4C3)nc21] | 1-[(2,2-difluorocyclopropyl)methyl]-3-methyl-5-[2-(1,3-oxazol-2-ylcarbonyl)-1,2,3,3a,4,6a-hexahydrocyclopenta[c]pyrrol-5-yl]-1,3-dihydro-2H-imidazo[4,5-b]pyridin-2-one | C22H21F2N5O3 [M + H] calc 442.1688 obs 442.1711 |

Scheme 15

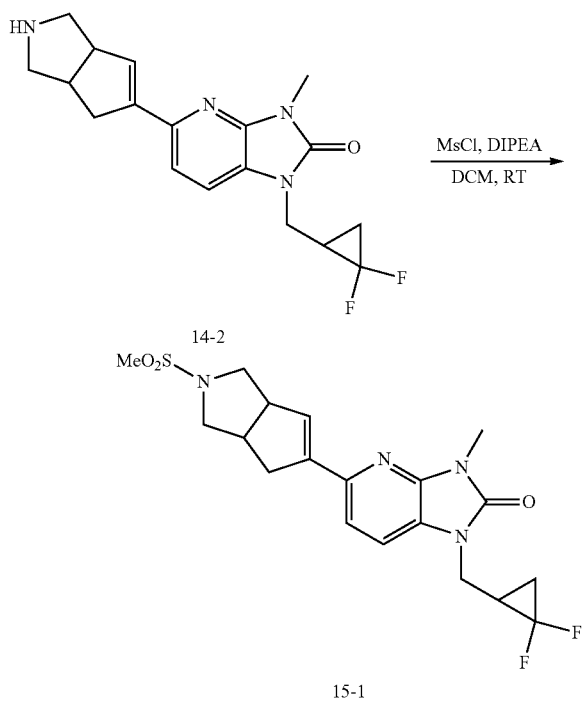

1-[(2,2-Difluorocyclopropyl)methyl]-3-methyl-5-[2-(methylsulfonyl)-1,2,3,3a,4,6a-hexahydrocyclopenta[c]pyrrol-5-yl]-1,3-dihydro-2H-imidazo[4,5-b]pyridin-2-one (15-1)

1-[(2,2-Difluorocyclopropyemethyl]-5-(1,2,3,3a,4,6a-hexahydrocyclo-penta-[c]pyrrol-5-yl)-3-methyl-1,3-dihydro-2H-imidazo[4,5-b]pyridin-2-one (14-2, 50 mg, 0.14 mmol, 1.0 equiv), and DIPEA (0.076 mL, 0.43 mmol, 3.0 equiv) were added to anhydrous methylene chloride (2 mL). Stirred for 5 min and methanesulfonyl chloride (12.0 μL, 0.16 mmol, 1.1 equiv) was added. After stirring for 10 min at room temperature, LCMS showed consumption of starting material. Purification by reverse-phase HPLC (20-100% $CH_3CN$:0.1% TFA in $H_2O$) provided 15-1 as a pale yellow oil. MS m/z (M+H): calculated=425.1456; observed=425.1465.

Scheme 16

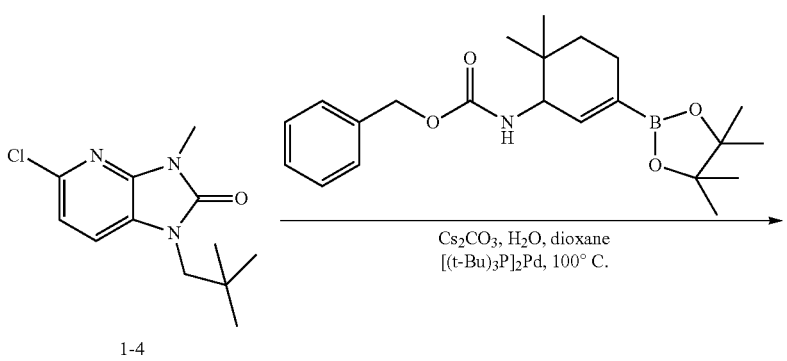

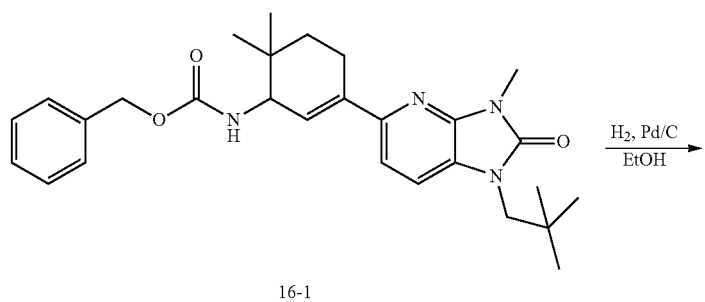

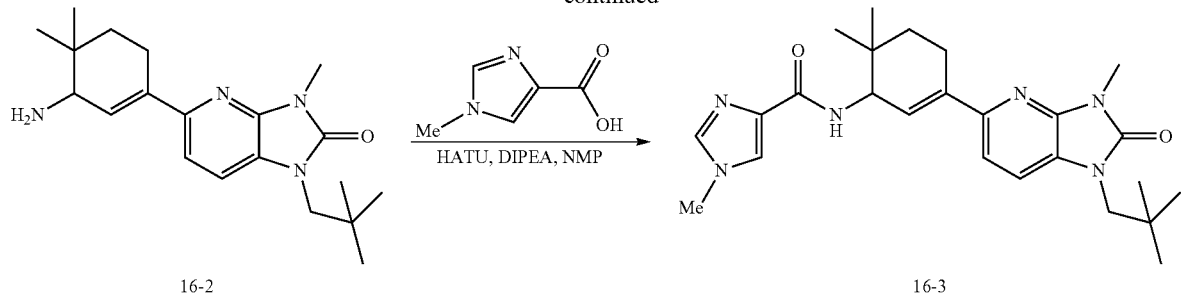

16-2 → 16-3

N-{5-[1-(2,2-dimethylpropyl)-3-methyl-2-oxo-2,3-dihydro-1H-imidazo[4,5-b]pyridin-5-yl]-2,2-dimethylcyclohexyl}-1-methyl-1H-imidazole-4-carboxamide (16-3)

Benzyl {3-[1-(2,2-dimethylpropyl)-3-methyl-2-oxo-2,3-dihydro-1H-imidazo[4,5-b]pyridin-5-yl]-6,6-dimethylcyclohex-2-en-1-yl}carbamate (16-1)

To a microwave vial was added 5-chloro-1-(2,2-dimethylpropyl)-3-methyl-1,3-dihydro-2H-imidazo[4,5-b]pyridin-2-one (1-4) (313 mg, 1.234 mmol), $Cs_2CO_3$ (804 mg, 2.467 mmol), benzyl [6,6-dimethyl-3-(4,4,5,5-tetramethyl-1,3,2-dioxaborolan-2-yl)cyclohex-2-en-1-yl]carbamate (668 mg, 1.734 mmol), & bis(tri-t-butylphosphine)palladium(0) (129 mg, 0.252 mmol), followed by anhydrous 1,4-dioxane (2.5 mL) & water (0.5 mL). The reaction mixture was then heated to 100° C. for 2×10 minutes under microwave irradiation. The reaction was then cooled to room temperature, diluted with MeOH & NMP, filtered & resulting residue was purified by reverse-phase chromatography (10-100% $CH_3CN$:0.1% TFA in $H_2O$) to yield benzyl {3-[1-(2,2-dimethylpropyl)-3-methyl-2-oxo-2,3-dihydro-1H-imidazo[4,5-b]pyridin-5-yl]-6,6-dimethylcyclohex-2-en-1-yl}carbamate (16-1) as a white solid/foam. HRMS m/z (M+H): calculated=477.2860; observed=477.2865.

5-(3-amino-4,4-dimethylcyclohexyl)-1-(2,2-dimethylpropyl)-3-methyl-1,3-dihydro-2H-imidazo[4,5-b]pyridin-2-one (16-2)

Procedure similar to that for tert-butyl 3-[1-(2,2-dimethylpropyl)-3-methyl-2-oxo-2,3-dihydro-1H-imidazo[4,5-b]pyridin-5-yl]piperidine-1-carboxylate (18-1) gave 5-(3-amino-4,4-dimethylcyclohexyl)-1-(2,2-dimethylpropyl)-3-methyl-1,3-dihydro-2H-imidazo[4,5-b]pyridin-2-one (16-2). HRMS (M+H)$^+$: observed=345.2650, calculated=345.2649.

N-{5-[1-(2,2-dimethylpropyl)-3-methyl-2-oxo-2,3-dihydro-1H-imidazo[4,5-b]pyridin-5-yl]-2,2-dimethylcyclohexyl}-1-methyl-1H-imidazole-4-carboxamide (16-3)

Procedure similar to that for N-{4-[1-(2,2-Dimethylpropyl)-3-methyl-2-oxo-2,3-dihydro-1H-imidazo[4,5-b]pyridin-5-yl]cyclohex-3-en-1-yl}-1-methyl-1H-imidazole-2-carboxamide (17-3) gave N-{5-[1-(2,2-dimethylpropyl)-3-methyl-2-oxo-2,3-dihydro-1H-imidazo[4,5-b]pyridin-5-yl]-2,2-dimethylcyclohexyl}-1-methyl-1H-imidazole-4-carboxamide (16-3). HRMS (M+H)$^+$: observed=453.2986, calculated=453.2973.

Scheme 17

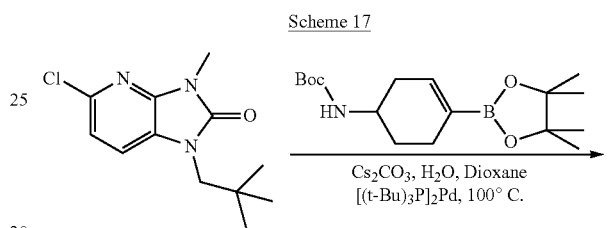

1-4

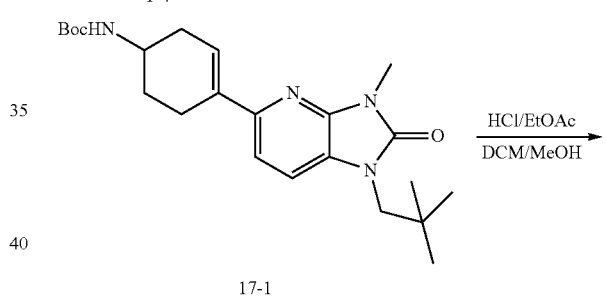

17-1

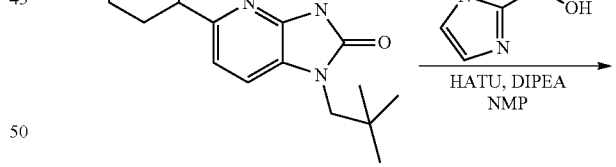

17-2

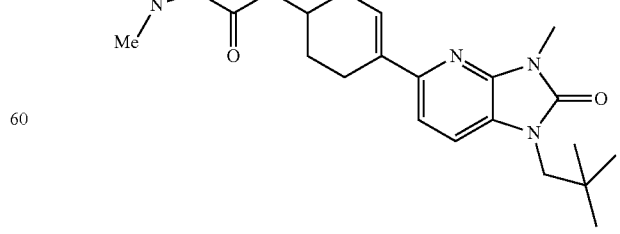

17-3

N-{4-[1-(2,2-Dimethylpropyl)-3-methyl-2-oxo-2,3-dihydro-1H-imidazo[4,5-b]pyridin-5-yl]cyclohex-3-en-1-yl}-1-methyl-1H-imidazole-2-carboxamide (17-3)

tert-Butyl {4-[1-(2,2-dimethylpropyl)-3-methyl-2-oxo-2,3-dihydro-1H-imidazo[4,5-b]pyridin-5-yl]cyclohex-3-en-1-yl}carbamate (17-1)

To a microwave vial was added 5-chloro-1-(2,2-dimethylpropyl)-3-methyl-1,3-dihydro-2H-imidazo[4,5-b]pyridin-2-one (1-4) (410 mg, 1.616 mmol), Cs$_2$CO$_3$ (1.14 g, 3.50 mmol), tert-butyl [4-(4,4,5,5-tetramethyl-1,3,2-dioxaborolan-2-yl)cyclohex-3-en-1-yl]carbamate (692 mg, 2.141 mmol), & bis(tri-t-butylphosphine)palladium(0) (183 mg, 0.358 mmol), followed by anhydrous 1,4-dioxane (2.5 mL) & water (0.5 mL). The reaction mixture was then heated to 100° C. for 10 minutes under microwave irradiation. The reaction was then cooled to room temperature, diluted with MeOH & NMP, filtered & resulting residue was purified by reverse-phase chromatography (10-100% CH$_3$CN:0.1% TFA in H$_2$O) to yield tert-Butyl {4-[1-(2,2-dimethylpropyl)-3-methyl-2-oxo-2,3-dihydro-1H-imidazo[4,5-b]pyridin-5-yl]cyclohex-3-en-1-yl}carbamate (17-1) as a yellow solid/foam. HRMS m/z (M+H): calculated=415.2704; observed=415.2705

5-(4-Aminocyclohex-1-en-1-yl)-1-(2,2-dimethylpropyl)-3-methyl-1,3-dihydro-2H-imidazo[4,5-b]pyridin-2-one (17-2)

To a round bottom flask was added tert-butyl {-4-[1-(2,2-dimethylpropyl)-3-methyl-2-oxo-2,3-dihydro-1H-imidazo[4,5-b]pyridin-5-yl]cyclohex-3-en-1-yl}carbamate (17-1) (338 mg, 0.815 mmol), DCM (2 mL), MeOH (2 mL), and a 4N solution of HCl in EtOAc (2.038 ml, 8.15 mmol). The reaction mixture was then capped & stirred at room temperature for several hours. The reaction was then concentrated to yield 5-(4-Aminocyclohex-1-en-1-yl)-1-(2,2-dimethylpropyl)-3-methyl-1,3-dihydro-2H-imidazo[4,5-b]pyridin-2-one (17-2) as a tan solid.

HRMS m/z (M+H): calculated=315.2179; observed=315.2177

N-{4-[1-(2,2-Dimethylpropyl)-3-methyl-2-oxo-2,3-dihydro-1H-imidazo[4,5-b]pyridin-5-yl]cyclohex-3-en-1-yl}-1-methyl-1H-imidazole-2-carboxamide (17-3)

To a round bottom flask were added 5-(4-Aminocyclohex-1-en-1-yl)-1-(2,2-dimethylpropyl)-3-methyl-1,3-dihydro-2H-imidazo[4,5-b]pyridin-2-one (17-2) (0.0010 g, 0.028 mmol), DIPEA (0.050 mL, 0.286 mmol), HATU (0.0013 g, 0.034 mmol), 1-methyl-1H-imidazole-2-carboxylic acid (0.00467 g, 0.037 mmol), and NMP (1 mL). The reaction was stirred at room temperature overnight (~14 hours), the reaction mixtures were then filtered & purified by reverse-phase chromatography (5-95% 0.1% TFA in H$_2$O:acetonitrile) to give N-{4-[1-(2,2-Dimethylpropyl)-3-methyl-2-oxo-2,3-dihydro-1H-imidazo[4,5-b]pyridin-5-yl]cyclohex-3-en-1-yl}-1-methyl-1H-imidazole-2-carboxamide (17-3). HRMS m/z (M+H): calculated=423.2503; observed=423.2507.

The following compounds were prepared by a reaction sequence analogous to that illustrated in Schemes 16 or 17:

TABLE 6

| # | Structure | Name | HRMS/LRMS |
|---|---|---|---|
| 17-4 | 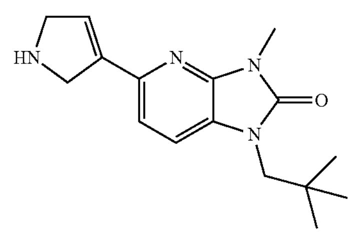 [SMILES: Cn1c(=O)n(CC(C)(C)C)c2ccc(C3=CCNC3)nc21] | 5-(2,5-dihydro-1H-pyrrol-3-yl)-1-(2,2-dimethylpropyl)-3-methyl-1,3-dihydro-2H-imidazo[4,5-b]pyridin-2-one | C16H22N4O [M + H] calc 287.1869 obs 287.1867 |
| 17-5 | 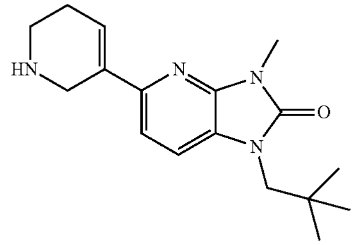 [SMILES: Cn1c(=O)n(CC(C)(C)C)c2ccc(C3=CCCNC3)nc21] | 1-(2,2-dimethylpropyl)-3-methyl-5-(1,2,5,6-tetrahydropyridin-3-yl)-1,3-dihydro-2H-imidazo[4,5-b]pyridin-2-one | C17H24N4O [M + H] calc 301.2025 obs 301.2021 |
| 17-6 | 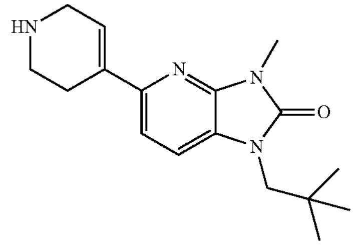 [SMILES: Cn1c(=O)n(CC(C)(C)C)c2ccc(C3=CCNCC3)nc21] | 1-(2,2-dimethylpropyl)-3-methyl-5-(1,2,3,6-tetrahydropyridin-4-yl)-1,3-dihydro-2H-imidazo[4,5-b]pyridin-2-one | C17H24N4O [M + H] calc 301.2025 obs 301.2021 |

TABLE 6-continued

| # | Structure | Name | HRMS/LRMS |
|---|---|---|---|
| 17-7 | 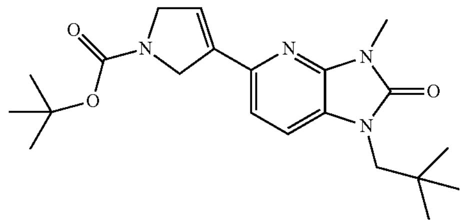 [SMILES: Cn1c(=O)n(CC(C)(C)C)c2ccc(C3=CCN(C(=O)OC(C)(C)C)C3)nc21] | tert-butyl 3-[1-(2,2-dimethylpropyl)-3-methyl-2-oxo-2,3-dihydro-1H-imidazo[4,5-b]pyridin-5-yl]-2,5-dihydro-1H-pyrrole-1-carboxylate | C21H30N4O3 [M + H] calc 387.2392 obs 387.2393 |
| 17-8 | 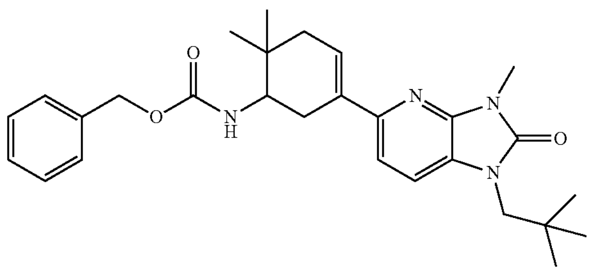 [SMILES: Cn1c(=O)n(CC(C)(C)C)c2ccc(C3=CCC(C)(C)C(NC(=O)OCc4ccccc4)C3)nc21] | benzyl {3-[1-(2,2-dimethylpropyl)-3-methyl-2-oxo-2,3-dihydro-1H-imidazo[4,5-b]pyridin-5-yl]-6,6-dimethylcyclohex-3-en-1-yl}carbamate | C28H36N4O3 [M + H] calc 477.2861 obs 477.2873 |
| 17-9 | 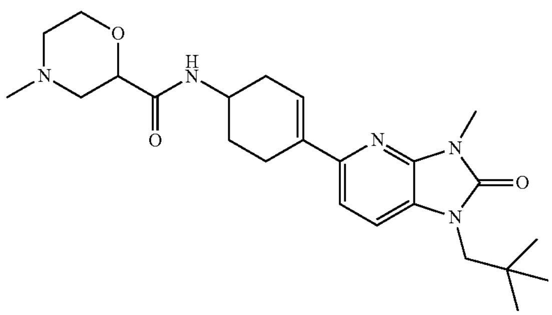 [SMILES: CN1CCOC(C(=O)NC2CC=C(c3ccc4c(n3)n(C)c(=O)n4CC(C)(C)C)CC2)C1] | N-{4-[1-(2,2-dimethylpropyl)-3-methyl-2-oxo-2,3-dihydro-1H-imidazo[4,5-b]pyridin-5-yl]cyclohex-3-en-1-yl}-4-methylmorpholine-2-carboxamide | C24H35N5O3 [M + H] calc 442.2814 obs 442.2823 |
| 17-10 | 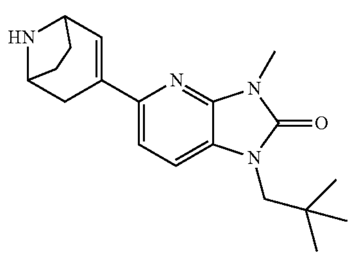 [SMILES: Cn1c(=O)n(CC(C)(C)C)c2ccc(C3=CC4CCC(C3)N4)nc21] | 5-(8-azabicyclo[3.2.1]oct-2-en-3-yl)-1-(2,2-dimethylpropyl)-3-methyl-1,3-dihydro-2H-imidazo[4,5-b]pyridin-2-one | C19H26N4O [M + H] calc 327.2181 obs 327.2178 |
| 17-11 | 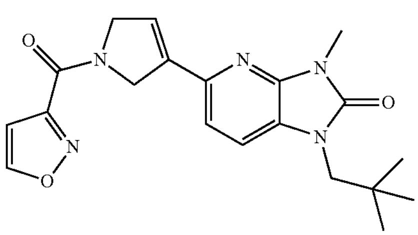 [SMILES: Cn1c(=O)n(CC(C)(C)C)c2ccc(C3=CCN(C(=O)c4ccon4)C3)nc21] | 1-(2,2-dimethylpropyl)-5-[1-(isoxazol-3-ylcarbonyl)-2,5-dihydro-1H-pyrrol-3-yl]-3-methyl-1,3-dihydro-2H-imidazo[4,5-b]pyridin-2-one | C20H23N5O3 [M + H] calc 382.1876 obs 382.1871 |
| 17-12 | 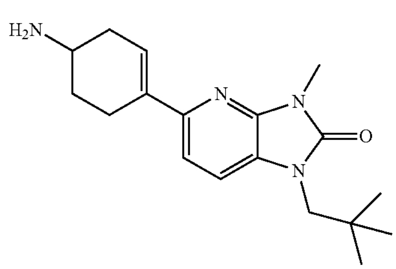 [SMILES: Cn1c(=O)n(CC(C)(C)C)c2ccc(C3=CCC(N)CC3)nc21] | 5-(4-aminocyclohex-1-en-1-yl)-1-(2,2-dimethylpropyl)-3-methyl-1,3-dihydro-2H-imidazo[4,5-b]pyridin-2-one | C18H26N4O [M + H] calc 315.2182 obs 315.2177 |

TABLE 6-continued

| # | Structure | Name | HRMS/LRMS |
|---|---|---|---|
| 17-13 | 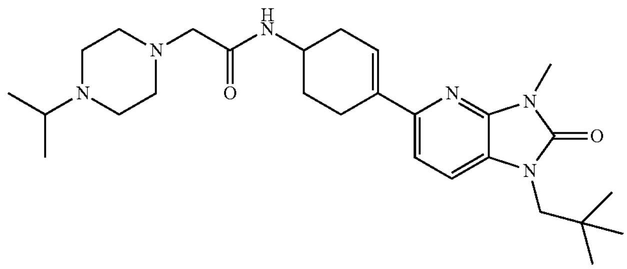 [SMILES: CC(C)N1CCN(CC(=O)NC2CC=C(c3ccc4c(n3)n(C)c(=O)n4CC(C)(C)C)CC2)CC1] | N-{4-[1-(2,2-dimethylpropyl)-3-methyl-2-oxo-2,3-dihydro-1H-imidazo[4,5-b]pyridin-5-yl]cyclohex-3-en-1-yl}-2-[4-(1-methylethyl)piperazin-1-yl]acetamide | C27H42N6O2 [M + H] calc 483.3442 obs 483.3449 |
| 17-14 | 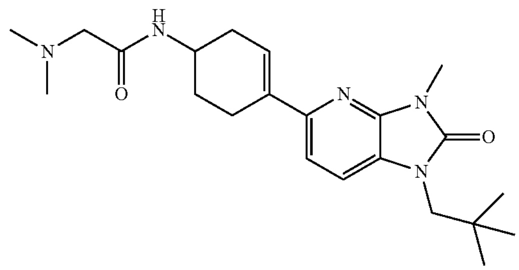 [SMILES: CN(C)CC(=O)NC1CC=C(c2ccc3c(n2)n(C)c(=O)n3CC(C)(C)C)CC1] | N-{4-[1-(2,2-dimethylpropyl)-3-methyl-2-oxo-2,3-dihydro-1H-imidazo[4,5-b]pyridin-5-yl]cyclohex-3-en-1-yl}-N~2~,N~2~-dimethylglycinamide | C22H33N5O2 [M + H] calc 400.2708 obs 400.2711 |
| 17-15 | 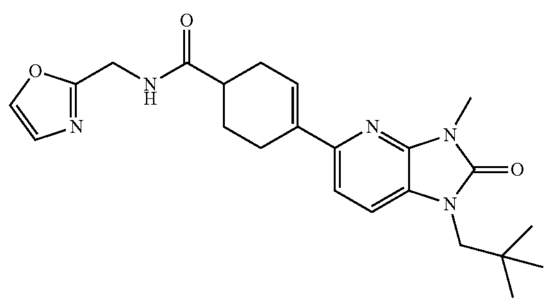 [SMILES: Cn1c(=O)n(CC(C)(C)C)c2ccc(C3=CCC(C(=O)NCc4ncco4)CC3)nc21] | 4-[1-(2,2-dimethylpropyl)-3-methyl-2-oxo-2,3-dihydro-1H-imidazo[4,5-b]pyridin-5-yl]-N-(1,3-oxazol-2-ylmethyl)cyclohex-3-ene-1-carboxamide | C23H29N5O3 [M + H] calc 424.2345 obs 424.2351 |
| 17-16 | 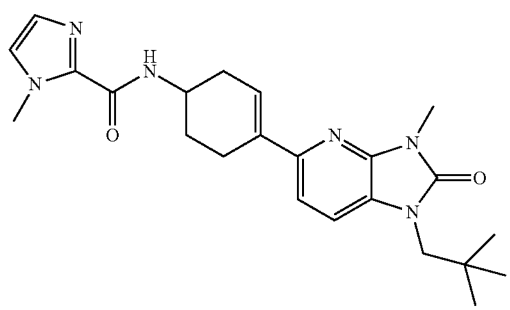 [SMILES: Cn1ccnc1C(=O)NC1CC=C(c2ccc3c(n2)n(C)c(=O)n3CC(C)(C)C)CC1] | N-{4-[1-(2,2-dimethylpropyl)-3-methyl-2-oxo-2,3-dihydro-1H-imidazo[4,5-b]pyridin-5-yl]cyclohex-3-en-1-yl}-1-methyl-1H-imidazole-2-carboxamide | C23H30N6O2 [M + H] calc 423.2505 obs 423.2507 |
| 17-17 | 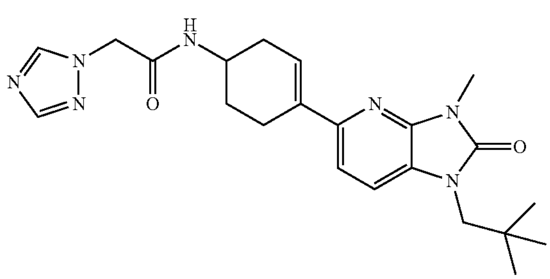 [SMILES: Cn1c(=O)n(CC(C)(C)C)c2ccc(C3=CCC(NC(=O)Cn4cncn4)CC3)nc21] | N-{4-[1-(2,2-dimethylpropyl)-3-methyl-2-oxo-2,3-dihydro-1H-imidazo[4,5-b]pyridin-5-yl]cyclohex-3-en-1-yl}-2-(1H-1,2,4-triazol-1-yl)acetamide | C22H29N7O2 [M + H] calc 424.2457 obs 424.2455 |

TABLE 6-continued

| # | Structure | Name | HRMS/LRMS |
|---|---|---|---|
| 17-18 | 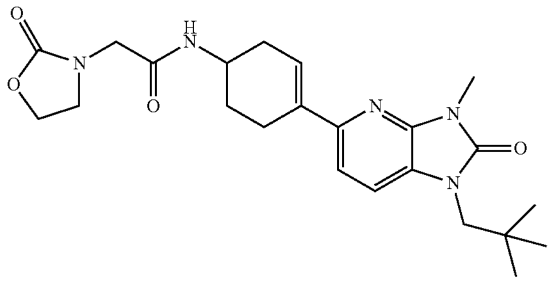 [SMILES: Cn1c(=O)n(CC(C)(C)C)c2ccc(C3=CCC(NC(=O)CN4CCOC4=O)CC3)nc21] | N-{4-[1-(2,2-dimethylpropyl)-3-methyl-2-oxo-2,3-dihydro-1H-imidazo[4,5-b]pyridin-5-yl]cyclohex-3-en-1-yl}-2-(2-oxo-1,3-oxazolidin-3-yl)acetamide | C23H31N5O4 [M + H] calc 442.245 obs 442.2458 |
| 17-19 | 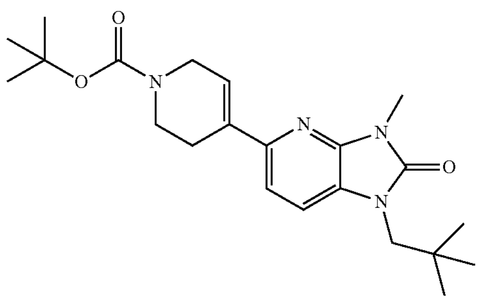 [SMILES: Cn1c(=O)n(CC(C)(C)C)c2ccc(C3=CCN(C(=O)OC(C)(C)C)CC3)nc21] | tert-butyl 4-[1-(2,2-dimethylpropyl)-3-methyl-2-oxo-2,3-dihydro-1H-imidazo[4,5-b]pyridin-5-yl]-3,6-dihydropyridine-1(2H)-carboxylate | C22H32N4O3 [M + H] calc 401.2548 obs 401.2556 |
| 17-20 | 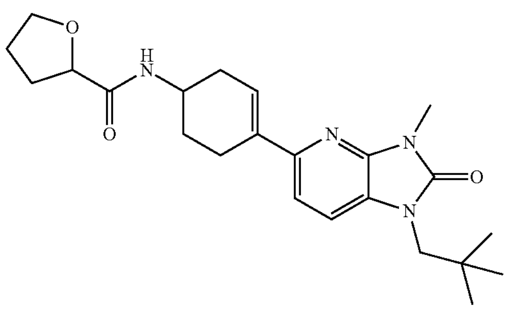 [SMILES: Cn1c(=O)n(CC(C)(C)C)c2ccc(C3=CCC(NC(=O)C4CCCO4)CC3)nc21] | N-{4-[1-(2,2-dimethylpropyl)-3-methyl-2-oxo-2,3-dihydro-1H-imidazo[4,5-b]pyridin-5-yl]cyclohex-3-en-1-yl}tetrahydrofuran-2-carboxamide | C23H32N4O3 [M + H] calc 413.2548 obs 413.2555 |
| 17-21 | 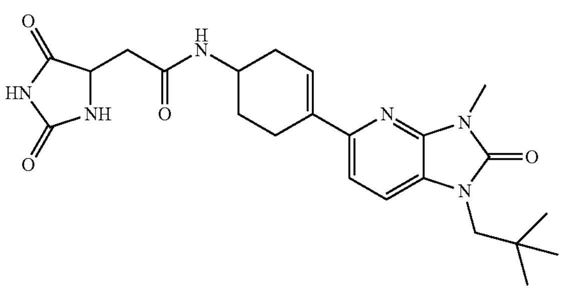 [SMILES: Cn1c(=O)n(CC(C)(C)C)c2ccc(C3=CCC(NC(=O)CC4NC(=O)NC4=O)CC3)nc21] | N-{4-[1-(2,2-dimethylpropyl)-3-methyl-2-oxo-2,3-dihydro-1H-imidazo[4,5-b]pyridin-5-yl]cyclohex-3-en-1-yl}-2-(2,5-dioxoimidazolidin-4-yl)acetamide | C23H30N6O4 [M + H] calc 455.2403 obs 455.2421 |
| 17-22 | 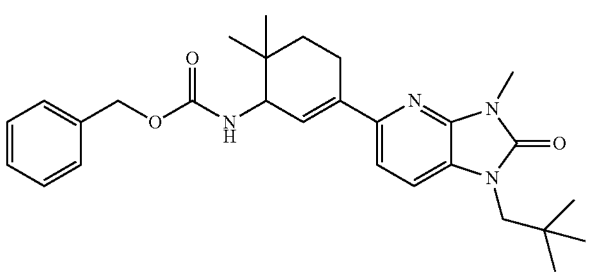 [SMILES: Cn1c(=O)n(CC(C)(C)C)c2ccc(C3=CC(NC(=O)OCc4ccccc4)C(C)(C)CC3)nc21] | benzyl {3-[1-(2,2-dimethylpropyl)-3-methyl-2-oxo-2,3-dihydro-1H-imidazo[4,5-b]pyridin-5-yl]-6,6-dimethylcyclohex-2-en-1-yl}carbamate | C28H36N4O3 [M + H] calc 477.2861 obs 477.2864 |

TABLE 6-continued

| # | Structure | Name | HRMS/LRMS |
|---|---|---|---|
| 17-23 | 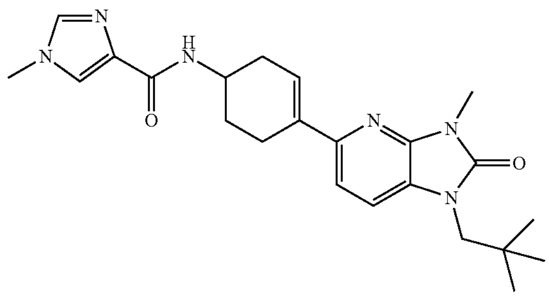 [SMILES: Cn1cnc(C(=O)NC2CC=C(c3ccc4c(n3)n(C)c(=O)n4CC(C)(C)C)CC2)c1] | N-{4-[1-(2,2-dimethylpropyl)-3-methyl-2-oxo-2,3-dihydro-1H-imidazo[4,5-b]pyridin-5-yl]cyclohex-3-en-1-yl}-1-methyl-1H-imidazole-4-carboxamide | C23H30N6O2 [M + H] calc 423.2505 obs 423.2514 |
| 17-24 | 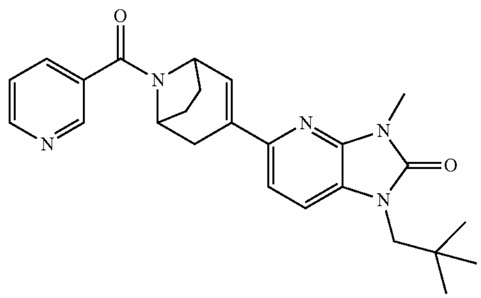 [SMILES: Cn1c(=O)n(CC(C)(C)C)c2ccc(C3=CC4CCC(C3)N4C(=O)c3cccnc3)nc21] | 1-(2,2-dimethylpropyl)-3-methyl-5-[8-(pyridin-3-ylcarbonyl)-8-azabicyclo[3.2.1]oct-2-en-3-yl]-1,3-dihydro-2H-imidazo[4,5-b]pyridin-2-one | C25H29N5O2 [M + H] calc 432.2396 obs 432.2401 |
| 17-25 | 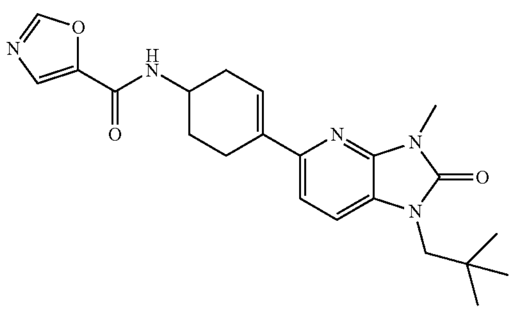 [SMILES: Cn1c(=O)n(CC(C)(C)C)c2ccc(C3=CCC(NC(=O)c4cnco4)CC3)nc21] | N-{4-[1-(2,2-dimethylpropyl)-3-methyl-2-oxo-2,3-dihydro-1H-imidazo[4,5-b]pyridin-5-yl]cyclohex-3-en-1-yl}-1,3-oxazole-5-carboxamide | C22H27N5O3 [M + H] calc 410.2189 obs 410.2201 |
| 17-26 | 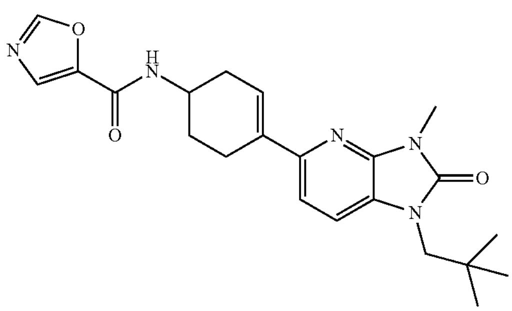 [SMILES: Cn1c(=O)n(CC(C)(C)C)c2ccc(C3=CCC(NC(=O)c4cnco4)CC3)nc21] | N-{4-[1-(2,2-dimethylpropyl)-3-methyl-2-oxo-2,3-dihydro-1H-imidazo[4,5-b]pyridin-5-yl]cyclohex-3-en-1-yl}-1,3-oxazole-5-carboxamide | C22H27N5O3 [M + H] calc 410.2189 obs 410.2201 |
| 17-27 | 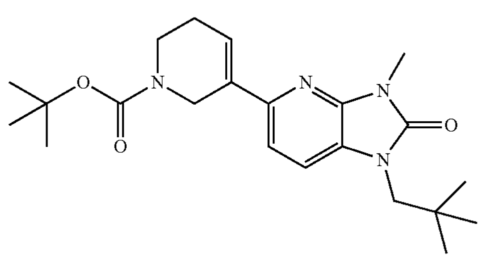 | tert-butyl 5-[1-(2,2-dimethylpropyl)-3-methyl-2-oxo-2,3-dihydro-1H-imidazo[4,5-b]pyridin-5-yl]-3,6-dihydropyridine-1(2H)-carboxylate | C22H32N4O3 [M + H] calc 401.2548 obs 401.2544 |

TABLE 6-continued

| # | Structure | Name | HRMS/LRMS |
|---|-----------|------|-----------|
| 17-28 | 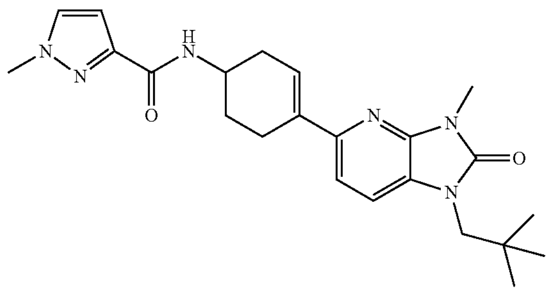 [SMILES: Cn1ccc(C(=O)NC2CC=C(c3ccc4c(n3)n(C)c(=O)n4CC(C)(C)C)CC2)n1] | N-{4-[1-(2,2-dimethylpropyl)-3-methyl-2-oxo-2,3-dihydro-1H-imidazo[4,5-b]pyridin-5-yl]cyclohex-3-en-1-yl}-1-methyl-1H-pyrazole-3-carboxamide | C23H30N6O2 [M + H] calc 423.2505 obs 423.2515 |
| 17-29 | 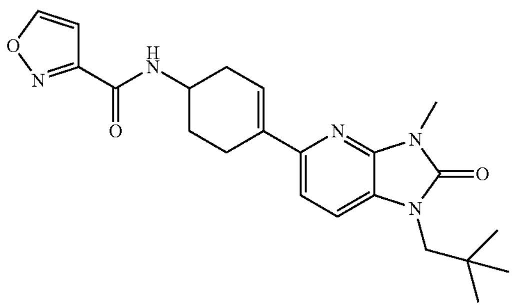 [SMILES: Cn1c(=O)n(CC(C)(C)C)c2ccc(C3=CCC(NC(=O)c4ccon4)CC3)nc21] | N-{4-[1-(2,2-dimethylpropyl)-3-methyl-2-oxo-2,3-dihydro-1H-imidazo[4,5-b]pyridin-5-yl]cyclohex-3-en-1-yl}isoxazole-3-carboxamide | C22H27N5O3 [M + H] calc 410.2189 obs 410.2185 |
| 17-30 | 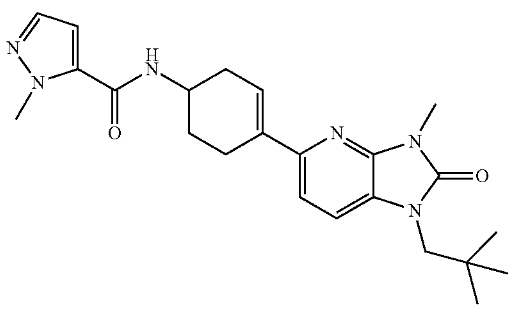 [SMILES: Cn1nccc1C(=O)NC1CC=C(c2ccc3c(n2)n(C)c(=O)n3CC(C)(C)C)CC1] | N-{4-[1-(2,2-dimethylpropyl)-3-methyl-2-oxo-2,3-dihydro-1H-imidazo[4,5-b]pyridin-5-yl]cyclohex-3-en-1-yl}-1-methyl-1H-pyrazole-5-carboxamide | C23H30N6O2 [M + H] calc 423.2505 obs 423.2509 |
| 17-31 | 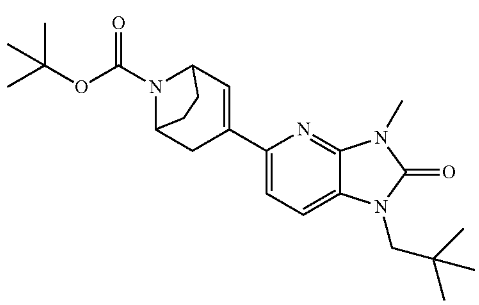 [SMILES: Cn1c(=O)n(CC(C)(C)C)c2ccc(C3=CC4CCC(C3)N4C(=O)OC(C)(C)C)nc21] | tert-butyl 3-[1-(2,2-dimethylpropyl)-3-methyl-2-oxo-2,3-dihydro-1H-imidazo[4,5-b]pyridin-5-yl]-8-azabicyclo[3.2.1]oct-2-ene-8-carboxylate | C24H34N4O3 [M + H] calc 427.2704 obs 427.2701 |
| 17-32 | 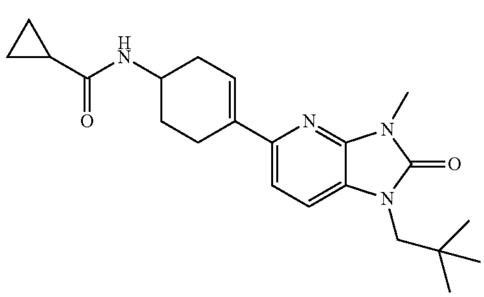 [SMILES: Cn1c(=O)n(CC(C)(C)C)c2ccc(C3=CCC(NC(=O)C4CC4)CC3)nc21] | N-{4-[1-(2,2-dimethylpropyl)-3-methyl-2-oxo-2,3-dihydro-1H-imidazo[4,5-b]pyridin-5-yl]cyclohex-3-en-1-yl}cyclopropanecarboxamide | C22H30N4O2 [M + H] calc 383.2443 obs 383.2445 |

TABLE 6-continued

| # | Structure | Name | HRMS/LRMS |
|---|---|---|---|
| 17-33 | 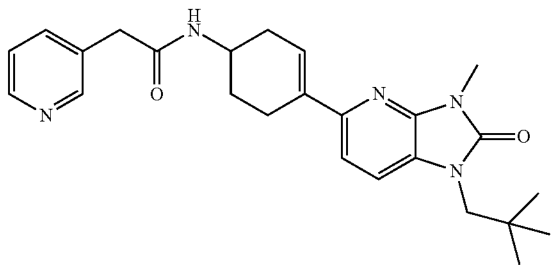 [SMILES: Cn1c(=O)n(CC(C)(C)C)c2ccc(C3=CCC(NC(=O)Cc4cccnc4)CC3)nc21] | N-{4-[1-(2,2-dimethylpropyl)-3-methyl-2-oxo-2,3-dihydro-1H-imidazo[4,5-b]pyridin-5-yl]cyclohex-3-en-1-yl}-2-pyridin-3-ylacetamide | C25H31N5O2 [M + H] calc 434.2552 obs 434.2556 |
| 17-34 | 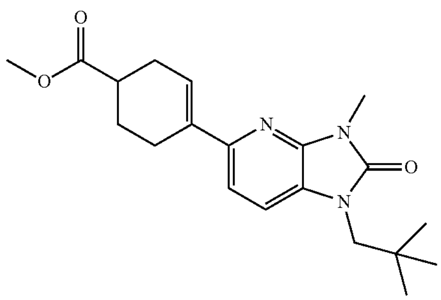 | methyl 4-[1-(2,2-dimethylpropyl)-3-methyl-2-oxo-2,3-dihydro-1H-imidazo[4,5-b]pyridin-5-yl]cyclohex-3-ene-1-carboxylate | C20H27N3O3 [M + H] calc 358.2127 obs 358.2126 |
| 17-35 | 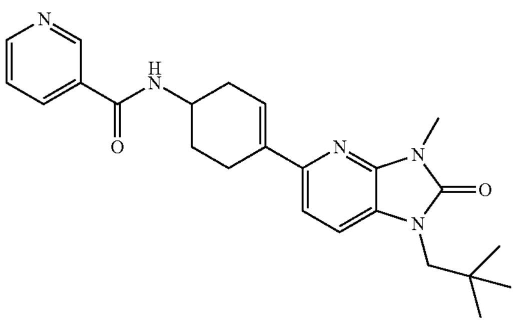 [SMILES: Cn1c(=O)n(CC(C)(C)C)c2ccc(C3=CCC(NC(=O)c4cccnc4)CC3)nc21] | N-{4-[1-(2,2-dimethylpropyl)-3-methyl-2-oxo-2,3-dihydro-1H-imidazo[4,5-b]pyridin-5-yl]cyclohex-3-en-1-yl}pyridine-3-carboxamide | C24H29N5O2 [M + H] calc 420.2396 obs 420.2400 |
| 17-36 | 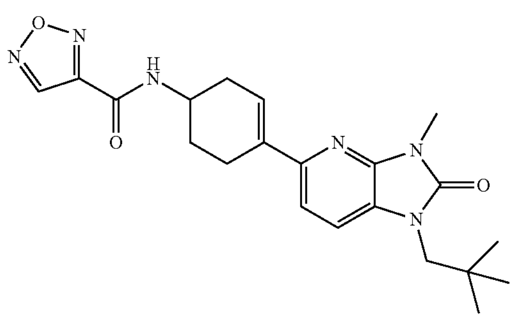 [SMILES: Cn1c(=O)n(CC(C)(C)C)c2ccc(C3=CCC(NC(=O)c4cnon4)CC3)nc21] | N-{4-[1-(2,2-dimethylpropyl)-3-methyl-2-oxo-2,3-dihydro-1H-imidazo[4,5-b]pyridin-5-yl]cyclohex-3-en-1-yl}-1,2,5-oxadiazole-3-carboxamide | C21H26N6O3 [M + H] calc 411.2141 obs 411.2147 |
| 17-37 | 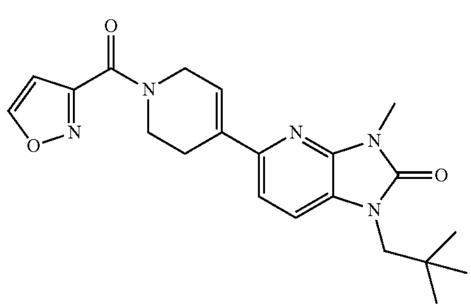 [SMILES: Cn1c(=O)n(CC(C)(C)C)c2ccc(C3=CCN(C(=O)c4ccon4)CC3)nc21] | 1-(2,2-dimethylpropyl)-5-[1-(isoxazol-3-ylcarbonyl)-1,2,3,6-tetrahydropyridin-4-yl]-3-methyl-1,3-dihydro-2H-imidazo[4,5-b]pyridin-2-one | C21H25N5O3 [M + H] calc 396.2032 obs 396.2023 |

TABLE 6-continued

| # | Structure | Name | HRMS/LRMS |
|---|---|---|---|
| 17-38 | 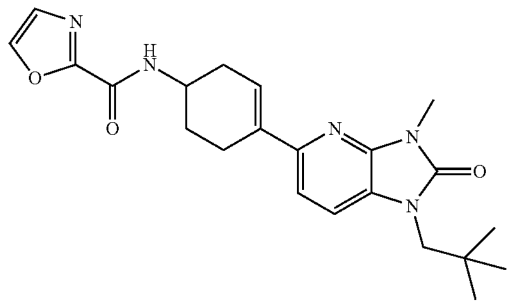 [SMILES: Cn1c(=O)n(CC(C)(C)C)c2ccc(C3=CCC(NC(=O)c4ncco4)CC3)nc21] | N-{4-[1-(2,2-dimethylpropyl)-3-methyl-2-oxo-2,3-dihydro-1H-imidazo[4,5-b]pyridin-5-yl]cyclohex-3-en-1-yl}-1,3-oxazole-2-carboxamide | C22H27N5O3 [M + H] calc 410.2189 obs 410.2195 |
| 17-39 | 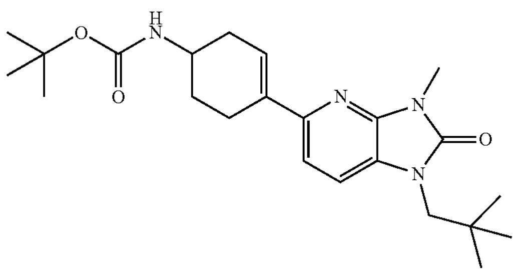 [SMILES: Cn1c(=O)n(CC(C)(C)C)c2ccc(C3=CCC(NC(=O)OC(C)(C)C)CC3)nc21] | tert-butyl {4-[1-(2,2-dimethylpropyl)-3-methyl-2-oxo-2,3-dihydro-1H-imidazo[4,5-b]pyridin-5-yl]cyclohex-3-en-1-yl}carbamate | C23H34N4O3 [M + H] calc 415.2705 obs 415.2707 |
| 17-40 | 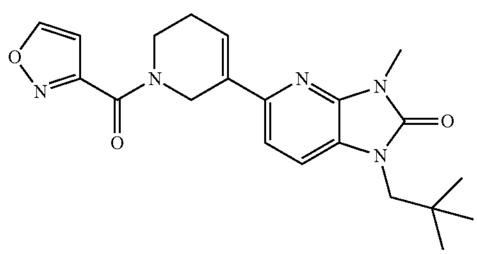 | 1-(2,2-dimethylpropyl)-5-[1-(isoxazol-3-ylcarbonyl)-1,2,5,6-tetrahydropyridin-3-yl]-3-methyl-1,3-dihydro-2H-imidazo[4,5-b]pyridin-2-one | C21H25N5O3 [M + H] calc 396.2032 obs 396.2025 |
| 17-41 | 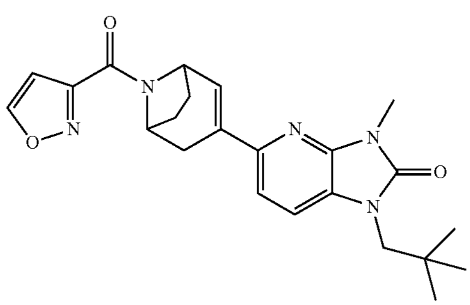 [SMILES: Cn1c(=O)n(CC(C)(C)C)c2ccc(C3=CC4CCC(C3)N4C(=O)c3ccon3)nc21] | 1-(2,2-dimethylpropyl)-5-[8-(isoxazol-3-ylcarbonyl)-8-azabicyclo[3.2.1]oct-2-en-3-yl]-3-methyl-1,3-dihydro-2H-imidazo[4,5-b]pyridin-2-one | C23H27N5O3 [M + H] calc 422.2188 obs 422.2185 |
| 17-42 | 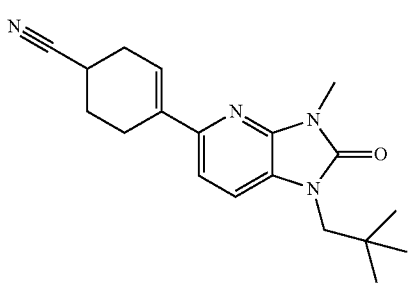 [SMILES: Cn1c(=O)n(CC(C)(C)C)c2ccc(C3=CCC(C#N)CC3)nc21] | 4-[1-(2,2-dimethylpropyl)-3-methyl-2-oxo-2,3-dihydro-1H-imidazo[4,5-b]pyridin-5-yl]cyclohex-3-ene-1-carbonitrile | C19H24N4O [M + H] calc 325.2023 obs 325.2022 |

TABLE 6-continued

| # | Structure | Name | HRMS/LRMS |
|---|---|---|---|
| 17-43 | 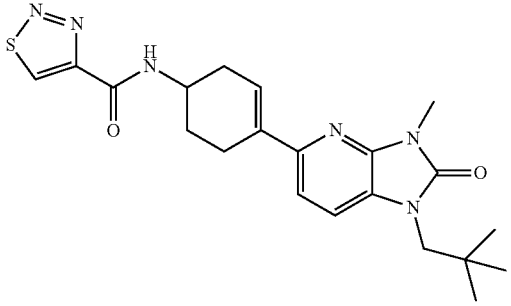 [SMILES: Cn1c(=O)n(CC(C)(C)C)c2ccc(C3=CCC(NC(=O)c4csnn4)CC3)nc21] | N-{4-[1-(2,2-dimethylpropyl)-3-methyl-2-oxo-2,3-dihydro-1H-imidazo[4,5-b]pyridin-5-yl]cyclohex-3-en-1-yl}-1,2,3-thiadiazole-4-carboxamide | C21H26N6O2S [M + H] calc 427.1911 obs 427.1916 |
| 17-44 | 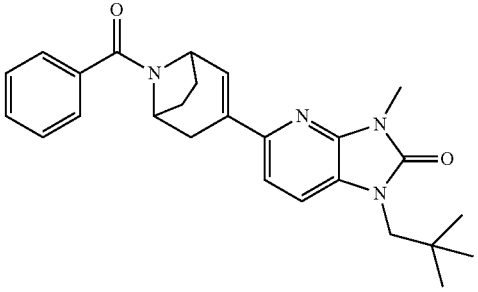 [SMILES: Cn1c(=O)n(CC(C)(C)C)c2ccc(C3=CC4CCC(C3)N4C(=O)c3ccccc3)nc21] | 1-(2,2-dimethylpropyl)-3-methyl-5-[8-(phenylcarbonyl)-8-azabicyclo[3.2.1]oct-2-en-3-yl]-1,3-dihydro-2H-imidazo[4,5-b]pyridin-2-one | C26H30N4O2 [M + H] calc 431.2443 obs 431.2451 |
| 17-45 | 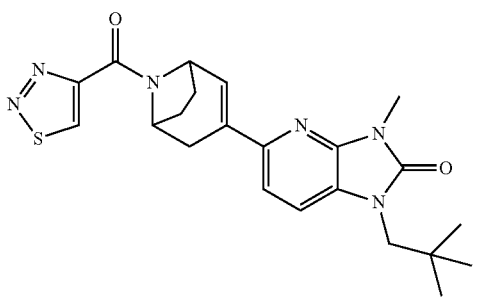 [SMILES: Cn1c(=O)n(CC(C)(C)C)c2ccc(C3=CC4CCC(C3)N4C(=O)c3csnn3)nc21] | 1-(2,2-dimethylpropyl)-3-methyl-5-[8-(1,2,3-thiadiazol-4-ylcarbonyl)-8-azabicyclo[3.2.1]oct-2-en-3-yl]-1,3-dihydro-2H-imidazo[4,5-b]pyridin-2-one | C22H26N6O2S [M + H] calc 439.1913 obs 439.1916 |
| 17-46 | 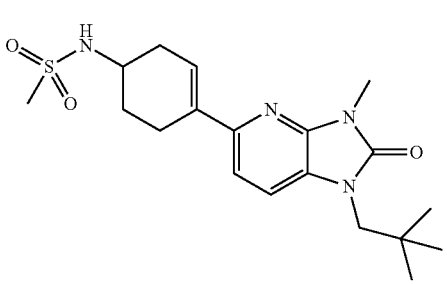 [SMILES: Cn1c(=O)n(CC(C)(C)C)c2ccc(C3=CCC(NS(C)(=O)=O)CC3)nc21] | N-{4-[1-(2,2-dimethylpropyl)-3-methyl-2-oxo-2,3-dihydro-1H-imidazo[4,5-b]pyridin-5-yl]cyclohex-3-en-1-yl}methanesulfonamide | C19H28N4O3S [M + H] calc 393.1957 obs 393.1955 |
| 17-47 | 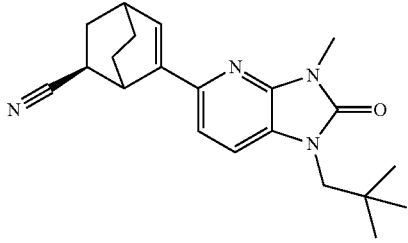 [SMILES: Cn1c(=O)n(CC(C)(C)C)c2ccc(C3=CC4CCC3[C@@H](C#N)C4)nc21] | (2S)-6-[1-(2,2-dimethylpropyl)-3-methyl-2-oxo-2,3-dihydro-1H-imidazo[4,5-b]pyridin-5-yl]bicyclo[2.2.2]oct-5-ene-2-carbonitrile | C21H26N4O [M + H] calc 351.2181 obs 351.2193 |

TABLE 6-continued

| # | Structure | Name | HRMS/LRMS |
|---|---|---|---|
| 17-48 | 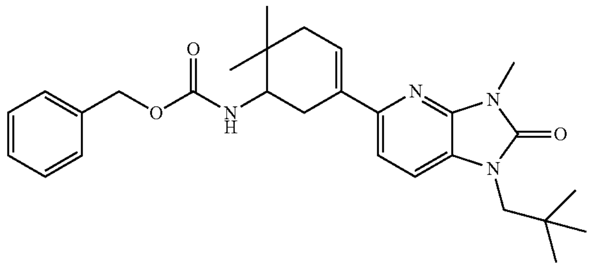 [SMILES: Cn1c(=O)n(CC(C)(C)C)c2ccc(C3=CCC(C)(C)C(NC(=O)OCc4ccccc4)C3)nc21] | benzyl {3-[1-(2,2-dimethylpropyl)-3-methyl-2-oxo-2,3-dihydro-1H-imidazo[4,5-b]pyridin-5-yl]-6,6-dimethylcyclohex-3-en-1-yl}carbamate | C28H36N4O3 [M + H] calc 477.2861 obs 477.2874 |
| 17-49 | 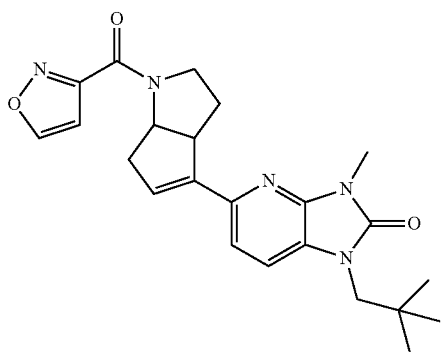 [SMILES: Cn1c(=O)n(CC(C)(C)C)c2ccc(C3=CCC4C3CCN4C(=O)c3ccon3)nc21] | 1-(2,2-dimethylpropyl)-5-[1-(isoxazol-3-ylcarbonyl)-1,2,3,3a,6,6a-hexahydrocyclopenta[b]pyrrol-4-yl]-3-methyl-1,3-dihydro-2H-imidazo[4,5-b]pyridin-2-one | C23H27N5O3 [M + H] calc 422.2189 obs 422.2202 |
| 17-50 | 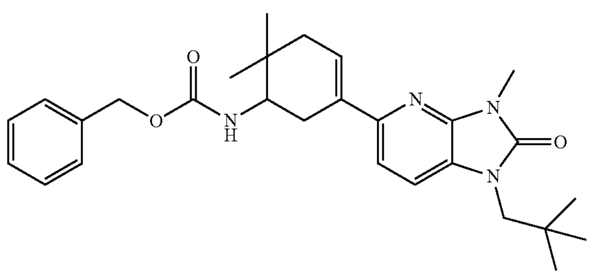 [SMILES: Cn1c(=O)n(CC(C)(C)C)c2ccc(C3=CCC(C)(C)C(NC(=O)OCc4ccccc4)C3)nc21] | benzyl {3-[1-(2,2-dimethylpropyl)-3-methyl-2-oxo-2,3-dihydro-1H-imidazo[4,5-b]pyridin-5-yl]-6,6-dimethylcyclohex-3-en-1-yl}carbamate | C28H36N4O3 [M + H] calc 477.2861 obs 477.2874 |
| 17-51 | 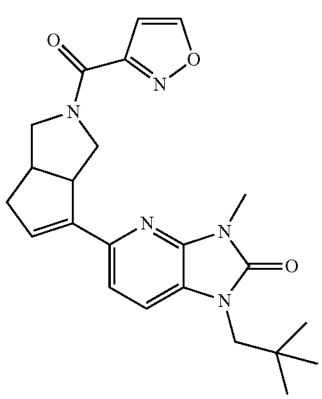 [SMILES: Cn1c(=O)n(CC(C)(C)C)c2ccc(C3=CCC4CN(C(=O)c5ccon5)CC34)nc21] | 1-(2,2-dimethylpropyl)-5-[2-(isoxazol-3-ylcarbonyl)-1,2,3,3a,6,6a-hexahydrocyclopenta[c]pyrrol-4-yl]-3-methyl-1,3-dihydro-2H-imidazo[4,5-b]pyridin-2-one | C23H27N5O3 [M + H] calc 422.2189 obs 422.2201 |

TABLE 6-continued

| # | Structure | Name | HRMS/LRMS |
|---|-----------|------|-----------|
| 17-52 | 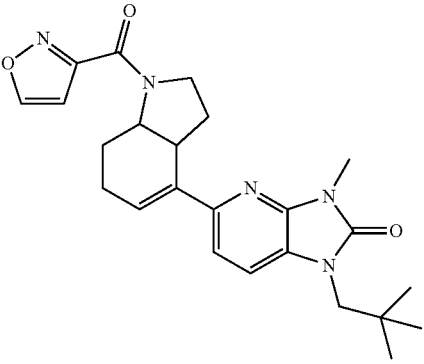 [SMILES: Cn1c(=O)n(CC(C)(C)C)c2ccc(C3=CCCC4C3CCN4C(=O)c3ccon3)nc21] | 1-(2,2-dimethylpropyl)-5-[1-(isoxazol-3-ylcarbonyl)-2,3,3a,6,7,7a-hexahydro-1H-indol-4-yl]-3-methyl-1,3-dihydro-2H-imidazo[4,5-b]pyridin-2-one | C24H29N5O3 [M + H] calc 436.2345 obs 436.2361 |
| 17-53 | 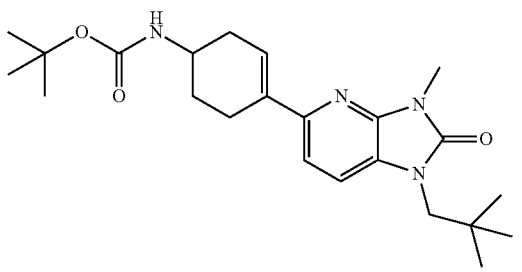 [SMILES: Cn1c(=O)n(CC(C)(C)C)c2ccc(C3=CCC(NC(=O)OC(C)(C)C)CC3)nc21] | tert-butyl {4-[1-(2,2-dimethylpropyl)-3-methyl-2-oxo-2,3-dihydro-1H-imidazo[4,5-b]pyridin-5-yl]cyclohex-3-en-1-yl}carbamate | C23H34N4O3 [M + H] calc 415.2705 obs 415.2707 |
| 17-54 | 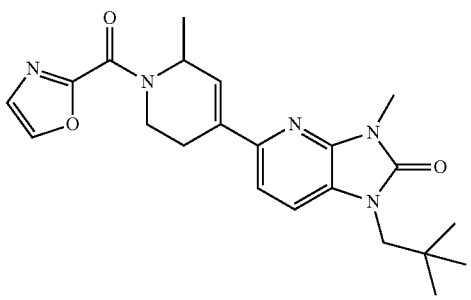 [SMILES: CC1C=C(c2ccc3c(n2)n(C)c(=O)n3CC(C)(C)C)CCN1C(=O)c1ncco1] | 1-(2,2-dimethylpropyl)-3-methyl-5-[6-methyl-1-(1,3-oxazol-2-ylcarbonyl)-1,2,3,6-tetrahydropyridin-4-yl]-1,3-dihydro-2H-imidazo[4,5-b]pyridin-2-one | C22H27N5O3 [M + H] calc 410.2188 obs 410.2186 |
| 17-55 | 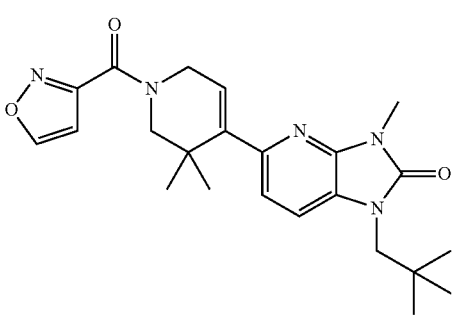 [SMILES: Cn1c(=O)n(CC(C)(C)C)c2ccc(C3=CCN(C(=O)c4ccon4)CC3(C)C)nc21] | 1-(2,2-dimethylpropyl)-5-[1-(isoxazol-3-ylcarbonyl)-3,3-dimethyl-1,2,3,6-tetrahydropyridin-4-yl]-3-methyl-1,3-dihydro-2H-imidazo[4,5-b]pyridin-2-one | C23H29N5O3 [M + H] calc 424.2343 obs 424.2341 |

TABLE 6-continued

| # | Structure | Name | HRMS/LRMS |
|---|---|---|---|
| 17-56 | 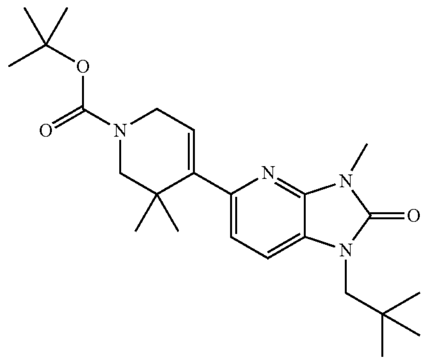 [SMILES: Cn1c(=O)n(CC(C)(C)C)c2ccc(C3=CCN(C(=O)OC(C)(C)C)CC3(C)C)nc21] | tert-butyl 4-[1-(2,2-dimethylpropyl)-3-methyl-2-oxo-2,3-dihydro-1H-imidazo[4,5-b]pyridin-5-yl]-3,3-dimethyl-3,6-dihydropyridine-1(2H)-carboxylate | C24H36N4O3 [M + H] calc 429.2860 obs 429.2860 |

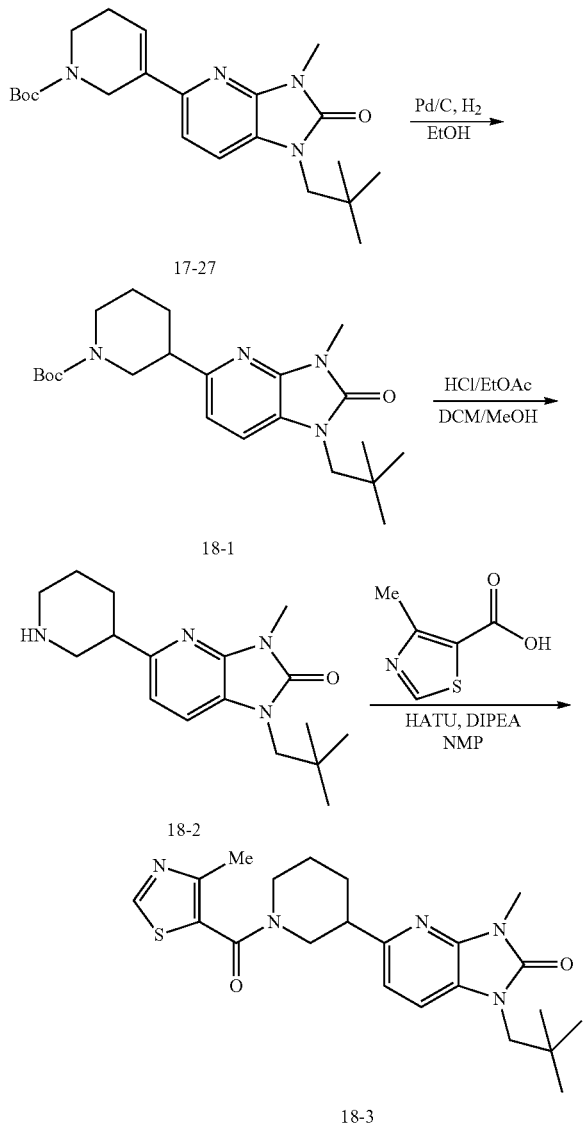

1-(2,2-Dimethylpropyl)-3-methyl-5-{1-[(4-methyl-1,3-thiazol-5-yl)-carbonyl]-piperidin-3-yl}-1,3-dihydro-2H-imidazo[4,5-b]pyridin-2-one (18-3)

tert-butyl 3-[1-(2,2-dimethylpropyl)-3-methyl-2-oxo-2,3-dihydro-1H-imidazo[4,5-b]pyridin-5-yl]piperidine-1-carboxylate (18-1)

To a round bottom flask containing tert-butyl 5-[1-(2,2-dimethylpropyl)-3-methyl-2-oxo-2,3-dihydro-1H-imidazo[4,5-b]pyridin-5-yl]-3,6-dihydropyridine-1(2H)-carboxylate (17-27) (1 g, 2.497 mmol), was added EtOH (25 mL) & Palladium on Carbon (10% by weight on carbon) (0.25 g, 0.2349 mmol). A balloon containing hydrogen gas was then attached and purged 3× with vacuum/hydrogen. The reaction mixture was permitted to stir at room temperature for 1 hour, then purged 3× with vacuum/nitrogen, diluted with EtOH, filtered & concentrated to yield tert-butyl 3-[1-(2,2-dimethylpropyl)-3-methyl-2-oxo-2,3-dihydro-1H-imidazo[4,5-b]pyridin-5-yl]piperidine-1-carboxylate (18-1). LRMS (M+H)$^+$: observed=403.3, calculated=403.5.

1-(2,2-dimethylpropyl)-3-methyl-5-piperidin-3-yl-1,3-dihydro-2H-imidazo[4,5-b]pyridin-2-one (18-2)

Procedure similar to that for 5-(4-Aminocyclohex-1-en-1-yl)-1-(2,2-dimethylpropyl)-3-methyl-1,3-dihydro-2H-imidazo[4,5-b]pyridin-2-one (17-2) gave 1-(2,2-dimethylpropyl)-3-methyl-5-piperidin-3-yl-1,3-dihydro-2H-imidazo[4,5-b]pyridin-2-one (18-2). LRMS (M+H)$^+$: observed=303.2, calculated=303.4.

1-(2,2-Dimethylpropyl)-3-methyl-5-{1-[(4-methyl-1,3-thiazol-5-yl)carbonyl]-piperidin-3-yl}-1,3-dihydro-2H-imidazo[4,5-b]pyridin-2-one (18-3)

Procedure similar to that for N-{4-[1-(2,2-Dimethylpropyl)-3-methyl-2-oxo-2,3-dihydro-1H-imidazo[4,5-b]pyridin-5-yl]cyclohex-3-en-1-yl}-1-methyl-1H-imidazole-2-carboxamide (17-3) gave 1-(2,2-Dimethylpropyl)-3-methyl-5-{1-[(4-methyl-1,3-thiazol-5-yl)carbonyl]-piperidin-3-yl}-1,3-dihydro-2H-imidazo[4,5-b]pyridin-2-one (18-3). HRMS (M+H)$^+$: observed=428.2107, calculated=428.2115. $^1$H NMR (499 MHz, DMSO): δ 9.07 (s, 1H); 7.46 (s, 1H); 6.96 (s, 1H); 3.61 (s, 2H); 2.93-2.81 (m, 1H); 2.38 (s, 4H); 2.07-1.98 (m, 2H); 1.91-1.79 (m, 3H); 1.64-1.48 (m, 2H); 0.94 (s, 9H). The Me-substituent normally has a NMR resonance at δ 3.40, but this was not observed here due to presaturation at 3.40-3.50 ppm (for H₂O).

The following compounds were prepared by synthetic transformations analogous to those illustrated in Schemes 17 and 18:

TABLE 7

| # | Structure | Name | HRMS/LRMS |
|---|-----------|------|-----------|
| 18-4 | 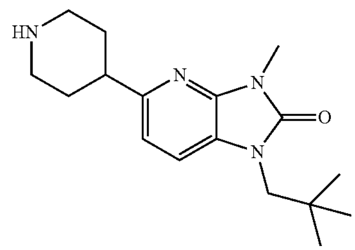 [SMILES: Cn1c(=O)n(CC(C)(C)C)c2ccc(C3CCNCC3)nc21] | 1-(2,2-dimethylpropyl)-3-methyl-5-piperidin-4-yl-1,3-dihydro-2H-imidazo[4,5-b]pyridin-2-one | C17H26N4O [M + H] calc 303.2181 obs 303.2178 |
| 18-5 | 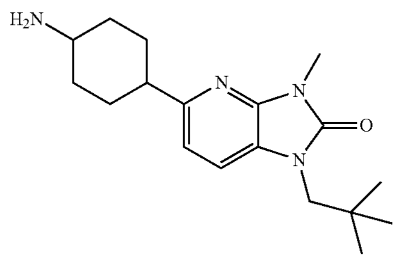 [SMILES: Cn1c(=O)n(CC(C)(C)C)c2ccc(C3CCC(N)CC3)nc21] | 5-(4-aminocyclohexyl)-1-(2,2-dimethylpropyl)-3-methyl-1,3-dihydro-2H-imidazo[4,5-b]pyridin-2-one | C18H28N4O [M + H] calc 317.2338 obs 317.2337 |
| 18-6 | 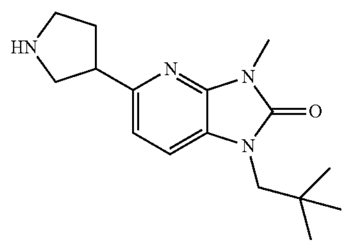 [SMILES: Cn1c(=O)n(CC(C)(C)C)c2ccc(C3CCNC3)nc21] | 1-(2,2-dimethylpropyl)-3-methyl-5-pyrrolidin-3-yl-1,3-dihydro-2H-imidazo[4,5-b]pyridin-2-one | C16H24N4O [M + H] calc 289.2025 obs 289.2027 |
| 18-7 | 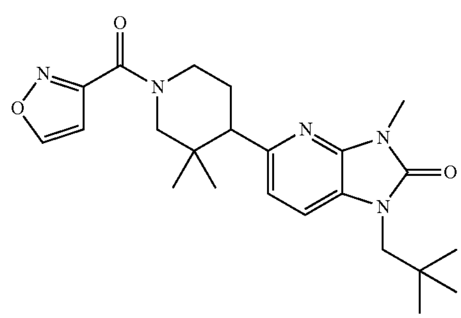 | 1-(2,2-dimethylpropyl)-5-[1-(isoxazol-3-ylcarbonyl)-3,3-dimethylpiperidin-4-yl]-3-methyl-1,3-dihydro-2H-imidazo[4,5-b]pyridin-2-one | C27H37N5O4 [M + H] calc 496.2919 obs 496.2930 |
| 18-8 | 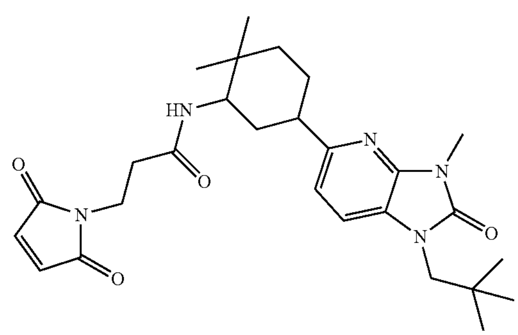 | N-{5-[1-(2,2-dimethylpropyl)-3-methyl-2-oxo-2,3-dihydro-1H-imidazo[4,5-b]pyridin-5-yl]-2,2-dimethylcyclohexyl}-3-(2,5-dioxo-2,5-dihydro-1H-pyrrol-1-yl)propanamide | C26H39N7O2 [M + H] calc 482.3239 obs 482.3244 |

TABLE 7-continued

| # | Structure | Name | HRMS/LRMS |
|---|---|---|---|
| 18-9 | 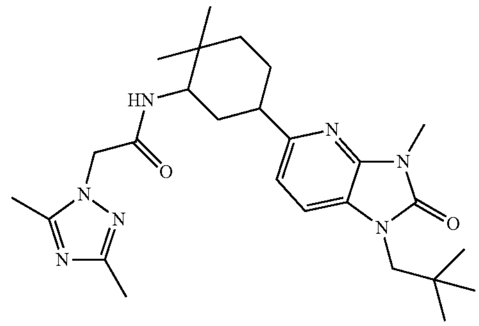 | N-{5-[1-(2,2-dimethylpropyl)-3-methyl-2-oxo-2,3-dihydro-1H-imidazo[4,5-b]pyridin-5-yl]-2,2-dimethylcyclohexyl}-2-(3,5-dimethyl-1H-1,2,4-triazol-1-yl)acetamide | C25H37N7O2 [M + H] calc 468.3082 obs 468.3088 |
| 18-10 | 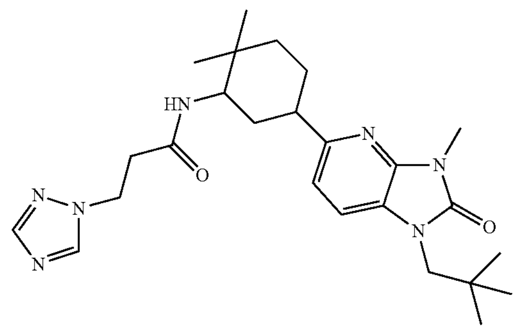 | N-{5-[1-(2,2-dimethylpropyl)-3-methyl-2-oxo-2,3-dihydro-1H-imidazo[4,5-b]pyridin-5-yl]-2,2-dimethylcyclohexyl}-3-(1H-1,2,4-triazol-1-yl)propanamide | C27H41N5O3 [M + H] calc 484.3282 obs 484.3289 |
| 18-11 | 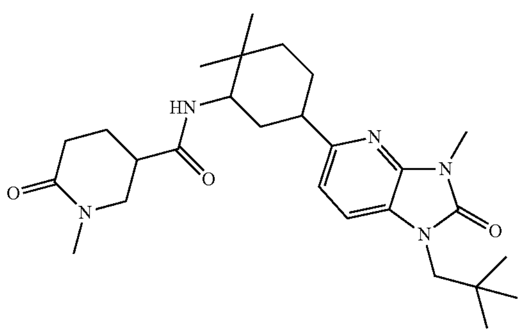 | N-{5-[1-(2,2-dimethylpropyl)-3-methyl-2-oxo-2,3-dihydro-1H-imidazo[4,5-b]pyridin-5-yl]-2,2-dimethylcyclohexyl}-1-methyl-6-oxopiperidine-3-carboxamide | C21H27N5O2S [M + H] calc 414.196 obs 414.1954 |
| 18-12 | 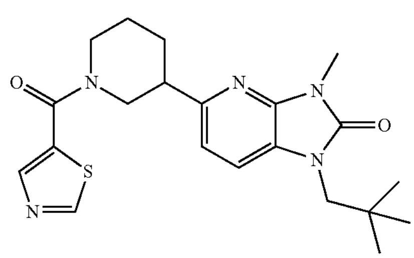 | 1-(2,2-dimethylpropyl)-3-methyl-5-[1-(1,3-thiazol-5-ylcarbonyl)piperidin-3-yl]-1,3-dihydro-2H-imidazo[4,5-b]pyridin-2-one | C22H31N7O2 [M + H] calc 426.2613 obs 426.2605 |
| 18-13 | 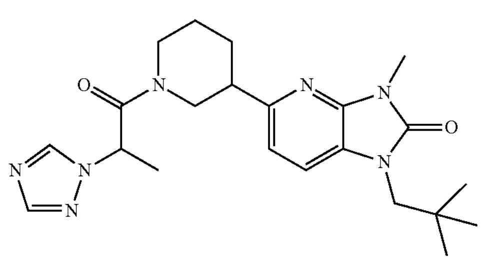 | 1-(2,2-dimethylpropyl)-3-methyl-5-{1-[2-(1H-1,2,4-triazol-1-yl)propanoyl]piperidin-3-yl}-1,3-dihydro-2H-imidazo[4,5-b]pyridin-2-one | C31H42N6O3 [M + H] calc 547.3392 obs 547.3405 |

TABLE 7-continued

| # | Structure | Name | HRMS/LRMS |
|---|---|---|---|
| 18-14 | 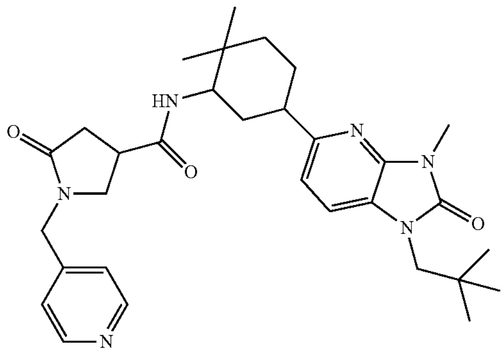 | N-{5-[1-(2,2-dimethylpropyl)-3-methyl-2-oxo-2,3-dihydro-1H-imidazo[4,5-b]pyridin-5-yl]-2,2-dimethylcyclohexyl}-5-oxo-1-(pyridin-4-ylmethyl)pyrrolidine-3-carboxamide | C27H36N8O2 [M + H] calc 505.3035 obs 505.3053 |
| 18-15 | 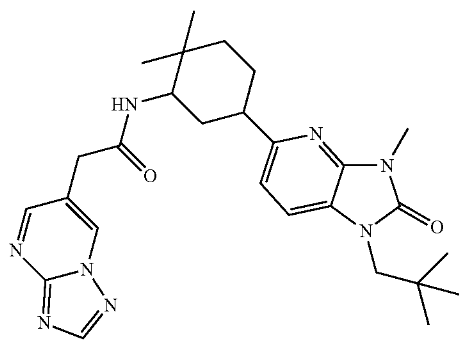 | N-{5-[1-(2,2-dimethylpropyl)-3-methyl-2-oxo-2,3-dihydro-1H-imidazo[4,5-b]pyridin-5-yl]-2,2-dimethylcyclohexyl}-2-[1,2,4]triazolo[1,5-a]pyrimidin-6-ylacetamide | C21H27N5O2S [M + H] calc 414.196 obs 414.1955 |
| 18-16 | 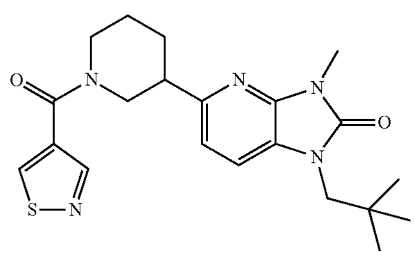 | 1-(2,2-dimethylpropyl)-5-[1-(isothiazol-4-ylcarbonyl)piperidin-3-yl]-3-methyl-1,3-dihydro-2H-imidazo[4,5-b]pyridin-2-one | C26H41N5O2 [M + H] calc 456.3333 obs 456.3340 |
| 18-17 | 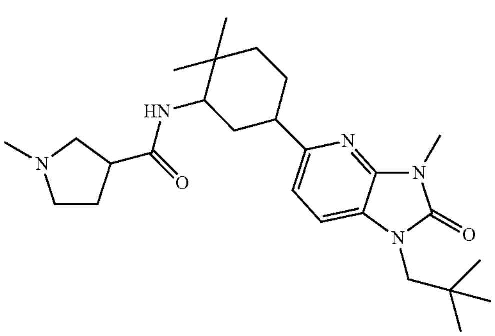 | N-{5-[1-(2,2-dimethylpropyl)-3-methyl-2-oxo-2,3-dihydro-1H-imidazo[4,5-b]pyridin-5-yl]-2,2-dimethylcyclohexyl}-1-methylpyrrolidine-3-carboxamide | C19H28N4O2 [M + H] calc 345.2287 obs 345.2281 |
| 18-18 | 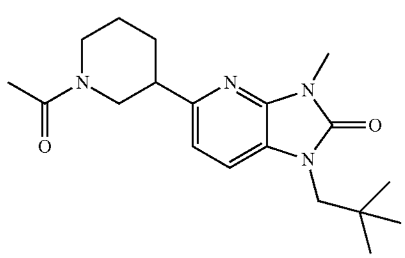 | 5-(1-acetylpiperidin-3-yl)-1-(2,2-dimethylpropyl)-3-methyl-1,3-dihydro-2H-imidazo[4,5-b]pyridin-2-one | C22H35N5O2 [M + H] calc 402.2865 obs 402.2868 |

TABLE 7-continued

| # | Structure | Name | HRMS/LRMS |
|---|---|---|---|
| 18-19 | 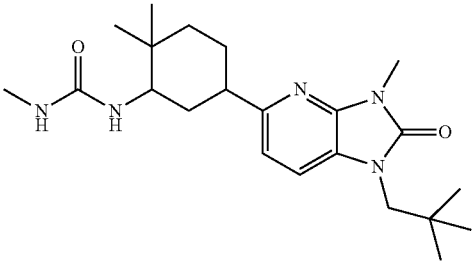 | 1-{5-[1-(2,2-dimethylpropyl)-3-methyl-2-oxo-2,3-dihydro-1H-imidazo[4,5-b]pyridin-5-yl]-2,2-dimethylcyclohexyl}-3-methylurea | C31H41N5O3 [M + H] calc 532.3282 obs 532.3280 |
| 18-20 | 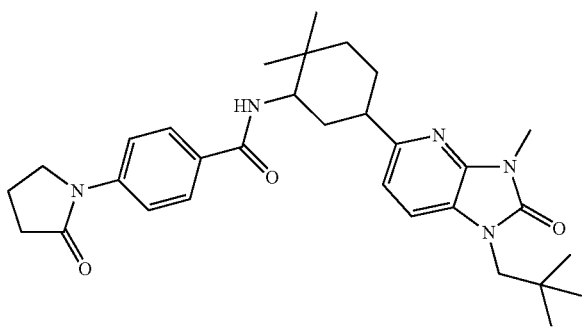 | N-{5-[1-(2,2-dimethylpropyl)-3-methyl-2-oxo-2,3-dihydro-1H-imidazo[4,5-b]pyridin-5-yl]-2,2-dimethylcyclohexyl}-4-(2-oxopyrrolidin-1-yl)benzamide | C31H40N6O3 [M + H] calc 545.3235 obs 545.3230 |
| 18-21 | 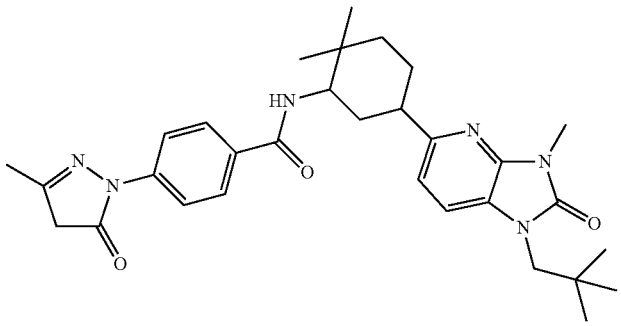 | N-{5-[1-(2,2-dimethylpropyl)-3-methyl-2-oxo-2,3-dihydro-1H-imidazo[4,5-b]pyridin-5-yl]-2,2-dimethylcyclohexyl}-4-(3-methyl-5-oxo-4,5-dihydro-1H-pyrazol-1-yl)benzamide | C20H27N7O2 [M + H] calc 398.2301 obs 398.2295 |
| 18-22 | 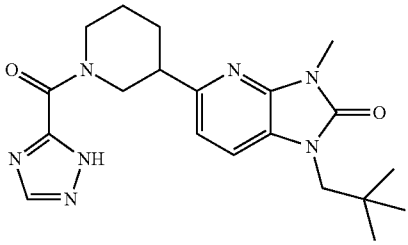 | 1-(2,2-dimethylpropyl)-3-methyl-5-[1-(1H-1,2,4-triazol-5-ylcarbonyl)piperidin-3-yl]-1,3-dihydro-2H-imidazo[4,5-b]pyridin-2-one | C22H30N6O2 [M + H] calc 411.2504 obs 411.2496 |
| 18-23 | 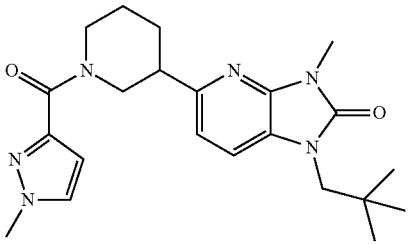 | 1-(2,2-dimethylpropyl)-3-methyl-5-{1-[(1-methyl-1H-pyrazol-3-yl)carbonyl]piperidin-3-yl}-1,3-dihydro-2H-imidazo[4,5-b]pyridin-2-one | C21H32N4O4S [M + H] calc 437.2218 obs 437.2213 |

| # | Structure | Name | HRMS/LRMS |
|---|---|---|---|
| 18-24 | 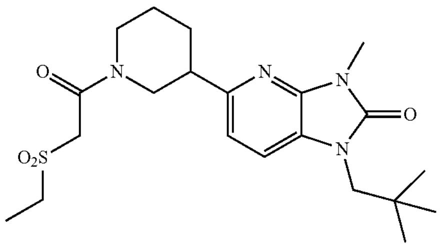 | 1-(2,2-dimethylpropyl)-5-{1-[(ethylsulfonyl)acetyl]piperidin-3-yl}-3-methyl-1,3-dihydro-2H-imidazo[4,5-b]pyridin-2-one | C22H32N4O3 [M + H] calc 401.2548 obs 401.2545 |
| 18-25 | 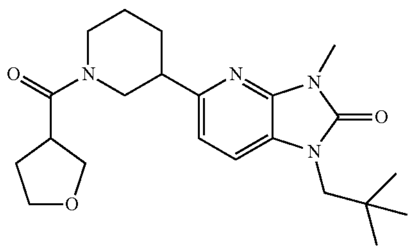 | 1-(2,2-dimethylpropyl)-3-methyl-5-[1-(tetrahydrofuran-3-ylcarbonyl)piperidin-3-yl]-1,3-dihydro-2H-imidazo[4,5-b]pyridin-2-one | C20H32N4O [M + H] calc 345.265 obs 345.2652 |
| 18-26 | 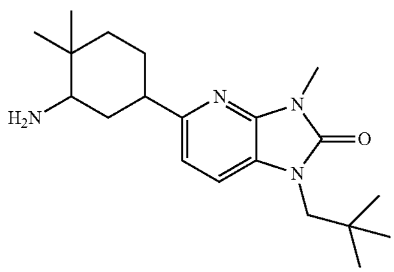 | 5-(3-amino-4,4-dimethylcyclohexyl)-1-(2,2-dimethylpropyl)-3-methyl-1,3-dihydro-2H-imidazo[4,5-b]pyridin-2-one | C21H28N6O2 [M + H] calc 397.2348 obs 397.2341 |
| 18-27 | 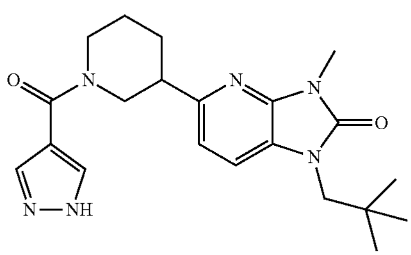 | 1-(2,2-dimethylpropyl)-3-methyl-5-[1-(1H-pyrazol-4-ylcarbonyl)piperidin-3-yl]-1,3-dihydro-2H-imidazo[4,5-b]pyridin-2-one | C22H34N4O2 [M + H] calc 387.2755 obs 387.2752 |
| 18-28 | 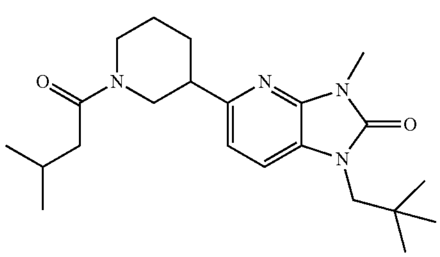 | 1-(2,2-dimethylpropyl)-3-methyl-5-[1-(3-methylbutanoyl)piperidin-3-yl]-1,3-dihydro-2H-imidazo[4,5-b]pyridin-2-one | C30H37N5O3 [M + H] calc 516.297 obs 516.2981 |
| 18-29 | 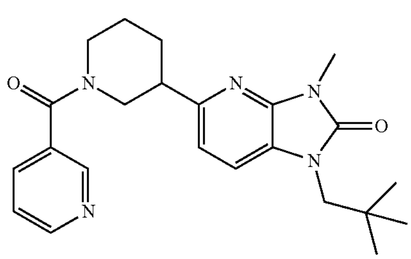 | 1-(2,2-dimethylpropyl)-3-methyl-5-[1-(pyridin-3-ylcarbonyl)piperidin-3-yl]-1,3-dihydro-2H-imidazo[4,5-b]pyridin-2-one | C30H37N5O3 [M + H] calc 516.297 obs 516.2981 |

TABLE 7-continued

| # | Structure | Name | HRMS/LRMS |
|---|---|---|---|
| 18-30 | 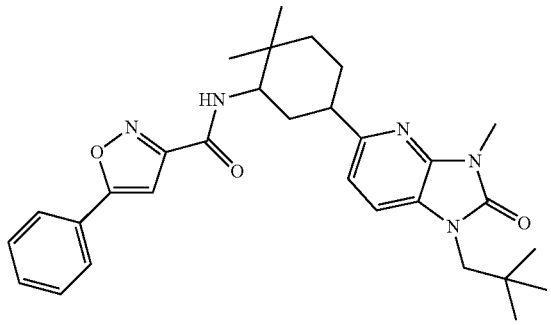 | N-{5-[1-(2,2-dimethylpropyl)-3-methyl-2-oxo-2,3-dihydro-1H-imidazo[4,5-b]pyridin-5-yl]-2,2-dimethylcyclohexyl}-5-phenylisoxazole-3-carboxamide | C22H30N6O2 [M + H] calc 411.2504 obs 411.2497 |
| 18-31 | 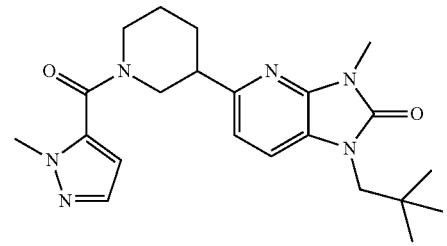 | 1-(2,2-dimethylpropyl)-3-methyl-5-{1-[(1-methyl-1H-pyrazol-5-yl)carbonyl]piperidin-3-yl}-1,3-dihydro-2H-imidazo[4,5-b]pyridin-2-one | C32H43N5O3 [M + H] calc 546.3439 obs 546.3434 |
| 18-32 | 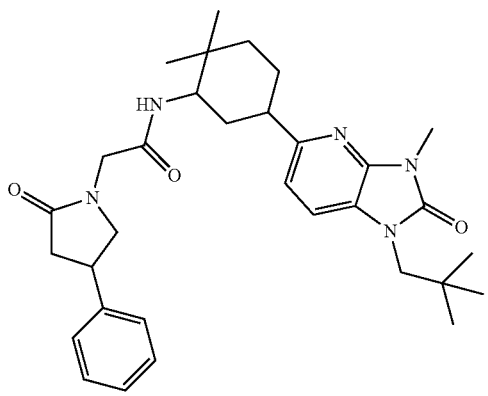 | N-{5-[1-(2,2-dimethylpropyl)-3-methyl-2-oxo-2,3-dihydro-1H-imidazo[4,5-b]pyridin-5-yl]-2,2-dimethylcyclohexyl}-2-(2-oxo-4-phenylpyrrolidin-1-yl)acetamide | C20H32N4O [M + H] calc 345.265 obs 345.2650 |
| 18-33 | 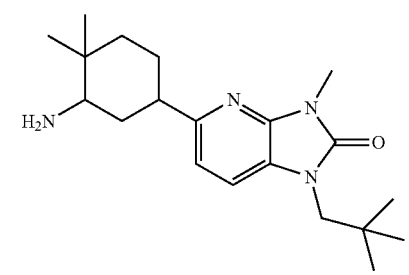 | 5-(3-amino-4,4-dimethylcyclohexyl)-1-(2,2-dimethylpropyl)-3-methyl-1,3-dihydro-2H-imidazo[4,5-b]pyridin-2-one | C21H27N5O3 [M + H] calc 398.2188 obs 398.2186 |
| 18-34 | 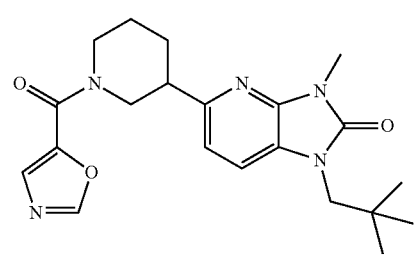 | 1-(2,2-dimethylpropyl)-3-methyl-5-[1-(1,3-oxazol-5-ylcarbonyl)piperidin-3-yl]-1,3-dihydro-2H-imidazo[4,5-b]pyridin-2-one | C25H29N5O2 [M + H] calc 432.2396 obs 432.2392 |

TABLE 7-continued

| # | Structure | Name | HRMS/LRMS |
|---|---|---|---|
| 18-35 | 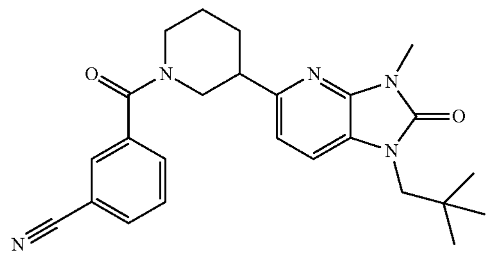 | 3-({3-[1-(2,2-dimethylpropyl)-3-methyl-2-oxo-2,3-dihydro-1H-imidazo[4,5-b]pyridin-5-yl]piperidin-1-yl}carbonyl)benzonitrile | C28H46N6O2 [M + H] calc 499.3755 obs 499.3754 |
| 18-36 | 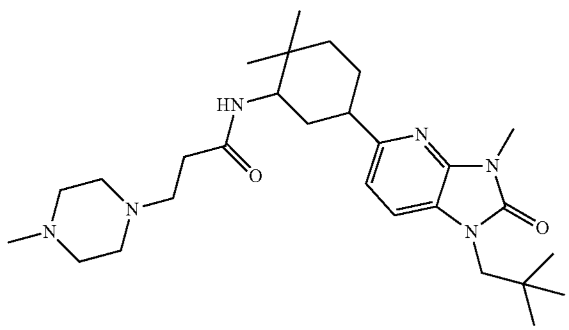 | N-{5-[1-(2,2-dimethylpropyl)-3-methyl-2-oxo-2,3-dihydro-1H-imidazo[4,5-b]pyridin-5-yl]-2,2-dimethylcyclohexyl}-3-(4-methylpiperazin-1-yl)propanamide | C23H34N4O3 [M + H] calc 415.2704 obs 415.2702 |
| 18-37 | 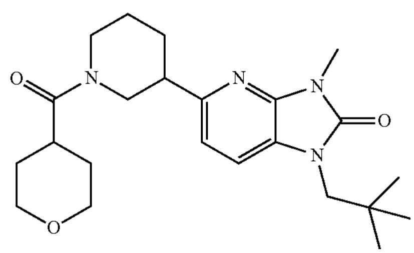 | 1-(2,2-dimethylpropyl)-3-methyl-5-[1-(tetrahydro-2H-pyran-4-ylcarbonyl)piperidin-3-yl]-1,3-dihydro-2H-imidazo[4,5-b]pyridin-2-one | C22H30N6O2 [M + H] calc 411.2504 obs 411.2497 |
| 18-38 | 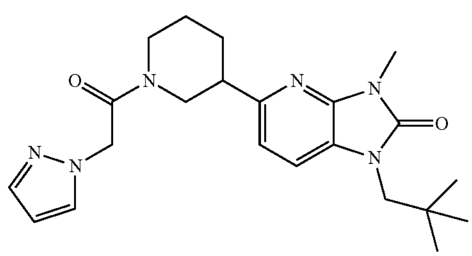 | 1-(2,2-dimethylpropyl)-3-methyl-5-[1-(1H-pyrazol-1-ylacetyl)piperidin-3-yl]-1,3-dihydro-2H-imidazo[4,5-b]pyridin-2-one | C28H38N4O3 [M + H] calc 479.3017 obs 479.3009 |
| 18-39 | 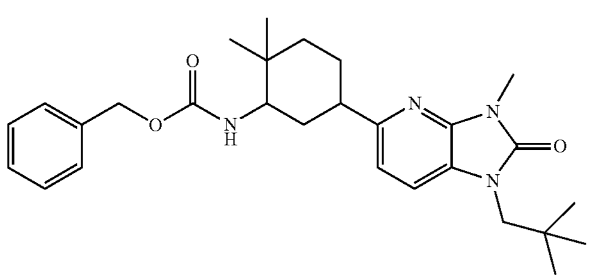 | benzyl {5-[1-(2,2-dimethylpropyl)-3-methyl-2-oxo-2,3-dihydro-1H-imidazo[4,5-b]pyridin-5-yl]-2,2-dimethylcyclohexyl}carbamate | C22H30N6O2 [M + H] calc 411.2504 obs 411.2494 |

TABLE 7-continued

| # | Structure | Name | HRMS/LRMS |
|---|---|---|---|
| 18-40 | 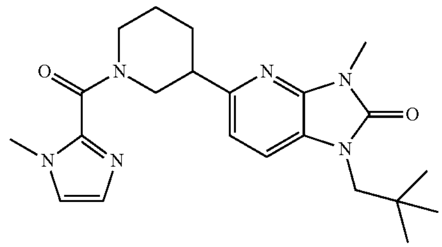 | 1-(2,2-dimethylpropyl)-3-methyl-5-{1-[(1-methyl-1H-imidazol-2-yl)carbonyl]piperidin-3-yl}-1,3-dihydro-2H-imidazo[4,5-b]pyridin-2-one | C20H26N6O3 [M + H] calc 399.2141 obs 399.2133 |
| 18-41 | 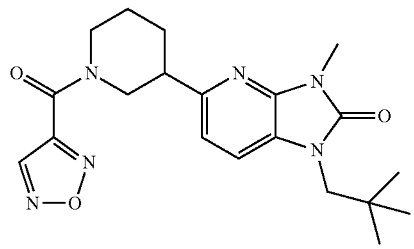 | 1-(2,2-dimethylpropyl)-3-methyl-5-[1-(1,2,5-oxadiazol-3-ylcarbonyl)piperidin-3-yl]-1,3-dihydro-2H-imidazo[4,5-b]pyridin-2-one | C28H35F3N4O3 [M + H] calc 533.2735 obs 533.2731 |
| 18-42 | 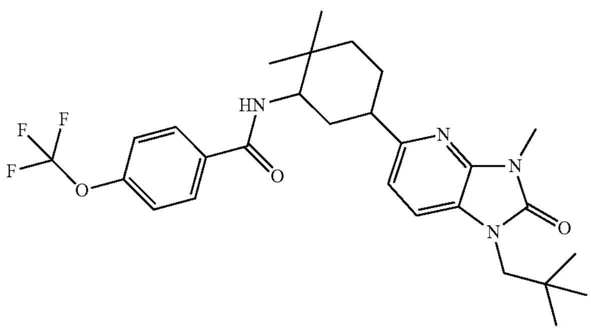 | N-{5-[1-(2,2-dimethylpropyl)-3-methyl-2-oxo-2,3-dihydro-1H-imidazo[4,5-b]pyridin-5-yl]-2,2-dimethylcyclohexyl}-4-(trifluoromethoxy)benzamide | C24H35N7O2 [M + H] calc 454.2926 obs 454.2935 |
| 18-43 | 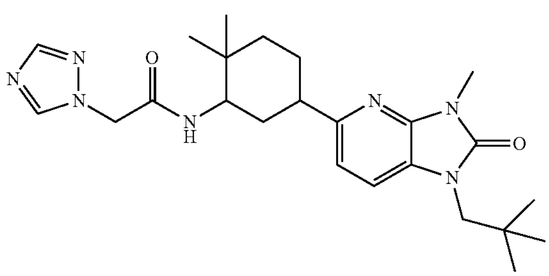 | N-{5-[1-(2,2-dimethylpropyl)-3-methyl-2-oxo-2,3-dihydro-1H-imidazo[4,5-b]pyridin-5-yl]-2,2-dimethylcyclohexyl}-2-(1H-1,2,4-triazol-1-yl)acetamide | C32H42N6O2 [M + H] calc 543.3442 obs 543.3449 |
| 18-44 | 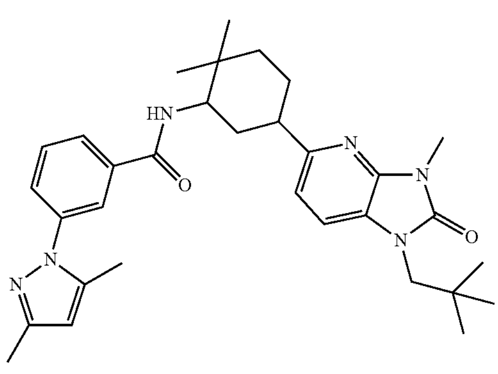 | N-{5-[1-(2,2-dimethylpropyl)-3-methyl-2-oxo-2,3-dihydro-1H-imidazo[4,5-b]pyridin-5-yl]-2,2-dimethylcyclohexyl}-3-(3,5-dimethyl-1H-pyrazol-1-yl)benzamide | C28H45N5O2 [M + H] calc 484.3646 obs 484.3640 |

TABLE 7-continued

| # | Structure | Name | HRMS/LRMS |
|---|---|---|---|
| 18-45 | 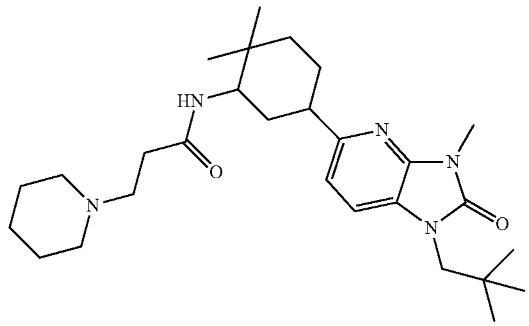 | N-{5-[1-(2,2-dimethylpropyl)-3-methyl-2-oxo-2,3-dihydro-1H-imidazo[4,5-b]pyridin-5-yl]-2,2-dimethylcyclohexyl}-3-piperidin-1-ylpropanamide | C29H48N6O2 [M + H] calc 513.3911 obs 513.3912 |
| 18-46 | 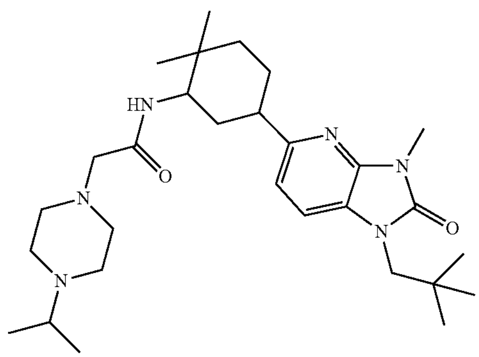 | N-{5-[1-(2,2-dimethylpropyl)-3-methyl-2-oxo-2,3-dihydro-1H-imidazo[4,5-b]pyridin-5-yl]-2,2-dimethylcyclohexyl}-2-[4-(1-methylethyl)piperazin-1-yl]acetamide | C30H37N5O2 [M + H] calc 500.3021 obs 500.3023 |
| 18-47 | 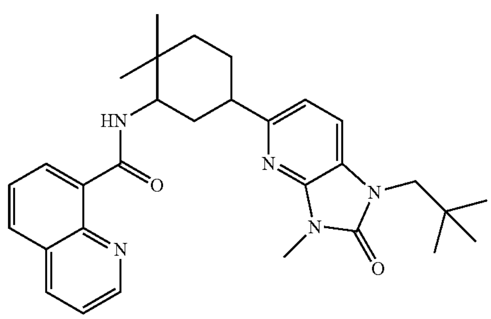 | N-{5-[1-(2,2-dimethylpropyl)-3-methyl-2-oxo-2,3-dihydro-1H-imidazo[4,5-b]pyridin-5-yl]-2,2-dimethylcyclohexyl}quinoline-8-carboxamide | C27H43N5O2 [M + H] calc 470.349 obs 470.3489 |
| 18-48 | 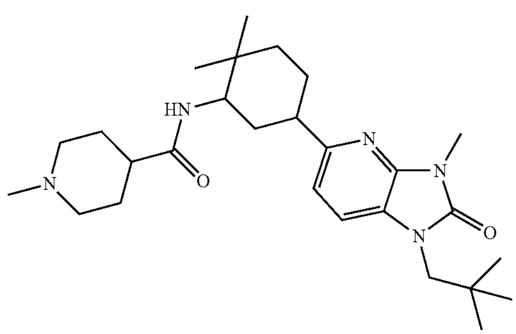 | N-{5-[1-(2,2-dimethylpropyl)-3-methyl-2-oxo-2,3-dihydro-1H-imidazo[4,5-b]pyridin-5-yl]-2,2-dimethylcyclohexyl}-1-methylpiperidine-4-carboxamide | C30H37N5O3 [M + H] calc 516.297 obs 516.2980 |

TABLE 7-continued

| # | Name | HRMS/LRMS |
|---|---|---|
| 18-49 | N-{5-[1-(2,2-dimethylpropyl)-3-methyl-2-oxo-2,3-dihydro-1H-imidazo[4,5-b]pyridin-5-yl]-2,2-dimethylcyclohexyl}-2-phenyl-1,3-oxazole-4-carboxamide | C21H32N4O3 [M + H] calc 389.2548 obs 389.2545 |
| 18-50 | tert-butyl 3-[1-(2,2-dimethylpropyl)-3-methyl-2-oxo-2,3-dihydro-1H-imidazo[4,5-b]pyridin-5-yl]pyrrolidine-1-carboxylate | C20H26N6O2S [M + H] calc 415.1913 obs 415.1909 |
| 18-51 | 1-(2,2-dimethylpropyl)-3-methyl-5-[1-(1,2,3-thiadiazol-4-ylcarbonyl)piperidin-3-yl]-1,3-dihydro-2H-imidazo[4,5-b]pyridin-2-one | C30H39N7O2 [M + H] calc 530.3239 obs 530.3247 |
| 18-52 | N-{5-[1-(2,2-dimethylpropyl)-3-methyl-2-oxo-2,3-dihydro-1H-imidazo[4,5-b]pyridin-5-yl]-2,2-dimethylcyclohexyl}-2-(5-phenyl-4H-1,2,4-triazol-3-yl)acetamide | C22H34N4O2 [M + H] calc 387.2755 obs 387.2751 |
| 18-53 | 5-[1-(2,2-dimethyl-propanoyl)piperidin-3-yl]-1-(2,2-dimethylpropyl)-3-methyl-1,3-dihydro-2H-imidazo[4,5-b]pyridin-2-one | C23H34N4O3 [M + H] calc 415.2704 obs 415.2701 |

TABLE 7-continued

| # | Structure | Name | HRMS/LRMS |
|---|---|---|---|
| 18-54 | 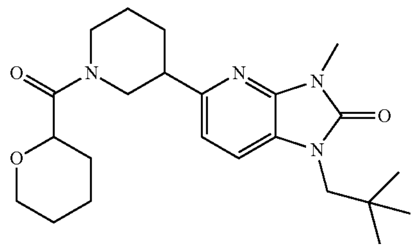 | 1-(2,2-dimethylpropyl)-3-methyl-5-[1-(tetrahydro-2H-pyran-2-ylcarbonyl)piperidin-3-yl]-1,3-dihydro-2H-imidazo[4,5-b]pyridin-2-one | C24H36N4O3 [M + H] calc 429.2861 obs 429.2869 |
| 18-55 | 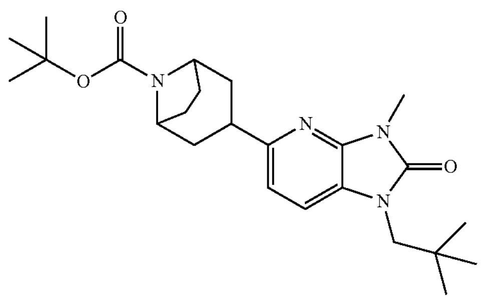 | tert-butyl 3-[1-(2,2-dimethylpropyl)-3-methyl-2-oxo-2,3-dihydro-1H-imidazo[4,5-b]pyridin-5-yl]-8-azabicyclo[3.2.1]octane-8-carboxylate | C25H36N6O2 [M + H] calc 453.2974 obs 453.2980 |
| 18-56 | 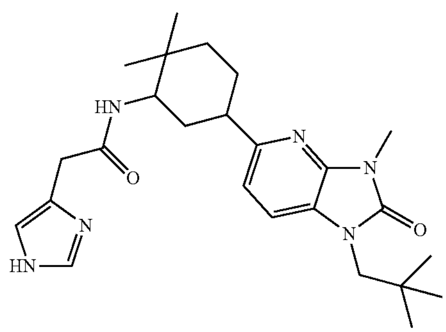 [SMILES: Cn1c(=O)n(CC(C)(C)C)c2ccc(C3CCC(C)(C)C(NC(=O)Cc4c[nH]cn4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-2-(1H-imidazol-4-yl)acetamide | C27H43N5O2 [M + H] calc 470.349 obs 470.3496 |
| 18-57 | 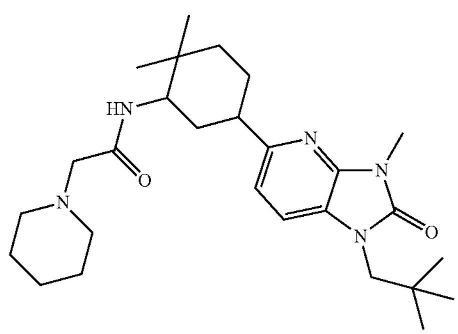 | N-{5-[1-(2,2-dimethylpropyl)-3-methyl-2-oxo-2,3-dihydro-1H-imidazo[4,5-b]pyridin-5-yl]-2,2-dimethylcyclohexyl}-2-piperidin-1-ylacetamide | C29H38N6O2 [M + H] calc 503.313 obs 503.3122 |
| 18-58 | 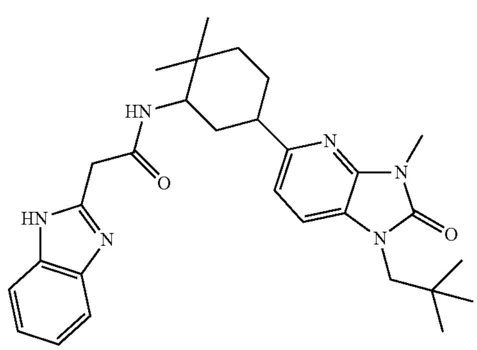 | 2-(1H-benzimidazol-2-yl)-N-{5-[1-(2,2-dimethylpropyl)-3-methyl-2-oxo-2,3-dihydro-1H-imidazo[4,5-b]pyridin-5-yl]-2,2-dimethylcyclohexyl}acetamide | C31H41N5O3 [M + H] calc 532.3282 obs 532.3291 |

TABLE 7-continued

| # | Structure | Name | HRMS/LRMS |
|---|---|---|---|
| 18-59 | 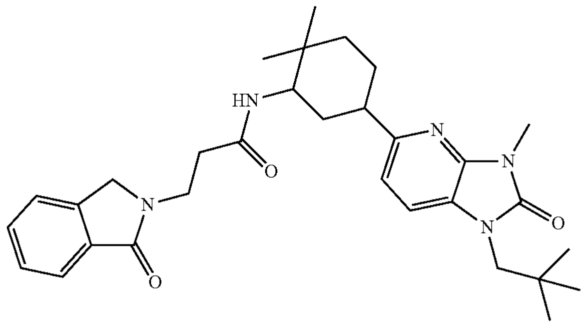 | N-{5-[1-(2,2-dimethylpropyl)-3-methyl-2-oxo-2,3-dihydro-1H-imidazo[4,5-b]pyridin-5-yl]-2,2-dimethylcyclohexyl}-3-(1-oxo-1,3-dihydro-2H-isoindol-2-yl)propanamide | C27H40N6O2 [M + H] calc 481.3286 obs 481.3293 |
| 18-60 | 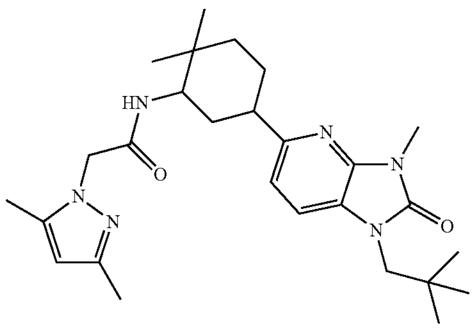 | N-{5-[1-(2,2-dimethylpropyl)-3-methyl-2-oxo-2,3-dihydro-1H-imidazo[4,5-b]pyridin-5-yl]-2,2-dimethylcyclohexyl}-2-(3,5-dimethyl-1H-pyrazol-1-yl)acetamide | C27H37N5O2 [M + H] calc 464.3021 obs 464.3025 |
| 18-61 | 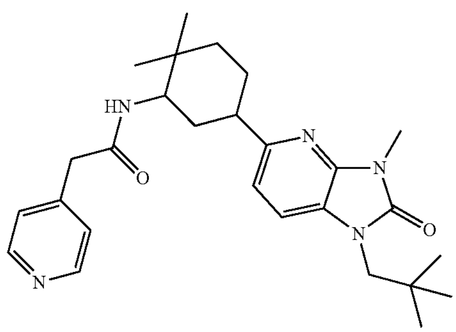 | N-{5-[1-(2,2-dimethylpropyl)-3-methyl-2-oxo-2,3-dihydro-1H-imidazo[4,5-b]pyridin-5-yl]-2,2-dimethylcyclohexyl}-2-pyridin-4-ylacetamide | C32H46N6O2 [M + H] calc 547.3755 obs 547.3756 |
| 18-62 | 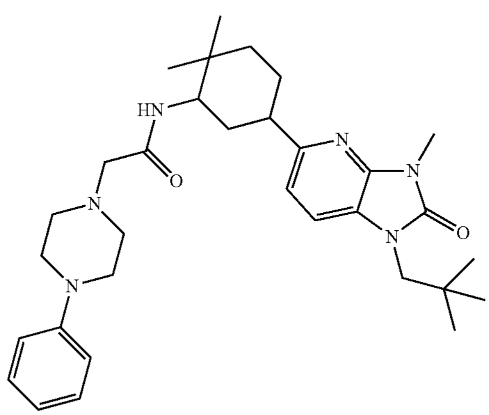 | N-{5-[1-(2,2-dimethylpropyl)-3-methyl-2-oxo-2,3-dihydro-1H-imidazo[4,5-b]pyridin-5-yl]-2,2-dimethylcyclohexyl}-2-(4-phenylpiperazin-1-yl)acetamide | C23H36N4O2 [M + H] calc 401.2912 obs 401.2906 |

TABLE 7-continued

| # | Structure | Name | HRMS/LRMS |
|---|---|---|---|
| 18-63 | 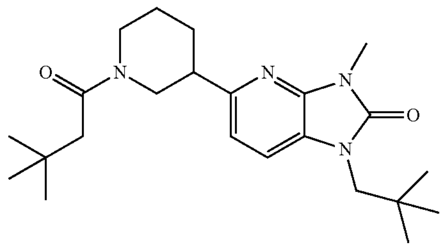 | 5-[1-(3,3-dimethyl-butanoyl)piperidin-3-yl]-1-(2,2-dimethyl-propyl)-3-methyl-1,3-dihydro-2H-imidazo[4,5-b]pyridin-2-one | C27H41N5O3 [M + H] calc 484.3282 obs 484.3290 |
| 18-64 | 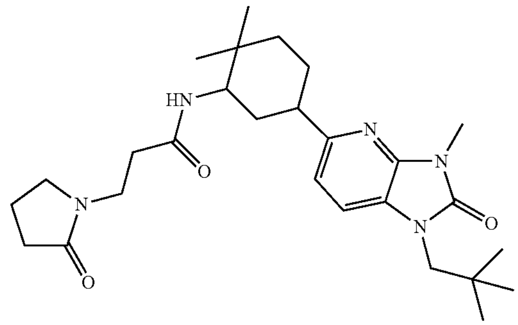 | N-{5-[1-(2,2-dimethylpropyl)-3-methyl-2-oxo-2,3-dihydro-1H-imidazo[4,5-b]pyridin-5-yl]-2,2-dimethylcyclohexyl}-3-(2-oxopyrrolidin-1-yl)propanamide | C27H37N5O2 [M + H] calc 464.3021 obs 464.3020 |
| 18-65 | 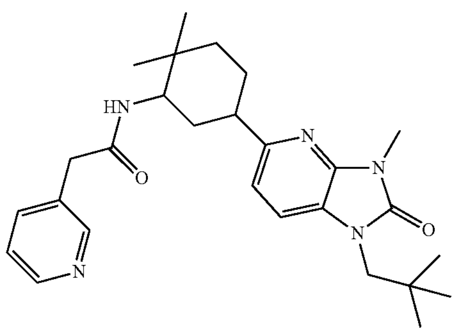 | N-{5-[1-(2,2-dimethylpropyl)-3-methyl-2-oxo-2,3-dihydro-1H-imidazo[4,5-b]pyridin-5-yl]-2,2-dimethylcyclohexyl}-2-pyridin-3-ylacetamide | C24H36N4O4 [M + H] calc 445.281 obs 445.2809 |
| 18-66 | 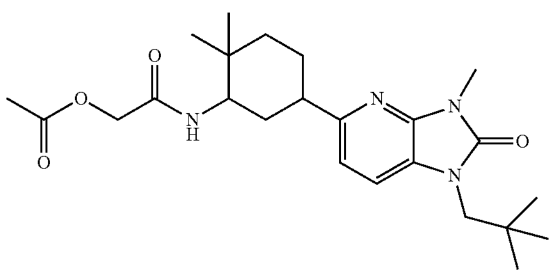 | 2-({5-[1-(2,2-dimethylpropyl)-3-methyl-2-oxo-2,3-dihydro-1H-imidazo[4,5-b]pyridin-5-yl]-2,2-dimethyl-cyclohexyl}amino)-2-oxoethyl acetate | C28H43N5O3 [M + H] calc 498.3439 obs 498.3439 |
| 18-67 | 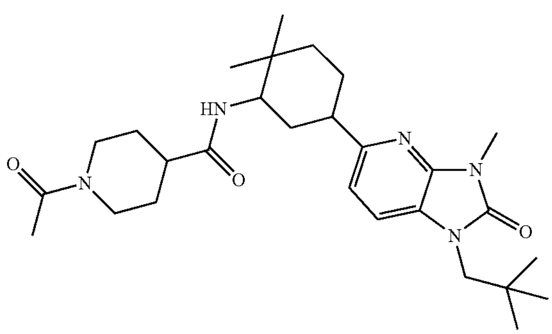 | 1-acetyl-N-{5-[1-(2,2-dimethylpropyl)-3-methyl-2-oxo-2,3-dihydro-1H-imidazo[4,5-b]pyridin-5-yl]-2,2-dimethyl-cyclohexyl}piperidine-4-carboxamide | C28H39N5O2 [M + H] calc 478.3177 obs 478.3180 |

TABLE 7-continued

| # | Structure | Name | HRMS/LRMS |
|---|---|---|---|
| 18-68 | 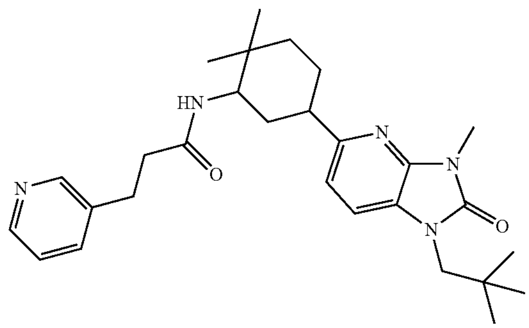 | N-{5-[1-(2,2-dimethylpropyl)-3-methyl-2-oxo-2,3-dihydro-1H-imidazo[4,5-b]pyridin-5-yl]-2,2-dimethylcyclohexyl}-3-pyridin-3-ylpropanamide | C24H34N6O3 [M + H] calc 455.2766 obs 455.2780 |
| 18-69 | 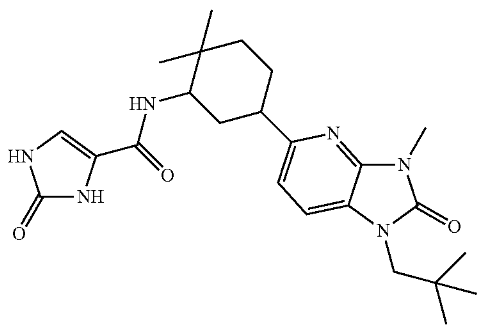 | N-{5-[1-(2,2-dimethylpropyl)-3-methyl-2-oxo-2,3-dihydro-1H-imidazo[4,5-b]pyridin-5-yl]-2,2-dimethylcyclohexyl}-2-oxo-2,3-dihydro-1H-imidazole-4-carboxamide | C24H36N4O3 [M + H] calc 429.2861 obs 429.2872 |
| 18-70 | 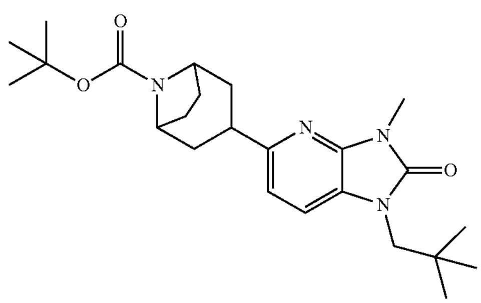 | tert-butyl 3-[1-(2,2-dimethylpropyl)-3-methyl-2-oxo-2,3-dihydro-1H-imidazo[4,5-b]pyridin-5-yl]-8-azabicyclo[3.2.1]octane-8-carboxylate | C20H25N5O3 [M + H] calc 384.2032 obs 384.2027 |
| 18-71 | 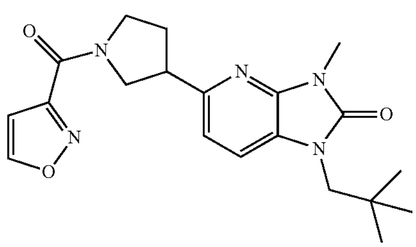 | 1-(2,2-dimethylpropyl)-5-[1-(isoxazol-3-ylcarbonyl)pyrrolidin-3-yl]-3-methyl-1,3-dihydro-2H-imidazo[4,5-b]pyridin-2-one | C26H37N5O [M + H] calc 436.3072 obs 436.3070 |
| 18-72 | 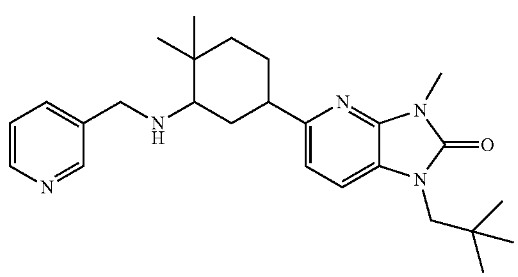 | 1-(2,2-dimethylpropyl)-5-{4,4-dimethyl-3-[(pyridin-3-ylmethyl)amino]cyclohexyl}-3-methyl-1,3-dihydro-2H-imidazo[4,5-b]pyridin-2-one | C25H37N5O4 [M + H] calc 472.2919 obs 472.2927 |

TABLE 7-continued

| # | Structure | Name | HRMS/LRMS |
|---|---|---|---|
| 18-73 | 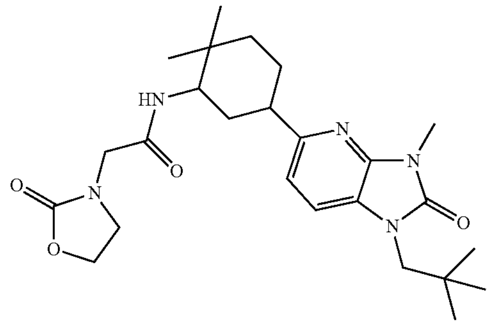 | N-{5-[1-(2,2-dimethylpropyl)-3-methyl-2-oxo-2,3-dihydro-1H-imidazo[4,5-b]pyridin-5-yl]-2,2-dimethylcyclohexyl}-2-(2-oxo-1,3-oxazolidin-3-yl)acetamide | C21H27N5O3 [M + H] calc 398.2188 obs 398.2184 |
| 18-74 | 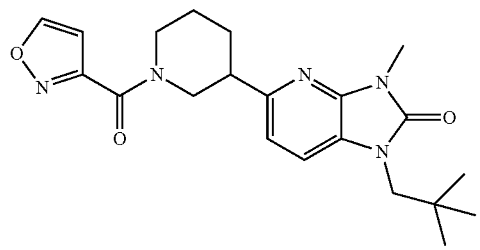 | 1-(2,2-dimethylpropyl)-5-[1-(isoxazol-3-ylcarbonyl)piperidin-3-yl]-3-methyl-1,3-dihydro-2H-imidazo[4,5-b]pyridin-2-one | C31H43N5O3 [M + H] calc 534.3439 obs 534.3449 |
| 18-75 | 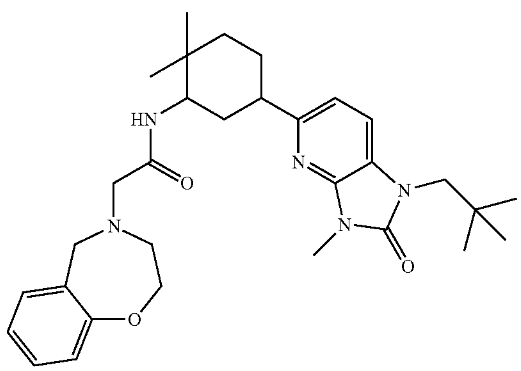 | 2-(2,3-dihydro-1,4-benzoxazepin-4(5H)-yl)-N-{5-[1-(2,2-dimethylpropyl)-3-methyl-2-oxo-2,3-dihydro-1H-imidazo[4,5-b]pyridin-5-yl]-2,2-dimethylcyclohexyl}acetamide | C23H35F3N4O3S [M + H] calc 505.2456 obs 505.2463 |
| 18-76 | 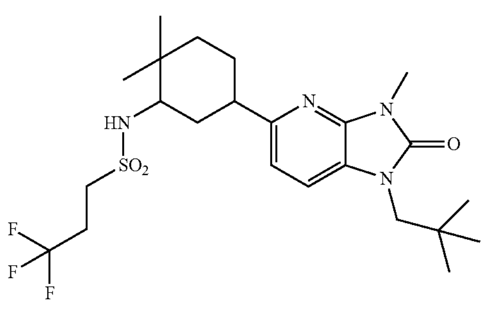 | N-{5-[1-(2,2-dimethylpropyl)-3-methyl-2-oxo-2,3-dihydro-1H-imidazo[4,5-b]pyridin-5-yl]-2,2-dimethylcyclohexyl}-3,3,3-trifluoropropane-1-sulfonamide | C23H28N4O2 [M + H] calc 393.2287 obs 393.2288 |
| 18-77 | 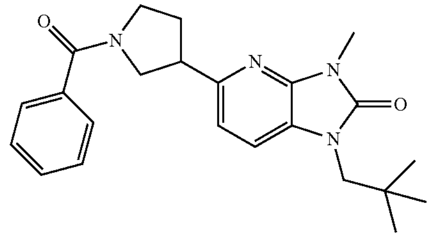 | 1-(2,2-dimethylpropyl)-3-methyl-5-[1-(phenylcarbonyl)pyrrolidin-3-yl]-1,3-dihydro-2H-imidazo[4,5-b]pyridin-2-one | C29H39N5O3 [M + H] calc 506.3126 obs 506.3126 |

TABLE 7-continued

| # | Structure | Name | HRMS/LRMS |
|---|---|---|---|
| 18-78 | 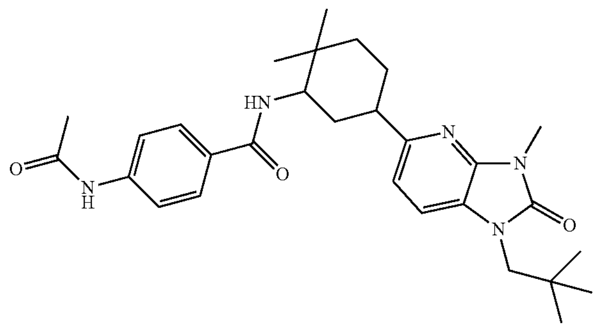 | 4-(acetylamino)-N-{5-[1-(2,2-dimethylpropyl)-3-methyl-2-oxo-2,3-dihydro-1H-imidazo[4,5-b]pyridin-5-yl]-2,2-dimethyl-cyclohexyl}benzamide | C24H30N4O2 [M + H] calc 407.2443 obs 407.2437 |
| 18-79 | 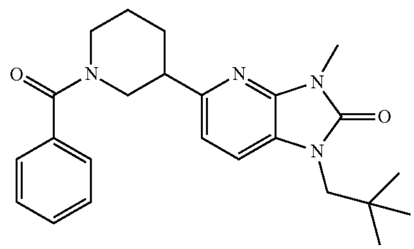 | 1-(2,2-dimethylpropyl)-3-methyl-5-[1-(phenyl-carbonyl)piperidin-3-yl]-1,3-dihydro-2H-imidazo[4,5-b]pyridin-2-one | C30H42N4O3 [M + H] calc 507.333 obs 507.3327 |
| 18-80 | 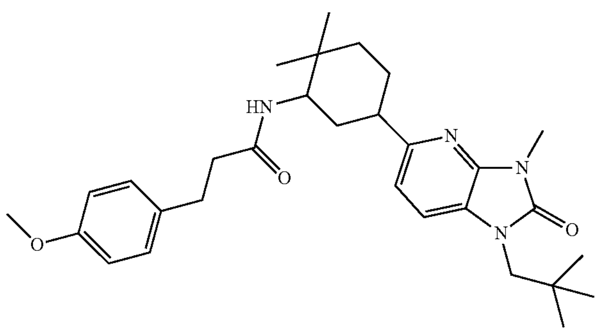 | N-{5-[1-(2,2-dimethylpropyl)-3-methyl-2-oxo-2,3-dihydro-1H-imidazo[4,5-b]pyridin-5-yl]-2,2-dimethylcyclohexyl}-3-(4-methoxy-phenyl)propanamide | C26H38N6O2 [M + H] calc 467.313 obs 467.3135 |
| 18-81 | 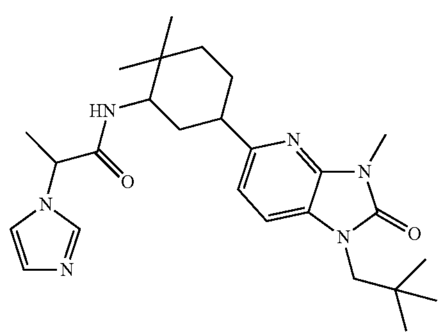 | N-{5-[1-(2,2-dimethylpropyl)-3-methyl-2-oxo-2,3-dihydro-1H-imidazo[4,5-b]pyridin-5-yl]-2,2-dimethylcyclohexyl}-2-(1H-imidazol-1-yl)propanamide | C27H38N4O3S [M + H] calc 499.2738 obs 499.2747 |
| 18-82 | 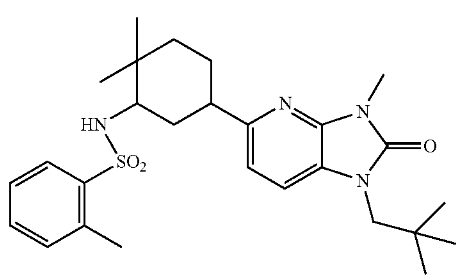 | N-{5-[1-(2,2-dimethylpropyl)-3-methyl-2-oxo-2,3-dihydro-1H-imidazo[4,5-b]pyridin-5-yl]-2,2-dimethylcyclohexyl}-2-methylbenzene-sulfonamide | C25H36N6O2 [M + H] calc 453.2974 obs 453.2981 |

TABLE 7-continued

| # | Structure | Name | HRMS/LRMS |
|---|---|---|---|
| 18-83 | 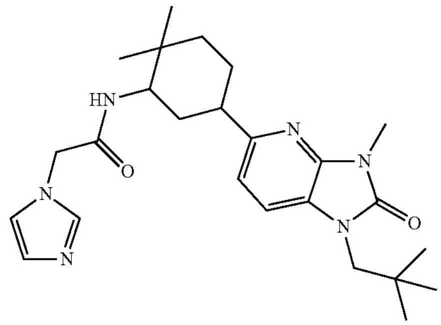 | N-{5-[1-(2,2-dimethylpropyl)-3-methyl-2-oxo-2,3-dihydro-1H-imidazo[4,5-b]pyridin-5-yl]-2,2-dimethylcyclohexyl}-2-(1H-imidazol-1-yl)acetamide | C27H37N5O2 [M + H] calc 464.3021 obs 464.3026 |
| 18-84 | 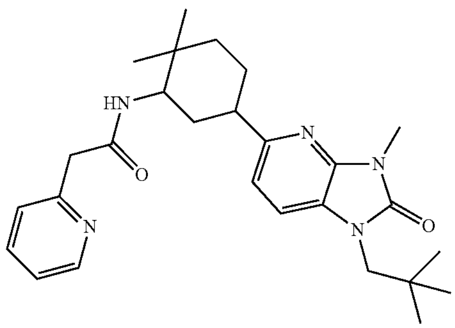 | N-{5-[1-(2,2-dimethylpropyl)-3-methyl-2-oxo-2,3-dihydro-1H-imidazo[4,5-b]pyridin-5-yl]-2,2-dimethylcyclohexyl}-2-pyridin-2-ylacetamide | C25H34N6O2 [M + H] calc 451.2817 obs 451.2820 |
| 18-85 | 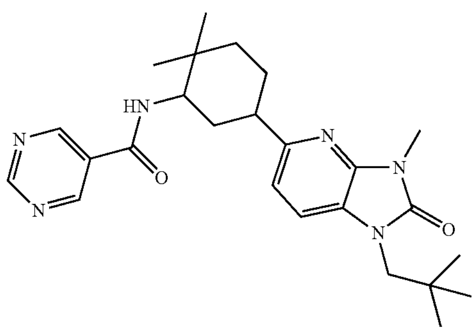 | N-{5-[1-(2,2-dimethylpropyl)-3-methyl-2-oxo-2,3-dihydro-1H-imidazo[4,5-b]pyridin-5-yl]-2,2-dimethylcyclohexyl}pyrimidine-5-carboxamide | C21H27N5O3 [M + H] calc 398.2188 obs 398.2187 |
| 18-86 | 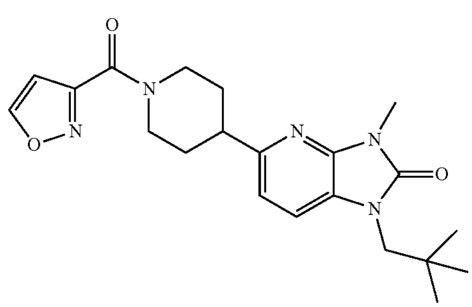 | 1-(2,2-dimethylpropyl)-5-[1-(isoxazol-3-ylcarbonyl)piperidin-4-yl]-3-methyl-1,3-dihydro-2H-imidazo[4,5-b]pyridin-2-one | C31H44N6O2 [M + H] calc 533.3599 obs 533.3596 |

TABLE 7-continued

| # | Structure | Name | HRMS/LRMS |
|---|---|---|---|
| 18-87 | 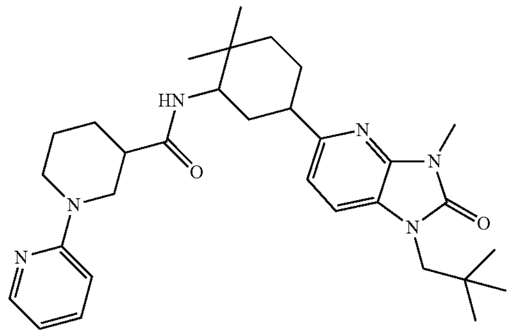 | N-{5-[1-(2,2-dimethylpropyl)-3-methyl-2-oxo-2,3-dihydro-1H-imidazo[4,5-b]pyridin-5-yl]-2,2-dimethylcyclohexyl}-1-pyridin-2-ylpiperidine-3-carboxamide | C24H39N5O2 [M + H] calc 430.3177 obs 430.3181 |
| 18-88 | 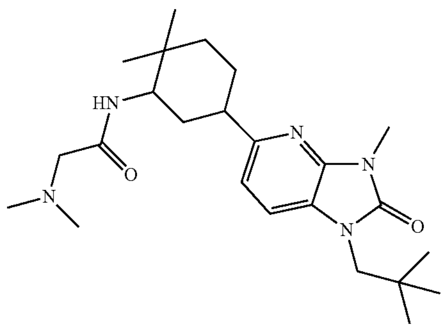 | N-{5-[1-(2,2-dimethylpropyl)-3-methyl-2-oxo-2,3-dihydro-1H-imidazo[4,5-b]pyridin-5-yl]-2,2-dimethylcyclohexyl}-N~2~,N~2~-dimethylglycinamide | C30H38N6O2 [M + H] calc 515.313 obs 515.3130 |
| 18-89 | 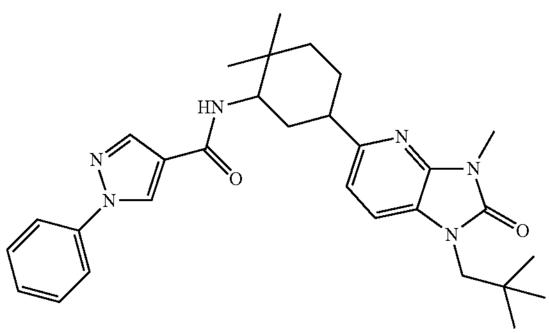 | N-{5-[1-(2,2-dimethylpropyl)-3-methyl-2-oxo-2,3-dihydro-1H-imidazo[4,5-b]pyridin-5-yl]-2,2-dimethylcyclohexyl}-1-phenyl-1H-pyrazole-4-carboxamide | C25H38N4O3 [M + H] calc 443.3017 obs 443.3013 |
| 18-90 | 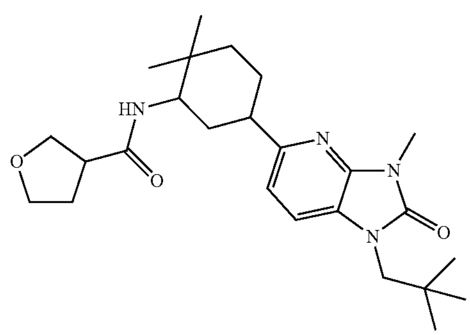 | N-{5-[1-(2,2-dimethylpropyl)-3-methyl-2-oxo-2,3-dihydro-1H-imidazo[4,5-b]pyridin-5-yl]-2,2-dimethylcyclohexyl}tetrahydrofuran-3-carboxamide | C30H38N6O2 [M + H] calc 515.313 obs 515.3130 |

TABLE 7-continued

| # | Structure | Name | HRMS/LRMS |
|---|---|---|---|
| 18-91 | 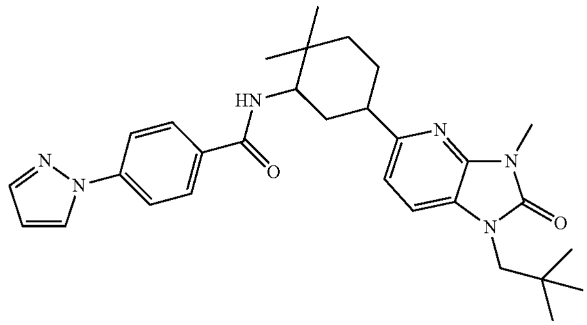 | N-{5-[1-(2,2-dimethylpropyl)-3-methyl-2-oxo-2,3-dihydro-1H-imidazo[4,5-b]pyridin-5-yl]-2,2-dimethylcyclohexyl}-4-(1H-pyrazol-1-yl)benzamide | C25H40N4O3 [M + H] calc 445.3173 obs 445.3169 |
| 18-92 | 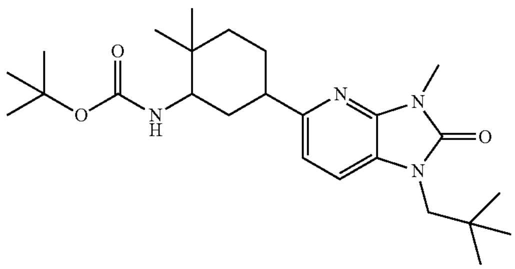 | tert-butyl {5-[1-(2,2-dimethylpropyl)-3-methyl-2-oxo-2,3-dihydro-1H-imidazo[4,5-b]pyridin-5-yl]-2,2-dimethyl-cyclohexyl}carbamate | C31H39N5O2S [M + H] calc 546.2898 obs 546.2900 |
| 18-93 | 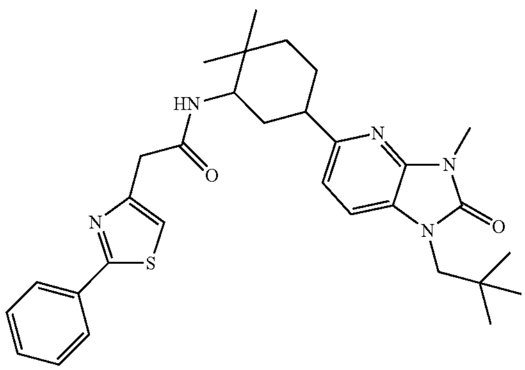 | N-{5-[1-(2,2-dimethylpropyl)-3-methyl-2-oxo-2,3-dihydro-1H-imidazo[4,5-b]pyridin-5-yl]-2,2-dimethylcyclohexyl}-2-(2-phenyl-1,3-thiazol-4-yl)acetamide | C29H45N5O3 [M + H] calc 512.3595 obs 512.3603 |
| 18-94 | 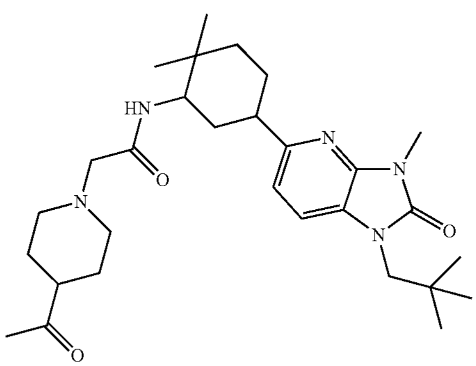 | 2-(4-acetylpiperidin-1-yl)-N-{5-[1-(2,2-dimethylpropyl)-3-methyl-2-oxo-2,3-dihydro-1H-imidazo[4,5-b]pyridin-5-yl]-2,2-dimethyl-cyclohexyl}acetamide | C22H34N4O2 [M + H] calc 387.2756 obs 387.2755 |
| 18-95 | 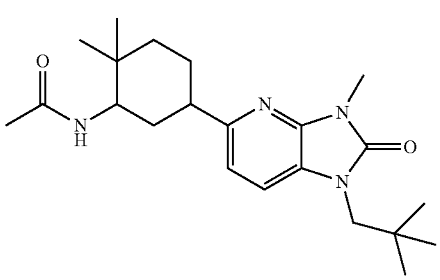 | N-{5-[1-(2,2-dimethylpropyl)-3-methyl-2-oxo-2,3-dihydro-1H-imidazo[4,5-b]pyridin-5-yl]-2,2-dimethyl-cyclohexyl}acetamide | C31H43N5O2 [M + H] calc 518.349 obs 518.3501 |

TABLE 7-continued

| # | Structure | Name | HRMS/LRMS |
|---|---|---|---|
| 18-96 | 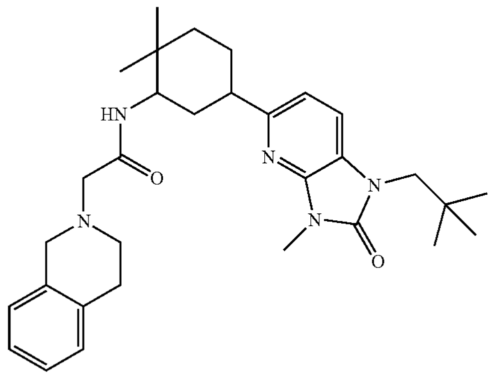 | 2-(3,4-dihydroisoquinolin-2(1H)-yl)-N-{5-[1-(2,2-dimethylpropyl)-3-methyl-2-oxo-2,3-dihydro-1H-imidazo[4,5-b]pyridin-5-yl]-2,2-dimethyl-cyclohexyl}acetamide | C25H36N6O4 [M + H] calc 485.2872 obs 485.2867 |
| 18-97 | 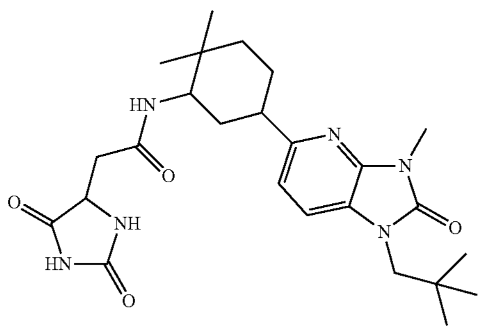 [SMILES: Cn1c(=O)n(CC(C)(C)C)c2ccc(C3CCC(C)(C)C(NC(=O)CC4NC(=O)NC4=O)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-2-(2,5-dioxoimidazolidin-4-yl)acetamide | C26H38N6O2 [M + H] calc 467.313 obs 467.3132 |
| 18-98 | 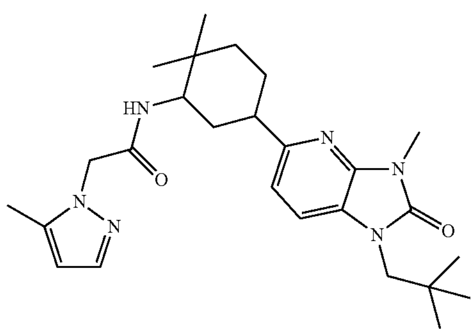 | N-{5-[1-(2,2-dimethylpropyl)-3-methyl-2-oxo-2,3-dihydro-1H-imidazo[4,5-b]pyridin-5-yl]-2,2-dimethylcyclohexyl}-2-(5-methyl-1H-pyrazol-1-yl)acetamide | C24H33N5O3 [M + H] calc 440.2657 obs 440.2663 |
| 18-99 | 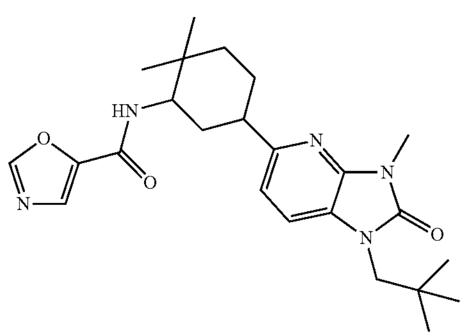 | N-{5-[1-(2,2-dimethylpropyl)-3-methyl-2-oxo-2,3-dihydro-1H-imidazo[4,5-b]pyridin-5-yl]-2,2-dimethylcyclohexyl}-1,3-oxazole-5-carboxamide | C26H37N5O2S [M + H] calc 484.2742 obs 484.2747 |

TABLE 7-continued

| # | Structure | Name | HRMS/LRMS |
|---|---|---|---|
| 18-100 | 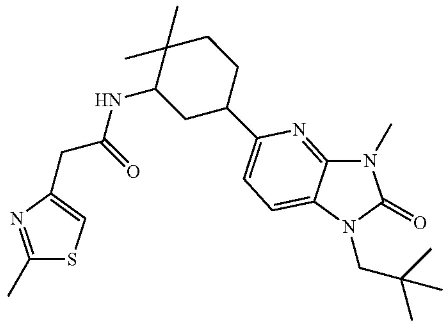 | N-{5-[1-(2,2-dimethylpropyl)-3-methyl-2-oxo-2,3-dihydro-1H-imidazo[4,5-b]pyridin-5-yl]-2,2-dimethylcyclohexyl}-2-(2-methyl-1,3-thiazol-4-yl)acetamide | C27H39N5O2S [M + H] calc 498.2898 obs 498.2904 |
| 18-101 | 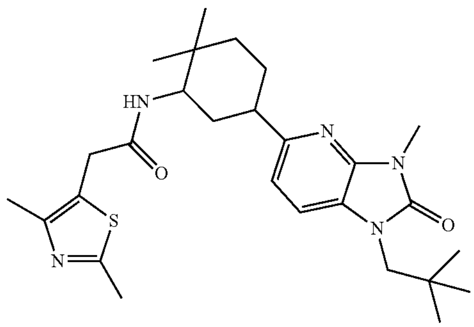 | N-{5-[1-(2,2-dimethylpropyl)-3-methyl-2-oxo-2,3-dihydro-1H-imidazo[4,5-b]pyridin-5-yl]-2,2-dimethylcyclohexyl}-2-(2,4-dimethyl-1,3-thiazol-5-yl)acetamide | C26H38N6O2 [M + H] calc 467.313 obs 467.3130 |
| 18-102 | 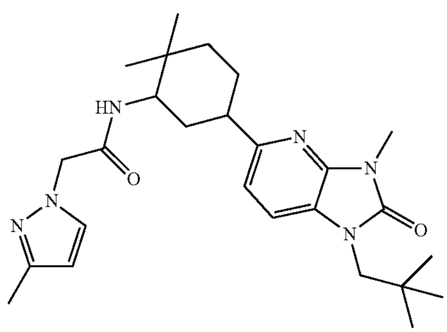 | N-{5-[1-(2,2-dimethylpropyl)-3-methyl-2-oxo-2,3-dihydro-1H-imidazo[4,5-b]pyridin-5-yl]-2,2-dimethylcyclohexyl}-2-(3-methyl-1H-pyrazol-1-yl)acetamide | C30H37N5O3 [M + H] calc 516.297 obs 516.2979 |
| 18-103 | 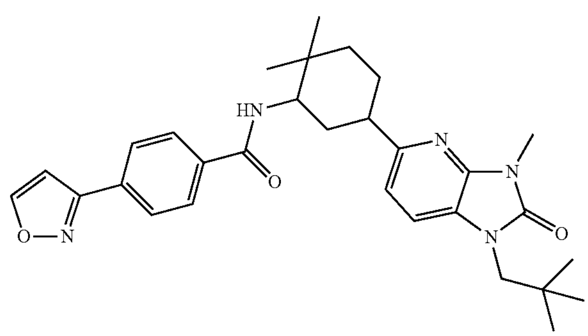 | N-{5-[1-(2,2-dimethylpropyl)-3-methyl-2-oxo-2,3-dihydro-1H-imidazo[4,5-b]pyridin-5-yl]-2,2-dimethylcyclohexyl}-4-isoxazol-3-ylbenzamide | C23H34N4O2 [M + H] calc 399.2755 obs 399.2749 |
| 18-104 | 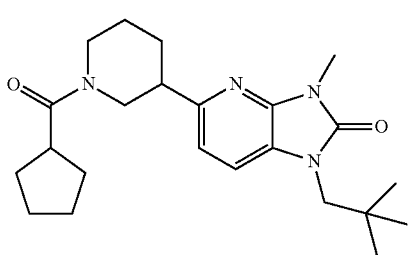 | 5-[1-(cyclopentylcarbonyl)piperidin-3-yl]-1-(2,2-dimethylpropyl)-3-methyl-1,3-dihydro-2H-imidazo[4,5-b]pyridin-2-one | C22H34N4O3 [M + H] calc 403.2705 obs 403.2699 |

TABLE 7-continued

| # | Structure | Name | HRMS/LRMS |
|---|---|---|---|
| 18-105 | 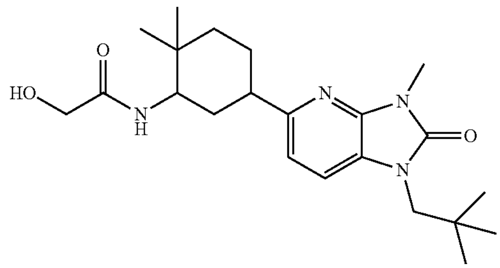 | N-{5-[1-(2,2-dimethylpropyl)-3-methyl-2-oxo-2,3-dihydro-1H-imidazo[4,5-b]pyridin-5-yl]-2,2-dimethylcyclohexyl}-2-hydroxyacetamide | C26H38N6O2 [M + H] calc 467.313 obs 467.3136 |
| 18-106 | 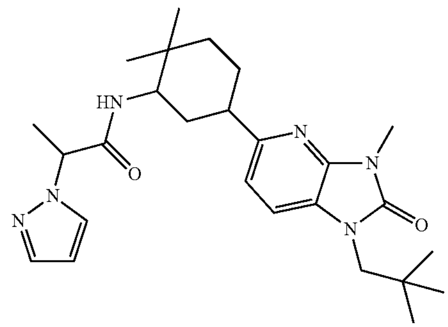 | N-{5-[1-(2,2-dimethylpropyl)-3-methyl-2-oxo-2,3-dihydro-1H-imidazo[4,5-b]pyridin-5-yl]-2,2-dimethylcyclohexyl}-2-(1H-pyrazol-1-yl)propanamide | C29H38N6O2 [M + H] calc 503.313 obs 503.3135 |
| 18-107 | 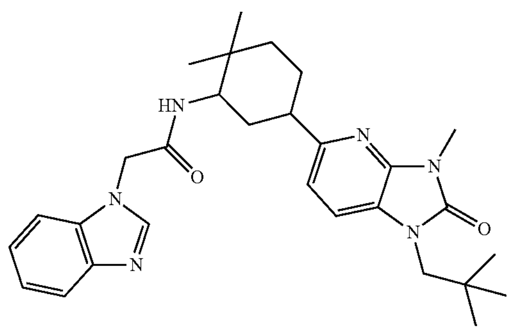 | 2-(1H-benzimidazol-1-yl)-N-{5-[1-(2,2-dimethylpropyl)-3-methyl-2-oxo-2,3-dihydro-1H-imidazo[4,5-b]pyridin-5-yl]-2,2-dimethyl-cyclohexyl}acetamide | C30H37N5O2 [M + H] calc 500.3021 obs 500.3027 |
| 18-108 | 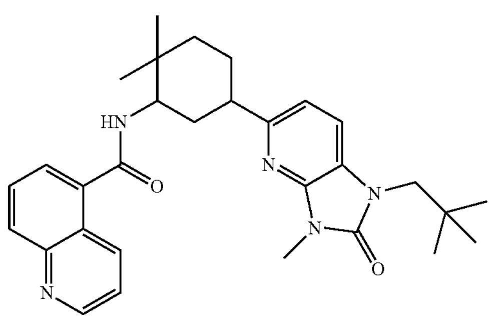 | N-{5-[1-(2,2-dimethylpropyl)-3-methyl-2-oxo-2,3-dihydro-1H-imidazo[4,5-b]pyridin-5-yl]-2,2-dimethyl-cyclohexyl}quinoline-5-carboxamide | C24H30N4O2 [M + H] calc 407.2443 obs 407.2442 |
| 18-109 | 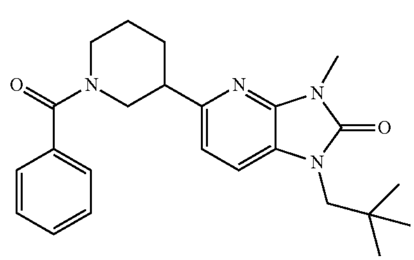 | 1-(2,2-dimethylpropyl)-3-methyl-5-[1-(phenyl-carbonyl)piperidin-3-yl]-1,3-dihydro-2H-imidazo[4,5-b]pyridin-2-one | C22H34N4O3 [M + H] calc 403.2704 obs 403.2713 |

TABLE 7-continued

| # | Structure | Name | HRMS/LRMS |
|---|---|---|---|
| 18-110 | 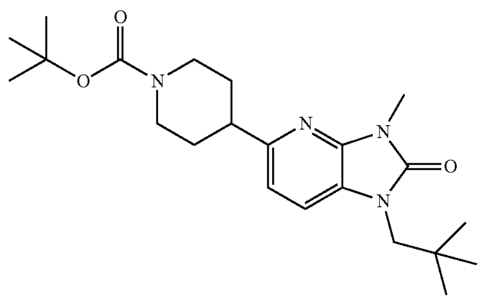 | tert-butyl 4-[1-(2,2-dimethylpropyl)-3-methyl-2-oxo-2,3-dihydro-1H-imidazo[4,5-b]pyridin-5-yl]piperidine-1-carboxylate | C29H38N6O2 [M + H] calc 503.313 obs 503.3137 |
| 18-111 | 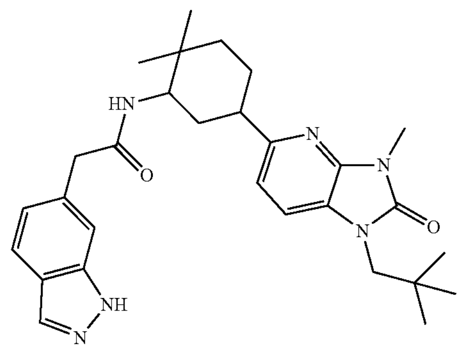 | N-{5-[1-(2,2-dimethylpropyl)-3-methyl-2-oxo-2,3-dihydro-1H-imidazo[4,5-b]pyridin-5-yl]-2,2-dimethylcyclohexyl}-2-(1H-indazol-6-yl)acetamide | C29H37N7O2 [M + H] calc 516.3083 obs 516.3087 |
| 18-112 | 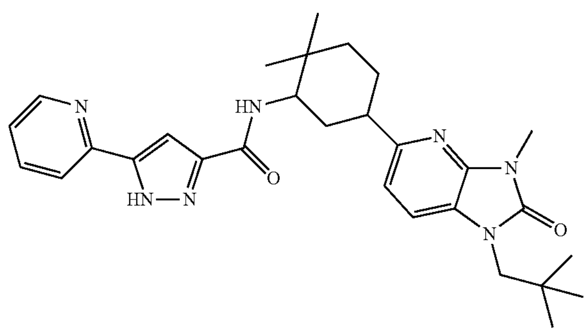 | N-{5-[1-(2,2-dimethylpropyl)-3-methyl-2-oxo-2,3-dihydro-1H-imidazo[4,5-b]pyridin-5-yl]-2,2-dimethylcyclohexyl}-5-pyridin-2-yl-1H-pyrazole-3-carboxamide | C28H36N6O2 [M + H] calc 489.2974 obs 489.2970 |
| 18-113 | 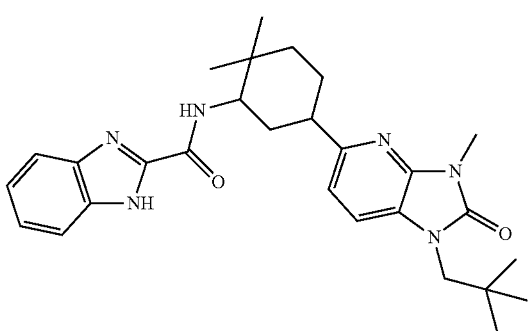 | N-{5-[1-(2,2-dimethylpropyl)-3-methyl-2-oxo-2,3-dihydro-1H-imidazo[4,5-b]pyridin-5-yl]-2,2-dimethylcyclohexyl}-1H-benzimidazole-2-carboxamide | C22H34N4O3 [M + H] calc 403.2704 obs 403.2699 |
| 18-114 | 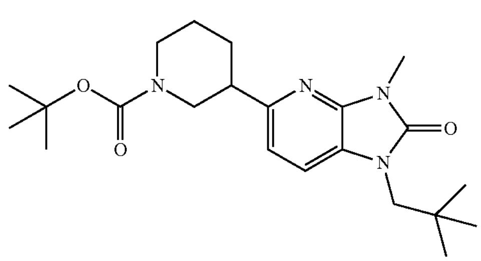 [SMILES: Cn1c(=O)n(CC(C)(C)C)c2ccc(C3CCCN(C(=O)OC(C)(C)C)C3)nc21] | tert-butyl 3-[1-(2,2-dimethylpropyl)-3-methyl-2-oxo-2,3-dihydro-1H-imidazo[4,5-b]pyridin-5-yl]piperidine-1-carboxylate | C22H34N4O3 [M + H] calc 403.2704 obs 403.2699 |

| # | Structure | Name | HRMS/LRMS |
|---|---|---|---|
| 18-115 | 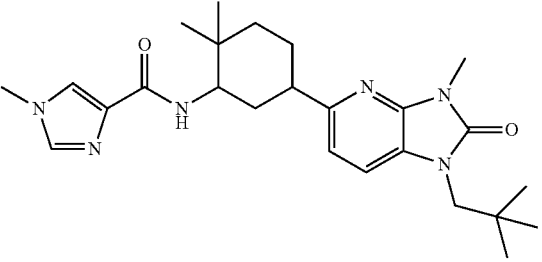 [SMILES: Cn1cnc(C(=O)NC2CC(c3ccc4c(n3)n(C)c(=O)n4CC(C)(C)C)CCC2(C)C)c1] | N-{5-[1-(2,2-dimethylpropyl)-3-methyl-2-oxo-2,3-dihydro-1H-imidazo[4,5-b]pyridin-5-yl]-2,2-dimethylcyclohexyl}-1-methyl-1H-imidazole-4-carboxamide | C25H36N6O2 [M + H] calc 453.2974 obs 453.2986 |
| 18-116 | 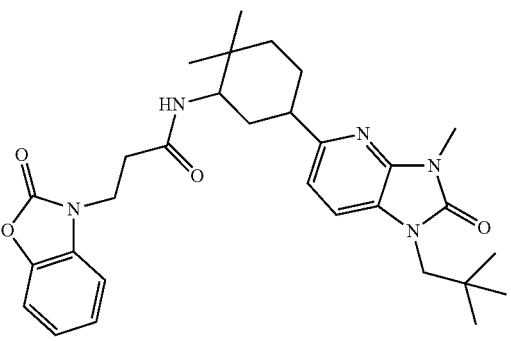 [SMILES: Cn1c(=O)n(CC(C)(C)C)c2ccc(C3CCC(C)(C)C(NC(=O)CCn4c(=O)oc5ccccc54)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-3-(2-oxo-1,3-benzoxazol-3(2H)-yl)propanamide | C30H39N5O4 [M + H] calc 534.3075 obs 534.3075 |
| 18-117 | 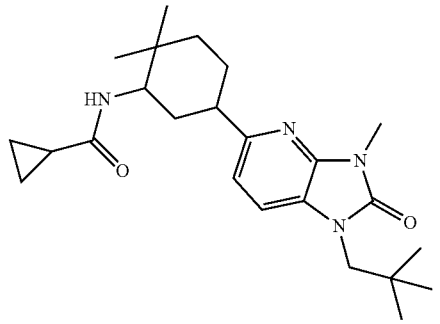 [SMILES: Cn1c(=O)n(CC(C)(C)C)c2ccc(C3CCC(C)(C)C(NC(=O)C4CC4)C3)nc21] | N-{5-[1-(2,2-dimethylpropyl)-3-methyl-2-oxo-2,3-dihydro-1H-imidazo[4,5-b]pyridin-5-yl]-2,2-dimethyl-cyclohexyl}cyclo-propanecarboxamide | C24H36N4O2 [M + H] calc 413.2912 obs 413.2911 |
| 18-118 | 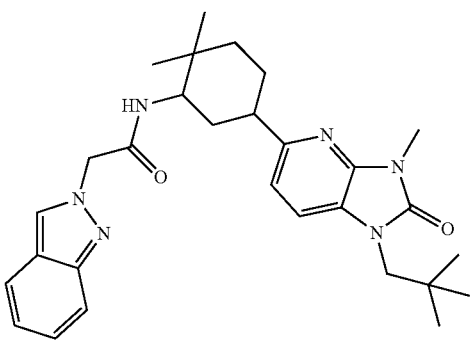 [SMILES: Cn1c(=O)n(CC(C)(C)C)c2ccc(C3CCC(C)(C)C(NC(=O)Cn4cc5ccccc5n4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-2-(2H-indazol-2-yl)acetamide | C29H38N6O2 [M + H] calc 503.313 obs 503.3137 |
| 18-119 | 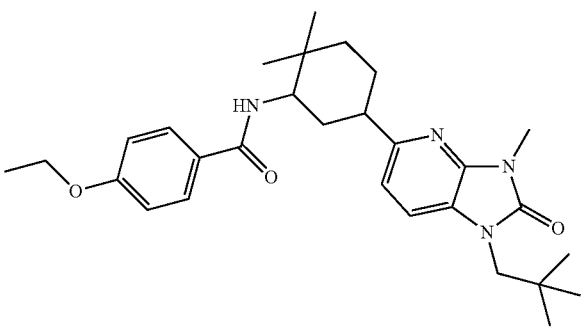 [SMILES: CCOc1ccc(C(=O)NC2CC(c3ccc4c(n3)n(C)c(=O)n4CC(C)(C)C)CCC2(C)C)cc1] | N-{5-[1-(2,2-dimethylpropyl)-3-methyl-2-oxo-2,3-dihydro-1H-imidazo[4,5-b]pyridin-5-yl]-2,2-dimethylcyclohexyl}-4-ethoxybenzamide | C29H40N4O3 [M + H] calc 493.3173 obs 493.3169 |

TABLE 7-continued

| # | Structure | Name | HRMS/LRMS |
|---|-----------|------|-----------|
| 18-120 | 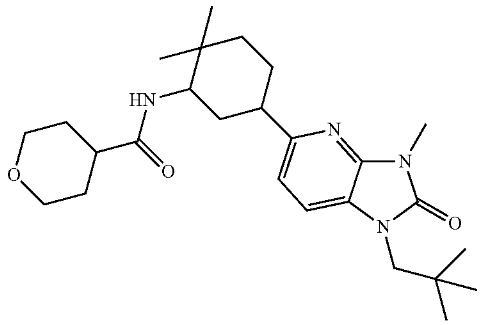 [SMILES: Cn1c(=O)n(CC(C)(C)C)c2ccc(C3CCC(C)(C)C(NC(=O)C4CCOCC4)C3)nc21] | N-{5-[1-(2,2-dimethylpropyl)-3-methyl-2-oxo-2,3-dihydro-1H-imidazo[4,5-b]pyridin-5-yl]-2,2-dimethyl-cyclohexyl}tetrahydro-2H-pyran-4-carboxamide | C26H40N4O3 [M + H] calc 457.3173 obs 457.3181 |
| 18-121 | 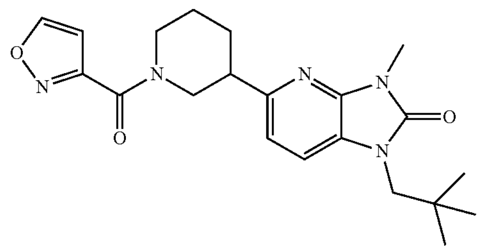 [SMILES: Cn1c(=O)n(CC(C)(C)C)c2ccc(C3CCCN(C(=O)c4ccon4)C3)nc21] | 1-(2,2-dimethylpropyl)-5-[1-(isoxazol-3-ylcarbonyl)piperidin-3-yl]-3-methyl-1,3-dihydro-2H-imidazo[4,5-b]pyridin-2-one | C21H27N5O3 [M + H] calc 398.2188 obs 398.2183 |
| 18-122 | 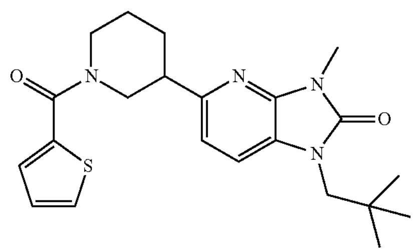 [SMILES: Cn1c(=O)n(CC(C)(C)C)c2ccc(C3CCCN(C(=O)c4cccs4)C3)nc21] | 1-(2,2-dimethylpropyl)-3-methyl-5-[1-(thiophen-2-ylcarbonyl)piperidin-3-yl]-1,3-dihydro-2H-imidazo[4,5-b]pyridin-2-one | C22H28N4O2S [M + H] calc 413.2007 obs 413.2004 |
| 18-123 | 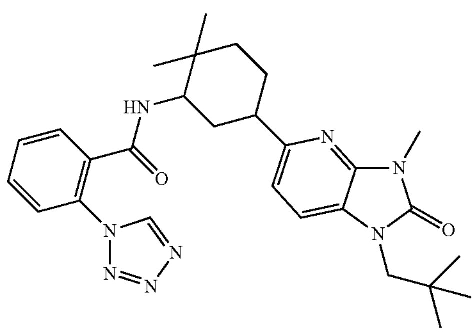 [SMILES: Cn1c(=O)n(CC(C)(C)C)c2ccc(C3CCC(C)(C)C(NC(=O)c4ccccc4-n4cnnn4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-2-(1H-tetrazol-1-yl)benzamide | C28H36N8O2 [M + H] calc 517.3035 obs 517.3031 |
| 18-124 | 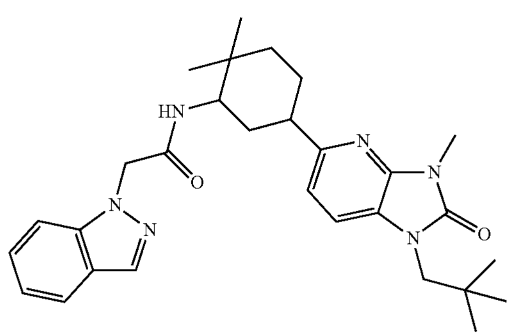 [SMILES: Cn1c(=O)n(CC(C)(C)C)c2ccc(C3CCC(C)(C)C(NC(=O)Cn4ncc5ccccc54)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-2-(1H-indazol-1-yl)acetamide | C29H38N6O2 [M + H] calc 503.313 obs 503.3137 |

TABLE 7-continued

| # | Structure | Name | HRMS/LRMS |
|---|-----------|------|-----------|
| 18-125 | 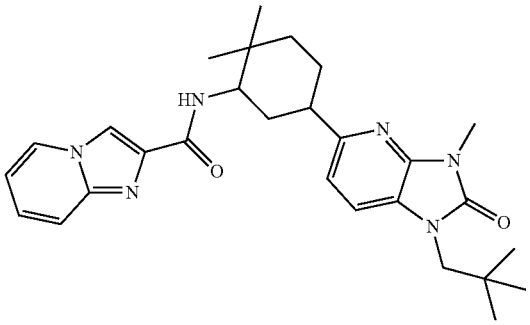 [SMILES: Cn1c(=O)n(CC(C)(C)C)c2ccc(C3CCC(C)(C)C(NC(=O)c4cn5ccccc5n4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}imidazo[1,2-a]pyridine-2-carboxamide | C28H36N6O2 [M + H] calc 489.2974 obs 489.2981 |
| 18-126 | 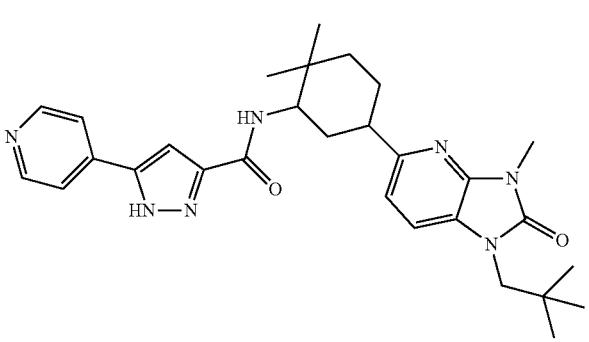 [SMILES: Cn1c(=O)n(CC(C)(C)C)c2ccc(C3CCC(C)(C)C(NC(=O)c4cc(-c5ccncc5)[nH]n4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-5-pyridin-4-yl-1H-pyrazole-3-carboxamide | C29H37N7O2 [M + H] calc 516.3083 obs 516.3088 |
| 18-127 | 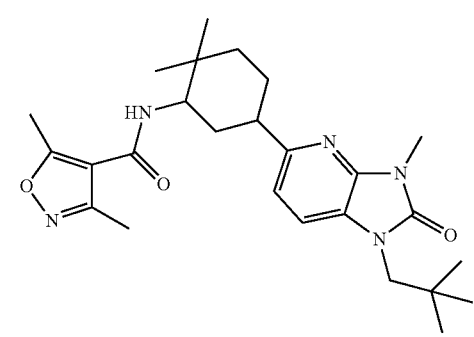 [SMILES: Cc1noc(C)c1C(=O)NC1CC(c2ccc3c(n2)n(C)c(=O)n3CC(C)(C)C)CCC1(C)C] | N-{5-[1-(2,2-dimethylpropyl)-3-methyl-2-oxo-2,3-dihydro-1H-imidazo[4,5-b]pyridin-5-yl]-2,2-dimethylcyclohexyl}-3,5-dimethylisoxazole-4-carboxamide | C26H37N5O3 [M + H] calc 468.297 obs 468.2968 |
| 18-128 | 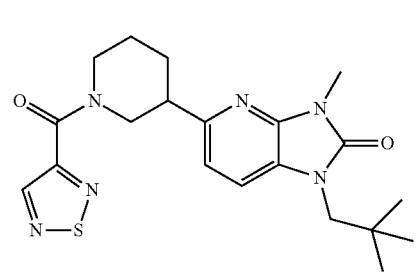 [SMILES: Cn1c(=O)n(CC(C)(C)C)c2ccc(C3CCCN(C(=O)c4cnsn4)C3)nc21] | 1-(2,2-dimethylpropyl)-3-methyl-5-[1-(1,2,5-thiadiazol-3-ylcarbonyl)piperidin-3-yl]-1,3-dihydro-2H-imidazo[4,5-b]pyridin-2-one | C20H26N6O2S [M + H] calc 415.1913 obs 415.1907 |
| 18-129 | 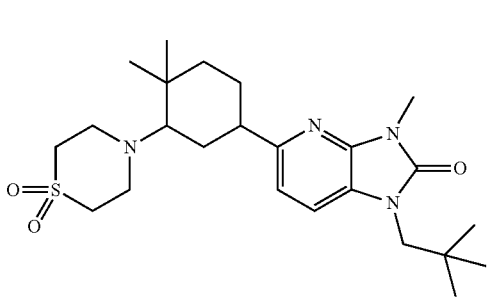 [SMILES: Cn1c(=O)n(CC(C)(C)C)c2ccc(C3CCC(C)(C)C(N4CCS(=O)(=O)CC4)C3)nc21] | 1-(2,2-dimethylpropyl)-5-[3-(1,1-dioxidothiomorpholin-4-yl)-4,4-dimethylcyclohexyl]-3-methyl-1,3-dihydro-2H-imidazo[4,5-b]pyridin-2-one | C24H38N4O3S [M + H] calc 463.2738 obs 463.2734 |

TABLE 7-continued

| # | Structure | Name | HRMS/LRMS |
|---|---|---|---|
| 18-130 | 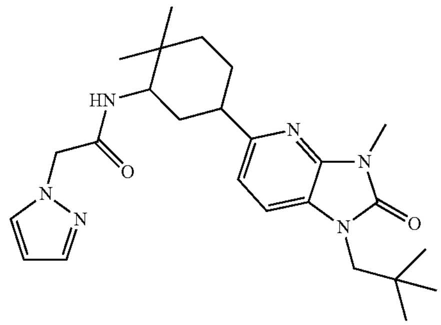 [SMILES: Cn1c(=O)n(CC(C)(C)C)c2ccc(C3CCC(C)(C)C(NC(=O)Cn4cccn4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-2-(1H-pyrazol-1-yl)acetamide | C25H36N6O2 [M + H] calc 453.2974 obs 453.2979 |
| 18-131 | 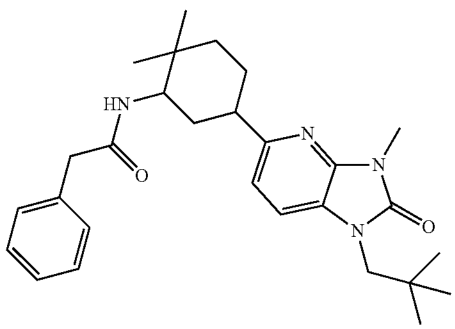 [SMILES: Cn1c(=O)n(CC(C)(C)C)c2ccc(C3CCC(C)(C)C(NC(=O)Cc4ccccc4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-2-phenylacetamide | C28H38N4O2 [M + H] calc 463.3068 obs 463.3068 |
| 18-132 | 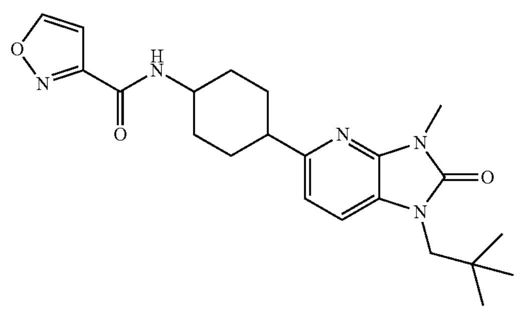 [SMILES: Cn1c(=O)n(CC(C)(C)C)c2ccc(C3CCC(NC(=O)c4ccon4)CC3)nc21] | N-{4-[1-(2,2-dimethylpropyl)-3-methyl-2-oxo-2,3-dihydro-1H-imidazo[4,5-b]pyridin-5-yl]cyclohexyl}isoxazole-3-carboxamide | C22H29N5O3 [M + H] calc 412.2345 obs 412.2344 |
| 18-133 | 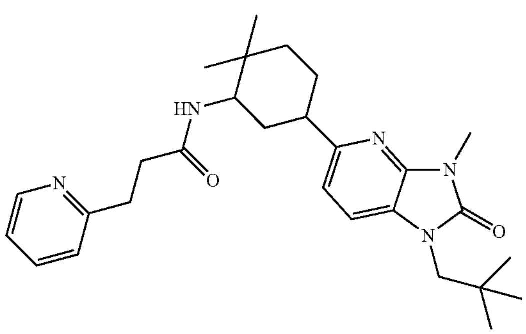 [SMILES: Cn1c(=O)n(CC(C)(C)C)c2ccc(C3CCC(C)(C)C(NC(=O)CCc4ccccn4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-3-pyridin-2-ylpropanamide | C28H39N5O2 [M + H] calc 478.3177 obs 478.3182 |
| 18-134 | 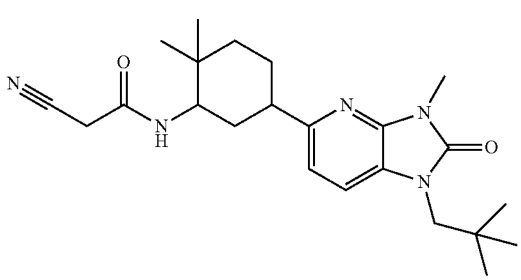 [SMILES: Cn1c(=O)n(CC(C)(C)C)c2ccc(C3CCC(C)(C)C(NC(=O)CC#N)C3)nc21] | 2-cyano-N-{5-[1-(2,2-dimethylpropyl)-3-methyl-2-oxo-2,3-dihydro-1H-imidazo[4,5-b]pyridin-5-yl]-2,2-dimethylcyclohexyl}acetamide | C23H33N5O2 [M + H] calc 412.2708 obs 412.2709 |

TABLE 7-continued

| # | Structure | Name | HRMS/LRMS |
|---|---|---|---|
| 18-135 | 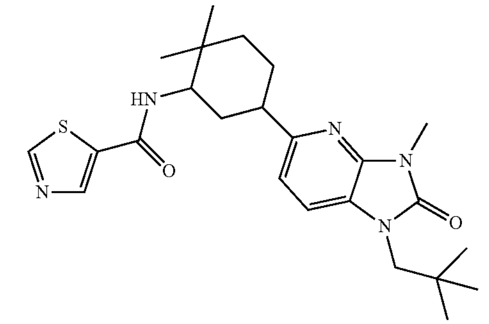 [SMILES: Cn1c(=O)n(CC(C)(C)C)c2ccc(C3CCC(C)(C)C(NC(=O)c4cncs4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-1,3-thiazole-5-carboxamide | C24H33N5O2S [M + H] calc 456.2429 obs 456.2430 |
| 18-136 | 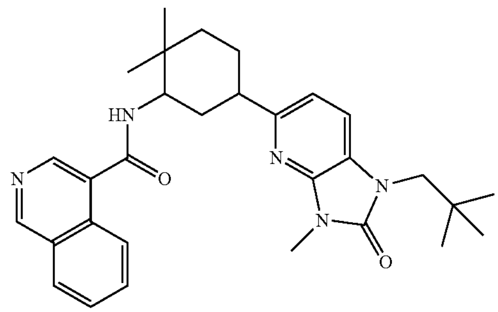 [SMILES: Cn1c(=O)n(CC(C)(C)C)c2ccc(C3CCC(C)(C)C(NC(=O)c4cncc5ccccc45)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}isoquinoline-4-carboxamide | C30H37N5O2 [M + H] calc 500.3021 obs 500.3024 |
| 18-137 | 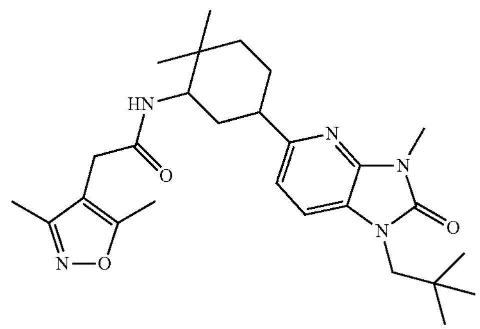 [SMILES: Cc1noc(C)c1CC(=O)NC1CC(c2ccc3c(n2)n(C)c(=O)n3CC(C)(C)C)CCC1(C)C] | 2-(3,5-dimethylisoxazol-4-yl)-N-{5-[1-(2,2-dimethylpropyl)-3-methyl-2-oxo-2,3-dihydro-1H-imidazo[4,5-b]pyridin-5-yl]-2,2-dimethylcyclohexyl}acetamide | C27H39N5O3 [M + H] calc 482.3126 obs 482.3131 |
| 18-138 | 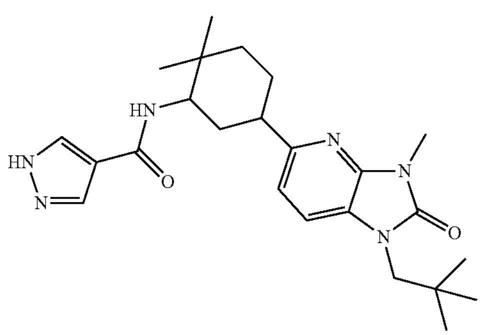 [SMILES: Cn1c(=O)n(CC(C)(C)C)c2ccc(C3CCC(C)(C)C(NC(=O)c4cn[nH]c4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-1H-pyrazole-4-carboxamide | C24H34N6O2 [M + H] calc 439.2817 obs 439.2823 |
| 18-139 | 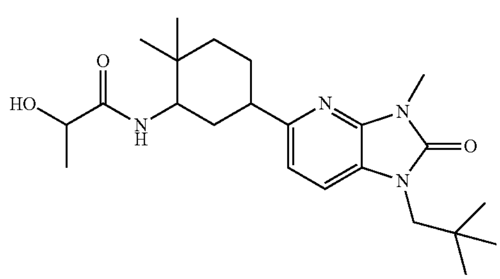 [SMILES: CC(O)C(=O)NC1CC(c2ccc3c(n2)n(C)c(=O)n3CC(C)(C)C)CCC1(C)C] | N-{5-[1-(2,2-dimethylpropyl)-3-methyl-2-oxo-2,3-dihydro-1H-imidazo[4,5-b]pyridin-5-yl]-2,2-dimethylcyclohexyl}-2-hydroxypropanamide | C23H36N4O3 [M + H] calc 417.2861 obs 417.2857 |

TABLE 7-continued

| # | Structure | Name | HRMS/LRMS |
|---|---|---|---|
| 18-140 | 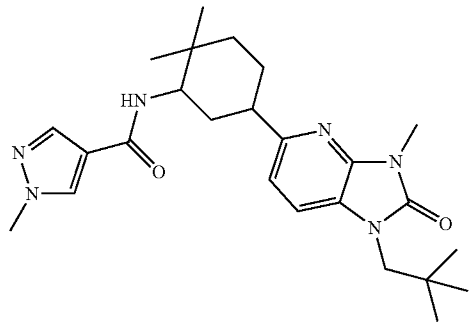 [SMILES: Cn1cc(C(=O)NC2CC(c3ccc4c(n3)n(C)c(=O)n4CC(C)(C)C)CCC2(C)C)cn1] | N-{5-[1-(2,2-dimethylpropyl)-3-methyl-2-oxo-2,3-dihydro-1H-imidazo[4,5-b]pyridin-5-yl]-2,2-dimethylcyclohexyl}-1-methyl-1H-pyrazole-4-carboxamide | C25H36N6O2 [M + H] calc 453.2974 obs 453.2981 |
| 18-141 | 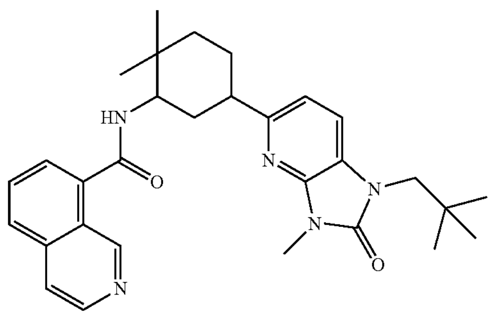 [SMILES: Cn1c(=O)n(CC(C)(C)C)c2ccc(C3CCC(C)(C)C(NC(=O)c4cccc5ccncc45)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}isoquinoline-8-carboxamide | C30H37N5O2 [M + H] calc 500.3021 obs 500.3028 |
| 18-142 | 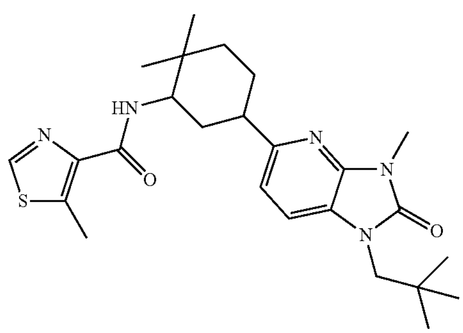 [SMILES: Cc1scnc1C(=O)NC1CC(c2ccc3c(n2)n(C)c(=O)n3CC(C)(C)C)CCC1(C)C] | N-{5-[1-(2,2-dimethylpropyl)-3-methyl-2-oxo-2,3-dihydro-1H-imidazo[4,5-b]pyridin-5-yl]-2,2-dimethylcyclohexyl}-5-methyl-1,3-thiazole-4-carboxamide | C25H35N5O2S [M + H] calc 470.2585 obs 470.2586 |
| 18-143 | 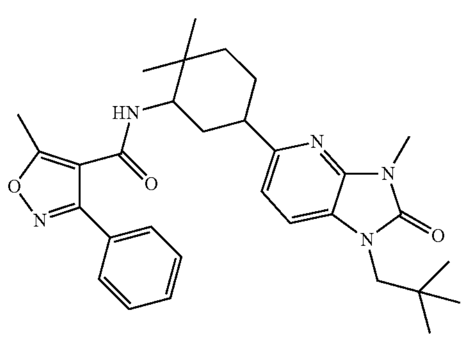 [SMILES: Cc1onc(-c2ccccc2)c1C(=O)NC1CC(c2ccc3c(n2)n(C)c(=O)n3CC(C)(C)C)CCC1(C)C] | N-{5-[1-(2,2-dimethylpropyl)-3-methyl-2-oxo-2,3-dihydro-1H-imidazo[4,5-b]pyridin-5-yl]-2,2-dimethylcyclohexyl}-5-methyl-3-phenylisoxazole-4-carboxamide | C31H39N5O3 [M + H] calc 530.3126 obs 530.3126 |

TABLE 7-continued

| # | Structure | Name | HRMS/LRMS |
|---|---|---|---|
| 18-144 | 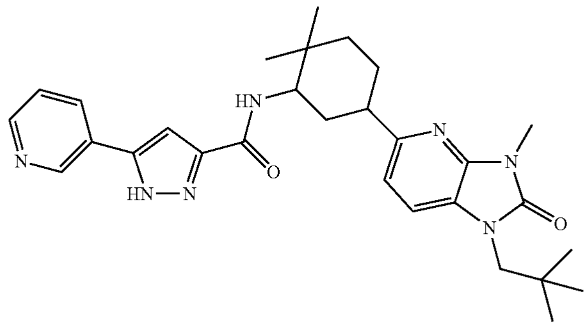 [SMILES: Cn1c(=O)n(CC(C)(C)C)c2ccc(C3CCC(C)(C)C(NC(=O)c4cc(-c5cccnc5)[nH]n4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-5-pyridin-3-yl-1H-pyrazole-3-carboxamide | C29H37N7O2 [M + H] calc 516.3083 obs 516.3089 |
| 18-145 | 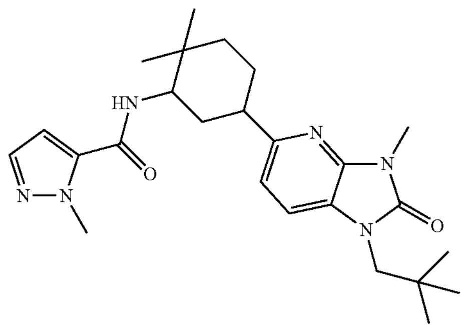 [SMILES: Cn1nccc1C(=O)NC1CC(c2ccc3c(n2)n(C)c(=O)n3CC(C)(C)C)CCC1(C)C] | N-{5-[1-(2,2-dimethylpropyl)-3-methyl-2-oxo-2,3-dihydro-1H-imidazo[4,5-b]pyridin-5-yl]-2,2-dimethylcyclohexyl}-1-methyl-1H-pyrazole-5-carboxamide | C25H36N6O2 [M + H] calc 453.2974 obs 453.2974 |
| 18-146 | 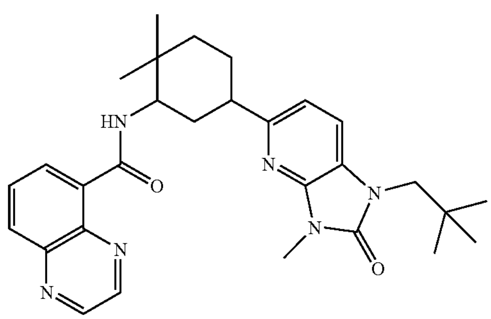 [SMILES: Cn1c(=O)n(CC(C)(C)C)c2ccc(C3CCC(C)(C)C(NC(=O)c4cccc5nccnc45)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}quinoxaline-5-carboxamide | C29H36N6O2 [M + H] calc 501.2974 obs 501.2976 |
| 18-147 | 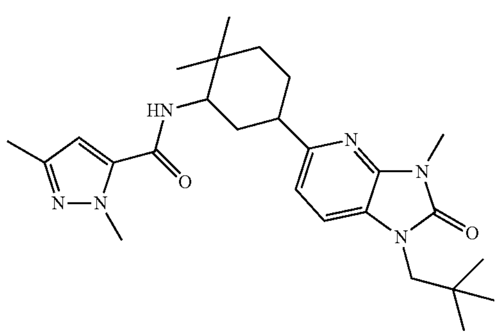 [SMILES: Cc1cc(C(=O)NC2CC(c3ccc4c(n3)n(C)c(=O)n4CC(C)(C)C)CCC2(C)C)n(C)n1] | N-{5-[1-(2,2-dimethylpropyl)-3-methyl-2-oxo-2,3-dihydro-1H-imidazo[4,5-b]pyridin-5-yl]-2,2-dimethylcyclohexyl}-1,3-dimethyl-1H-pyrazole-5-carboxamide | C26H38N6O2 [M + H] calc 467.313 obs 467.3130 |

TABLE 7-continued

| # | Structure | Name | HRMS/LRMS |
|---|---|---|---|
| 18-148 | 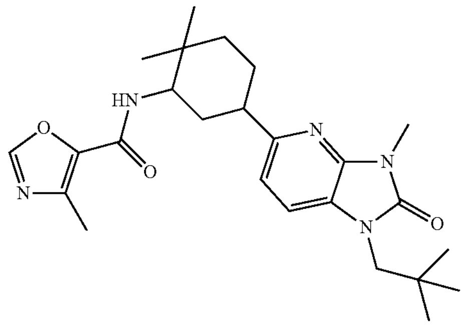 [SMILES: Cc1ncoc1C(=O)NC1CC(c2ccc3c(n2)n(C)c(=O)n3CC(C)(C)C)CCC1(C)C] | N-{5-[1-(2,2-dimethylpropyl)-3-methyl-2-oxo-2,3-dihydro-1H-imidazo[4,5-b]pyridin-5-yl]-2,2-dimethylcyclohexyl}-4-methyl-1,3-oxazole-5-carboxamide | C25H35N5O3 [M + H] calc 454.2814 obs 454.2821 |
| 18-149 | 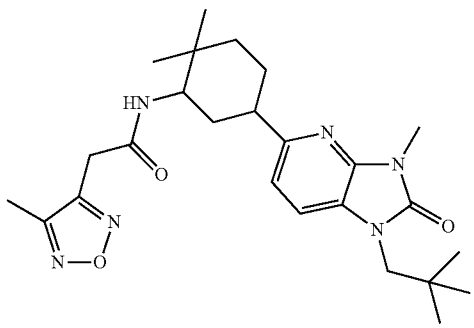 [SMILES: Cc1nonc1CC(=O)NC1CC(c2ccc3c(n2)n(C)c(=O)n3CC(C)(C)C)CCC1(C)C] | N-{5-[1-(2,2-dimethylpropyl)-3-methyl-2-oxo-2,3-dihydro-1H-imidazo[4,5-b]pyridin-5-yl]-2,2-dimethylcyclohexyl}-2-(4-methyl-1,2,5-oxadiazol-3-yl)acetamide | C25H36N6O3 [M + H] calc 469.2923 obs 469.2925 |
| 18-150 | 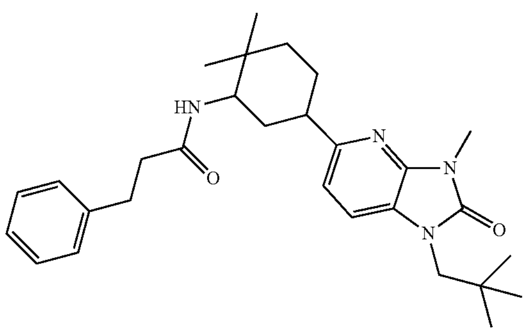 [SMILES: Cn1c(=O)n(CC(C)(C)C)c2ccc(C3CCC(C)(C)C(NC(=O)CCc4ccccc4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-3-phenylpropanamide | C29H40N4O2 [M + H] calc 477.3224 obs 477.3225 |
| 18-151 | 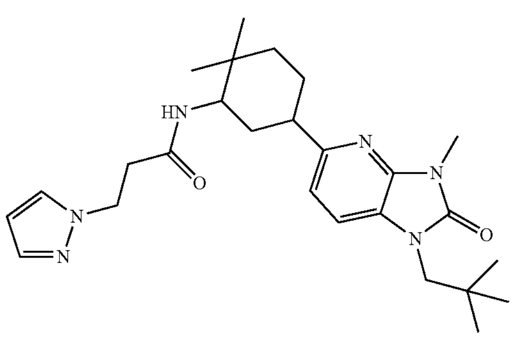 [SMILES: Cn1c(=O)n(CC(C)(C)C)c2ccc(C3CCC(C)(C)C(NC(=O)CCn4cccn4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-3-(1H-pyrazol-1-yl)propanamide | C26H38N6O2 [M + H] calc 467.313 obs 467.3135 |

TABLE 7-continued

| # | Structure | Name | HRMS/LRMS |
|---|---|---|---|
| 18-152 | 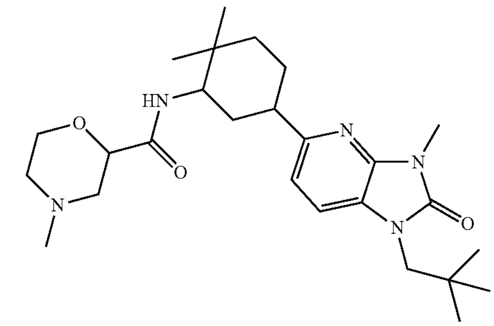 [SMILES: CN1CCOC(C(=O)NC2CC(c3ccc4c(n3)n(C)c(=O)n4CC(C)(C)C)CCC2(C)C)C1] | N-{5-[1-(2,2-dimethylpropyl)-3-methyl-2-oxo-2,3-dihydro-1H-imidazo[4,5-b]pyridin-5-yl]-2,2-dimethylcyclohexyl}-4-methylmorpholine-2-carboxamide | C26H41N5O3 [M + H] calc 472.3282 obs 472.3282 |
| 18-153 | 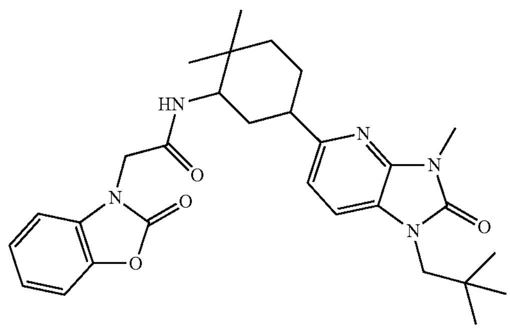 [SMILES: Cn1c(=O)n(CC(C)(C)C)c2ccc(C3CCC(C)(C)C(NC(=O)Cn4c(=O)oc5ccccc54)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-2-(2-oxo-1,3-benzoxazol-3(2H)-yl)acetamide | C29H37N5O4 [M + H] calc 520.2919 obs 520.2913 |
| 18-154 | 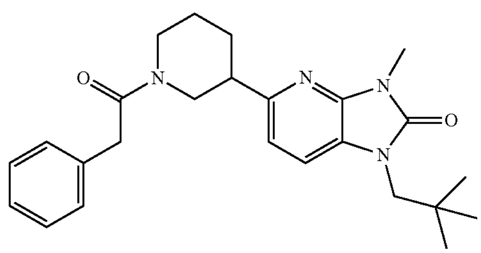 [SMILES: Cn1c(=O)n(CC(C)(C)C)c2ccc(C3CCCN(C(=O)Cc4ccccc4)C3)nc21] | 1-(2,2-dimethylpropyl)-3-methyl-5-[1-(phenylacetyl)piperidin-3-yl]-1,3-dihydro-2H-imidazo[4,5-b]pyridin-2-one | C25H32N4O2 [M + H] calc 421.2599 obs 421.2599 |
| 18-155 | 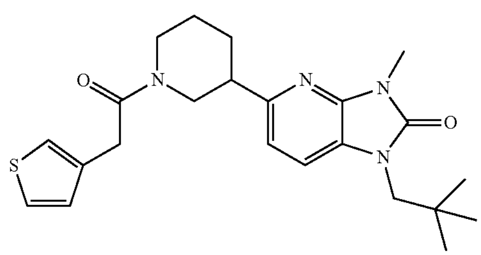 [SMILES: Cn1c(=O)n(CC(C)(C)C)c2ccc(C3CCCN(C(=O)Cc4ccsc4)C3)nc21] | 1-(2,2-dimethylpropyl)-3-methyl-5-[1-(thiophen-3-ylacetyl)piperidin-3-yl]-1,3-dihydro-2H-imidazo[4,5-b]pyridin-2-one | C23H30N4O2S [M + H] calc 427.2164 obs 427.2157 |
| 18-156 | 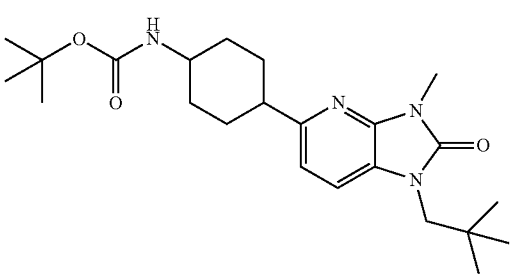 [SMILES: Cn1c(=O)n(CC(C)(C)C)c2ccc(C3CCC(NC(=O)OC(C)(C)C)CC3)nc21] | tert-butyl {4-[1-(2,2-dimethylpropyl)-3-methyl-2-oxo-2,3-dihydro-1H-imidazo[4,5-b]pyridin-5-yl]cyclohexyl}carbamate | C23H36N4O3 [M + H] calc 417.2861 obs 417.2864 |

TABLE 7-continued

| # | Structure | Name | HRMS/LRMS |
|---|---|---|---|
| 18-157 | 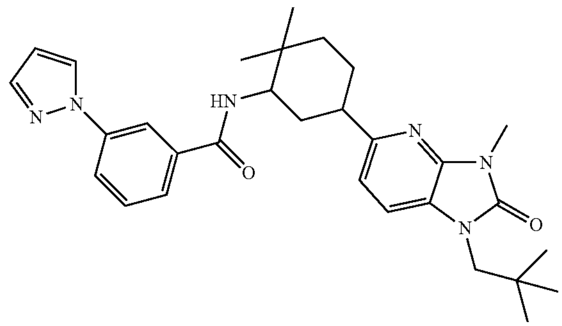 [SMILES: Cn1c(=O)n(CC(C)(C)C)c2ccc(C3CCC(C)(C)C(NC(=O)c4cccc(-n5cccn5)c4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-3-(1H-pyrazol-1-yl)benzamide | C30H38N6O2 [M + H] calc 515.313 obs 515.3143 |
| 18-158 | 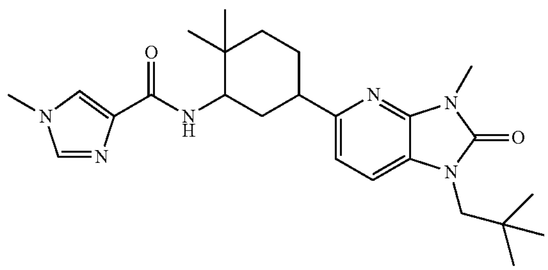 [SMILES: Cn1cnc(C(=O)NC2CC(c3ccc4c(n3)n(C)c(=O)n4CC(C)(C)C)CCC2(C)C)c1] | N-{5-[1-(2,2-dimethylpropyl)-3-methyl-2-oxo-2,3-dihydro-1H-imidazo[4,5-b]pyridin-5-yl]-2,2-dimethylcyclohexyl}-1-methyl-1H-imidazole-4-carboxamide | C25H36N6O2 [M + H] calc 453.2974 obs 453.2987 |
| 18-159 | 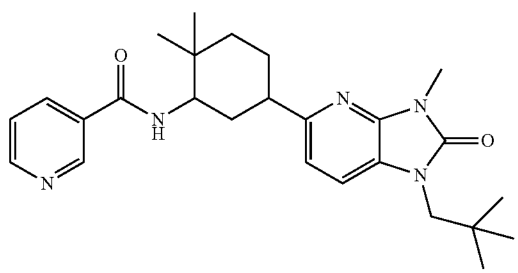 [SMILES: Cn1c(=O)n(CC(C)(C)C)c2ccc(C3CCC(C)(C)C(NC(=O)c4cccnc4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}pyridine-3-carboxamide | C26H35N5O2 [M + H] calc 450.2865 obs 450.2863 |
| 18-160 | 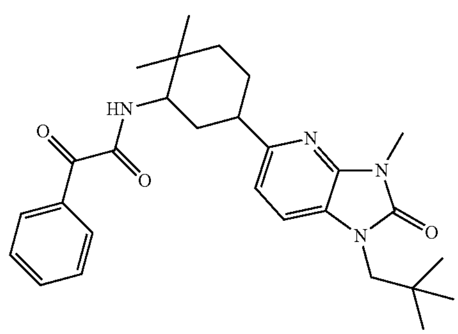 [SMILES: Cn1c(=O)n(CC(C)(C)C)c2ccc(C3CCC(C)(C)C(NC(=O)C(=O)c4ccccc4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-2-oxo-2-phenylacetamide | C28H36N4O3 [M + H] calc 477.2861 obs 477.2855 |
| 18-161 | 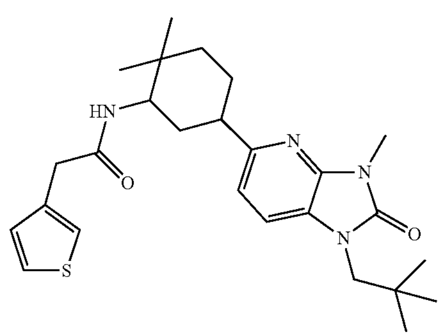 [SMILES: Cn1c(=O)n(CC(C)(C)C)c2ccc(C3CCC(C)(C)C(NC(=O)Cc4ccsc4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-2-thiophen-3-ylacetamide | C26H36N4O2S [M + H] calc 469.2633 obs 469.2639 |

TABLE 7-continued

| # | Structure | Name | HRMS/LRMS |
|---|---|---|---|
| 18-162 | 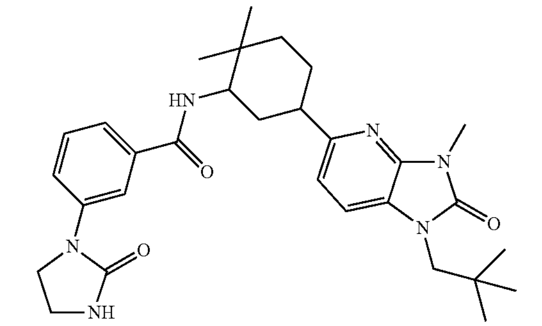 [SMILES: Cn1c(=O)n(CC(C)(C)C)c2ccc(C3CCC(C)(C)C(NC(=O)c4cccc(N5CCNC5=O)c4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-3-(2-oxoimidazolidin-1-yl)benzamide | C30H40N6O3 [M + H] calc 533.3235 obs 533.3233 |
| 18-163 | 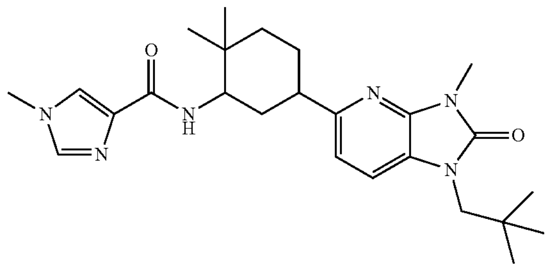 [SMILES: Cn1cnc(C(=O)NC2CC(c3ccc4c(n3)n(C)c(=O)n4CC(C)(C)C)CCC2(C)C)c1] | N-{5-[1-(2,2-dimethylpropyl)-3-methyl-2-oxo-2,3-dihydro-1H-imidazo[4,5-b]pyridin-5-yl]-2,2-dimethylcyclohexyl}-1-methyl-1H-imidazole-4-carboxamide | C25H36N6O2 [M + H] calc 453.2974 obs 453.2986 |
| 18-164 | 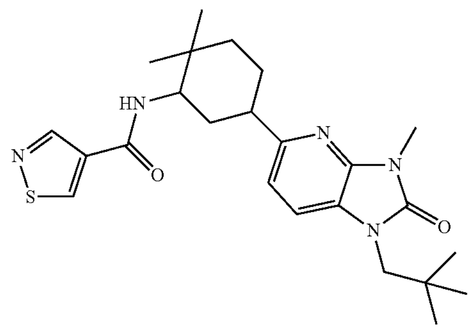 [SMILES: Cn1c(=O)n(CC(C)(C)C)c2ccc(C3CCC(C)(C)C(NC(=O)c4cnsc4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}isothiazole-4-carboxamide | C24H33N5O2S [M + H] calc 456.2429 obs 456.2434 |
| 18-165 | 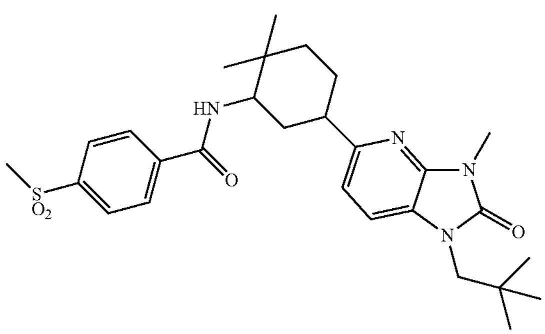 [SMILES: Cn1c(=O)n(CC(C)(C)C)c2ccc(C3CCC(C)(C)C(NC(=O)c4ccc(S(C)(=O)=O)cc4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-4-(methylsulfonyl)benzamide | C28H38N4O4S [M + H] calc 527.2687 obs 527.2680 |
| 18-166 | 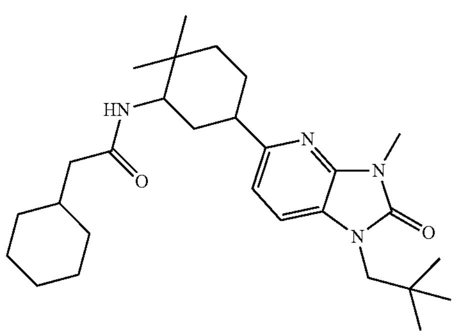 [SMILES: Cn1c(=O)n(CC(C)(C)C)c2ccc(C3CCC(C)(C)C(NC(=O)CC4CCCCC4)C3)nc21] | 2-cyclohexyl-N-{5-[1-(2,2-dimethylpropyl)-3-methyl-2-oxo-2,3-dihydro-1H-imidazo[4,5-b]pyridin-5-yl]-2,2-dimethylcyclohexyl}acetamide | C28H44N4O2 [M + H] calc 469.3537 obs 469.3545 |

TABLE 7-continued

| # | Structure | Name | HRMS/LRMS |
|---|---|---|---|
| 18-167 | 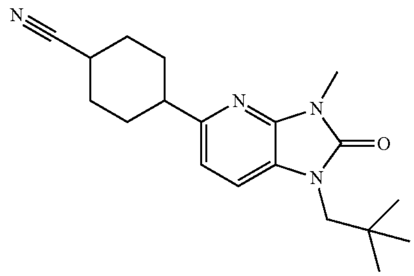 [SMILES: Cn1c(=O)n(CC(C)(C)C)c2ccc(C3CCC(C#N)CC3)nc21] | 4-[1-(2,2-dimethylpropyl)-3-methyl-2-oxo-2,3-dihydro-1H-imidazo[4,5-b]pyridin-5-yl]cyclohexanecarbonitrile | C19H26N4O [M + H] calc 327.2182 obs 327.2181 |
| 18-168 | 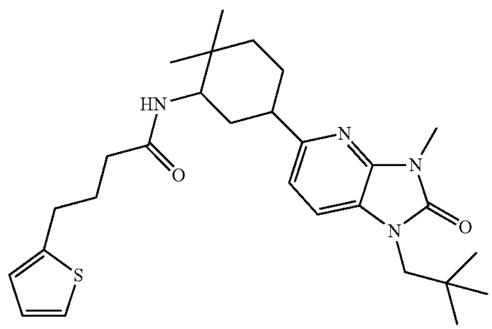 [SMILES: Cn1c(=O)n(CC(C)(C)C)c2ccc(C3CCC(C)(C)C(NC(=O)CCCc4cccs4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-4-thiophen-2-ylbutanamide | C28H40N4O2S [M + H] calc 497.2945 obs 497.2942 |
| 18-169 | 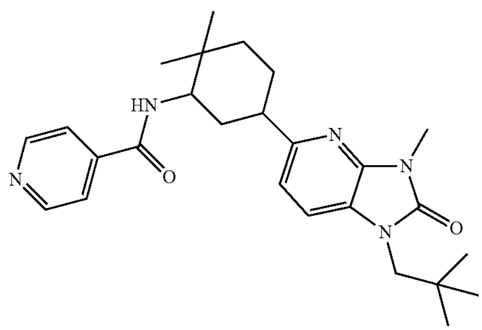 [SMILES: Cn1c(=O)n(CC(C)(C)C)c2ccc(C3CCC(C)(C)C(NC(=O)c4ccncc4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}pyridine-4-carboxamide | C26H35N5O2 [M + H] calc 450.2865 obs 450.2872 |
| 18-170 | 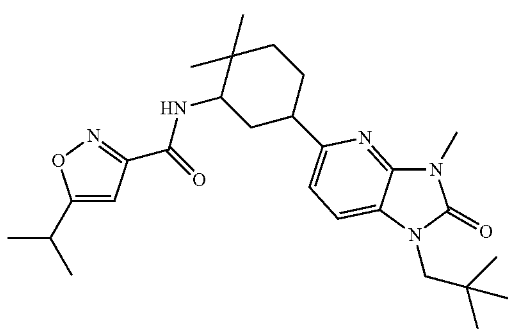 [SMILES: CC(C)c1cc(C(=O)NC2CC(c3ccc4c(n3)n(C)c(=O)n4CC(C)(C)C)CCC2(C)C)no1] | N-{5-[1-(2,2-dimethylpropyl)-3-methyl-2-oxo-2,3-dihydro-1H-imidazo[4,5-b]pyridin-5-yl]-2,2-dimethylcyclohexyl}-5-(1-methylethyl)isoxazole-3-carboxamide | C27H39N5O3 [M + H] calc 482.3126 obs 482.3128 |
| 18-171 | 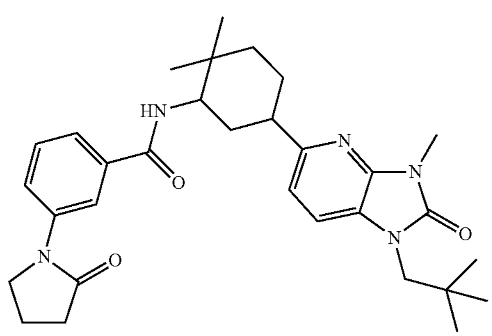 [SMILES: Cn1c(=O)n(CC(C)(C)C)c2ccc(C3CCC(C)(C)C(NC(=O)c4cccc(N5CCCC5=O)c4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-3-(2-oxopyrrolidin-1-yl)benzamide | C31H41N5O3 [M + H] calc 532.3282 obs 532.3282 |

TABLE 7-continued

| # | Structure | Name | HRMS/LRMS |
|---|---|---|---|
| 18-172 | 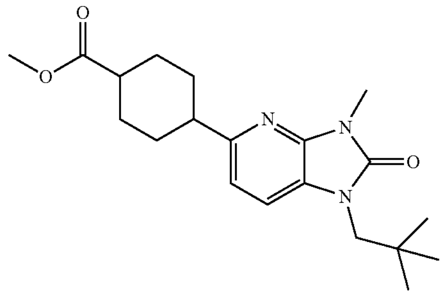 [SMILES: COC(=O)C1CCC(c2ccc3c(n2)n(C)c(=O)n3CC(C)(C)C)CC1] | methyl 4-[1-(2,2-dimethylpropyl)-3-methyl-2-oxo-2,3-dihydro-1H-imidazo[4,5-b]pyridin-5-yl]cyclohexane-carboxylate | C20H29N3O3 [M + H] calc 360.2283 obs 360.2279 |
| 18-173 | 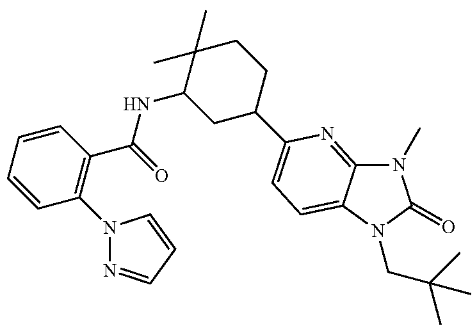 [SMILES: Cn1c(=O)n(CC(C)(C)C)c2ccc(C3CCC(C)(C)C(NC(=O)c4ccccc4-n4cccn4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-2-(1H-pyrazol-1-yl)benzamide | C30H38N6O2 [M + H] calc 515.313 obs 515.3127 |
| 18-174 | 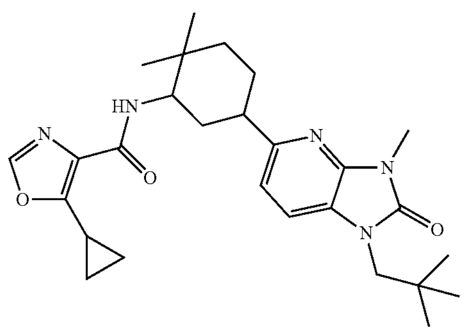 [SMILES: Cn1c(=O)n(CC(C)(C)C)c2ccc(C3CCC(C)(C)C(NC(=O)c4ncoc4C4CC4)C3)nc21] | 5-cyclopropyl-N-{5-[1-(2,2-dimethylpropyl)-3-methyl-2-oxo-2,3-dihydro-1H-imidazo[4,5-b]pyridin-5-yl]-2,2-dimethylcyclohexyl}-1,3-oxazole-4-carboxamide | C27H37N5O3 [M + H] calc 480.297 obs 480.2972 |
| 18-175 | 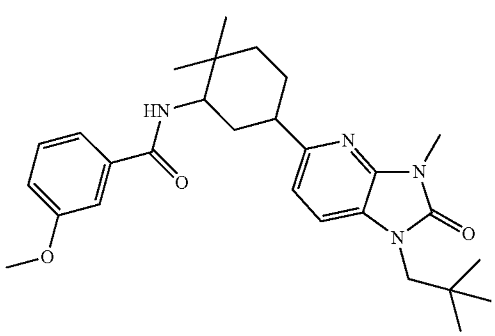 [SMILES: COc1cccc(C(=O)NC2CC(c3ccc4c(n3)n(C)c(=O)n4CC(C)(C)C)CCC2(C)C)c1] | N-{5-[1-(2,2-dimethylpropyl)-3-methyl-2-oxo-2,3-dihydro-1H-imidazo[4,5-b]pyridin-5-yl]-2,2-dimethylcyclohexyl}-3-methoxybenzamide | C28H38N4O3 [M + H] calc 479.3017 obs 479.3014 |
| 18-176 | 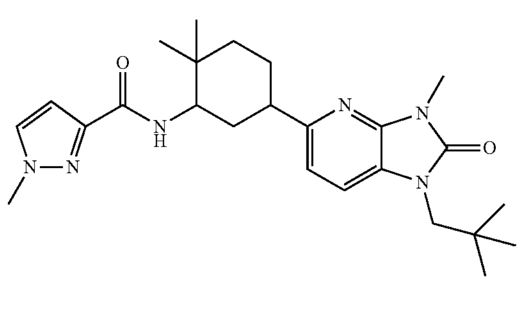 [SMILES: Cn1ccc(C(=O)NC2CC(c3ccc4c(n3)n(C)c(=O)n4CC(C)(C)C)CCC2(C)C)n1] | N-{5-[1-(2,2-dimethylpropyl)-3-methyl-2-oxo-2,3-dihydro-1H-imidazo[4,5-b]pyridin-5-yl]-2,2-dimethylcyclohexyl}-1-methyl-1H-pyrazole-3-carboxamide | C25H36N6O2 [M + H] calc 453.2974 obs 453.2980 |

TABLE 7-continued

| # | Structure | Name | HRMS/LRMS |
|---|---|---|---|
| 18-177 | 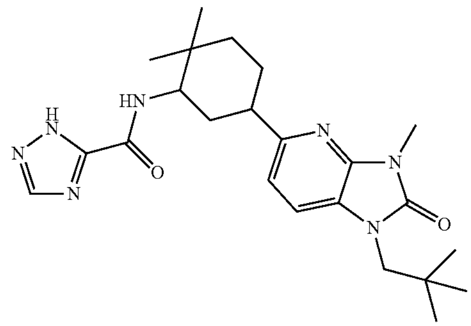 [SMILES: Cn1c(=O)n(CC(C)(C)C)c2ccc(C3CCC(C)(C)C(NC(=O)c4ncn[nH]4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-1H-1,2,4-triazole-5-carboxamide | C23H33N7O2 [M + H] calc 440.2769 obs 440.2778 |
| 18-178 | 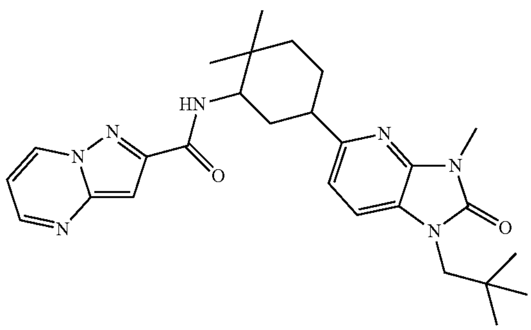 [SMILES: Cn1c(=O)n(CC(C)(C)C)c2ccc(C3CCC(C)(C)C(NC(=O)c4cc5ncccn5n4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}pyrazolo[1,5-a]pyrimidine-2-carboxamide | C27H35N7O2 [M + H] calc 490.2925 obs 490.2930 |
| 18-179 | 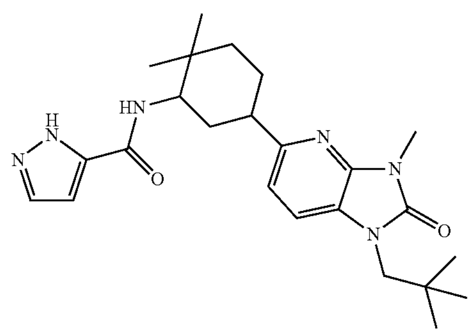 [SMILES: Cn1c(=O)n(CC(C)(C)C)c2ccc(C3CCC(C)(C)C(NC(=O)c4ccn[nH]4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-1H-pyrazole-5-carboxamide | C24H34N6O2 [M + H] calc 439.2816 obs 439.2823 |
| 18-180 | 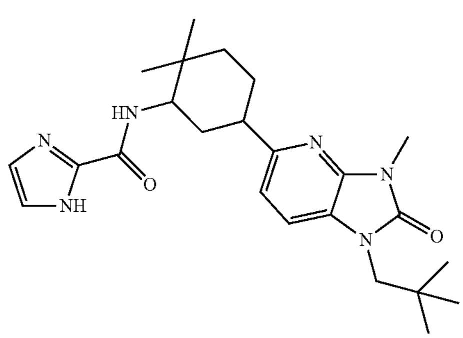 [SMILES: Cn1c(=O)n(CC(C)(C)C)c2ccc(C3CCC(C)(C)C(NC(=O)c4ncc[nH]4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-1H-imidazole-2-carboxamide | C24H34N6O2 [M + H] calc 439.2816 obs 439.2822 |

TABLE 7-continued

| # | Structure | Name | HRMS/LRMS |
|---|---|---|---|
| 18-181 | 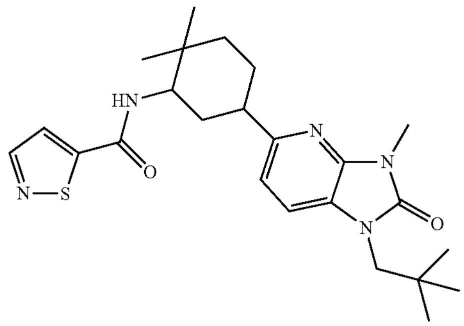 [SMILES: Cn1c(=O)n(CC(C)(C)C)c2ccc(C3CCC(C)(C)C(NC(=O)c4ccns4)C3)nc21] | N-{5-[1-(2,2-dimethylpropyl)-3-methyl-2-oxo-2,3-dihydro-1H-imidazo[4,5-b]pyridin-5-yl]-2,2-dimethyl-cyclohexyl}isothiazole-5-carboxamide | C24H33N5O2S [M + H] calc 456.3439 obs 534.3449 |
| 18-182 | 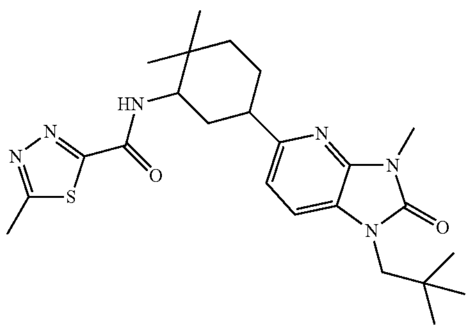 [SMILES: Cc1nnc(C(=O)NC2CC(c3ccc4c(n3)n(C)c(=O)n4CC(C)(C)C)CCC2(C)C)s1] | N-{5-[1-(2,2-dimethylpropyl)-3-methyl-2-oxo-2,3-dihydro-1H-imidazo[4,5-b]pyridin-5-yl]-2,2-dimethylcyclohexyl}-5-methyl-1,3,4-thiadiazole-2-carboxamide | C24H34N6O2S [M + H] calc 471.2537 obs 471.2542 |
| 18-183 | 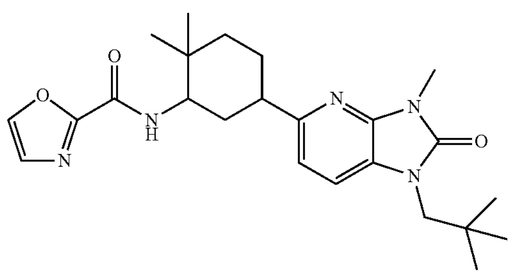 [SMILES: Cn1c(=O)n(CC(C)(C)C)c2ccc(C3CCC(C)(C)C(NC(=O)c4ncco4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-1,3-oxazole-2-carboxamide | C24H33N5O3 [M + H] calc 440.2657 obs 440.2656 |
| 18-184 | 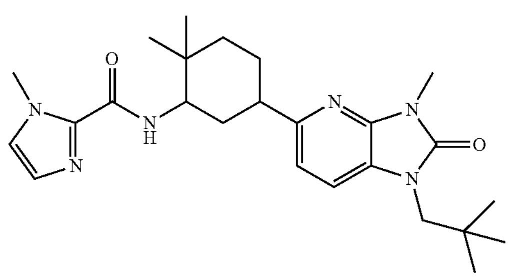 [SMILES: Cn1ccnc1C(=O)NC1CC(c2ccc3c(n2)n(C)c(=O)n3CC(C)(C)C)CCC1(C)C] | N-{5-[1-(2,2-dimethylpropyl)-3-methyl-2-oxo-2,3-dihydro-1H-imidazo[4,5-b]pyridin-5-yl]-2,2-dimethylcyclohexyl}-1-methyl-1H-imidazole-2-carboxamide | C25H36N6O2 [M + H] calc 453.2974 obs 453.2980 |
| 18-185 | 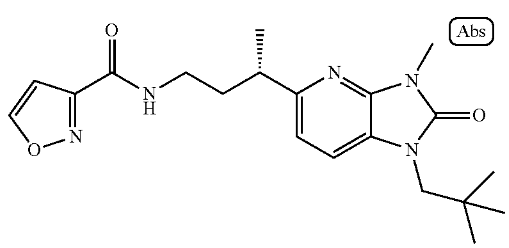 | N-{5-[1-(2,2-dimethylpropyl)-3-methyl-2-oxo-2,3-dihydro-1H-imidazo[4,5-b]pyridin-5-yl]-2,2-dimethyl-cyclohexyl}quinoline-6-carboxamide | C30H37N5O2 [M + H] calc 500.3020 obs 500.3020 |

TABLE 7-continued

| # | Structure | Name | HRMS/LRMS |
|---|-----------|------|-----------|
| 18-186 | 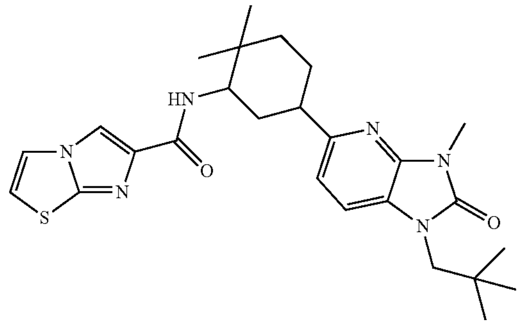 [SMILES: Cn1c(=O)n(CC(C)(C)C)c2ccc(C3CCC(C)(C)C(NC(=O)c4cn5ccsc5n4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}imidazo[2,1-b][1,3]thiazole-6-carboxamide | C26H34N6O2S [M + H] calc 495.2537 obs 495.2542 |
| 18-187 | 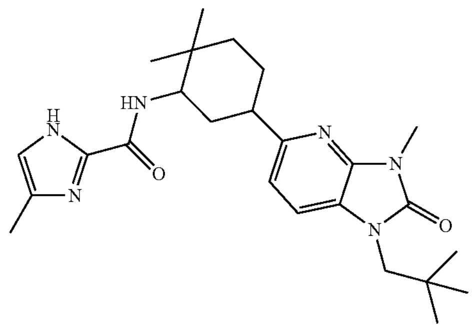 [SMILES: Cc1c[nH]c(C(=O)NC2CC(c3ccc4c(n3)n(C)c(=O)n4CC(C)(C)C)CCC2(C)C)n1] | N-{5-[1-(2,2-dimethylpropyl)-3-methyl-2-oxo-2,3-dihydro-1H-imidazo[4,5-b]pyridin-5-yl]-2,2-dimethylcyclohexyl}-4-methyl-1H-imidazole-2-carboxamide | C25H36N6O2 [M + H] calc 453.2973 obs 453.2979 |
| 18-188 | 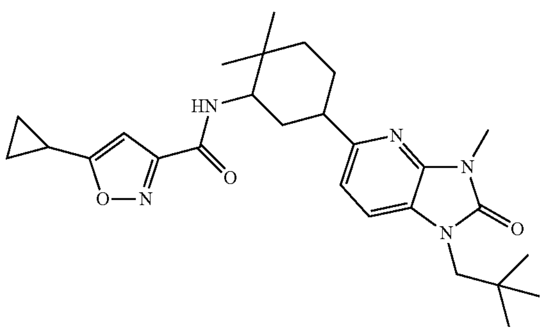 [SMILES: Cn1c(=O)n(CC(C)(C)C)c2ccc(C3CCC(C)(C)C(NC(=O)c4cc(C5CC5)on4)C3)nc21] | 5-cyclopropyl-N-{5-[1-(2,2-dimethylpropyl)-3-methyl-2-oxo-2,3-dihydro-1H-imidazo[4,5-b]pyridin-5-yl]-2,2-dimethylcyclohexyl}isoxazole-3-carboxamide | C27H37N5O3 [M + H] calc 480.2969 obs 480.2973 |
| 18-189 | 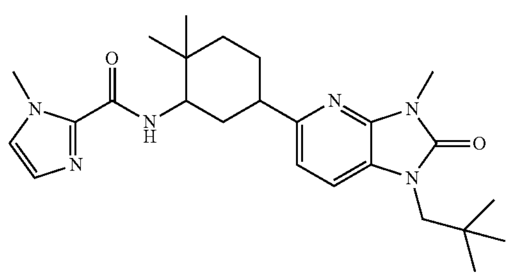 [SMILES: Cn1ccnc1C(=O)NC1CC(c2ccc3c(n2)n(C)c(=O)n3CC(C)(C)C)CCC1(C)C] | N-{5-[1-(2,2-dimethylpropyl)-3-methyl-2-oxo-2,3-dihydro-1H-imidazo[4,5-b]pyridin-5-yl]-2,2-dimethylcyclohexyl}-1-methyl-1H-imidazole-2-carboxamide | C25H36N6O2 [M + H] calc 453.2973 obs 453.2976 |
| 18-190 | 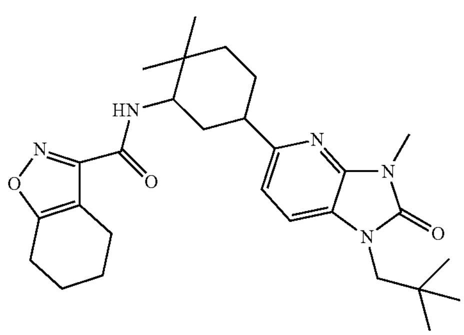 [SMILES: Cn1c(=O)n(CC(C)(C)C)c2ccc(C3CCC(C)(C)C(NC(=O)c4noc5c4CCCC5)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-4,5,6,7-tetrahydro-1,2-benzisoxazole-3-carboxamide | C28H39N5O3 [M + H] calc 494.3126 obs 494.3128 |

TABLE 7-continued

| # | Structure | Name | HRMS/LRMS |
|---|---|---|---|
| 18-191 | 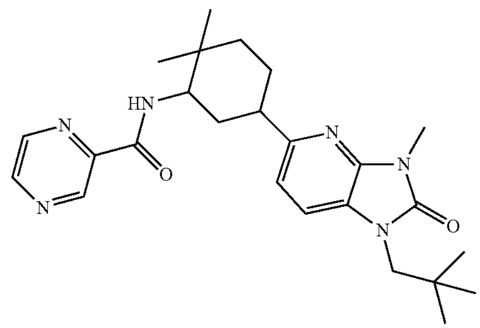 | N-{5-[1-(2,2-dimethylpropyl)-3-methyl-2-oxo-2,3-dihydro-1H-imidazo[4,5-b]pyridin-5-yl]-2,2-dimethylcyclohexyl}pyrazine-2-carboxamide | C25H34N6O2 [M + H] calc 451.2816 obs 451.2815 |
| 18-192 | 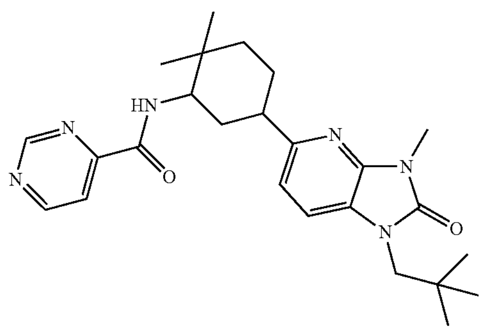 [SMILES: Cn1c(=O)n(CC(C)(C)C)c2ccc(C3CCC(C)(C)C(NC(=O)c4ccncn4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}pyrimidine-4-carboxamide | C25H34N6O2 [M + H] calc 451.2816 obs 451.2818 |
| 18-193 | 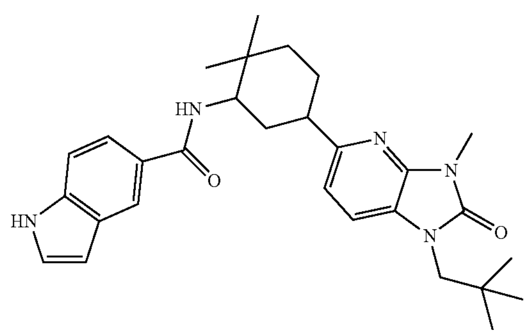 [SMILES: Cn1c(=O)n(CC(C)(C)C)c2ccc(C3CCC(C)(C)C(NC(=O)c4ccc5[nH]ccc5c4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-1H-indole-5-carboxamide | C29H37N5O2 [M + H] calc 488.3021 obs 488.3017 |
| 18-194 | 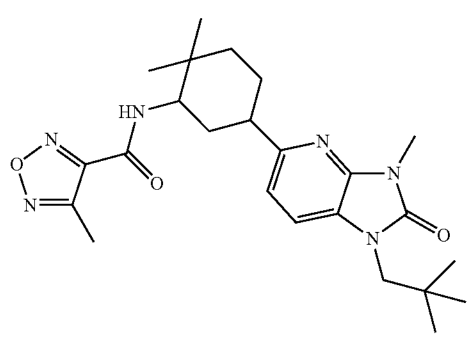 [SMILES: Cc1nonc1C(=O)NC1CC(c2ccc3c(n2)n(C)c(=O)n3CC(C)(C)C)CCC1(C)C] | N-{5-[1-(2,2-dimethylpropyl)-3-methyl-2-oxo-2,3-dihydro-1H-imidazo[4,5-b]pyridin-5-yl]-2,2-dimethylcyclohexyl}-4-methyl-1,2,5-oxadiazole-3-carboxamide | C24H34N6O3 [M + H] calc 455.2766 obs 455.2766 |

TABLE 7-continued

| # | Structure | Name | HRMS/LRMS |
|---|---|---|---|
| 18-195 | 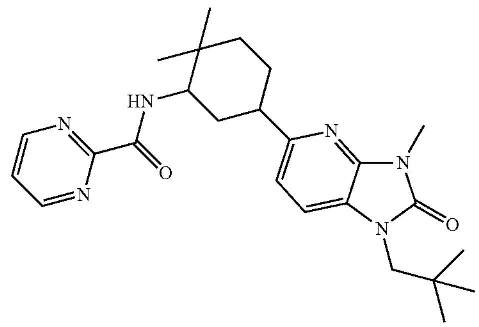 [SMILES: Cn1c(=O)n(CC(C)(C)C)c2ccc(C3CCC(C)(C)C(NC(=O)c4ncccn4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}pyrimidine-2-carboxamide | C25H34N6O2 [M + H] calc 451.2817 obs 451.2825 |
| 18-196 | 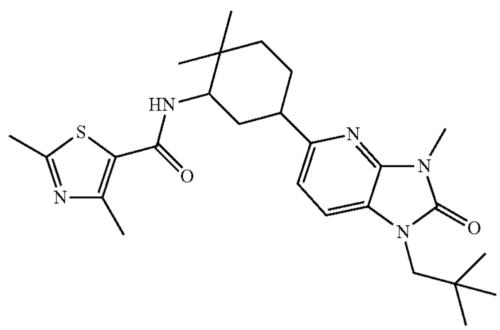 [SMILES: Cc1nc(C)c(C(=O)NC2CC(c3ccc4c(n3)n(C)c(=O)n4CC(C)(C)C)CCC2(C)C)s1] | N-{5-[1-(2,2-dimethylpropyl)-3-methyl-2-oxo-2,3-dihydro-1H-imidazo[4,5-b]pyridin-5-yl]-2,2-dimethylcyclohexyl}-2,4-dimethyl-1,3-thiazole-5-carboxamide | C26H37N5O2S [M + H] calc 484.2742 obs 484.2746 |
| 18-197 | 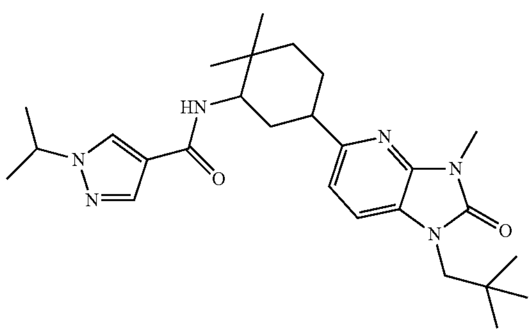 [SMILES: CC(C)n1cc(C(=O)NC2CC(c3ccc4c(n3)n(C)c(=O)n4CC(C)(C)C)CCC2(C)C)cn1] | N-{5-[1-(2,2-dimethylpropyl)-3-methyl-2-oxo-2,3-dihydro-1H-imidazo[4,5-b]pyridin-5-yl]-2,2-dimethylcyclohexyl}-1-(1-methylethyl)-1H-pyrazole-4-carboxamide | C27H40N6O2 [M + H] calc 481.3286 obs 481.3295 |
| 18-198 | 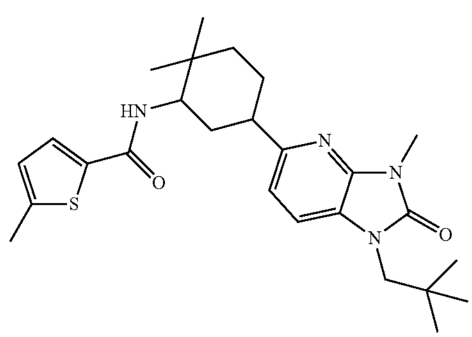 [SMILES: Cc1ccc(C(=O)NC2CC(c3ccc4c(n3)n(C)c(=O)n4CC(C)(C)C)CCC2(C)C)s1] | N-{5-[1-(2,2-dimethylpropyl)-3-methyl-2-oxo-2,3-dihydro-1H-imidazo[4,5-b]pyridin-5-yl]-2,2-dimethylcyclohexyl}-5-methylthiophene-2-carboxamide | C26H36N4O2S [M + H] calc 469.2633 obs 469.2630 |

TABLE 7-continued

| # | Structure | Name | HRMS/LRMS |
|---|---|---|---|
| 18-199 | 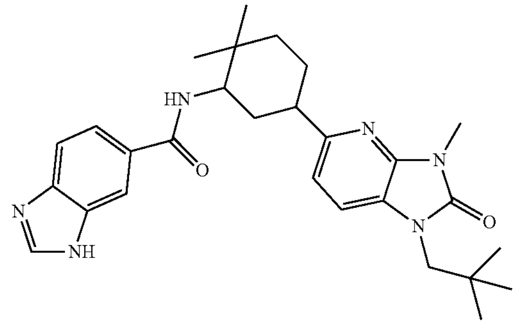 [SMILES: Cn1c(=O)n(CC(C)(C)C)c2ccc(C3CCC(C)(C)C(NC(=O)c4ccc5nc[nH]c5c4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-1H-benzimidazole-6-carboxamide | C28H36N6O2 [M + H] calc 489.2974 obs 489.2974 |
| 18-200 | 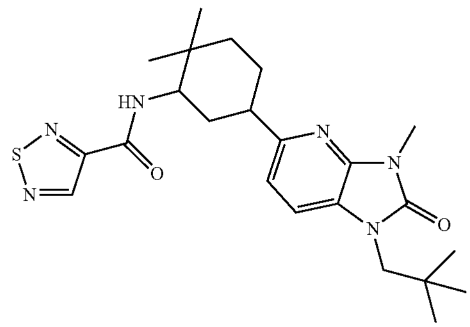 [SMILES: Cn1c(=O)n(CC(C)(C)C)c2ccc(C3CCC(C)(C)C(NC(=O)c4cnsn4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-1,2,5-thiadiazole-3-carboxamide | C23H32N6O2S [M + H] calc 457.2382 obs 457.2383 |
| 18-201 | 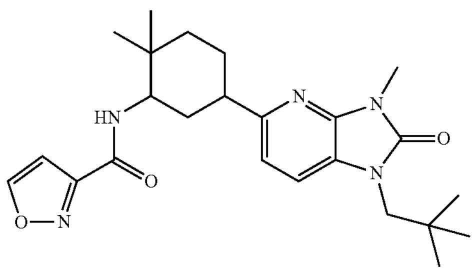 [SMILES: Cn1c(=O)n(CC(C)(C)C)c2ccc(C3CCC(C)(C)C(NC(=O)c4ccon4)C3)nc21] | N-{5-[1-(2,2-dimethylpropyl)-3-methyl-2-oxo-2,3-dihydro-1H-imidazo[4,5-b]pyridin-5-yl]-2,2-dimethyl-cyclohexyl}isoxazole-3-carboxamide | C24H33N5O3 [M + H] calc 440.2657 obs 440.2659 |
| 18-202 | 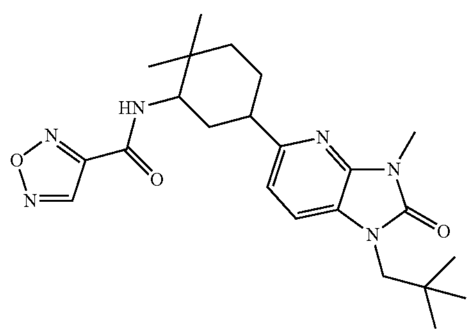 [SMILES: Cn1c(=O)n(CC(C)(C)C)c2ccc(C3CCC(C)(C)C(NC(=O)c4cnon4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-1,2,5-oxadiazole-3-carboxamide | C23H32N6O3 [M + H] calc 441.261 obs 441.2619 |
| 18-203 | 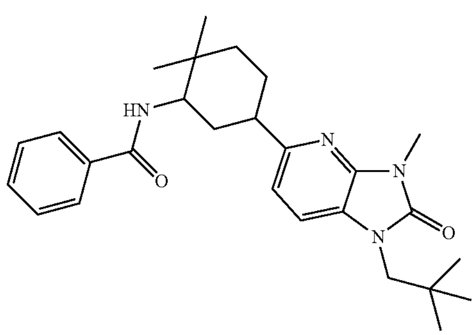 [SMILES: Cn1c(=O)n(CC(C)(C)C)c2ccc(C3CCC(C)(C)C(NC(=O)c4ccccc4)C3)nc21] | N-{5-[1-(2,2-dimethylpropyl)-3-methyl-2-oxo-2,3-dihydro-1H-imidazo[4,5-b]pyridin-5-yl]-2,2-dimethyl-cyclohexyl}benzamide | C27H36N4O2 [M + H] calc 449.2912 obs 449.2907 |

TABLE 7-continued

| # | Structure | Name | HRMS/LRMS |
|---|---|---|---|
| 18-204 | 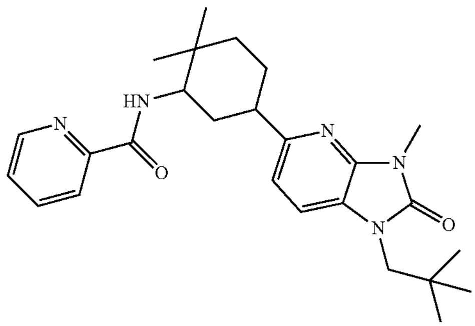 [SMILES: Cn1c(=O)n(CC(C)(C)C)c2ccc(C3CCC(C)(C)C(NC(=O)c4ccccn4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}pyridine-2-carboxamide | C26H35N5O2 [M + H] calc 450.2865 obs 450.2873 |
| 18-205 | 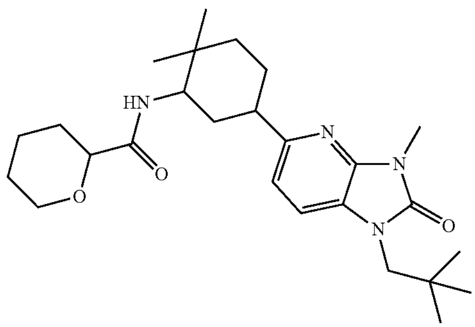 [SMILES: Cn1c(=O)n(CC(C)(C)C)c2ccc(C3CCC(C)(C)C(NC(=O)C4CCCCO4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}tetrahydro-2H-pyran-2-carboxamide | C26H40N4O3 [M + H] calc 457.3173 obs 457.3181 |
| 18-206 | 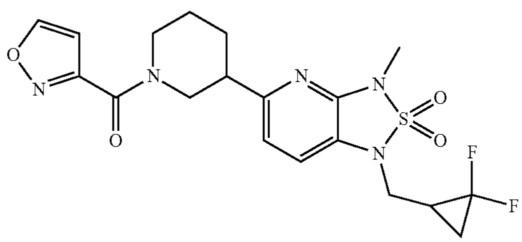 | N-{5-[1-(2,2-dimethylpropyl)-3-methyl-2-oxo-2,3-dihydro-1H-imidazo[4,5-b]pyridin-5-yl]-2,2-dimethylcyclohexyl}-5-ethylisoxazole-3-carboxamide | C26H37N5O3 [M + H] calc 468.297 obs 468.2982 |
| 18-207 | 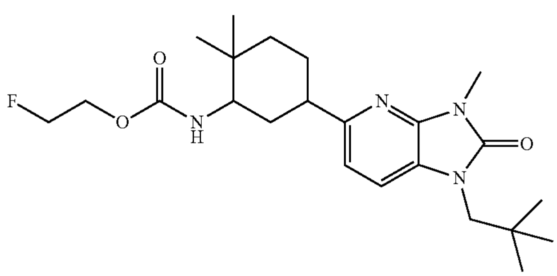 [SMILES: Cn1c(=O)n(CC(C)(C)C)c2ccc(C3CCC(C)(C)C(NC(=O)OCCF)C3)nc21] | 2-fluoroethyl {5-[1-(2,2-dimethylpropyl)-3-methyl-2-oxo-2,3-dihydro-1H-imidazo[4,5-b]pyridin-5-yl]-2,2-dimethylcyclohexyl}carbamate | C23H35FN4O3 [M + H] calc 435.2767 obs 435.2775 |
| 18-208 | 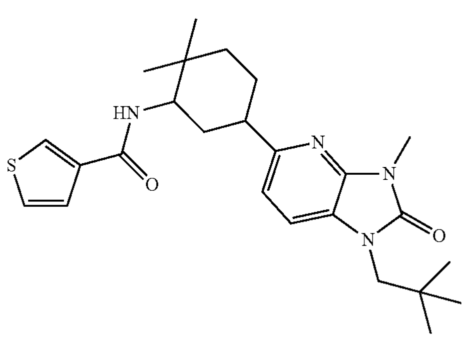 [SMILES: Cn1c(=O)n(CC(C)(C)C)c2ccc(C3CCC(C)(C)C(NC(=O)c4ccsc4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}thiophene-3-carboxamide | C25H34N4O2S [M + H] calc 455.2476 obs 455.2473 |

TABLE 7-continued

| # | Name | HRMS/LRMS |
|---|------|-----------|
| 18-209 | N-{5-[1-(2,2-dimethylpropyl)-3-methyl-2-oxo-2,3-dihydro-1H-imidazo[4,5-b]pyridin-5-yl]-2,2-dimethylcyclohexyl}-5-methyl-1,2,3-thiadiazole-4-carboxamide | C24H34N6O2S [M + H] calc 471.2538 obs 471.2540 |
| 18-210 | N-{5-[1-(2,2-dimethylpropyl)-3-methyl-2-oxo-2,3-dihydro-1H-imidazo[4,5-b]pyridin-5-yl]-2,2-dimethylcyclohexyl}-1,2,3-thiadiazole-4-carboxamide | C23H32N6O2S [M + H] calc 457.2382 obs 457.2386 |
| 18-211 | 1-(2,2-dimethylpropyl)-3-methyl-5-[2-methyl-1-(1,3-oxazol-2-ylcarbonyl)piperidin-4-yl]-1,3-dihydro-2H-imidazo[4,5-b]pyridin-2-one | C22H29N5O3 [M + H] calc 412.2345 obs 412.2339 |
| 18-212 | 1-(2,2-dimethylpropyl)-5-[1-(isoxazol-3-ylcarbonyl)-2-methylpiperidin-4-yl]-3-methyl-1,3-dihydro-2H-imidazo[4,5-b]pyridin-2-one | C22H29N5O3 [M + H] calc 412.2345 obs 412.2343 |

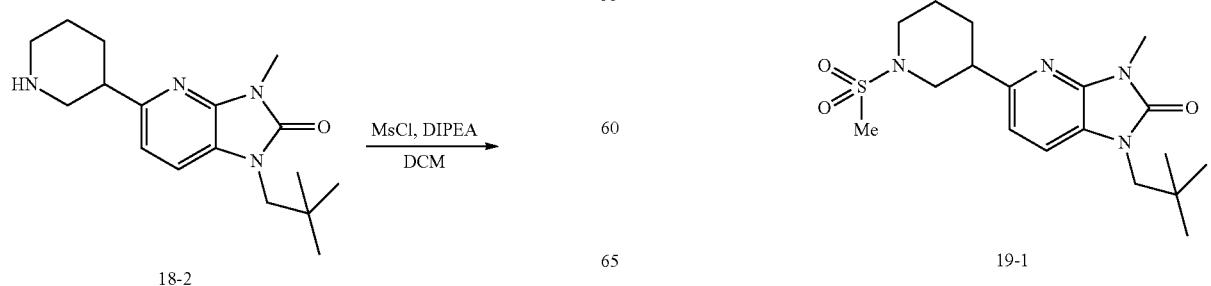

Scheme 19

1-(2,2-Dimethylpropyl)-3-methyl-5-[1-(methylsulfonyl)piperidin-3-yl]-1,3-dihydro-2H-imidazo[4,5-b]pyridin-2-one (19-1)

To a flask was added methanesulfonyl chloride (3.74 mg, 0.033 mmol), NMP (0.5 mL), then (18-2) (7.6 mg, 0.025 mmol), & DIPEA (40 μl, 0.229 mmol). The reaction mixture was stirred at room temperature for 3 hours, then diluted with MeOH & purified by reverse phase chromatography (5-95% CH$_3$CN:0.1% TFA in H$_2$O) to give 1-(2,2-Dimethylpropyl)-3-methyl-5-[1-(methylsulfonyl)piperidin-3-yl]-1,3-dihydro-2H-imidazo[4,5-b]pyridin-2-one (19-1). HRMS (M+H)$^+$: observed=381.1956, calculated=381.1955. $^1$H NMR (499 MHz, DMSO): δ 7.48 (d, J=7.9 Hz, 1H); 7.02 (d, J=7.9 Hz, 1H); 3.71-3.68 (m, 1H); 3.64-3.56 (m, 3H); 3.34 (s, 3H); 2.93-2.83 (m, 5H); 2.78-2.72 (m, 1H); 2.00-1.92 (m, 1H); 1.89-1.82 (m, 1H); 1.76-1.60 (m, 2H); 0.95 (s, 9H).

The following compounds were prepared by synthetic transformations analogous to those illustrated in Schemes 17, 18 and 19:

TABLE 8

| # | Structure | Name | HRMS/LRMS |
|---|---|---|---|
| 19-2 | 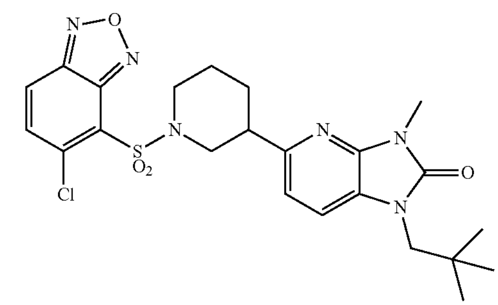 [SMILES: Cn1c(=O)n(CC(C)(C)C)c2ccc(C3CCCN(S(=O)(=O)c4c(Cl)ccc5nonc45)C3)nc21] | 5-{1-[(5-chloro-2,1,3-benzoxadiazol-4-yl)sulfonyl]piperidin-3-yl}-1-(2,2-dimethylpropyl)-3-methyl-1,3-dihydro-2H-imidazo[4,5-b]pyridin-2-one | C23H27ClN6O4S [M + H] calc 519.1578 obs 519.1575 |
| 19-3 | 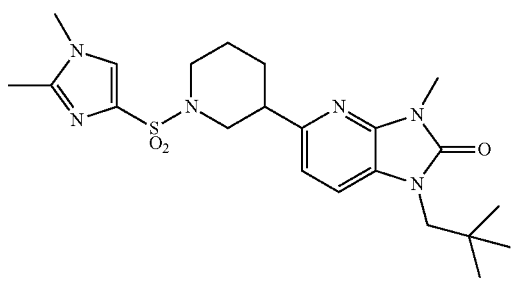 [SMILES: Cc1nc(S(=O)(=O)N2CCCC(c3ccc4c(n3)n(C)c(=O)n4CC(C)(C)C)C2)cn1C] | 5-{1-[(1,2-dimethyl-1H-imidazol-4-yl)sulfonyl]piperidin-3-yl}-1-(2,2-dimethylpropyl)-3-methyl-1,3-dihydro-2H-imidazo[4,5-b]pyridin-2-one | C22H32N6O3S [M + H] calc 461.2331 obs 461.2330 |
| 19-4 | 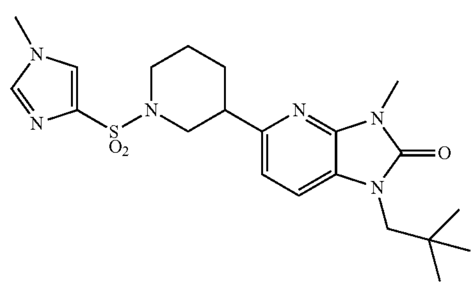 [SMILES: Cn1cnc(S(=O)(=O)N2CCCC(c3ccc4c(n3)n(C)c(=O)n4CC(C)(C)C)C2)c1] | 1-(2,2-dimethylpropyl)-3-methyl-5-{1-[(1-methyl-1H-imidazol-4-yl)sulfonyl]piperidin-3-yl}-1,3-dihydro-2H-imidazo[4,5-b]pyridin-2-one | C21H30N6O3S [M + H] calc 447.2174 obs 447.2169 |
| 19-5 | 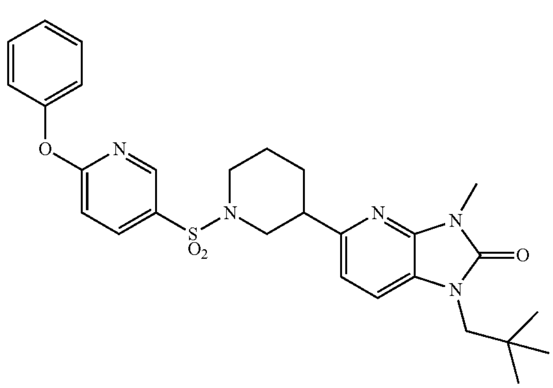 [SMILES: Cn1c(=O)n(CC(C)(C)C)c2ccc(C3CCCN(S(=O)(=O)c4ccc(Oc5ccccc5)nc4)C3)nc21] | 1-(2,2-dimethylpropyl)-3-methyl-5-{1-[(6-phenoxypyridin-3-yl)sulfonyl]piperidin-3-yl}-1,3-dihydro-2H-imidazo[4,5-b]pyridin-2-one | C28H33N5O4S [M + H] calc 536.2327 obs 536.2325 |

TABLE 8-continued

| # | Structure | Name | HRMS/LRMS |
|---|---|---|---|
| 19-6 | 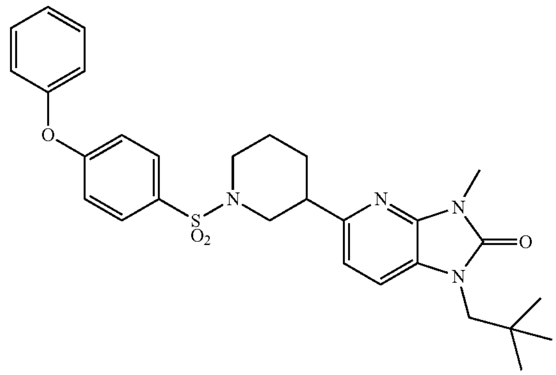 [SMILES: Cn1c(=O)n(CC(C)(C)C)c2ccc(C3CCCN(S(=O)(=O)c4ccc(Oc5ccccc5)cc4)C3)nc21] | 1-(2,2-dimethylpropyl)-3-methyl-5-{1-[(4-phenoxyphenyl)sulfonyl]piperidin-3-yl}-1,3-dihydro-2H-imidazo[4,5-b]pyridin-2-one | C29H34N4O4S [M + H] calc 535.2374 obs 535.2373 |
| 19-7 | 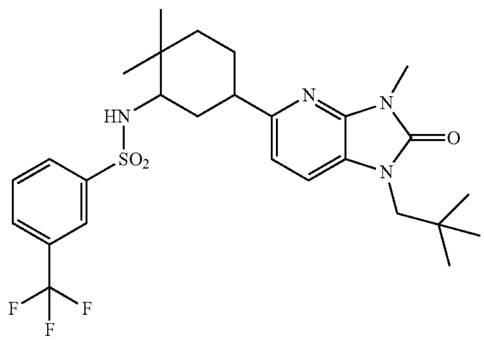 [SMILES: Cn1c(=O)n(CC(C)(C)C)c2ccc(C3CCC(C)(C)C(NS(=O)(=O)c4cccc(C(F)(F)F)c4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-3-(trifluoromethyl)benzenesulfonamide | C27H35F3N4O3S [M + H] calc 553.2456 obs 553.2458 |
| 19-8 | 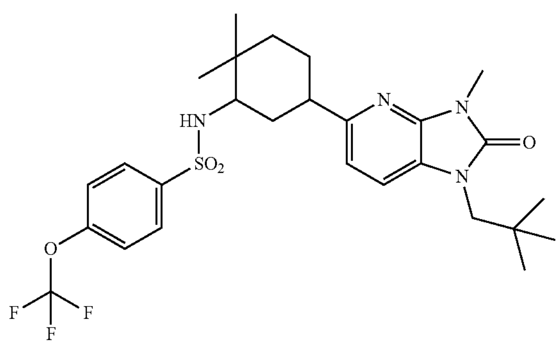 [SMILES: Cn1c(=O)n(CC(C)(C)C)c2ccc(C3CCC(C)(C)C(NS(=O)(=O)c4ccc(OC(F)(F)F)cc4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-4-(trifluoromethoxy)benzenesulfonamide | C27H35F3N4O4S [M + H] calc 569.2405 obs 569.2410 |
| 19-9 | 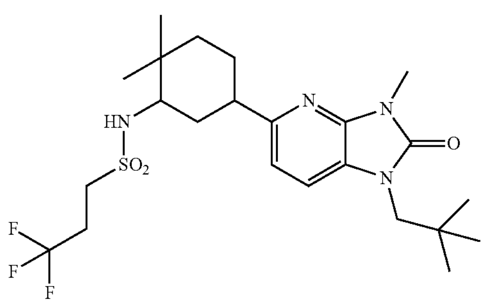 [SMILES: Cn1c(=O)n(CC(C)(C)C)c2ccc(C3CCC(C)(C)C(NS(=O)(=O)CCC(F)(F)F)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-3,3,3-trifluoropropane-1-sulfonamide | C23H35F3N4O3S [M + H] calc 505.2456 obs 505.2463 |
| 19-10 | 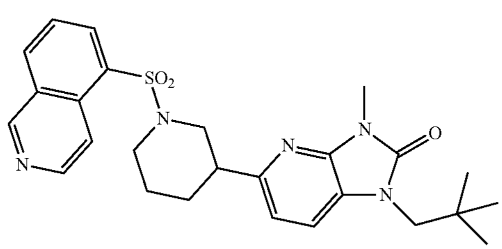 [SMILES: Cn1c(=O)n(CC(C)(C)C)c2ccc(C3CCCN(S(=O)(=O)c4cccc5cnccc45)C3)nc21] | 1-(2,2-dimethylpropyl)-5-[1-(isoquinolin-5-ylsulfonyl)piperidin-3-yl]-3-methyl-1,3-dihydro-2H-imidazo[4,5-b]pyridin-2-one | C26H31N5O3S [M + H] calc 494.2220 obs 494.2217 |

TABLE 8-continued

| # | Structure | Name | HRMS/LRMS |
|---|---|---|---|
| 19-11 | 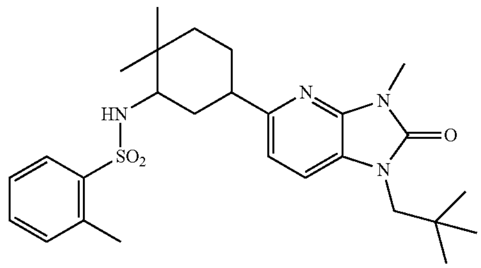 [SMILES: Cc1ccccc1S(=O)(=O)NC1CC(c2ccc3c(n2)n(C)c(=O)n3CC(C)(C)C)CCC1(C)C] | N-{5-[1-(2,2-dimethylpropyl)-3-methyl-2-oxo-2,3-dihydro-1H-imidazo[4,5-b]pyridin-5-yl]-2,2-dimethylcyclohexyl}-2-methylbenzenesulfonamide | C27H38N4O3S [M + H] calc 499.2738 obs 499.2747 |
| 19-12 | 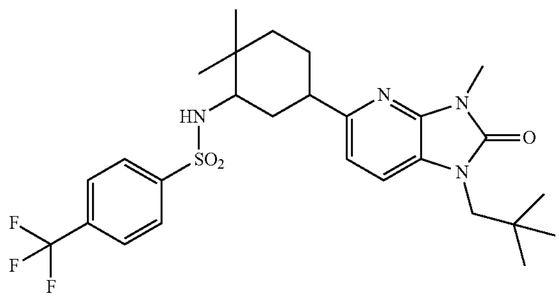 [SMILES: Cn1c(=O)n(CC(C)(C)C)c2ccc(C3CCC(C)(C)C(NS(=O)(=O)c4ccc(C(F)(F)F)cc4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-4-(trifluoromethyl)benzenesulfonamide | C27H35F3N4O3S [M + H] calc 553.2456 obs 553.2463 |
| 19-13 | 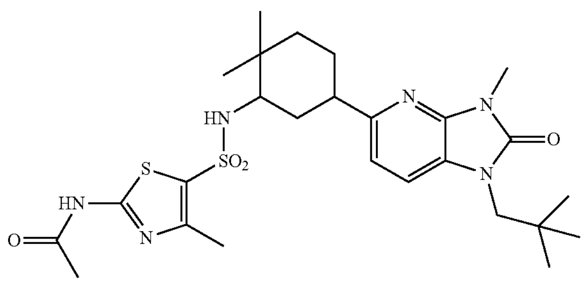 [SMILES: CC(=O)Nc1nc(C)c(S(=O)(=O)NC2CC(c3ccc4c(n3)n(C)c(=O)n4CC(C)(C)C)CCC2(C)C)s1] | N-[5-({5-[1-(2,2-dimethylpropyl)-3-methyl-2-oxo-2,3-dihydro-1H-imidazo[4,5-b]pyridin-5-yl]-2,2-dimethylcyclohexyl}sulfamoyl)-4-methyl-1,3-thiazol-2-yl]acetamide | C26H38N6O4S2 [M + H] calc 563.2469 obs 563.2473 |
| 19-14 | 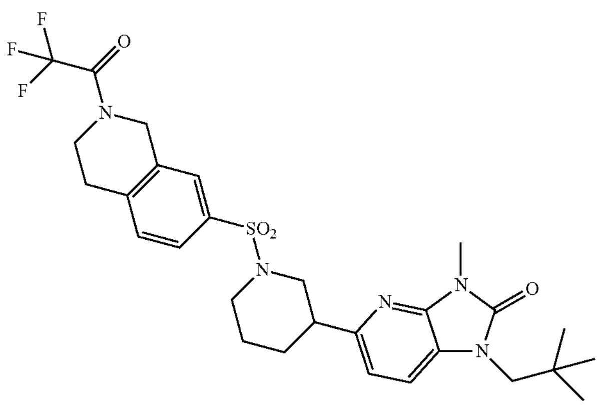 [SMILES: Cn1c(=O)n(CC(C)(C)C)c2ccc(C3CCCN(S(=O)(=O)c4ccc5c(c4)CN(C(=O)C(F)(F)F)CC5)C3)nc21] | 1-(2,2-dimethylpropyl)-3-methyl-5-(1-{[2-(trifluoroacetyl)-1,2,3,4-tetrahydroisoquinolin-7-yl]sulfonyl}piperidin-3-yl)-1,3-dihydro-2H-imidazo[4,5-b]pyridin-2-one | C28H34F3N5O4S [M + H] calc 594.2357 obs 594.2360 |
| 19-15 | 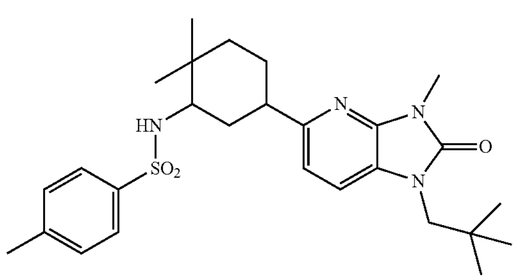 [SMILES: Cc1ccc(S(=O)(=O)NC2CC(c3ccc4c(n3)n(C)c(=O)n4CC(C)(C)C)CCC2(C)C)cc1] | N-{5-[1-(2,2-dimethylpropyl)-3-methyl-2-oxo-2,3-dihydro-1H-imidazo[4,5-b]pyridin-5-yl]-2,2-dimethylcyclohexyl}-4-methylbenzenesulfonamide | C27H38N4O3S [M + H] calc 499.2738 obs 499.2748 |

TABLE 8-continued

| # | Structure | Name | HRMS/LRMS |
|---|-----------|------|-----------|
| 19-16 | 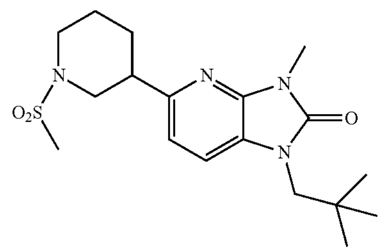 [SMILES: Cn1c(=O)n(CC(C)(C)C)c2ccc(C3CCCN(S(C)(=O)=O)C3)nc21] | 1-(2,2-dimethylpropyl)-3-methyl-5-[1-(methylsulfonyl)piperidin-3-yl]-1,3-dihydro-2H-imidazo[4,5-b]pyridin-2-one | C18H28N4O3S [M + H] calc 381.1956 obs 381.1956 |
| 19-17 | 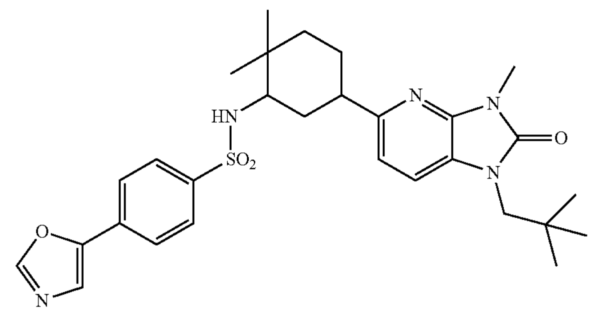 [SMILES: Cn1c(=O)n(CC(C)(C)C)c2ccc(C3CCC(C)(C)C(NS(=O)(=O)c4ccc(-c5cnco5)cc4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-4-(1,3-oxazol-5-yl)benzenesulfonamide | C29H37N5O4S [M + H] calc 552.264 obs 552.2632 |
| 19-18 | 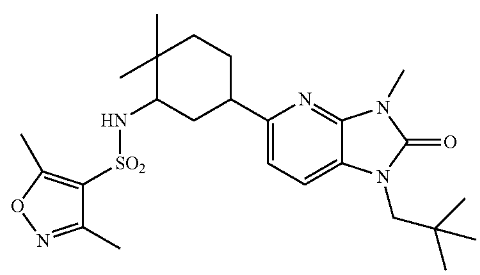 [SMILES: Cc1noc(C)c1S(=O)(=O)NC1CC(c2ccc3c(n2)n(C)c(=O)n3CC(C)(C)C)CCC1(C)C] | N-{5-[1-(2,2-dimethylpropyl)-3-methyl-2-oxo-2,3-dihydro-1H-imidazo[4,5-b]pyridin-5-yl]-2,2-dimethylcyclohexyl}-3,5-dimethylisoxazole-4-sulfonamide | C25H37N5O4S [M + H] calc 504.264 obs 504.2637 |
| 19-19 | 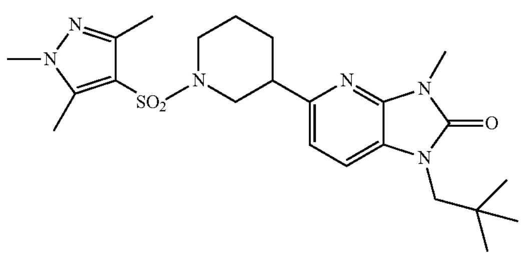 | 1-(2,2-dimethylpropyl)-3-methyl-5-{1-[(1,3,5-trimethyl-1H-pyrazol-4-yl)sulfonyl]piperidin-3-yl}-1,3-dihydro-2H-imidazo[4,5-b]pyridin-2-one | C23H34N6O3S [M + H] calc 475.2487 obs 475.2486 |
| 19-20 | 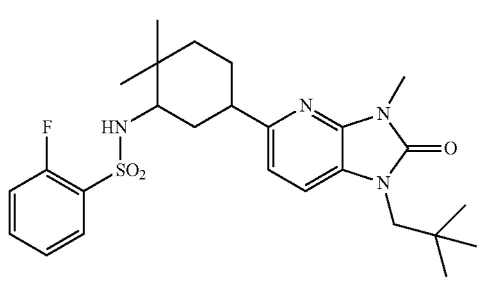 [SMILES: Cn1c(=O)n(CC(C)(C)C)c2ccc(C3CCC(C)(C)C(NS(=O)(=O)c4ccccc4F)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-2-fluorobenzenesulfonamide | C26H35FN4O3S [M + H] calc 503.2488 obs 503.2494 |
| 19-21 | 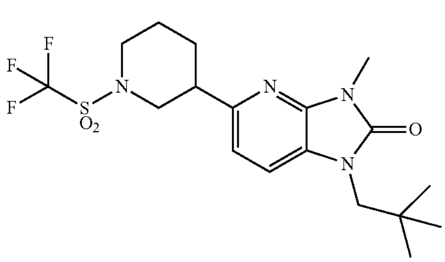 [SMILES: Cn1c(=O)n(CC(C)(C)C)c2ccc(C3CCCN(S(=O)(=O)C(F)(F)F)C3)nc21] | 1-(2,2-dimethylpropyl)-3-methyl-5-{1-[(trifluoromethyl)sulfonyl]piperidin-3-yl}-1,3-dihydro-2H-imidazo[4,5-b]pyridin-2-one | C18H25F3N4O3S [M + H] calc 435.1674 obs 435.1674 |

TABLE 8-continued

| # | Structure | Name | HRMS/LRMS |
|---|---|---|---|
| 19-22 | 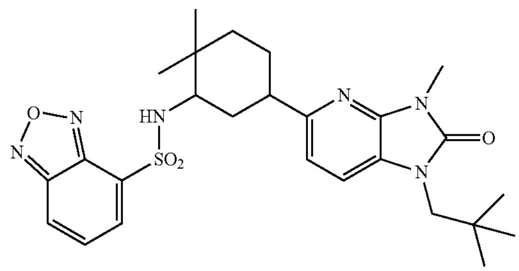 [SMILES: Cn1c(=O)n(CC(C)(C)C)c2ccc(C3CCC(C)(C)C(NS(=O)(=O)c4cccc5nonc45)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-2,1,3-benzoxadiazole-4-sulfonamide | C26H34N6O4S [M + H] calc 527.2436 obs 527.2445 |
| 19-23 | 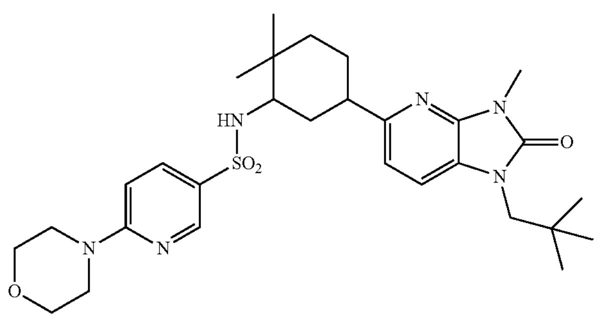 [SMILES: Cn1c(=O)n(CC(C)(C)C)c2ccc(C3CCC(C)(C)C(NS(=O)(=O)c4ccc(N5CCOCC5)nc4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-6-morpholin-4-ylpyridine-3-sulfonamide | C29H42N6O4S [M + H] calc 571.3061 obs 571.3065 |
| 19-24 | 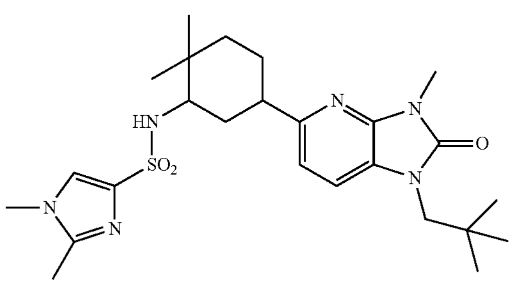 [SMILES: Cc1nc(S(=O)(=O)NC2CC(c3ccc4c(n3)n(C)c(=O)n4CC(C)(C)C)CCC2(C)C)cn1C] | N-{5-[1-(2,2-dimethylpropyl)-3-methyl-2-oxo-2,3-dihydro-1H-imidazo[4,5-b]pyridin-5-yl]-2,2-dimethylcyclohexyl}-1,2-dimethyl-1H-imidazole-4-sulfonamide | C25H38N6O3S [M + H] calc 503.28 obs 503.2806 |
| 19-25 | 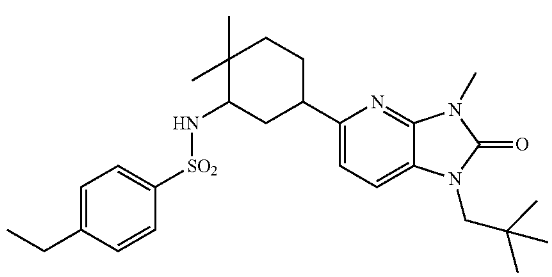 [SMILES: CCc1ccc(S(=O)(=O)NC2CC(c3ccc4c(n3)n(C)c(=O)n4CC(C)(C)C)CCC2(C)C)cc1] | N-{5-[1-(2,2-dimethylpropyl)-3-methyl-2-oxo-2,3-dihydro-1H-imidazo[4,5-b]pyridin-5-yl]-2,2-dimethylcyclohexyl}-4-ethylbenzenesulfonamide | C28H40 [M + H] calc 513.2894 obs 513.2899 |
| 19-26 | 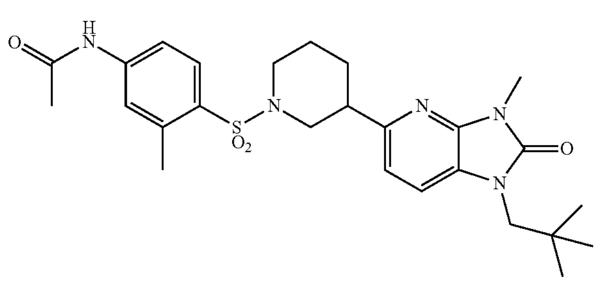 [SMILES: CC(=O)Nc1ccc(S(=O)(=O)N2CCCC(c3ccc4c(n3)n(C)c(=O)n4CC(C)(C)C)C2)c(C)c1] | N-[4-({3-[1-(2,2-dimethylpropyl)-3-methyl-2-oxo-2,3-dihydro-1H-imidazo[4,5-b]pyridin-5-yl]piperidin-1-yl}sulfonyl)-3-methylphenyl]acetamide | C26H35N5O4S [M + H] calc 514.2483 obs 514.2482 |

TABLE 8-continued

| # | Structure | Name | HRMS/LRMS |
|---|---|---|---|
| 19-27 | 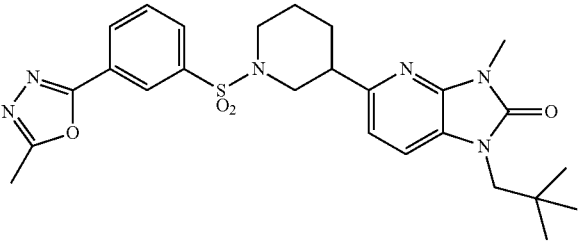 [SMILES: Cc1nnc(-c2cccc(S(=O)(=O)N3CCCC(c4ccc5c(n4)n(C)c(=O)n5CC(C)(C)C)C3)c2)o1] | 1-(2,2-dimethylpropyl)-3-methyl-5-(1-{[3-(5-methyl-1,3,4-oxadiazol-2-yl)phenyl]sulfonyl}piperidin-3-yl)-1,3-dihydro-2H-imidazo[4,5-b]pyridin-2-one | C26H32N6O4S [M + H] calc 525.228 obs 525.2281 |
| 19-28 | 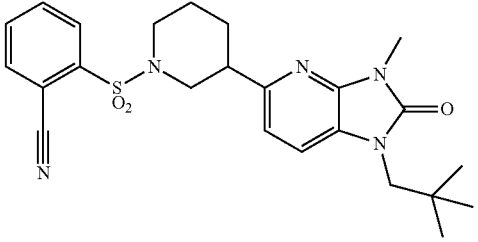 [SMILES: Cn1c(=O)n(CC(C)(C)C)c2ccc(C3CCCN(S(=O)(=O)c4ccccc4C#N)C3)nc21] | 2-({3-[1-(2,2-dimethylpropyl)-3-methyl-2-oxo-2,3-dihydro-1H-imidazo[4,5-b]pyridin-5-yl]piperidin-1-yl}sulfonyl)benzonitrile | C24H29N5O3S [M + H] calc 468.2065 obs 468.2065 |
| 19-29 | 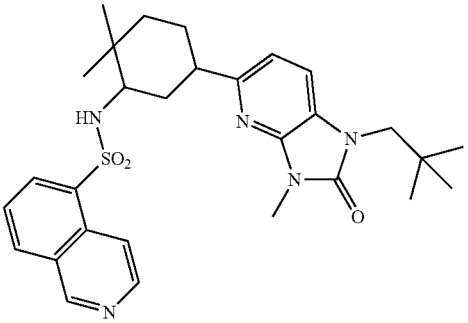 [SMILES: Cn1c(=O)n(CC(C)(C)C)c2ccc(C3CCC(C)(C)C(NS(=O)(=O)c4cccc5cnccc45)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}isoquinoline-5-sulfonamide | C29H37N5O3S [M + H] calc 536.2691 obs 536.2697 |
| 19-30 | 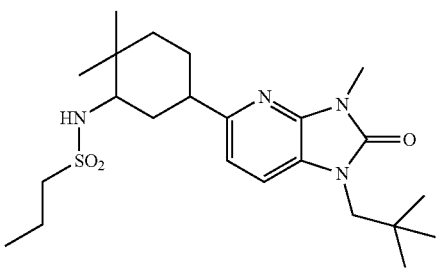 [SMILES: CCCS(=O)(=O)NC1CC(c2ccc3c(n2)n(C)c(=O)n3CC(C)(C)C)CCC1(C)C] | N-{5-[1-(2,2-dimethylpropyl)-3-methyl-2-oxo-2,3-dihydro-1H-imidazo[4,5-b]pyridin-5-yl]-2,2-dimethylcyclohexyl}propane-1-sulfonamide | C23H38N4O3S [M + H] calc 451.2738 obs 451.2737 |
| 19-31 | 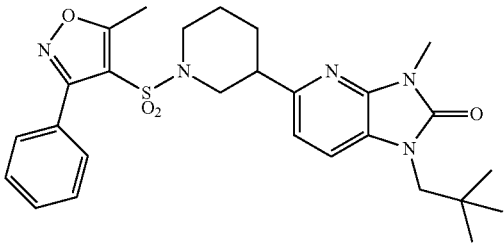 [SMILES: Cc1onc(-c2ccccc2)c1S(=O)(=O)N1CCCC(c2ccc3c(n2)n(C)c(=O)n3CC(C)(C)C)C1] | 1-(2,2-dimethylpropyl)-3-methyl-5-{1-[(5-methyl-3-phenylisoxazol-4-yl)sulfonyl]piperidin-3-yl}-1,3-dihydro-2H-imidazo[4,5-b]pyridin-2-one | C27H33N5O4S [M + H] calc 524.2327 obs 524.2323 |

TABLE 8-continued

| # | Structure | Name | HRMS/LRMS |
|---|---|---|---|
| 19-32 | 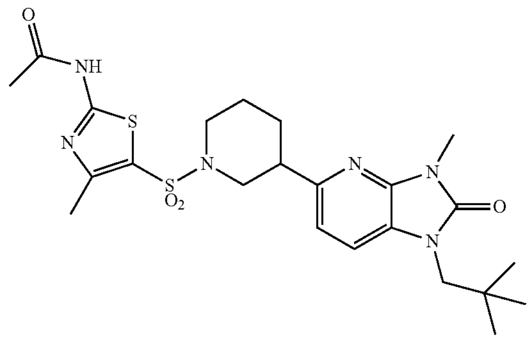 [SMILES: CC(=O)Nc1nc(C)c(S(=O)(=O)N2CCCC(c3ccc4c(n3)n(C)c(=O)n4CC(C)(C)C)C2)s1] | N-[5-({3-[1-(2,2-dimethylpropyl)-3-methyl-2-oxo-2,3-dihydro-1H-imidazo[4,5-b]pyridin-5-yl]piperidin-1-yl}sulfonyl)-4-methyl-1,3-thiazol-2-yl]acetamide | C23H32N6O4S2 [M + H] calc 521.2001 obs 521.2007 |
| 19-33 | 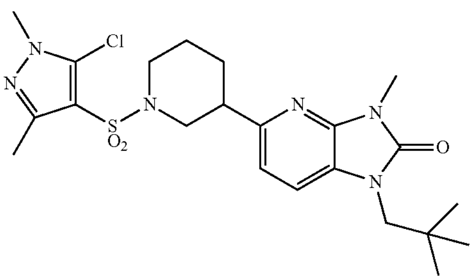 [SMILES: Cc1nn(C)c(Cl)c1S(=O)(=O)N1CCCC(c2ccc3c(n2)n(C)c(=O)n3CC(C)(C)C)C1] | 5-{1-[(5-chloro-1,3-dimethyl-1H-pyrazol-4-yl)sulfonyl]piperidin-3-yl}-1-(2,2-dimethylpropyl)-3-methyl-1,3-dihydro-2H-imidazo[4,5-b]pyridin-2-one | C22H31ClN6O3S [M + H] calc 495.1941 obs 495.1945 |
| 19-34 | 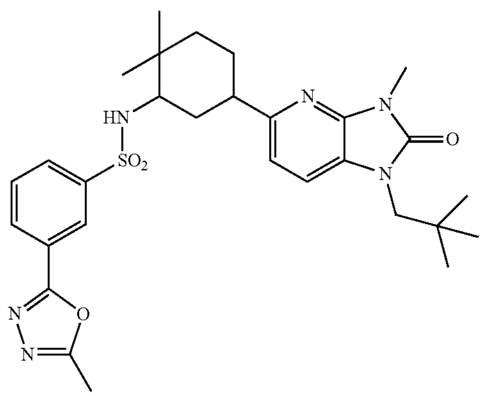 [SMILES: Cc1nnc(-c2cccc(S(=O)(=O)NC3CC(c4ccc5c(n4)n(C)c(=O)n5CC(C)(C)C)CCC3(C)C)c2)o1] | N-{5-[1-(2,2-dimethylpropyl)-3-methyl-2-oxo-2,3-dihydro-1H-imidazo[4,5-b]pyridin-5-yl]-2,2-dimethylcyclohexyl}-3-(5-methyl-1,3,4-oxadiazol-2-yl)benzenesulfonamide | C29H38N6O4S [M + H] calc 567.2748 obs 567.2757 |
| 19-35 | 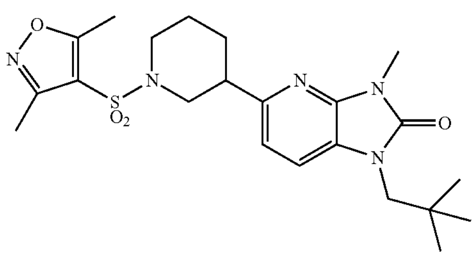 [SMILES: Cc1noc(C)c1S(=O)(=O)N1CCCC(c2ccc3c(n2)n(C)c(=O)n3CC(C)(C)C)C1] | 5-{1-[(3,5-dimethylisoxazol-4-yl)sulfonyl]piperidin-3-yl}-1-(2,2-dimethylpropyl)-3-methyl-1,3-dihydro-2H-imidazo[4,5-b]pyridin-2-one | C22H31N5O4S [M + H] calc 462.2171 obs 462.2169 |
| 19-36 | 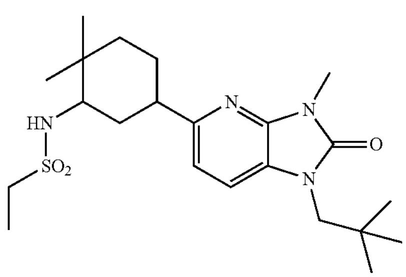 [SMILES: CCS(=O)(=O)NC1CC(c2ccc3c(n2)n(C)c(=O)n3CC(C)(C)C)CCC1(C)C] | N-{5-[1-(2,2-dimethylpropyl)-3-methyl-2-oxo-2,3-dihydro-1H-imidazo[4,5-b]pyridin-5-yl]-2,2-dimethylcyclohexyl}ethanesulfonamide | C22H36N4O3S [M + H] calc 437.2582 obs 437.2580 |

TABLE 8-continued

| # | Structure | Name | HRMS/LRMS |
|---|---|---|---|
| 19-37 | 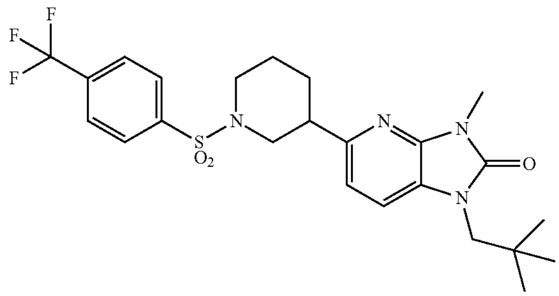 [SMILES: Cn1c(=O)n(CC(C)(C)C)c2ccc(C3CCCN(S(=O)(=O)c4ccc(C(F)(F)F)cc4)C3)nc21] | 1-(2,2-dimethylpropyl)-3-methyl-5-(1-{[4-(trifluoromethyl)phenyl]sulfonyl}piperidin-3-yl)-1,3-dihydro-2H-imidazo[4,5-b]pyridin-2-one | C24H29F3N4O3S [M + H] calc 511.1987 obs 511.1987 |
| 19-38 | 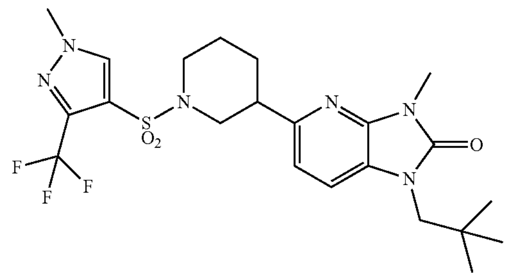 [SMILES: Cn1cc(S(=O)(=O)N2CCCC(c3ccc4c(n3)n(C)c(=O)n4CC(C)(C)C)C2)c(C(F)(F)F)n1] | 1-(2,2-dimethylpropyl)-3-methyl-5-(1-{[1-methyl-3-(trifluoromethyl)-1H-pyrazol-4-yl]sulfonyl}piperidin-3-yl)-1,3-dihydro-2H-imidazo[4,5-b]pyridin-2-one | C22H29F3N6O3S [M + H] calc 515.2049 obs 515.2047 |
| 19-39 | 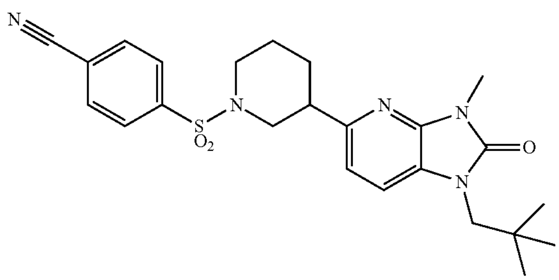 [SMILES: Cn1c(=O)n(CC(C)(C)C)c2ccc(C3CCCN(S(=O)(=O)c4ccc(C#N)cc4)C3)nc21] | 4-({3-[1-(2,2-dimethylpropyl)-3-methyl-2-oxo-2,3-dihydro-1H-imidazo[4,5-b]pyridin-5-yl]piperidin-1-yl}sulfonyl)benzonitrile | C24H29N5O3S [M + H] calc 468.2065 obs 468.2064 |
| 19-40 | 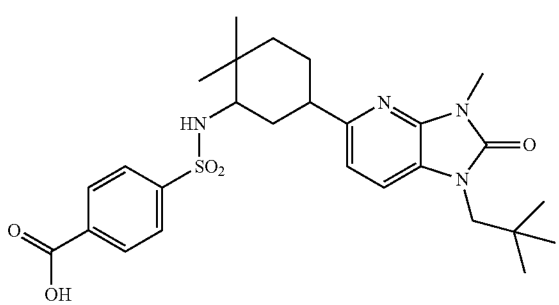 [SMILES: Cn1c(=O)n(CC(C)(C)C)c2ccc(C3CCC(C)(C)C(NS(=O)(=O)c4ccc(C(=O)O)cc4)C3)nc21] | 4-({5-[1-(2,2-dimethylpropyl)-3-methyl-2-oxo-2,3-dihydro-1H-imidazo[4,5-b]pyridin-5-yl]-2,2-dimethylcyclohexyl}sulfamoyl)benzoic acid | C27H36N4O5S [M + H] calc 529.248 obs 529.2494 |
| 19-41 | 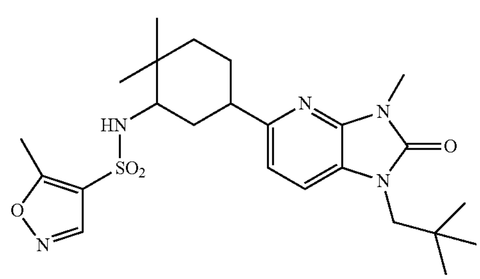 [SMILES: Cc1oncc1S(=O)(=O)NC1CC(c2ccc3c(n2)n(C)c(=O)n3CC(C)(C)C)CCC1(C)C] | N-{5-[1-(2,2-dimethylpropyl)-3-methyl-2-oxo-2,3-dihydro-1H-imidazo[4,5-b]pyridin-5-yl]-2,2-dimethylcyclohexyl}-5-methylisoxazole-4-sulfonamide | C24H35N5O4S [M + H] calc 490.2483 obs 490.2482 |

TABLE 8-continued

| # | Structure | Name | HRMS/LRMS |
|---|---|---|---|
| 19-42 | 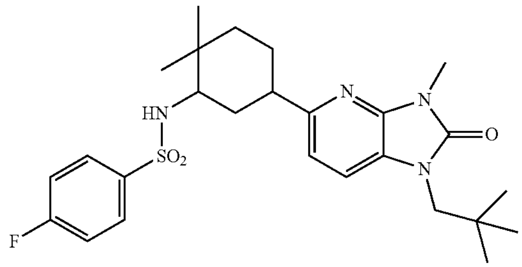 [SMILES: Cn1c(=O)n(CC(C)(C)C)c2ccc(C3CCC(C)(C)C(NS(=O)(=O)c4ccc(F)cc4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-4-fluorobenzenesulfonamide | C26H35FN4O3S [M + H] calc 503.2488 obs 503.2484 |
| 19-43 | 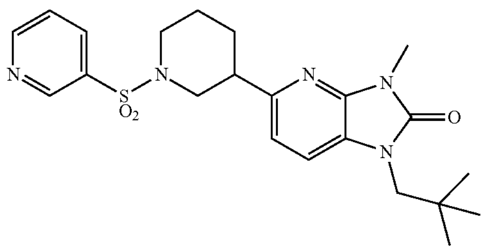 [SMILES: Cn1c(=O)n(CC(C)(C)C)c2ccc(C3CCCN(S(=O)(=O)c4cccnc4)C3)nc21] | 1-(2,2-dimethylpropyl)-3-methyl-5-[1-(pyridin-3-ylsulfonyl)piperidin-3-yl]-1,3-dihydro-2H-imidazo[4,5-b]pyridin-2-one | C22H29N5O3S [M + H] calc 444.2065 obs 444.2063 |
| 19-44 | 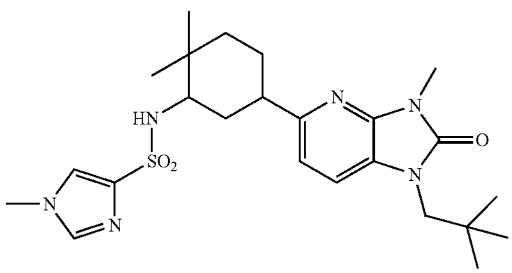 [SMILES: Cn1cnc(S(=O)(=O)NC2CC(c3ccc4c(n3)n(C)c(=O)n4CC(C)(C)C)CCC2(C)C)c1] | N-{5-[1-(2,2-dimethylpropyl)-3-methyl-2-oxo-2,3-dihydro-1H-imidazo[4,5-b]pyridin-5-yl]-2,2-dimethylcyclohexyl}-1-methyl-1H-imidazole-4-sulfonamide | C24H36N6O3S [M + H] calc 489.2643 obs 489.2654 |
| 19-45 | 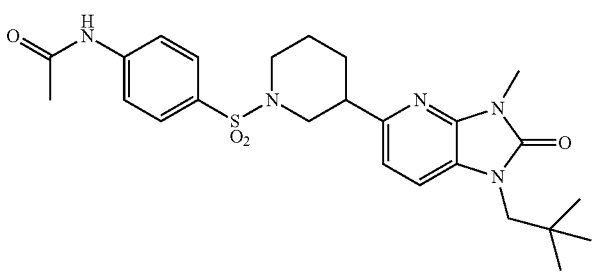 [SMILES: CC(=O)Nc1ccc(S(=O)(=O)N2CCCC(c3ccc4c(n3)n(C)c(=O)n4CC(C)(C)C)C2)cc1] | N-[4-({3-[1-(2,2-dimethylpropyl)-3-methyl-2-oxo-2,3-dihydro-1H-imidazo[4,5-b]pyridin-5-yl]piperidin-1-yl}sulfonyl)phenyl]acetamide | C25H33N5O4S [M + H] calc 500.2327 obs 500.2325 |
| 19-46 | 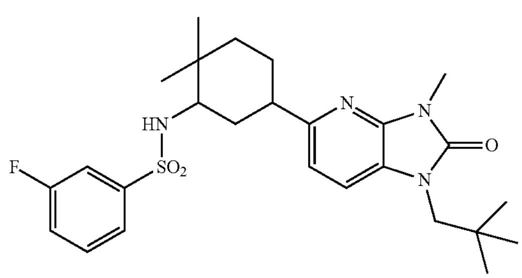 [SMILES: Cn1c(=O)n(CC(C)(C)C)c2ccc(C3CCC(C)(C)C(NS(=O)(=O)c4cccc(F)c4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-3-fluorobenzenesulfonamide | C26H35FN4O3S [M + H] calc 503.2488 obs 503.2485 |

TABLE 8-continued

| # | Structure | Name | HRMS/LRMS |
|---|---|---|---|
| 19-47 | 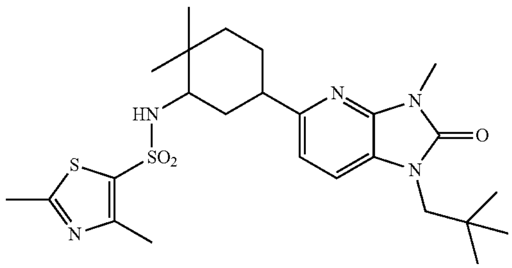 [SMILES: Cc1nc(C)c(S(=O)(=O)NC2CC(c3ccc4c(n3)n(C)c(=O)n4CC(C)(C)C)CCC2(C)C)s1] | N-{5-[1-(2,2-dimethylpropyl)-3-methyl-2-oxo-2,3-dihydro-1H-imidazo[4,5-b]pyridin-5-yl]-2,2-dimethylcyclohexyl}-2,4-dimethyl-1,3-thiazole-5-sulfonamide | C25H37N5O3S2 [M + H] calc 520.2411 obs 520.2420 |
| 19-48 | 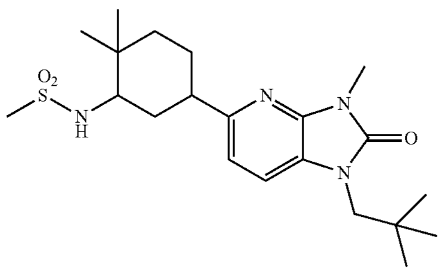 [SMILES: Cn1c(=O)n(CC(C)(C)C)c2ccc(C3CCC(C)(C)C(NS(C)(=O)=O)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}methanesulfonamide | C21H34N4O3S [M + H] calc 423.2425 obs 423.2428 |
| 19-49 | 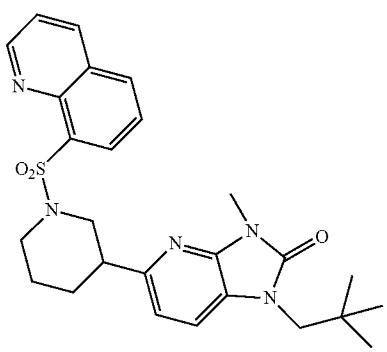 [SMILES: Cn1c(=O)n(CC(C)(C)C)c2ccc(C3CCCN(S(=O)(=O)c4cccc5cccnc45)C3)nc21] | 1-(2,2-dimethylpropyl)-3-methyl-5-[1-(quinolin-8-ylsulfonyl)piperidin-3-yl]-1,3-dihydro-2H-imidazo[4,5-b]pyridin-2-one | C26H31N5O3S [M + H] calc 494.2222 obs 494.2223 |
| 19-50 | 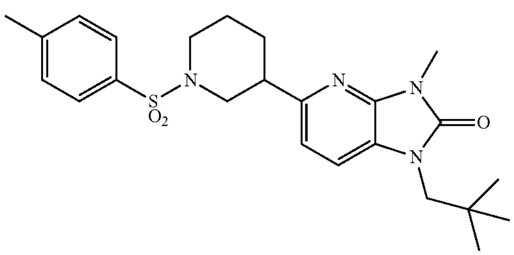 [SMILES: Cc1ccc(S(=O)(=O)N2CCCC(c3ccc4c(n3)n(C)c(=O)n4CC(C)(C)C)C2)cc1] | 1-(2,2-dimethylpropyl)-3-methyl-5-{1-[(4-methylphenyl)sulfonyl]piperidin-3-yl}-1,3-dihydro-2H-imidazo[4,5-b]pyridin-2-one | C24H32N4O3S [M + H] calc 457.2269 obs 457.2269 |
| 19-51 | 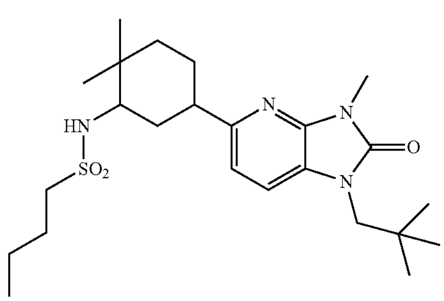 [SMILES: CCCCS(=O)(=O)NC1CC(c2ccc3c(n2)n(C)c(=O)n3CC(C)(C)C)CCC1(C)C] | N-{5-[1-(2,2-dimethylpropyl)-3-methyl-2-oxo-2,3-dihydro-1H-imidazo[4,5-b]pyridin-5-yl]-2,2-dimethylcyclohexyl}butane-1-sulfonamide | C24H40N4O3S [M + H] calc 465.2894 obs 465.2891 |

TABLE 8-continued

| # | Structure | Name | HRMS/LRMS |
|---|---|---|---|
| 19-52 | 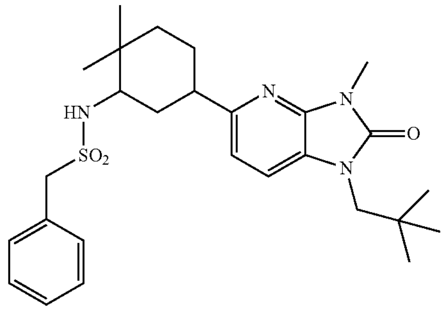 [SMILES: Cn1c(=O)n(CC(C)(C)C)c2ccc(C3CCC(C)(C)C(NS(=O)(=O)Cc4ccccc4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-1-phenylmethanesulfonamide | C27H38N4O3S [M + H] calc 499.2738 obs 499.2737 |
| 19-53 | 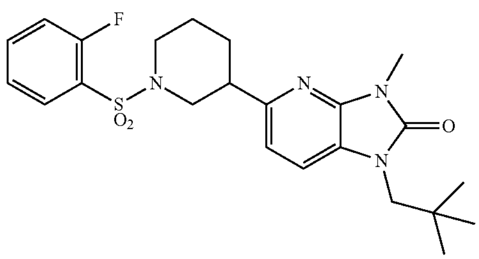 [SMILES: Cn1c(=O)n(CC(C)(C)C)c2ccc(C3CCCN(S(=O)(=O)c4ccccc4F)C3)nc21] | 1-(2,2-dimethylpropyl)-5-{1-[(2-fluorophenyl)sulfonyl]piperidin-3-yl}-3-methyl-1,3-dihydro-2H-imidazo[4,5-b]pyridin-2-one | C23H29FN4O3S [M + H] calc 461.2019 obs 461.2020 |
| 19-54 | 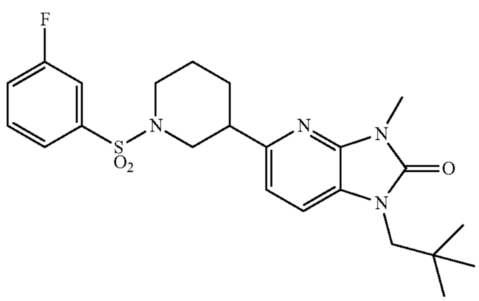 [SMILES: Cn1c(=O)n(CC(C)(C)C)c2ccc(C3CCCN(S(=O)(=O)c4cccc(F)c4)C3)nc21] | 1-(2,2-dimethylpropyl)-5-{1-[(3-fluorophenyl)sulfonyl]piperidin-3-yl}-3-methyl-1,3-dihydro-2H-imidazo[4,5-b]pyridin-2-one | C23H29FN4O3S [M + H] calc 461.2019 obs 461.2019 |
| 19-55 | 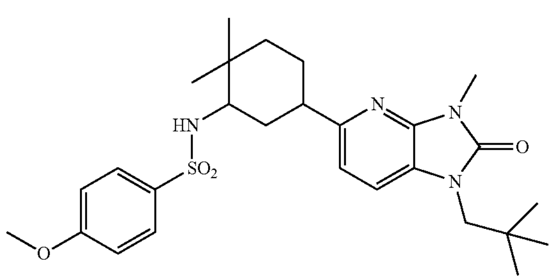 [SMILES: COc1ccc(S(=O)(=O)NC2CC(c3ccc4c(n3)n(C)c(=O)n4CC(C)(C)C)CCC2(C)C)cc1] | N-{5-[1-(2,2-dimethylpropyl)-3-methyl-2-oxo-2,3-dihydro-1H-imidazo[4,5-b]pyridin-5-yl]-2,2-dimethylcyclohexyl}-4-methoxybenzenesulfonamide | C27H38N4O4S [M + H] calc 515.2687 obs 515.2693 |
| 19-56 | 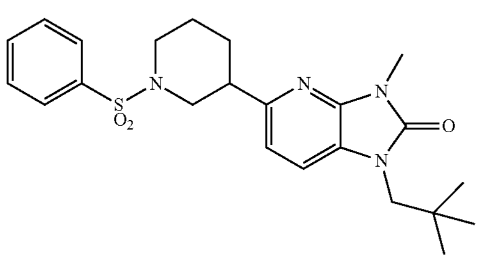 [SMILES: Cn1c(=O)n(CC(C)(C)C)c2ccc(C3CCCN(S(=O)(=O)c4ccccc4)C3)nc21] | 1-(2,2-dimethylpropyl)-3-methyl-5-[1-(phenylsulfonyl)piperidin-3-yl]-1,3-dihydro-2H-imidazo[4,5-b]pyridin-2-one | C23H30N4O3S [M + H] calc 443.2113 obs 443.2113 |

TABLE 8-continued

| # | Structure | Name | HRMS/LRMS |
|---|---|---|---|
| 19-57 | 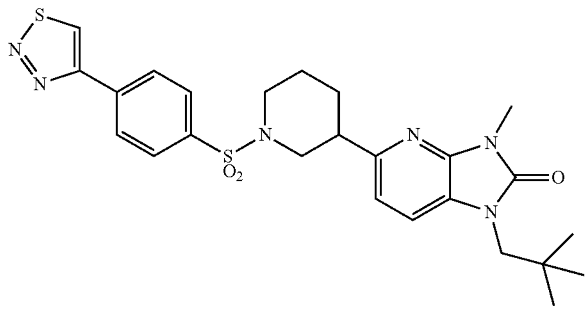 [SMILES: Cn1c(=O)n(CC(C)(C)C)c2ccc(C3CCCN(S(=O)(=O)c4ccc(-c5csnn5)cc4)C3)nc21] | 1-(2,2-dimethylpropyl)-3-methyl-5-(1-{[4-(1,2,3-thiadiazol-4-yl)phenyl]sulfonyl}piperidin-3-yl)-1,3-dihydro-2H-imidazo[4,5-b]pyridin-2-one | C25H30N6O3S2 [M + H] calc 527.1895 obs 527.1898 |
| 19-58 | 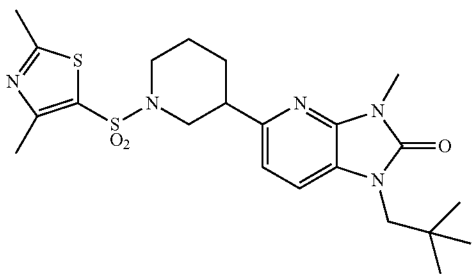 [SMILES: Cc1nc(C)c(S(=O)(=O)N2CCCC(c3ccc4c(n3)n(C)c(=O)n4CC(C)(C)C)C2)s1] | 1-(2,2-dimethylpropyl)-5-{1-[(2,4-dimethyl-1,3-thiazol-5-yl)sulfonyl]piperidin-3-yl}-3-methyl-1,3-dihydro-2H-imidazo[4,5-b]pyridin-2-one | C22H31N5O3S2 [M + H] calc 478.1942 obs 478.1943 |
| 19-59 | 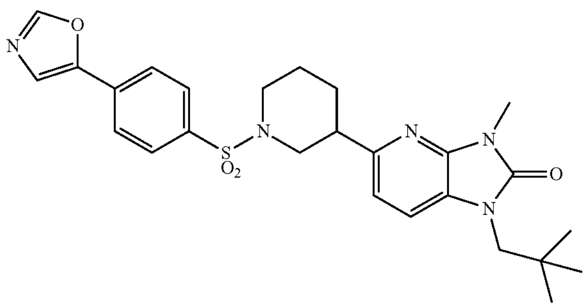 [SMILES: Cn1c(=O)n(CC(C)(C)C)c2ccc(C3CCCN(S(=O)(=O)c4ccc(-c5cnco5)cc4)C3)nc21] | 1-(2,2-dimethylpropyl)-3-methyl-5-(1-{[4-(1,3-oxazol-5-yl)phenyl]sulfonyl}piperidin-3-yl)-1,3-dihydro-2H-imidazo[4,5-b]pyridin-2-one | C26H31N5O4S [M + H] calc 510.2171 obs 510.2172 |
| 19-60 | 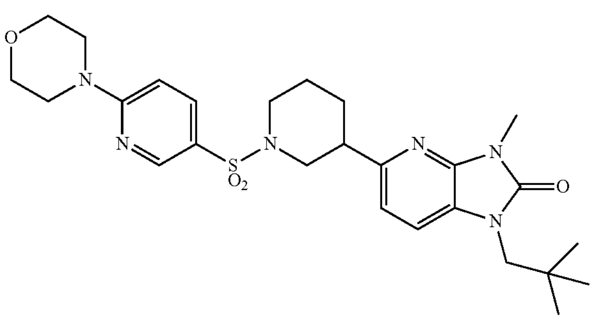 [SMILES: Cn1c(=O)n(CC(C)(C)C)c2ccc(C3CCCN(S(=O)(=O)c4ccc(N5CCOCC5)nc4)C3)nc21] | 1-(2,2-dimethylpropyl)-3-methyl-5-{1-[(6-morpholin-4-ylpyridin-3-yl)sulfonyl]piperidin-3-yl}-1,3-dihydro-2H-imidazo[4,5-b]pyridin-2-one | C26H36N6O4S [M + H] calc 529.2592 obs 529.2588 |
| 19-61 | 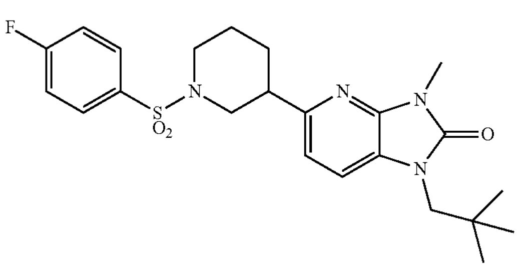 [SMILES: Cn1c(=O)n(CC(C)(C)C)c2ccc(C3CCCN(S(=O)(=O)c4ccc(F)cc4)C3)nc21] | 1-(2,2-dimethylpropyl)-5-{1-[(4-fluorophenyl)sulfonyl]piperidin-3-yl}-3-methyl-1,3-dihydro-2H-imidazo[4,5-b]pyridin-2-one | C23H29FN4O3S [M + H] calc 461.2019 obs 461.2019 |

TABLE 8-continued

| # | Structure | Name | HRMS/LRMS |
|---|---|---|---|
| 19-62 | 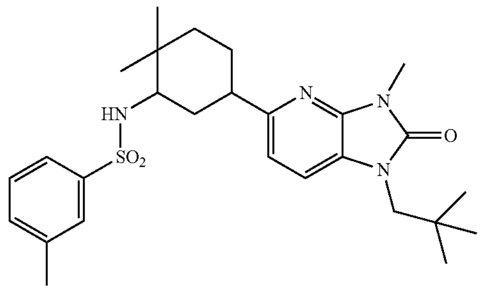 [SMILES: Cc1cccc(S(=O)(=O)NC2CC(c3ccc4c(n3)n(C)c(=O)n4CC(C)(C)C)CCC2(C)C)c1] | N-{5-[1-(2,2-dimethylpropyl)-3-methyl-2-oxo-2,3-dihydro-1H-imidazo[4,5-b]pyridin-5-yl]-2,2-dimethylcyclohexyl}-3-methylbenzenesulfonamide | C27H38N4O3S [M + H] calc 499.2738 obs 499.2741 |
| 19-63 | 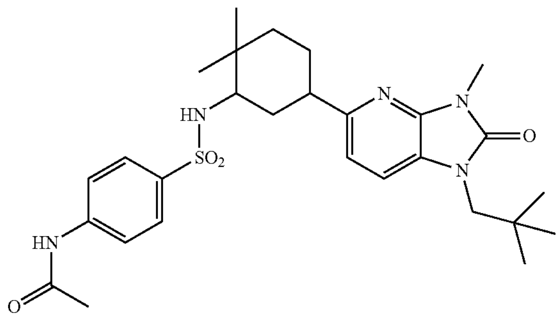 [SMILES: CC(=O)Nc1ccc(S(=O)(=O)NC2CC(c3ccc4c(n3)n(C)c(=O)n4CC(C)(C)C)CCC2(C)C)cc1] | N-[4-({5-[1-(2,2-dimethylpropyl)-3-methyl-2-oxo-2,3-dihydro-1H-imidazo[4,5-b]pyridin-5-yl]-2,2-dimethylcyclohexyl}sulfamoyl)phenyl]acetamide | C28H39N5O4S [M + H] calc 542.2796 obs 542.2801 |
| 19-64 | 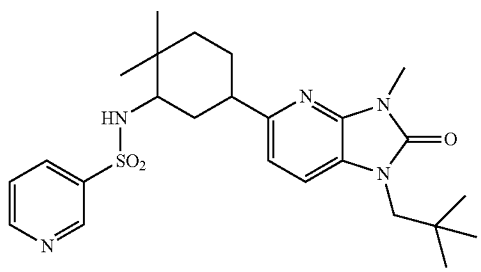 [SMILES: Cn1c(=O)n(CC(C)(C)C)c2ccc(C3CCC(C)(C)C(NS(=O)(=O)c4cccnc4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}pyridine-3-sulfonamide | C25H35N5O3S [M + H] calc 486.2534 obs 486.2541 |
| 19-65 | 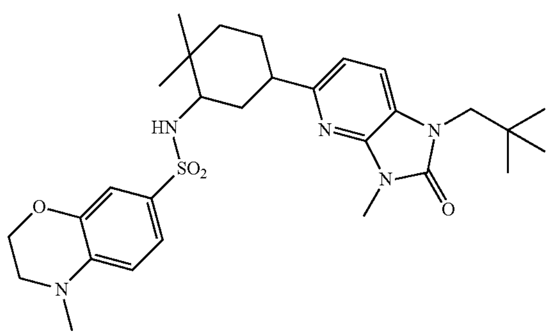 [SMILES: CN1CCOc2cc(S(=O)(=O)NC3CC(c4ccc5c(n4)n(C)c(=O)n5CC(C)(C)C)CCC3(C)C)ccc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-4-methyl-3,4-dihydro-2H-1,4-benzoxazine-7-sulfonamide | C29H41N5O4S [M + H] calc 556.2952 obs 556.2959 |
| 19-66 | 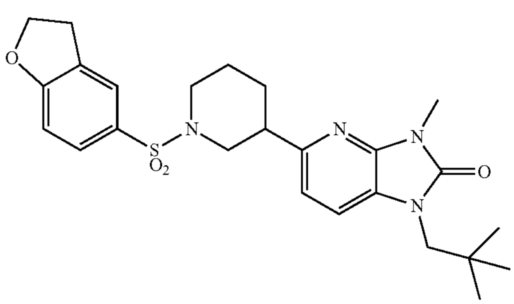 [SMILES: Cn1c(=O)n(CC(C)(C)C)c2ccc(C3CCCN(S(=O)(=O)c4ccc5c(c4)CCO5)C3)nc21] | 5-[1-(2,3-dihydro-1-benzofuran-5-ylsulfonyl)piperidin-3-yl]-1-(2,2-dimethylpropyl)-3-methyl-1,3-dihydro-2H-imidazo[4,5-b]pyridin-2-one | C25H32N4O4S [M + H] calc 485.2218 obs 485.2218 |

TABLE 8-continued

| # | Structure | Name | HRMS/LRMS |
|---|---|---|---|
| 19-67 | 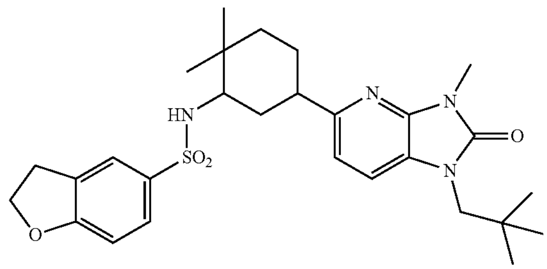 [SMILES: Cn1c(=O)n(CC(C)(C)C)c2ccc(C3CCC(C)(C)C(NS(=O)(=O)c4ccc5c(c4)CCO5)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-2,3-dihydro-1-benzofuran-5-sulfonamide | C28H38N4O4S [M + H] calc 527.2687 obs 527.2681 |
| 19-68 | 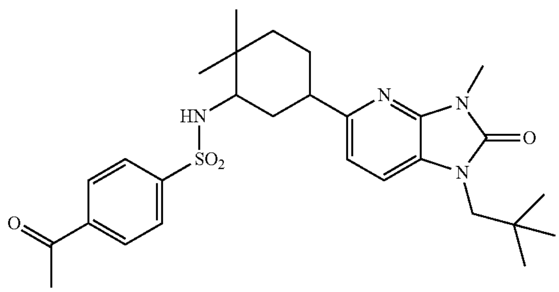 [SMILES: CC(=O)c1ccc(S(=O)(=O)NC2CC(c3ccc4c(n3)n(C)c(=O)n4CC(C)(C)C)CCC2(C)C)cc1] | 4-acetyl-N-{5-[1-(2,2-dimethylpropyl)-3-methyl-2-oxo-2,3-dihydro-1H-imidazo[4,5-b]pyridin-5-yl]-2,2-dimethylcyclohexyl}benzenesulfonamide | C28H38N4O4S [M + H] calc 527.2687 obs 527.2692 |
| 19-69 | 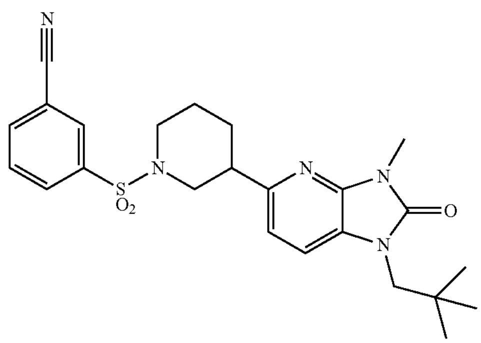 [SMILES: Cn1c(=O)n(CC(C)(C)C)c2ccc(C3CCCN(S(=O)(=O)c4cccc(C#N)c4)C3)nc21] | 3-({3-[1-(2,2-dimethylpropyl)-3-methyl-2-oxo-2,3-dihydro-1H-imidazo[4,5-b]pyridin-5-yl]piperidin-1-yl}sulfonyl)benzonitrile | C24H29N5O3S [M + H] calc 468.2065 obs 468.2064 |
| 19-70 | 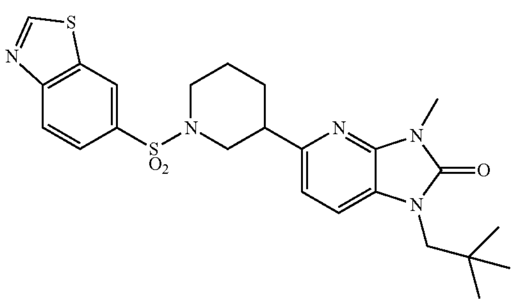 [SMILES: Cn1c(=O)n(CC(C)(C)C)c2ccc(C3CCCN(S(=O)(=O)c4ccc5ncsc5c4)C3)nc21] | 5-[1-(1,3-benzothiazol-6-ylsulfonyl)piperidin-3-yl]-1-(2,2-dimethylpropyl)-3-methyl-1,3-dihydro-2H-imidazo[4,5-b]pyridin-2-one | C24H29N5O3S2 [M + H] calc 500.1786 obs 500.1783 |
| 19-71 | 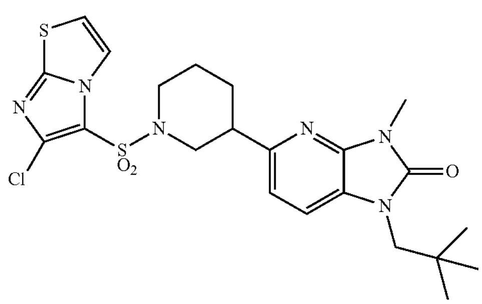 [SMILES: Cn1c(=O)n(CC(C)(C)C)c2ccc(C3CCCN(S(=O)(=O)c4c(Cl)nc5sccn45)C3)nc21] | 5-{1-[(6-chloroimidazo[2,1-b][1,3]thiazol-5-yl)sulfonyl]piperidin-3-yl}-1-(2,2-dimethylpropyl)-3-methyl-1,3-dihydro-2H-imidazo[4,5-b]pyridin-2-one | C22H27ClN6O3S2 [M + H] calc 523.1349 obs 523.1351 |

TABLE 8-continued

| # | Structure | Name | HRMS/LRMS |
|---|---|---|---|
| 19-72 | 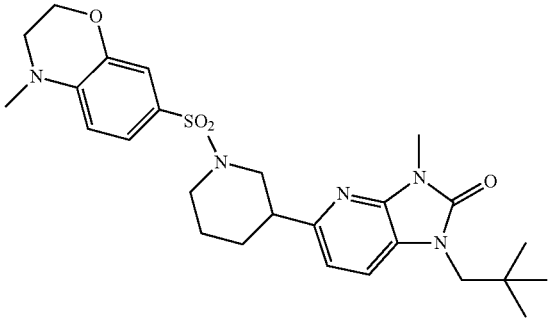 [SMILES: CN1CCOc2cc(S(=O)(=O)N3CCCC(c4ccc5c(n4)n(C)c(=O)n5CC(C)(C)C)C3)ccc21] | 1-(2,2-dimethylpropyl)-3-methyl-5-{1-[(4-methyl-3,4-dihydro-2H-1,4-benzoxazin-7-yl)sulfonyl]piperidin-3-yl}-1,3-dihydro-2H-imidazo[4,5-b]pyridin-2-one | C26H35N5O4S [M + H] calc 514.2483 obs 514.2479 |
| 19-73 | 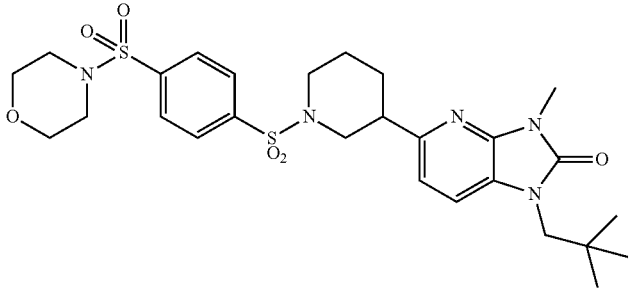 [SMILES: Cn1c(=O)n(CC(C)(C)C)c2ccc(C3CCCN(S(=O)(=O)c4ccc(S(=O)(=O)N5CCOCC5)cc4)C3)nc21] | 1-(2,2-dimethylpropyl)-3-methyl-5-(1-{[4-(morpholin-4-ylsulfonyl)phenyl]sulfonyl}piperidin-3-yl)-1,3-dihydro-2H-imidazo[4,5-b]pyridin-2-one | C27H37N5O6S2 [M + H] calc 592.2259 obs 592.2261 |
| 19-74 | 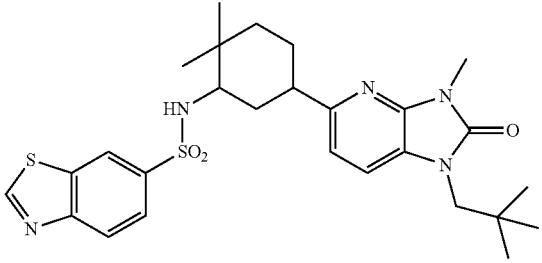 [SMILES: Cn1c(=O)n(CC(C)(C)C)c2ccc(C3CCC(C)(C)C(NS(=O)(=O)c4ccc5ncsc5c4)C3)nc21] | N-{5-[1-(2,2-dimethylpropyl)-3-methyl-2-oxo-2,3-dihydro-1H-imidazo[4,5-b]pyridin-5-yl]-2,2-dimethylcyclohexyl}-1,3-benzothiazole-6-sulfonamide | C27H35N5O3S2 [M + H] calc 542.2255 obs 542.2249 |
| 19-75 | 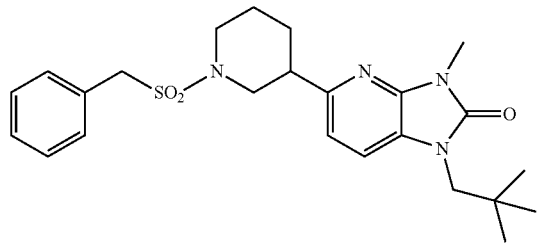 [SMILES: Cn1c(=O)n(CC(C)(C)C)c2ccc(C3CCCN(S(=O)(=O)Cc4ccccc4)C3)nc21] | 5-[1-(benzylsulfonyl)piperidin-3-yl]-1-(2,2-dimethylpropyl)-3-methyl-1,3-dihydro-2H-imidazo[4,5-b]pyridin-2-one | C24H32N4O3S [M + H] calc 457.2269 obs 457.2268 |
| 19-76 | 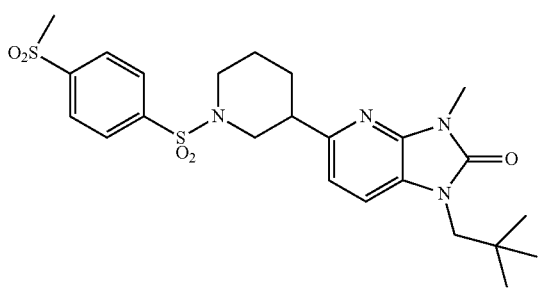 [SMILES: Cn1c(=O)n(CC(C)(C)C)c2ccc(C3CCCN(S(=O)(=O)c4ccc(S(C)(=O)=O)cc4)C3)nc21] | 1-(2,2-dimethylpropyl)-3-methyl-5-(1-{[4-(methylsulfonyl)phenyl]sulfonyl}piperidin-3-yl)-1,3-dihydro-2H-imidazo[4,5-b]pyridin-2-one | C24H32N4O5S2 [M + H] calc 521.1888 obs 521.1891 |

TABLE 8-continued

| # | Structure | Name | HRMS/LRMS |
|---|-----------|------|-----------|
| 19-77 | 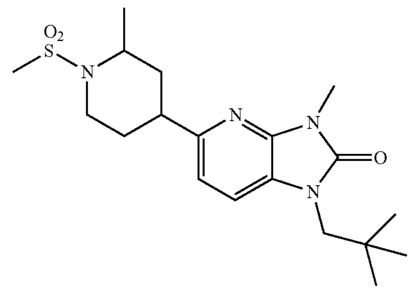 [SMILES: CC1CC(c2ccc3c(n2)n(C)c(=O)n3CC(C)(C)C)CCN1S(C)(=O)=O] | 1-(2,2-dimethylpropyl)-3-methyl-5-[2-methyl-1-(methylsulfonyl)piperidin-4-yl]-1,3-dihydro-2H-imidazo[4,5-b]pyridin-2-one | C19H30N4O3S [M + H] calc 395.2113 obs 395.2111 |

Scheme 20

17-31

20-1

20-2

20-3 i) BH₃-THF
ii) NaOH, H₂O₂

HCl/EtOAc
DCM/MeOH

HATU, DIPEA
NMP 1-(2,2-Dimethylpropyl)-5-[2-hydroxy-8-(isoxazol-3-ylcarbonyl)-8-azabicyclo-[3.2.1]oct-3-yl]-3-methyl-1,3-dihydro-2H-imidazo[4,5-b]pyridin-2-one (20-3)

tert-Butyl 3-[1-(2,2-dimethylpropyl)-3-methyl-2-oxo-2,3-dihydro-1H-imidazo-[4,5-b]pyridin-5-yl]-2-hydroxy-8-azabicyclo[3.2.1]octane-8-carboxylate (20-1)

To a round bottom flask was added tert-butyl 3-[1-(2,2-dimethylpropyl)-3-methyl-2-oxo-2,3-dihydro-1H-imidazo[4,5-b]pyridin-5-yl]-8-azabicyclo[3.2.1]oct-2-ene-8-carboxylate (17-31) (1.5 g, 3.52 mmol), and anhydrous THF (15 mL). The reaction mixture was then cooled to 0° C. under an atmosphere of nitrogen, and added borane tetrahydrofuran COMPLEX (1M in THF) (3.87 ml, 3.87 mmol) dropwise over 10 minutes while stirring. Stirred for ~10 minutes, then permitted to warm to room temperature for 30 minutes. Next cooled back to 0° C. and uncapped, and when open to atmosphere added hydrogen peroxide(35% by wt in H2O) (1.539 ml, 17.58 mmol) & sodium hydroxide (1M in H2O) (8.79 mL, 8.79 mmol) slowly over 20 minutes, then warmed to room temperature. The reaction was then permitted to stir overnight at room temperature (16 hours), then suspended in EtOAc, washed with a saturated solution of Na₂S₂O₃, then saturated NaHCO3, followed by water and brine, dried over Na₂SO₄, filtered and concentrated. The resulting residue was purified by silica gel chromatography (0-100% EtOAc/Hex) to yield tert-Butyl 3-[1-(2,2-dimethylpropyl)-3-methyl-2-oxo-2,3-dihydro-1H-imidazo-[4,5-b]pyridin-5-yl]-2-hydroxy-8-azabicyclo[3.2.1]octane-8-carboxylate (20-1). HRMS (M+H)⁺: observed=429.2865, calculated=429.2860.

1-(2,2-Dimethylpropyl)-5-(2-hydroxy-8-azabicyclo[3.2.1]oct-3-yl)-3-methyl-1,3-dihydro-2H-imidazo[4,5-b]pyridin-2-one (20-2)

Procedure similar to that for 5-(4-Aminocyclohex-1-en-1-yl)-1-(2,2-dimethylpropyl)-3-methyl-1,3-dihydro-2H-imidazo[4,5-b]pyridin-2-one (17-2) gave 1-(2,2-Dimethylpropyl)-5-(2-hydroxy-8-azabicyclo[3.2.1]oct-3-yl)-3-methyl-1,3-dihydro-2H-imidazo[4,5-b]pyridin-2-one (20-2). HRMS (M+H)⁺: observed=345.2286, calculated=345.2285.

1-(2,2-Dimethylpropyl)-5-[2-hydroxy-8-(isoxazol-3-ylcarbonyl)-8-azabicyclo-[3.2.1]oct-3-yl]-3-methyl-1,3-dihydro-2H-imidazo[4,5-b]pyridin-2-one (20-3)

Procedure similar to that for N-{4-[1-(2,2-Dimethylpropyl)-3-methyl-2-oxo-2,3-dihydro-1H-imidazo[4,5-b]pyridin-5-yl]cyclohex-3-en-1-yl}-1-methyl-1H-imidazole-2-carboxamide (17-3) gave 1-(2,2-Dimethylpropyl)-5-[2-hydroxy-8-(isoxazol-3-ylcarbonyl)-8-azabicyclo-[3.2.1]oct-3-yl]-3-methyl-1,3-dihydro-2H-imidazo[4,5-b]pyridin-2-one (20-3). HRMS (M+H)+: observed=440.2291, calculated=440.2292

The following compounds were prepared by a reaction sequence analogous to that illustrated in Scheme 20:

TABLE 9

| # | Structure | Name | HRMS/LRMS |
|---|-----------|------|-----------|
| 20-4 | 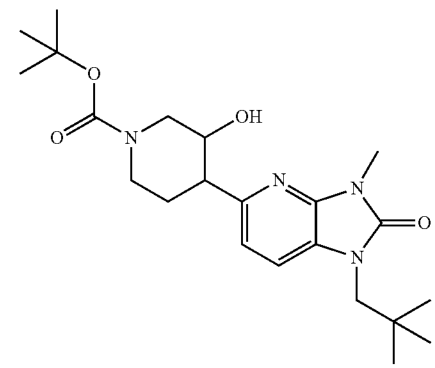 [SMILES: Cn1c(=O)n(CC(C)(C)C)c2ccc(C3CCN(C(=O)OC(C)(C)C)CC3O)nc21] | tert-butyl 4-[1-(2,2-dimethylpropyl)-3-methyl-2-oxo-2,3-dihydro-1H-imidazo[4,5-b]pyridin-5-yl]-3-hydroxypiperidine-1-carboxylate | C22H34N4O4 [M + H] calc 419.2653 obs 419.2647 |
| 20-5 | 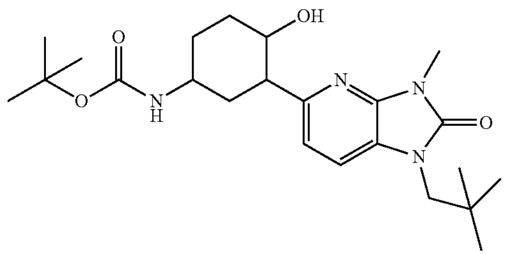 | tert-butyl {3-[1-(2,2-dimethylpropyl)-3-methyl-2-oxo-2,3-dihydro-1H-imidazo[4,5-b]pyridin-5-yl]-4-hydroxycyclohexyl} carbamate | C22H34N4O4 [M + H] calc 418.5 obs 419.4 |

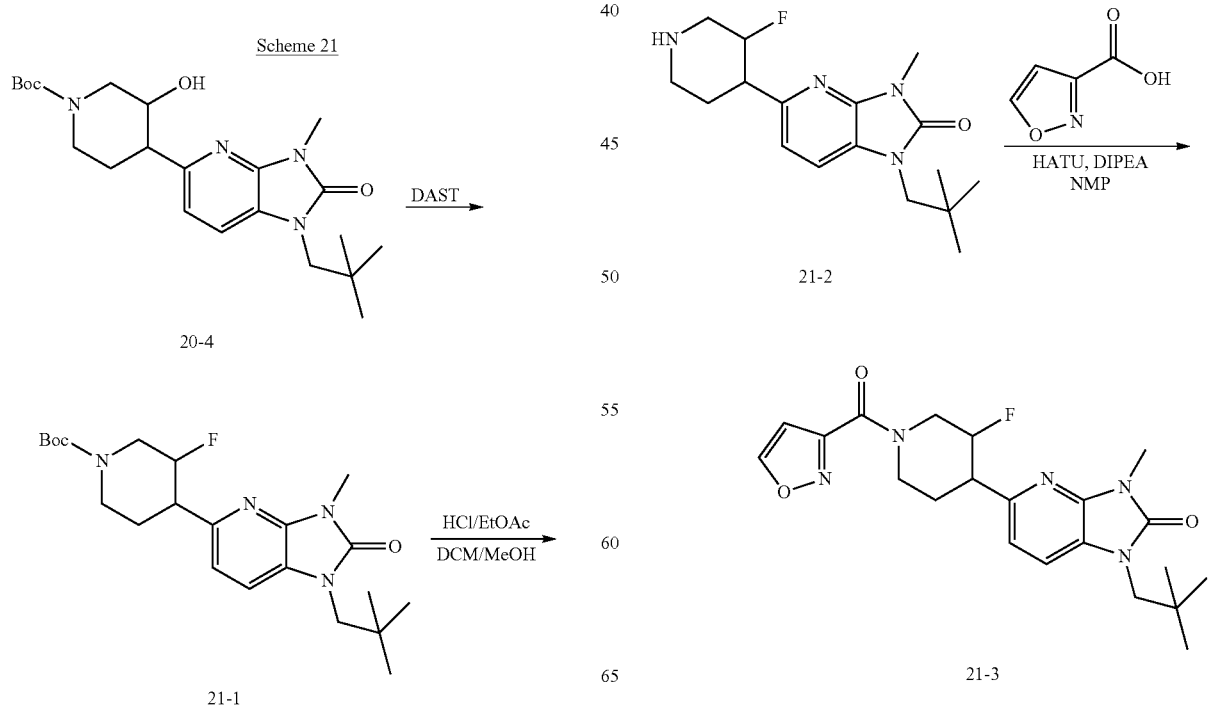

1-(2,2-Dimethylpropyl)-5-[3-fluoro-1-(isoxazol-3-ylcarbonyl)piperidin-4-yl]-3-methyl-1,3-dihydro-2H-imidazo[4,5-b]pyridin-2-one (21-3)

tert-Butyl 4-[1-(2,2-dimethylpropyl)-3-methyl-2-oxo-2,3-dihydro-1H-imidazo[4,5-b]pyridin-5-yl]-3-fluoropiperidine-1-carboxylate (21-1)

Procedure similar to that for tert-Butyl 4-{1-[(2,2-difluorocyclopropyl)-methyl]-3-methyl-2,2-dioxido-1,3-dihydro[1,2,5]thiadiazolo[3,4-b]pyridin-5-yl}-3-fluoropiperidine-1-carboxylate (29-1) gave tert-Butyl 4-[1-(2,2-dimethylpropyl)-3-methyl-2-oxo-2,3-dihydro-1H-imidazo[4,5-b]pyridin-5-yl]-3-fluoropiperidine-1-carboxylate (21-1). LRMS (M+H)$^+$: observed=421.3, calculated=421.5.

1-(2,2-Dimethylpropyl)-5-(3-fluoropiperidin-4-yl)-3-methyl-1,3-dihydro-2H-imidazo[4,5-b]pyridin-2-one (21-2)

Procedure similar to that for 5-(4-Aminocyclohex-1-en-1-yl)-1-(2,2-dimethylpropyl)-3-methyl-1,3-dihydro-2H-imidazo[4,5-b]pyridin-2-one (17-2) gave 1-(2,2-Dimethylpropyl)-5-(3-fluoropiperidin-4-yl)-3-methyl-1,3-dihydro-2H-imidazo[4,5-b]pyridin-2-one (21-2). HRMS (M+H)$^+$: observed=321.2086, calculated=321.2085.

1-(2,2-Dimethylpropyl)-5-[3-fluoro-1-(isoxazol-3-ylcarbonyl)piperidin-4-yl]-3-methyl-1,3-dihydro-2H-imidazo[4,5-b]pyridin-2-one (21-3)

Procedure similar to that for N-{4-[1-(2,2-Dimethylpropyl)-3-methyl-2-oxo-2,3-dihydro-1H-imidazo[4,5-b]pyridin-5-yl]cyclohex-3-en-1-yl}-1-methyl-1H-imidazole-2-carboxamide (17-3) gave 1-(2,2-Dimethylpropyl)-5-[3-fluoro-1-(isoxazol-3-ylcarbonyl)piperidin-4-yl]-3-methyl-1,3-dihydro-2H-imidazo[4,5-b]pyridin-2-one (21-3). HRMS (M+H)$^+$: observed=416.2091, calculated=416.2092.

The following compounds were prepared by a reaction sequence analogous to that illustrated in Scheme 21:

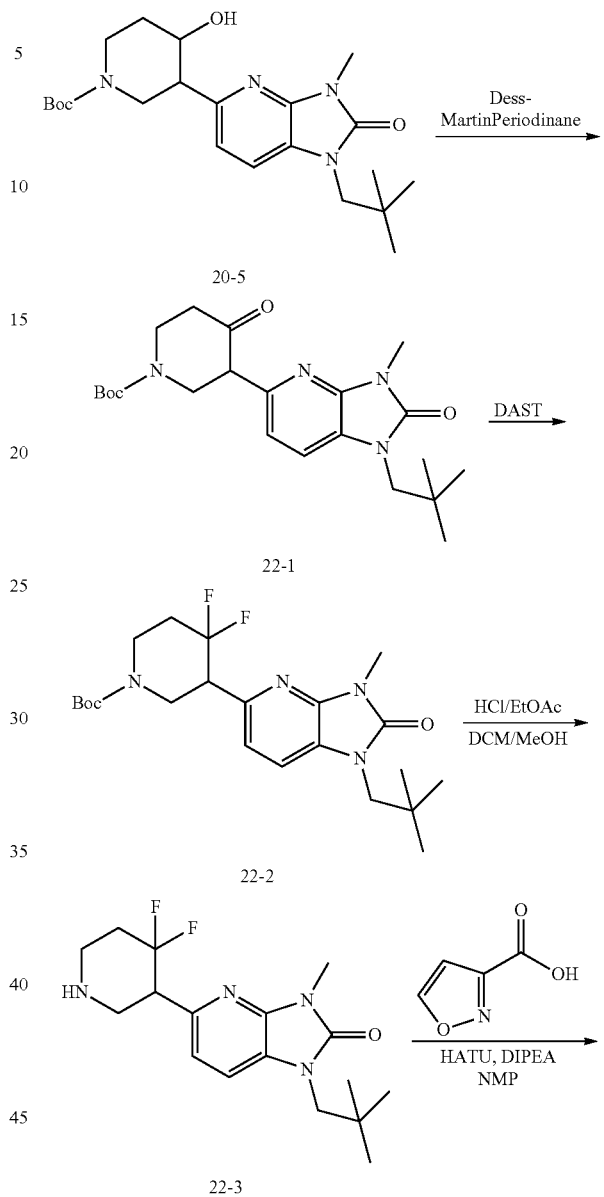

Scheme 22

TABLE 10

| # | Structure | Name | HRMS/LRMS |
|---|-----------|------|-----------|
| 21-4 | 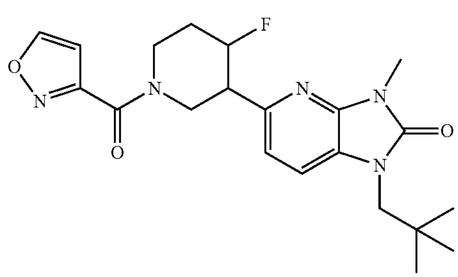 [SMILES: Cn1c(=O)n(CC(C)(C)C)c2ccc(C3CN(C(=O)c4ccon4)CCC3F)nc21] | 1-(2,2-dimethylpropyl)-5-[4-fluoro-1-(isoxazol-3-ylcarbonyl)piperidin-3-yl]-3-methyl-1,3-dihydro-2H-imidazo[4,5-b]pyridin-2-one | C21H26FN5O3 [M + H] calc 416.2092 obs 416.2091 |

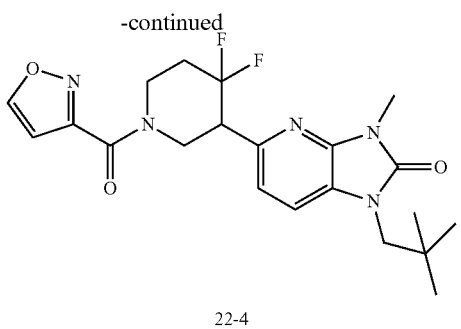

22-4

5-[4,4-Difluoro-1-(isoxazol-3-ylcarbonyl)piperidin-3-yl]-1-(2,2-dimethylpropyl)-3-methyl-1,3-dihydro-2H-imidazo[4,5-b]pyridin-2-one (22-4)

tert-butyl 3-[1-(2,2-dimethylpropyl)-3-methyl-2-oxo-2,3-dihydro-1H-imidazo[4,5-b]pyridin-5-yl]-4-oxopiperidine-1-carboxylate (22-1)

To a round bottom flask was added tert-butyl 3-[1-(2,2-dimethylpropyl)-3-methyl-2-oxo-2,3-dihydro-1H-imidazo[4,5-b]pyridin-5-yl]-4-hydroxypiperidine-1-carboxylate (20-5) (25 mg, 0.060 mmol), DCM (1 mL), and Dess-MartinPeriodinane (27.9 mg, 0.066 mmol), and the resulting mixture was then stirred under an atmosphere of nitrogen at room temperature for 15 hours. The reaction mixture was then suspended in EtOAc, and washed with a saturated solution of Na2S2O3, followed by a saturated solution of sodium bicarbonate, then water, and finally brine. Organics dried over sodium sulfate, filtered & concentrated to give crude tert-butyl 3-[1-(2,2-dimethylpropyl)-3-methyl-2-oxo-2,3-dihydro-1H-imidazo[4,5-b]pyridin-5-yl]-4-oxopiperidine-1-carboxylate (22-1). LRMS (M+H)$^+$: observed=417.4, calculated=417.5.

tert-butyl 3-[1-(2,2-dimethylpropyl)-3-methyl-2-oxo-2,3-dihydro-1H-imidazo[4,5-b]pyridin-5-yl]-4-oxopiperidine-1-carboxylate (22-2)

To a round bottom flask was added tert-butyl 3-[1-(2,2-dimethylpropyl)-3-methyl-2-oxo-2,3-dihydro-1H-imidazo[4,5-b]pyridin-5-yl]-4-oxopiperidine-1-carboxylate (22-1) (25 mg, 0.060 mmol), anhydrous DCM (1 mL), the reaction mixture was cooled to −78 C while stirring under an atmosphere of nitrogen, then added DAST (0.024 ml, 0.180 mmol) dropwise. Reaction mixture was continued to stir at −78 C for 10 minutes, then permitted to warm to room temperature overnight (16 hours). The reaction mixture was then quenched with 1N NaOH, then suspended in EtOAc, washed with water, then brine; dried over Na2SO4, filtered & concentrated. The resulting residue was then purified by reverse-phase chromatography (10-100% CH$_3$CN:0.1% TFA in H$_2$O) to yield tert-butyl 3-[1-(2,2-dimethylpropyl)-3-methyl-2-oxo-2,3-dihydro-1H-imidazo[4,5-b]pyridin-5-yl]-4-oxopiperidine-1-carboxylate (22-2). LRMS (M+H)$^+$: observed=439.3, calculated=439.5.

5-(4,4-difluoropiperidin-3-yl)-1-(2,2-dimethylpropyl)-3-methyl-1,3-dihydro-2H-imidazo[4,5-b]pyridin-2-one (22-3)

Procedure similar to that for 5-(4-Aminocyclohex-1-en-1-yl)-1-(2,2-dimethylpropyl)-3-methyl-1,3-dihydro-2H-imidazo[4, 5-1)]pyridin-2-one (17-2) gave 5-(4,4-difluoropiperidin-3-yl)-1-(2,2-dimethylpropyl)-3-methyl-1,3-dihydro-2H-imidazo[4,5-b]pyridin-2-one (22-3). LRMS (M+H)$^+$: observed=339.3, calculated=339.4.

5-[4,4-Difluoro-1-(isoxazol-3-ylcarbonyl)piperidin-3-yl]-1-(2,2-dimethylpropyl)-3-methyl-1,3-dihydro-2H-imidazo[4,5-b]pyridin-2-one (22-4)

Procedure similar to that for N-{4-[1-(2,2-Dimethylpropyl)-3-methyl-2-oxo-2,3-dihydro-1H-imidazo[4,5-b]pyridin-5-yl]cyclohex-3-en-1-yl}-1-methyl-1H-imidazole-2-carboxamide (17-3) gave 5-[4,4-Difluoro-1-(isoxazol-3-ylcarbonyl)piperidin-3-yl]-1-(2,2-dimethylpropyl)-3-methyl-1,3-dihydro-2H-imidazo[4,5-b]pyridin-2-one (22-4). HRMS (M+H)$^+$: observed=434.1994, calculated=434.1998.

Scheme 23

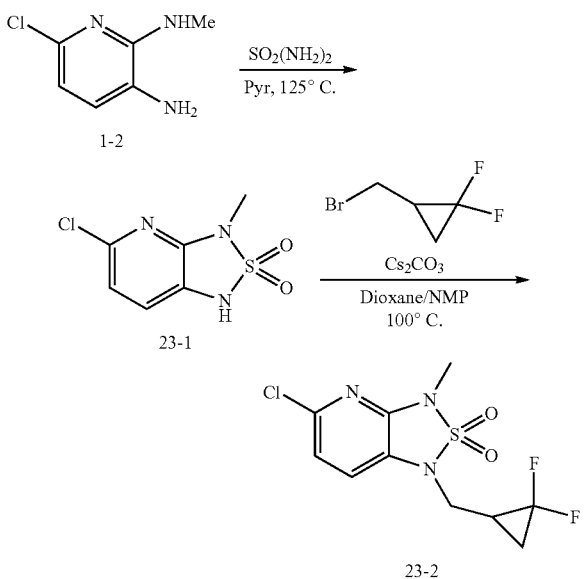

23-2

5-Chloro-1-[(2,2-difluorocyclopropyl)methyl]-3-methyl-1,3-dihydro-[1,2,5]thiadiazolo[3,4-b]pyridine 2,2-dioxide (23-2)

5-Chloro-3-methyl-1,3-dihydro[1,2,5]thiadiazolo[3,4-b]pyridine 2,2-dioxide (21-1)

To a round bottom flask was added 6-chloro-N$^2$-methylpyridine-2,3-diamine (1-2) (2.043 g, 12.96 mmol), sulfamide (2.69 g, 28.0 mmol), and anhydrous pyridine (20 ml). The reaction mixture was refluxed at 125 C in a hot oil bath with stirring under an atmosphere of nitrogen with a water cooled reflux condenser attached overnight (16 hours). The reaction mixture was then cooled to room temperature and suspended in EtOAc (250 mL) & 6N HCl in water (250 mL) and filtered. Filtrate was then separated, organics dried over sodium sulfate, filtered & concentrated. The resulting residue was then purified with silica gel chromatography (0-20% Isopropanol/DCM) & concentrated to yield 5-chloro-3-methyl-1,3-dihydro[1,2,5]thiadiazolo[3,4-b]pyridine 2,2-dioxide (23-1). HRMS (M+H)$^+$: observed=219.9946, calculated=219.9942.

5-chloro-1-[(2,2-difluorocyclopropyl)methyl]-3-methyl-1,3-dihydro-[1,2,5]thiadiazolo[3,4-b]pyridine 2,2-dioxide (23-2)

Procedure similar to that for 5-chloro-1-(2,2-dimethylpropyl)-3-methyl-1,3-dihydro-2H-imidazo[4,5-b]-pyridin-2-one (1-4) gave 5-chloro-1-[(2,2-difluorocyclopropyl)methyl]-3-methyl-1,3-dihydro[1,2,5]thiadiazolo[3,4-b]pyridine 2,2-dioxide (23-2). HRMS (M+H)$^+$: observed=310.0220, calculated=310.0223.

Scheme 24

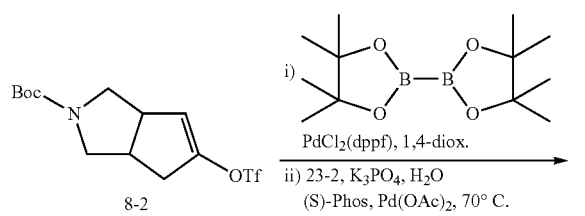

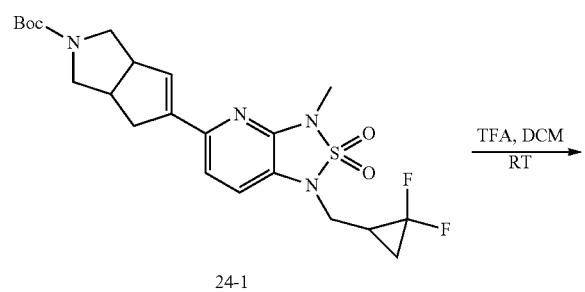

24-1

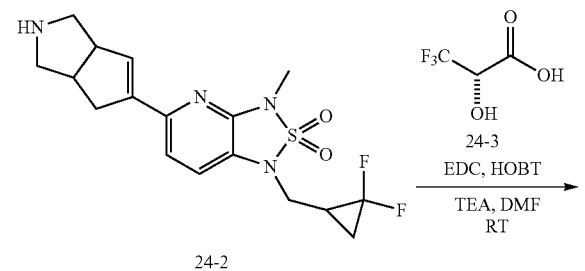

24-2

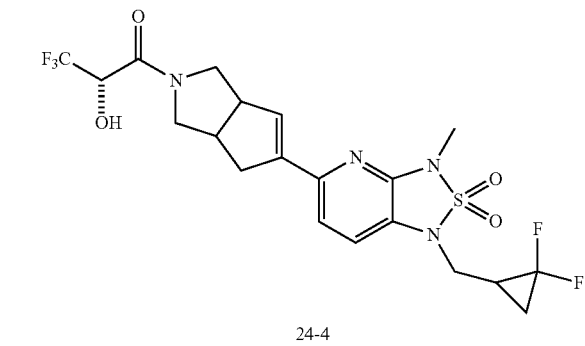

24-4

(2S)-1-[5-{1-[(2,2-Difluorocyclopropyl)methyl]-3-methyl-2,2-dioxido-1,3-dihydro[1,2,5]thiadiazolo[3,4-b]pyridin-5-yl}-3,3a,4,6a-tetrahydro-cyclopenta-[c]pyrrol-2(1H)-yl]-3,3,3-trifluoro-2-hydroxypropan-1-one (24-4)

tert-Butyl 5-{1-[(2,2-difluorocyclopropyl)methyl]-3-methyl-2,2-dioxido-1,3-dihydro[1,2,5]thiadiazolo[3,4-b]pyridin-5-yl}-3,3a,4,6a-tetrahydrocyclopenta[c]-pyrrole-2(1H)-carboxylate (24-1)

tert-Butyl 5-{[(Trifluoromethyl)sulfonyl]oxy}-3,3a,4,6a-tetrahydrocyclo-penta[c]pyrrole-2(1H)-carboxylate (8-2, 1.3 g, 3.64 mmol, 1.0 equiv), bis(pinocolato)diboron (1.0 g, 4.0 mmol, 1.1 equiv), potassium acetate (1.1 g, 10.91 mmol, 3.0 equiv) and PdCl$_2$(dppf) (0.19 g, 0.26 mmol, 0.07 equiv) were added to anhydrous 1,4-dioxane (4.6 mL) and heated to 60° C. After 18 h, the reaction contents were cooled to RT, followed by the subsequent addition of water (0.93 mL), 5-chloro-1-[(2,2-difluorocyclopropyl)methyl]-3-methyl-1,3-dihydro[1,2,5]-thiadiazole[3,4-b]pyridine 2,2-dioxide (23-2, 1.1 g, 3.64 mmol, 1.0 equiv), K$_3$PO$_4$ (1.9 g, 9.09 mmol, 2.5 equiv), (S)-Phos (0.15 g, 0.36 mmol, 0.10 equiv) and palladium(II) acetate (4.1 mg, 0.18 mmol, 0.05 equiv). The resulting mixture was heated to 70° C. for 9 h. Following this duration, LCMS showed consumption of starting material. The contents were then cooled to room temperature, diluted with ethyl acetate (20 mL), filtered through Celite and rinsed with ethyl acetate (3×5 mL) and water (1×5 mL). The filtrate layers were separated and the combined organics were washed with saturated NaHCO$_3$ (10 mL). The combined aqueous layers were then back-extracted with ethyl acetate (3×5 mL). The combined organics were dried over Na$_2$SO$_4$, filtered and concentrated in vacuo to give a dark orange oil. Purification by normal-phase chromatography (0-50% EtOAc:Hex) afforded 24-1 as a tan solid. MS m/z (M+H): calculated=482.5; observed=482.1.

1-[(2,2-Difluorocyclopropyl)methyl]-5-(1,2,3,3a,4,6a-hexahydrocyclo-penta-[c]pyrrol-5-yl)-3-methyl-1,3-dihydro[1,2,5]thiadiazolo[3,4-b]pyridine 2,2-dioxide (24-2)

tert-Butyl 5-{1-[(2,2-difluorocyclopropyl)methyl]-3-methyl-2,2-dioxido-1,3-dihydro[1,2,5]thiadiazolo[3,4-b]pyridin-5-yl}-3,3a,4,6a-tetrahydrocyclopenta[c]-pyrrole-2(1H)-carboxylate (24-1, 1.7 g, 3.4 mmol) was added to a mixture of DCM (28 mL) and TFA (7 mL) and stirred for 60 min. Following this duration, the contents were cautiously added to a mixture of saturated NaHCO$_3$ (50 mL) and ethyl acetate (50 mL). The layers were separated and the aqueous layer was back-extracted with ethyl acetate (2×30 mL). The combined organics were dried over Na$_2$SO$_4$, filtered and concentrated in vacuo to give an orange semi-solid. The material was carried forward without further purification.

(2S)-1-[5-{1-[(2,2-Difluorocyclopropyl)methyl]-3-methyl-2,2-dioxido-1,3-dihydro[1,2,5]thiadiazolo[3,4-b]pyridin-5-yl}-3,3a,4,6a-tetrahydrocyclopenta-[c]pyrrol-2(1H)-yl]-3,3,3-trifluoro-2-hydroxypropan-1-one (24-4)

1-[(2,2-Difluorocyclopropyl)methyl]-5-(1,2,3,3a,4,6a-hexahydrocyclo-penta-[c]pyrrol-5-yl)-3-methyl-1,3-dihydro[1,2,5]thiadiazolo[3,4-b]pyridine 2,2-dioxide (24-2, 0.79 g, 2.1 mmol, 1.0 equiv), (2S)-3,3,3-trifluoro-2-hydroxypropanoic acid (24-3, 0.30 g, 2.1 mmol, 1.0 equiv), EDC (0.40 g, 2.1 mmol, 1.0 equiv), HOBT (0.32 g, 2.1 mmol, 1.0 equiv) and triethylamine (0.58 mL, 4.2 mmol, 2.0 equiv) were added to anhydrous DMF (13.6 mL) and stirred at RT. After 18 h, the contents were partitioned between ethyl acetate (50 mL) and saturated NaHCO₃ (20 mL). The layers were separated and the aqueous layer was back-extracted with ethyl acetate (2×20 mL). The combined organics were washed with H₂O (5×20 mL), dried over Na₂SO₄, filtered and concentrated in vacuo to give a dark red oil. Purification by normal-phase chromatography (0-60% EtOAc:Hex) afforded 24-4 as a white solid. MS m/z (M+H): calculated=509.1276; observed=509.1281.

The following compounds were prepared from the appropriate triflate by a reaction sequence analogous to that illustrated in Scheme 24:

TABLE 11

| # | Structure | Name | HRMS/LRMS |
|---|-----------|------|-----------|
| 24-5 | 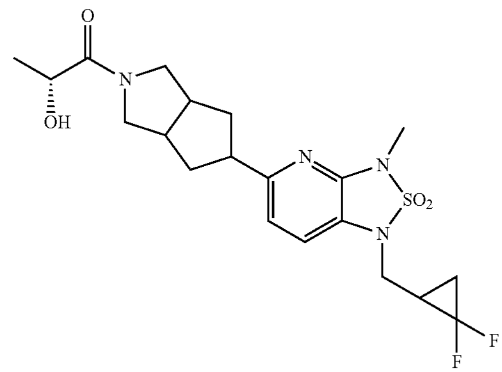 [SMILES: C[C@@H](O)C(=O)N1CC2CC(c3ccc4c(n3)N(C)S(=O)(=O)N4CC3CC3(F)F)CC2C1] | (2R)-1-[5-{1-[(2,2-difluorocyclopropyl)methyl]-3-methyl-2,2-dioxido-1,3-dihydro[1,2,5]thiadiazolo[3,4-b]pyridin-5-yl}hexahydrocyclopenta[c]pyrrol-2(1H)-yl]-1-oxopropan-2-ol | C20H26F2N4O4S [M + H] calc 457.1717 obs 457.1726 |
| 24-6 | 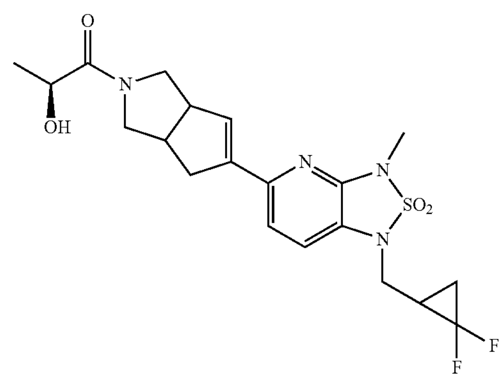 [SMILES: C[C@H](O)C(=O)N1CC2C=C(c3ccc4c(n3)N(C)S(=O)(=O)N4CC3CC3(F)F)CC2C1] | (2S)-1-[5-{-[(2,2-difluorocyclopropyl)methyl]-3-methyl-2,2-dioxido-1,3-dihydro[1,2,5]thiadiazolo[3,4-b]pyridin-5-yl}-3,3a,4,6a-tetrahydrocyclopenta[c]pyrrol-2(1H)-yl]-1-oxopropan-2-ol | C20H24F2N4O4S [M + H] calc 455.1561 obs 455.1561 |
| 24-7 | 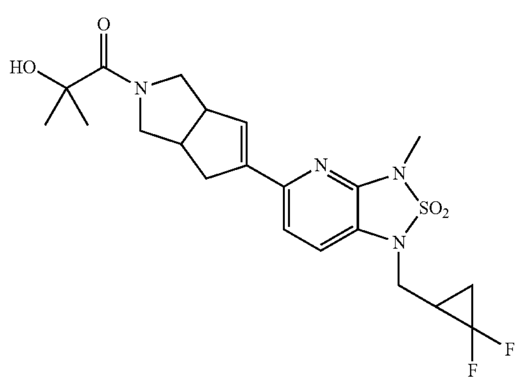 [SMILES: CN1c2nc(C3=CC4CN(C(=O)C(C)(C)O)CC4C3)ccc2N(CC2CC2(F)F)S1(=O)=O] | 1-[5-{1-[(2,2-difluorocyclopropyl)methyl]-3-methyl-2,2-dioxido-1,3-dihydro[1,2,5]thiadiazolo[3,4-b]pyridin-5-yl}-3,3a,4,6a-tetrahydrocyclopenta[c]pyrrol-2(1H)-yl]-2-methyl-1-oxopropan-2-ol | C21H26F2N4O4S [M + H] calc 469.1717 obs 469.1722 |

TABLE 11-continued

| # | Structure | Name | HRMS/LRMS |
|---|---|---|---|
| 24-8 | 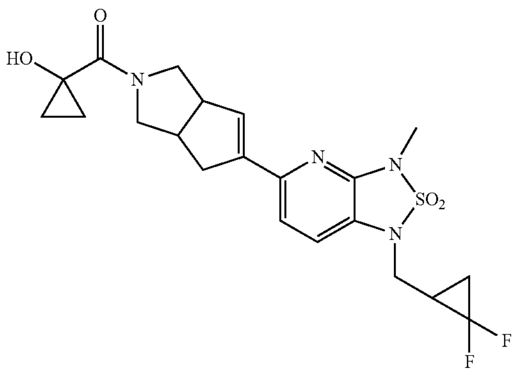 [SMILES: CN1c2nc(C3=CC4CN(C(=O)C5(O)CC5)CC4C3)ccc2N(CC2CC2(F)F)S1(=O)=O] | 1-{[5-{1-[(2,2-difluorocyclopropyl)methyl]-3-methyl-2,2-dioxido-1,3-dihydro[1,2,5]thiadiazolo[3,4-b]pyridin-5-yl}-3,3a,4,6a-tetrahydrocyclopenta[c]pyrrol-2(1H)-yl]carbonyl}cyclopropanol | C21H24F2N4O4S [M + H] calc 467.1561 obs 467.1569 |
| 24-9 | 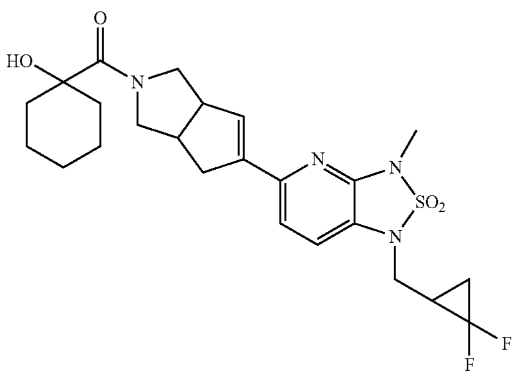 [SMILES: CN1c2nc(C3=CC4CN(C(=O)C5(O)CCCCC5)CC4C3)ccc2N(CC2CC2(F)F)S1(=O)=O] | 1-{[5-{1-[(2,2-difluorocyclopropyl)methyl]-3-methyl-2,2-dioxido-1,3-dihydro[1,2,5]thiadiazolo[3,4-b]pyridin-5-yl}-3,3a,4,6a-tetrahydrocyclopenta[c]pyrrol-2(1H)-yl]carbonyl}cyclohexanol | C24H30F2N4O4S [M + H] calc 509.2029 obs 509.2038 |
| 24-10 | 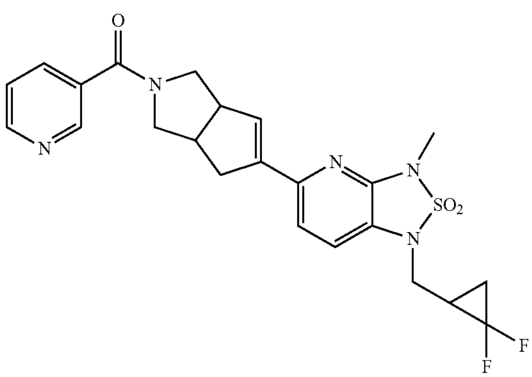 [SMILES: CN1c2nc(C3=CC4CN(C(=O)c5cccnc5)CC4C3)ccc2N(CC2CC2(F)F)S1(=O)=O] | 1-[(2,2-difluorocyclopropyl)methyl]-3-methyl-5-[2-(pyridin-3-ylcarbonyl)-1,2,3,3a,4,6a-hexahydrocyclopenta[c]pyrrol-5-yl]-1,3-dihydro[1,2,5]thiadiazolo[3,4-b]pyridine 2,2-dioxide | C23H23F2N5O3S [M + H] calc 488.1565 obs 488.1564 |
| 24-11 | 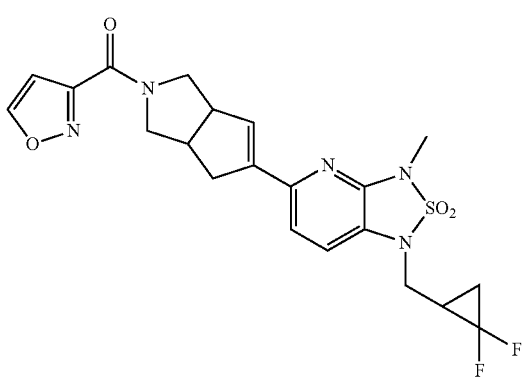 [SMILES: CN1c2nc(C3=CC4CN(C(=O)c5ccon5)CC4C3)ccc2N(CC2CC2(F)F)S1(=O)=O] | 1-[(2,2-difluorocyclopropyl)methyl]-5-[2-(isoxazol-3-ylcarbonyl)-1,2,3,3a,4,6a-hexahydrocyclopenta[c]pyrrol-5-yl]-3-methyl-1,3-dihydro[1,2,5]thiadiazolo[3,4-b]pyridine 2,2-dioxide | C21H21F2N5O3S [M + H] calc 478.1358 obs 478.1357 |

TABLE 11-continued

| # | Structure | Name | HRMS/LRMS |
|---|---|---|---|
| 24-12 | 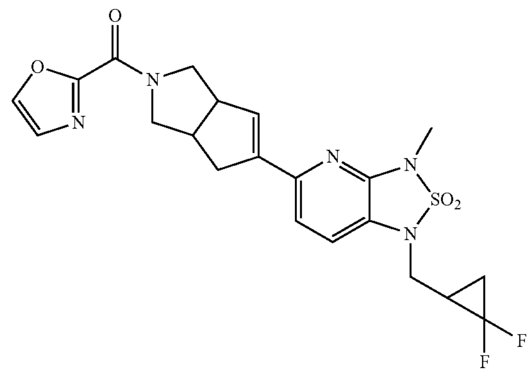 [SMILES: CN1c2nc(C3=CC4CN(C(=O)c5ncco5)CC4C3)ccc2N(CC2CC2(F)F)S1(=O)=O] | 1-[(2,2-difluorocyclopropyl)methyl]-3-methyl-5-[2-(1,3-oxazol-2-ylcarbonyl)-1,2,3,3a,4,6a-hexahydrocyclopenta[c]pyrrol-5-yl]-1,3-dihydro[1,2,5]thiadiazolo[3,4-b]pyridine 2,2-dioxide | C21H21F2N5O4S [M + H] calc 478.1358 obs 478.1360 |
| 24-13 | 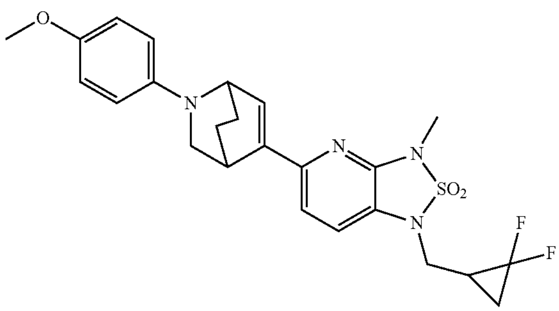 [SMILES: COc1ccc(N2CC3CCC2C=C3c2ccc3c(n2)N(C)S(=O)(=O)N3CC2CC2(F)F)cc1] | 1-[(2,2-difluorocyclopropyl)methyl]-5-[2-(4-methoxyphenyl)-2-azabicyclo[2.2.2]oct-5-en-5-yl]-3-methyl-1,3-dihydro[1,2,5]thiadiazolo[3,4-b]pyridine | C24H26F2N4O3S [M + H] calc 489.1768 obs 489.1776 |
| 24-14 | 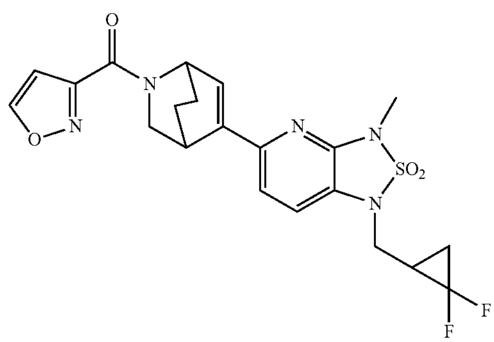 [SMILES: CN1c2nc(C3=CC4CCC3CN4C(=O)c3ccon3)ccc2N(CC2CC2(F)F)S1(=O)=O] | 1-[(2,2-difluorocyclopropyl)methyl]-5-[2-(isoxazol-3-ylcarbonyl)-2-azabicyclo[2.2.2]oct-5-en-5-yl]-3-methyl-1,3-dihydro[1,2,5]thiadiazolo[3,4-b]pyridine | C21H21F2N5O4S [M + H] calc 478.1358 obs 478.1367 |
| 24-15 | 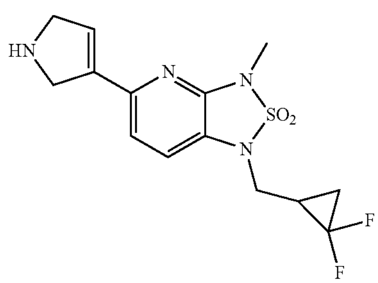 [SMILES: CN1c2nc(C3=CCNC3)ccc2N(CC2CC2(F)F)S1(=O)=O] | 1-[(2,2-difluorocyclopropyl)methyl]-5-(2,5-dihydro-1H-pyrrol-3-yl)-3-methyl-1,3-dihydro[1,2,5]thiadiazolo[3,4-b]pyridine 2,2-dioxide | C14H16F2N4O2S [M + H] calc 343.1038 obs 343.1037 |
| 24-16 | 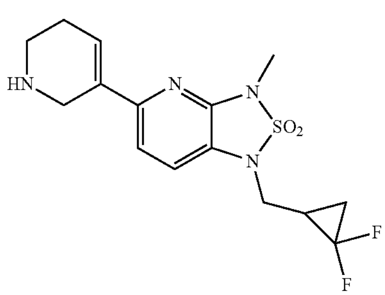 [SMILES: CN1c2nc(C3=CCCNC3)ccc2N(CC2CC2(F)F)S1(=O)=O] | 1-1(2,2-difluorocyclopropyl)methyl]-3-methyl-5-(1,2,5,6-tetrahydropyridin-3-yl)-1,3-dihydro[1,2,5]thiadiazolo[3,4-b]pyridine 2,2-dioxide | C15H18F2N4O2S [M + H] calc 357.1194 obs 357.1195 |

TABLE 11-continued

| # | Structure | Name | HRMS/LRMS |
|---|---|---|---|
| 24-17 | 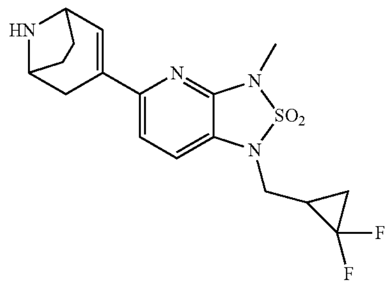 [SMILES: CN1c2nc(C3=CC4CCC(C3)N4)ccc2N(CC2CC2(F)F)S1(=O)=O] | 5-(8-azabicyclo[3.2.1]oct-2-en-3-yl)-1-[(2,2-difluorocyclopropyl)methyl]-3-methyl-1,3-dihydro[1,2,5]thiadiazolo[3,4-b]pyridine | C17H20F2N4O2S [M + H] calc 383.1351 obs 383.1348 |
| 24-18 | 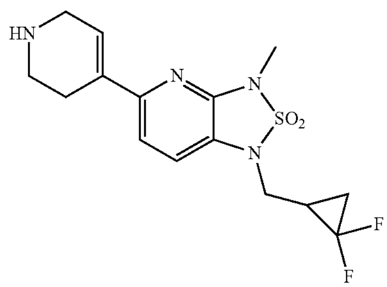 [SMILES: CN1c2nc(C3=CCNCC3)ccc2N(CC2CC2(F)F)S1(=O)=O] | 1-[(2,2-difluorocyclopropyl)methyl]-3-methyl-5-(1,2,3,6-tetrahydropyridin-4-yl)-1,3-dihydro[1,2,5]thiadiazolo[3,4-b]pyridine 2,2-dioxide | C15H18F2N4O2S [M + H] calc 357.1194 obs 357.1194 |
| 24-19 | 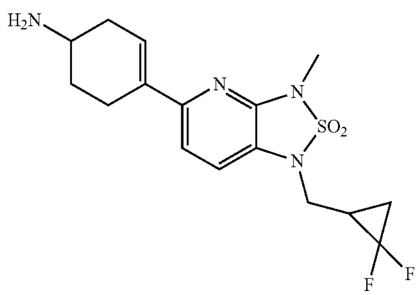 [SMILES: CN1c2nc(C3=CCC(N)CC3)ccc2N(CC2CC2(F)F)S1(=O)=O] | 4-{1-[(2,2-difluorocyclopropyl)methyl]-3-methyl-2,2-dioxido-1,3-dihydro[1,2,5]thiadiazolo[3,4-b]pyridin-5-yl}cyclohex-3-en-1-amine | C16H20F2N4O2S [M + H] calc 371.1351 obs 371.1351 |
| 24-20 | 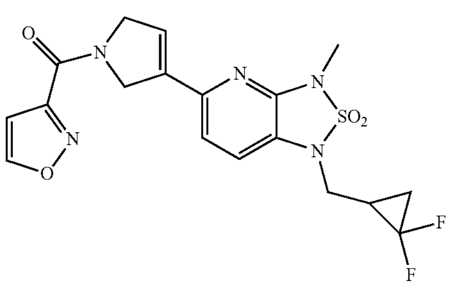 [SMILES: CN1c2nc(C3=CCN(C(=O)c4ccon4)C3)ccc2N(CC2CC2(F)F)S1(=O)=O] | 1-[(2,2-difluorocyclopropyl)methyl]-5-[1-(isoxazol-3-ylcarbonyl)-2,5-dihydro-1H-pyrrol-3-yl]-3-methyl-1,3-dihydro[1,2,5]thiadiazolo[3,4-b]pyridine 2,2-dioxide | C18H17F2N5O4S [M + H] calc 438.1045 obs 438.1036 |
| 24-21 | 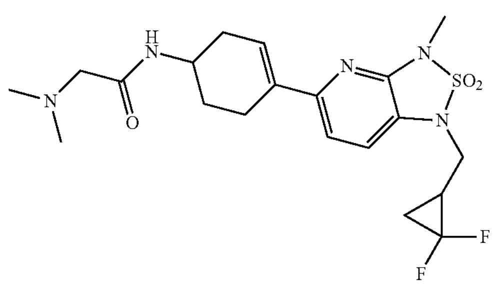 [SMILES: CN(C)CC(=O)NC1CC=C(c2ccc3c(n2)N(C)S(=O)(=O)N3CC2CC2(F)F)CC1] | N-(4-{1-[(2,2-difluorocyclopropyl)methyl]-3-methyl-2,2-dioxido-1,3-dihydro[1,2,5]thiadiazolo[3,4-b]pyridin-5-yl}cyclohex-3-en-1-yl)-N~2~,N~2~-dimethylglycinamide | C20H27F2N5O3S [M + H] calc 456.1877 obs 456.1872 |

| # | Structure | Name | HRMS/LRMS |
|---|---|---|---|
| 24-22 | 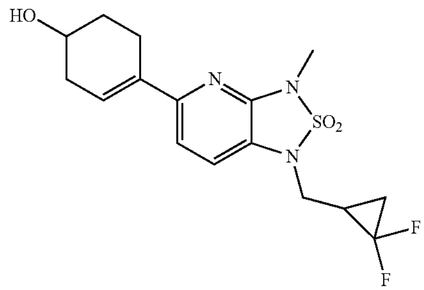 [SMILES: CN1c2nc(C3=CCC(O)CC3)ccc2N(CC2CC2(F)F)S1(=O)=O] | 4-{1-[(2,2-difluorocyclopropyl)methyl]-3-methyl-2,2-dioxido-1,3-dihydro[1,2,5]thiadiazolo[3,4-b]pyridin-5-yl}cyclohex-3-en-1-ol | C16H19F2N3O3S [M + H] calc 372.1191 obs 372.1188 |
| 24-23 | 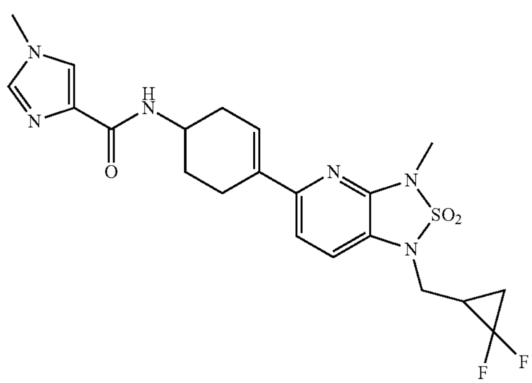 [SMILES: CN1c2nc(C3=CCC(NC(=O)c4cn(C)cn4)CC3)ccc2N(CC2CC2(F)F)S1(=O)=O] | N-(4-{1-[(2,2-difluorocyclopropyl)methyl]-3-methyl-2,2-dioxido-1,3-dihydro[1,2,5]thiadiazolo[3,4-b]pyridin-5-yl}cyclohex-3-en-1-yl)-1-methyl-1H-imidazole-4-carboxamide | C21H24F2N6O3S [M + H] calc 479.1674 obs 479.1686 |
| 24-24 | 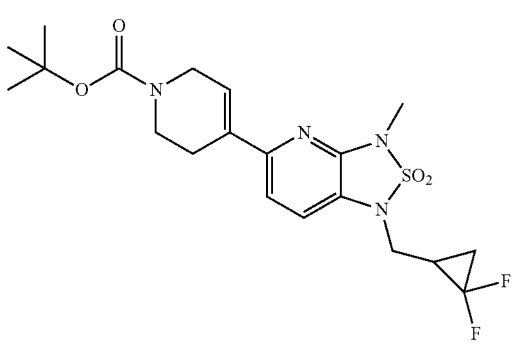 [SMILES: CN1c2nc(C3=CCN(C(=O)OC(C)(C)C)CC3)ccc2N(CC2CC2(F)F)S1(=O)=O] | tert-butyl 4-{1-[(2,2-difluorocyclopropyl)methyl]-3-methyl-2,2-dioxido-1,3-dihydro[1,2,5]thiadiazolo[3,4-b]pyridin-5-yl}-3,6-dihydropyridine-1(2H)-carboxylate | C20H26F2N4O4S [M + H] calc 457.1717 obs 457.1726 |
| 24-25 | 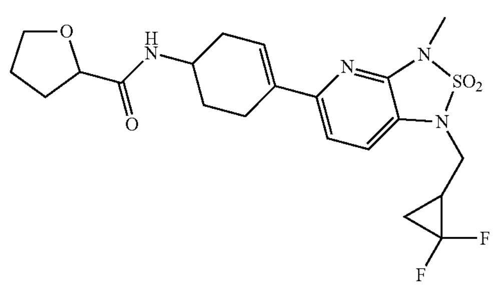 [SMILES: CN1c2nc(C3=CCC(NC(=O)C4CCCO4)CC3)ccc2N(CC2CC2(F)F)S1(=O)=O] | N-(4-{1-[(2,2-difluorocyclopropyl)methyl]-3-methyl-2,2-dioxido-1,3-dihydro[1,2,5]thiadiazolo[3,4-b]pyridin-5-yl}cyclohex-3-en-1-yl)tetrahydrofuran-2-carboxamide | C21H26F2N4O4S [M + H] calc 469.1717 obs 469.1714 |

TABLE 11-continued

| # | Structure | Name | HRMS/LRMS |
|---|---|---|---|
| 24-26 | 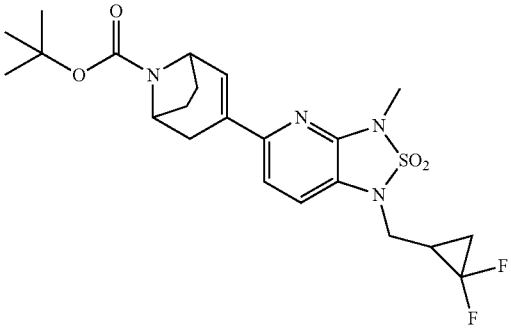 [SMILES: CN1c2nc(C3=CC4CCC(C3)N4C(=O)OC(C)(C)C)ccc2N(CC2CC2(F)F)S1(=O)=O] | tert-butyl 3-{1-[(2,2-difluorocyclopropyl)methyl]-3-methyl-2,2-dioxido-1,3-dihydro[1,2,5]thiadiazolo[3,4-b]pyridin-5-yl}-8-azabicyclo[3.2.1]oct-2-ene-8-carboxylate | C22H28F2N4O4S [M + H] calc 483.1874 obs 483.1878 |
| 24-27 | 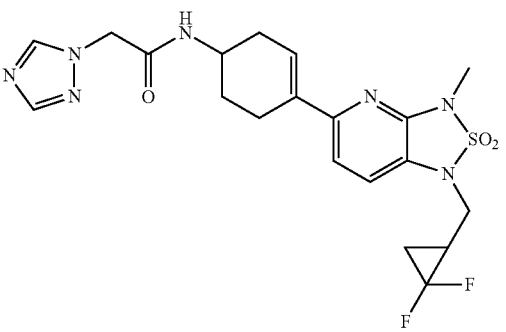 [SMILES: CN1c2nc(C3=CCC(NC(=O)Cn4cncn4)CC3)ccc2N(CC2CC2(F)F)S1(=O)=O] | N-(4-{1-[(2,2-difluorocyclopropyl)methyl]-3-methyl-2,2-dioxido-1,3-dihydro[1,2,5]thiadiazolo[3,4-b]pyridin-5-yl}cyclohex-3-en-1-yl)-2-(1H-1,2,4-triazol-1-yl)acetamide | C20H23F2N7O3S [M + H] calc 480.1626 obs 480.1618 |
| 24-28 | 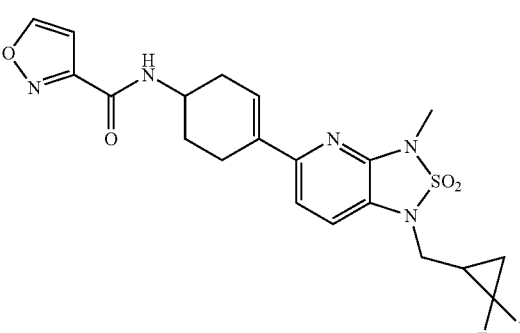 | N-(4-{1-[(2,2-difluorocyclopropyl)methyl]-3-methyl-2,2-dioxido-1,3-dihydro[1,2,5]thiadiazolo[3,4-b]pyridin-5-yl}cyclohex-3-en-1-yl)isoxazole-3-carboxamide | C20H21F2N5O4S [M + H] calc 466.1358 obs 466.1359 |
| 24-29 | 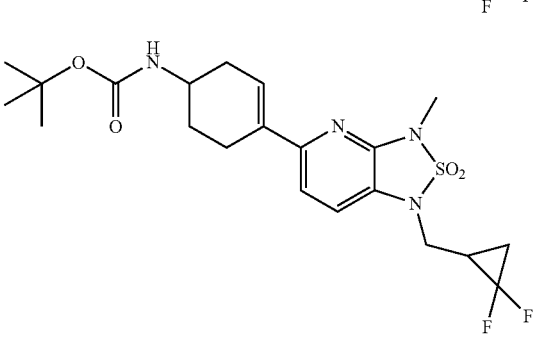 | tert-butyl (4-{1-[(2,2-difluorocyclopropyl)methyl]-3-methyl-2,2-dioxido-1,3-dihydro[1,2,5]thiadiazolo[3,4-b]pyridin-5-yl}cyclohex-3-en-1-yl)carbamate | C21H28F2N4O4S [M + H] calc 471.1874 obs 471.1883 |
| 24-30 | 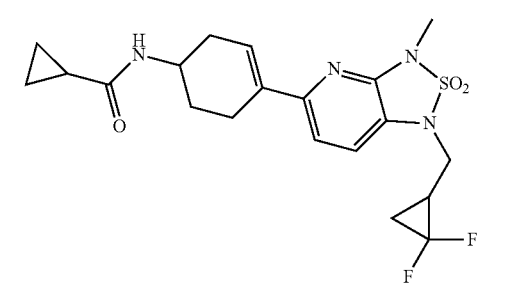 [SMILES: CN1c2nc(C3=CCC(NC(=O)C4CC4)CC3)ccc2N(CC2CC2(F)F)S1(=O)=O] | N-(4-{1-[(2,2-difluorocyclopropyl)methyl]-3-methyl-2,2-dioxido-1,3-dihydro[1,2,5]thiadiazolo[3,4-b]pyridin-5-yl}cyclohex-3-en-1-yl)cyclopropanecarboxamide | C20H24F2N4O3S [M + H] calc 439.1612 obs 439.1608 |

TABLE 11-continued

| # | Structure | Name | HRMS/LRMS |
|---|---|---|---|
| 24-31 | 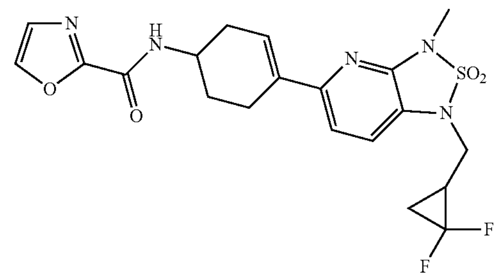 [SMILES: CN1c2nc(C3=CCC(NC(=O)c4ncco4)CC3)ccc2N(CC2CC2(F)F)S1(=O)=O] | N-(4-{1-[(2,2-difluorocyclopropyl)methyl]-3-methyl-2,2-dioxido-1,3-dihydro[1,2,5]thiadiazolo[3,4-b]pyridin-5-yl}cyclohex-3-en-1-yl)-1,3-oxazole-2-carboxamide | C20H21F2N5O4S [M + H] calc 466.1358 obs 466.1352 |
| 24-32 | 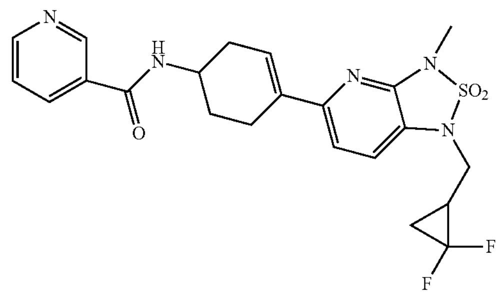 [SMILES: CN1c2nc(C3=CCC(NC(=O)c4cccnc4)CC3)ccc2N(CC2CC2(F)F)S1(=O)=O] | N-(4-{1-[(2,2-difluorocyclopropyl)methyl]-3-methyl-2,2-dioxido-1,3-dihydro[1,2,5]thiadiazolo[3,4-b]pyridin-5-yl}cyclohex-3-en-1-yl)pyridine-3-carboxamide | C22H23F2N5O3S [M + H] calc 476.1565 obs 476.1559 |
| 24-33 | 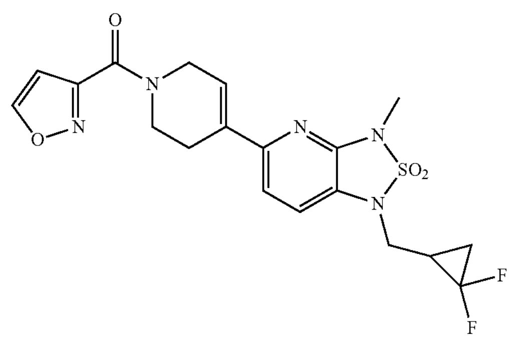 [SMILES: CN1c2nc(C3=CCN(C(=O)c4ccon4)CC3)ccc2N(CC2CC2(F)F)S1(=O)=O] | 1-[(2,2-difluorocyclopropyl)methyl]-5-[1-(isoxazol-3-ylcarbonyl)-1,2,3,6-tetrahydropyridin-4-yl]-3-methyl-1,3-dihydro[1,2,5]thiadiazolo[3,4-b]pyridine 2,2-dioxide | C19H19F2N5O4S [M + H] calc 452.1201 obs 452.1193 |
| 24-34 | 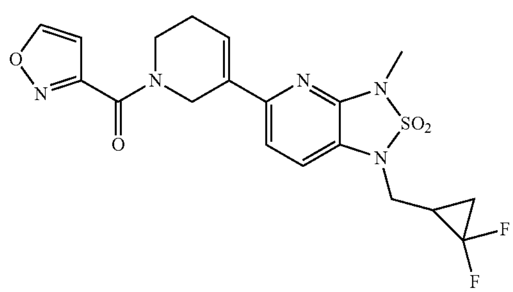 [SMILES: CN1c2nc(C3=CCCN(C(=O)c4ccon4)C3)ccc2N(CC2CC2(F)F)S1(=O)=O] | 1-[(2,2-difluorocyclopropyl)methyl]-5-[1-(isoxazol-3-ylcarbonyl)-1,2,5,6-tetrahydropyridin-3-yl]-3-methyl-1,3-dihydro[1,2,5]thiadiazolo[3,4-b]pyridine 2,2-dioxide | C19H19F2N5O4S [M + H] calc 452.1201 obs 452.1191 |
| 24-35 | 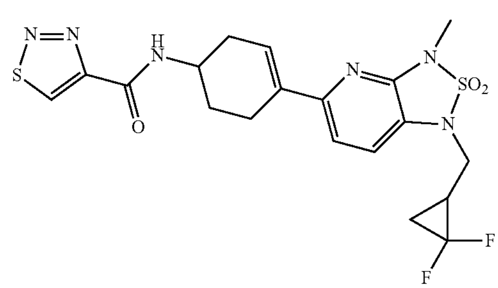 [SMILES: CN1c2nc(C3=CCC(NC(=O)c4csnn4)CC3)ccc2N(CC2CC2(F)F)S1(=O)=O] | N-(4-{1-[(2,2-difluorocyclopropyl)methyl]-3-methyl-2,2-dioxido-1,3-dihydro[1,2,5]thiadiazolo[3,4-b]pyridin-5-yl}cyclohex-3-en-1-yl)-1,2,3-thiadiazole-4-carboxamide | C19H20F2N6O3S2 [M + H] calc 483.1082 obs 483.1072 |

TABLE 11-continued

| # | Structure | Name | HRMS/LRMS |
|---|---|---|---|
| 24-36 | 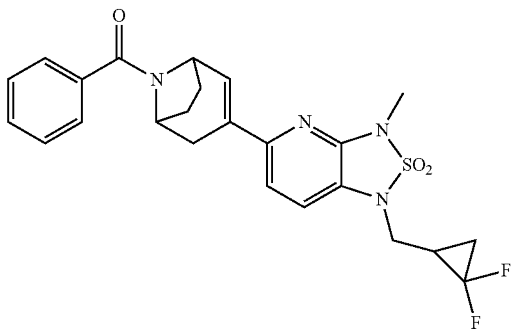 [SMILES: CN1c2nc(C3=CC4CCC(C3)N4C(=O)c3ccccc3)ccc2N(CC2CC2(F)F)S1(=O)=O] | 1-[(2,2-difluorocyclopropyl)methyl]-3-methyl-5-[8-(phenylcarbonyl)-8-azabicyclo[3.2.1]oct-2-en-3-yl]-1,3-dihydro[1,2,5]thiadiazolo[3,4-b]pyridine 2,2-dioxide | C24H24F2N4O3S [M + H] calc 487.1612 obs 487.1632 |
| 24-37 | 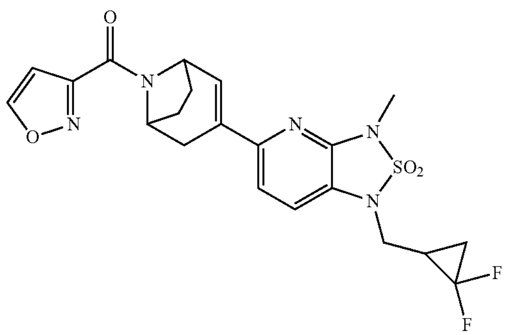 [SMILES: CN1c2nc(C3=CC4CCC(C3)N4C(=O)c3ccon3)ccc2N(CC2CC2(F)F)S1(=O)=O] | 1-[(2,2-difluorocyclopropyl)methyl]-5-[8-(isoxazol-3-ylcarbonyl)-8-azabicyclo[3.2.1]oct-2-en-3-yl]-3-methyl-1,3-dihydro[1,2,5]thiadiazolo[3,4-b]pyridine 2,2-dioxide | C21H21F2N5O4S [M + H] calc 478.1358 obs 478.1358 |

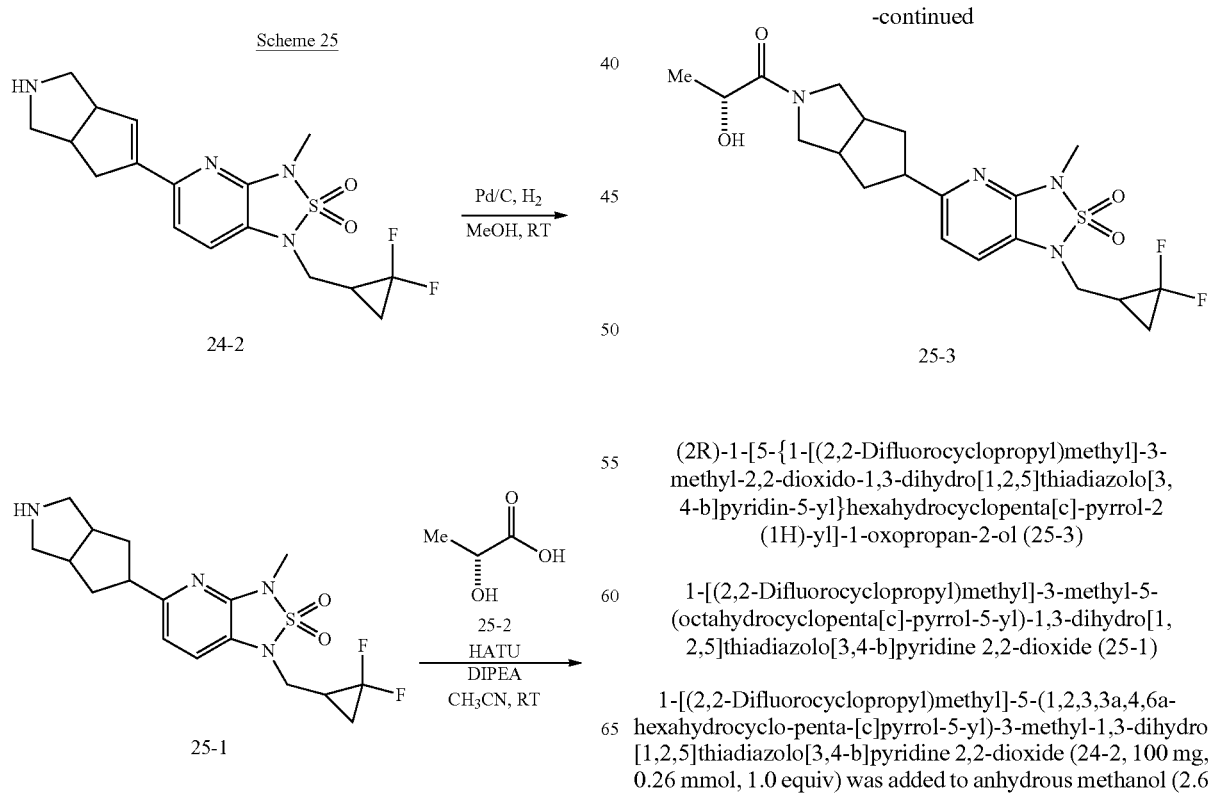

(2R)-1-[5-{1-[(2,2-Difluorocyclopropyl)methyl]-3-methyl-2,2-dioxido-1,3-dihydro[1,2,5]thiadiazolo[3,4-b]pyridin-5-yl}hexahydrocyclopenta[c]-pyrrol-2(1H)-yl]-1-oxopropan-2-ol (25-3)

1-[(2,2-Difluorocyclopropyl)methyl]-3-methyl-5-(octahydrocyclopenta[c]-pyrrol-5-yl)-1,3-dihydro[1,2,5]thiadiazolo[3,4-b]pyridine 2,2-dioxide (25-1)

1-[(2,2-Difluorocyclopropyl)methyl]-5-(1,2,3,3a,4,6a-hexahydrocyclo-penta-[c]pyrrol-5-yl)-3-methyl-1,3-dihydro[1,2,5]thiadiazolo[3,4-b]pyridine 2,2-dioxide (24-2, 100 mg, 0.26 mmol, 1.0 equiv) was added to anhydrous methanol (2.6 mL). To this solution was added 10% palladium(0) on carbon (55.7 mg, 0.052 mmol, 0.2 equiv) to give a black suspension. The reaction flask was evacuated and back-filled with hydrogen from a balloon. This process was repeated an additional 2 times. The resulting mixture was allowed to stir under an atmosphere of $H_2$ for 30 min. Following this duration, LCMS showed complete consumption of starting material. The reaction contents were filtered through Celite, washed with DCM and concentrated to give 25-1 as an off-white solid. The crude material was carried forward without additional purification.

(2R)-1-[5-{1-[(2,2-Difluorocyclopropyl)methyl]-3-methyl-2,2-dioxido-1,3-dihydro[1,2,5]thiadiazolo[3,4-b]pyridin-5-yl}hexahydrocyclopenta[c]pyrrol-2(1H)-yl]-1-oxopropan-2-ol (25-3)

1-[(2,2-Difluorocyclopropyl)methyl]-3-methyl-5-(octahydrocyclopenta[c]-pyrrol-5-yl)-1,3-dihydro[1,2,5]thia-

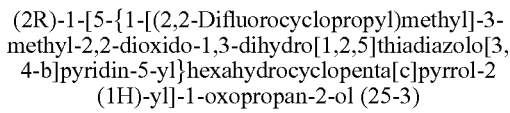

diazolo[3,4-b]pyridine 2,2-dioxide (25-1, 20 mg, 0.052 mmol, 1.0 equiv), (2R)-2-hydroxypropanoic acid (25-2, 7.0 mg, 0.078 mmol, 1.5 equiv), DIPEA (27 µL, 0.16 mmol, 3.0 equiv) and HATU (29.7 mg, 0.078 mmol, 1.5 equiv) were added to anhydrous acetonitrile (520 µL). After stirring for 10 min at room temperature, LCMS showed consumption of starting material. Purification by reverse-phase HPLC (20-100% $CH_3CN$:0.1% TFA in $H_2O$) provided 25-3 as a white solid. MS m/z (M+H): calculated=457.1716; observed=457.1726.

The following compounds were prepared from 23-2 and the appropriate triflate by a reaction sequence analogous to that illustrated in Schemes 24 and 25:

TABLE 12

| # | Structure | Name | HRMS/LRMS |
|---|---|---|---|
| 25-4 | 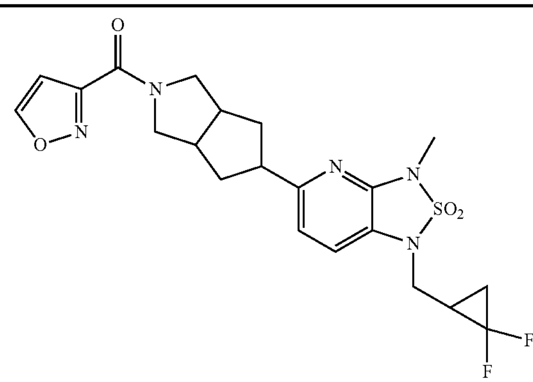 | 1-[(2,2-difluorocyclopropyl)methyl]-5-[2-(isoxazol-3-ylcarbonyl)octahydrocyclopenta[c]pyrrol-5-yl]-3-methyl-1,3-dihydro[1,2,5]thiadiazolo[3,4-b]pyridine 2,2-dioxide | C21H23F2N5O4S [M + H] calc 480.1514 obs 480.1521 |
| 25-5 | 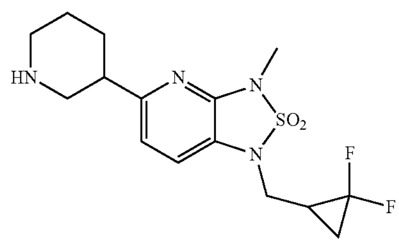 [SMILES: CN1c2nc(C3CCCNC3)ccc2N(CC2CC2(F)F)S1(=O)=O] | 1-[(2,2-difluorocyclopropyl)methyl]-3-methyl-5-piperidin-3-yl-1,3-dihydro[1,2,5]thiadiazolo[3,4-b]pyridine 2,2-dioxide | C15H20F2N4O2S [M + H] calc 359.1348 obs 359.1346 |
| 25-6 | 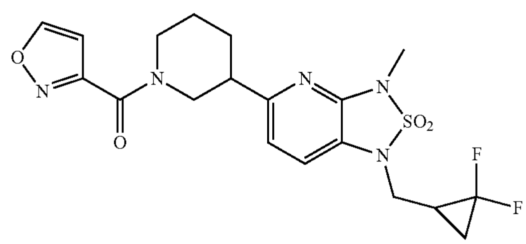 [SMILES: CN1c2nc(C3CCCN(C(=O)c4ccon4)C3)ccc2N(CC2CC2(F)F)S1(=O)=O] | 1-[(2,2-difluorocyclopropyl)methyl]-5-[1-(isoxazol-3-ylcarbonyl)piperidin-3-yl]-3-methyl-1,3-dihydro[1,2,5]thiadiazolo[3,4-b]pyridine 2,2-dioxide | C19H21F2N5O4S [M + H] calc 454.1355 obs 454.1350 |
| 25-7 | 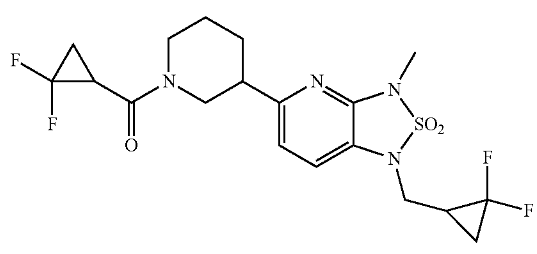 [SMILES: CN1c2nc(C3CCCN(C(=O)C4CC4(F)F)C3)ccc2N(CC2CC2(F)F)S1(=O)=O] | 5-{1-[(2,2-difluorocyclopropyl)carbonyl]piperidin-3-yl}-1-[(2,2-difluorocyclopropyl)methyl]-3-methyl-1,3-dihydro[1,2,5]thiadiazolo[3,4-b]pyridine 2,2-dioxide | C19H22F4N4O3S [M + H] calc 463.1422 obs 463.1419 |

Scheme 26

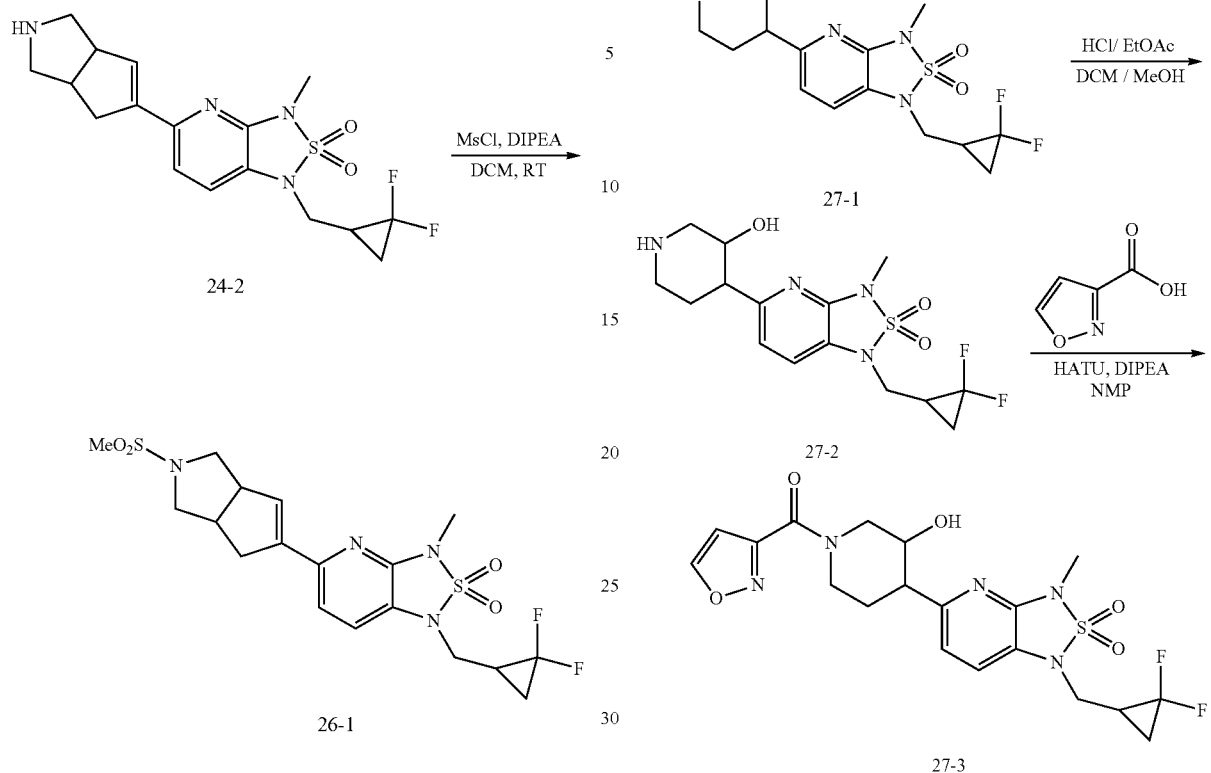

1-[(2,2-Difluorocyclopropyl)methyl]-3-methyl-5-[2-(methylsulfonyl)-1,2,3,3a,4,6a-hexahydrocyclopenta[c]pyrrol-5-yl]-1,3-dihydro[1,2,5]thiadiazolo[3,4-b]pyridine 2,2-dioxide (26-1)

1-[(2,2-Difluorocyclopropyl)methyl]-5-(1,2,3,3a,4,6a-hexahydrocyclo-penta-[c]pyrrol-5-yl)-3-methyl-1,3-dihydro[1,2,5]thiadiazolo[3,4-b]pyridine 2,2-dioxide (24-2, 40 mg, 0.11 mmol, 1.0 equiv) was added to anhydrous acetonitrile (1.0 mL) followed by the sequential addition of DIPEA (55 µL, 0.31 mmol, 3.0 equiv) and methanesulfonyl chloride (12 µL, 0.16 mmol, 1.5 equiv). After 10 min at RT, LCMS showed complete consumption of starting material. Purification by reverse-phase HPLC (10-100% CH$_3$CN:0.1% TFA in H$_2$O) afforded 26-1 as a white solid. MS ink (M+H): calculated=461.1123; observed=461.1129.

Scheme 27

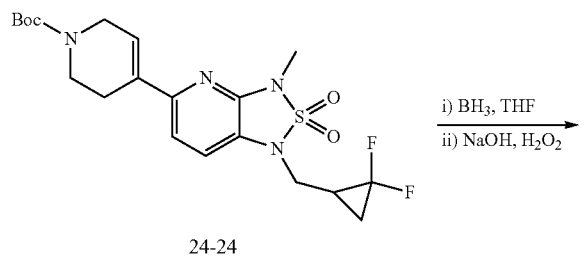

(4-{1-[(2,2-Difluorocyclopropyl)methyl]3-methyl-2,2-dioxido-1,3-dihydro-[1,2,5]thiadiazolo[3,4-b]pyridin-5-yl}-3-hydroxypiperidin-1-yl)(isoxazol-3-yl)methanone (27-3)

tert-Butyl 4-{1-[(2,2-Difluorocyclopropypmethyl]-3-methyl-2,2-dioxido-1,3-dihydro[1,2,5]thiadiazolo[3,4-b]pyridin-5-yl}-3-hydroxypiperidine-1-carboxylate (27-1)

Procedure similar to that for tert-Butyl 3-[1-(2,2-dimethylpropyl)-3-methyl-2-oxo-2,3-dihydro-1H-imidazo-[4,5-b]pyridin-5-yl]-2-hydroxy-8-azabicyclo[3.2.1]octane-8-carboxylate (20-1) gave tert-Butyl 4-{1-[(2,2-Difluorocyclopropyl)methyl]-3-methyl-2,2-dioxido-1,3-dihydro[1,2,5]thiadiazolo[3,4-b]pyridin-5-yl}-3-hydroxypiperidine-1-carboxylate (27-1). HRMS (M+H)$^+$: observed=475.1825, calculated=475.1821.

4-{1-[(2,2-Difluorocyclopropyl)methyl]-3-methyl-2,2-dioxido-1,3-dihydro[1,2,5]thiadiazolo[3,4-b]pyridin-5-yl}piperidin-3-ol (27-2)

Procedure similar to that for 5-(4-Aminocyclohex-1-en-1-yl)-1-(2,2-dimethylpropyl)-3-methyl-1,3-dihydro-2H-imidazo[4,5-b]pyridin-2-one (17-2) gave 4-{1-[(2,2-Difluorocyclopropyl)methyl]-3-methyl-2,2-dioxido-1,3-dihydro[1,2,5]-thiadiazole[3,4-b]pyridin-5-yl}piperidin-3-ol (27-2). HRMS (M+H)$^+$: observed=375.1295, calculated=375.1297.

(4-{1-[(2,2-Difluorocyclopropyl)methyl]-3-methyl-2,2-dioxido-1,3-dihydro-[1,2,5]thiadiazolo[3,4-b]pyridin-5-yl}-3-hydroxypiperidin-1-yl)(isoxazol-3-yl)methanone (27-3)

Procedure similar to that for N-{4-[1-(2,2-Dimethylpropyl)-3-methyl-2-oxo-2,3-dihydro-1H-imidazo[4,5-b]pyridin-5-yl]cyclohex-3-en-1-yl}-1-methyl-1H-imidazole-2-carboxamide (17-3) gave (4-{1-[(2,2-Difluorocyclopropymethyl]-3-methyl-2,2-dioxido-1,3-dihydro-[1,2,5]thiadiazolo[3,4-b]pyridin-5-yl}-3-hydroxypiperidin-1-yl)(isoxazol-3-yl)methanone (27-3). HRMS (M+H)$^+$: observed=470.1301, calculated=470.1304.

Scheme 28

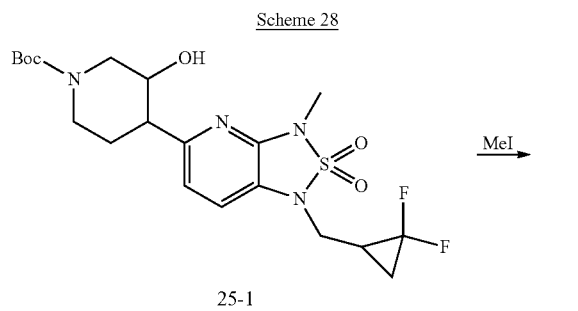

25-1

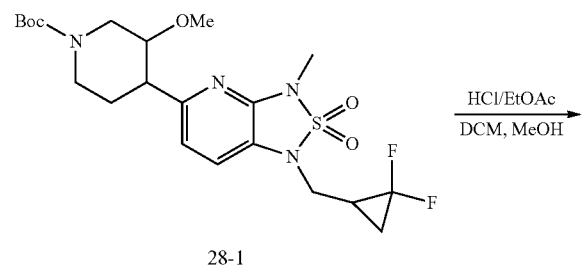

28-1

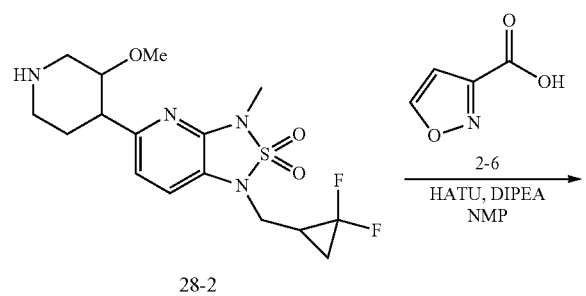

28-2

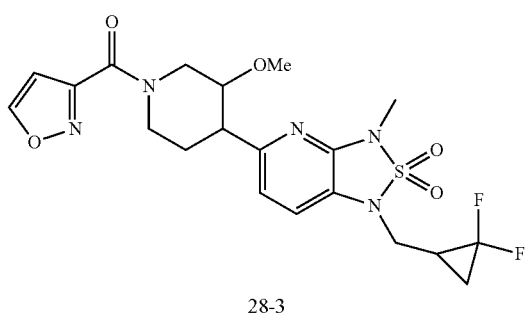

28-3

(4-{1-[(2,2-Difluorocyclopropypmethyl]-3-methyl-2,2-dioxido-1,3-dihydro-[1,2,5]thiadiazole[3,4-b]pyridin-5-yl}-3-methoxypiperidin-1-yl)(isoxazol-3-yl) methanone (28-3)

tert-Butyl 4-{1-[(2,2-difluorocyclopropyl)methyl]-3-methyl-2,2-dioxido-1,3-dihydro[1,2,5]thiadiazolo[3,4-b]pyridin-5-yl}-3-methoxypiperidine-1-carboxylate (28-1)

To a flask was added tert-butyl 4-{1-[(2,2-difluorocyclopropyl)methyl]-3-methyl-2,2-dioxido-1,3-dihydro[1,2,5]thiadiazolo[3,4-b]pyridin-5-yl}-3-hydroxypiperidine-1-carboxylate (27-1) (54 mg, 0.114 mmol), & anhydrous THF (2.5 mL). The reaction mixture was cooled to 0 C while stirring under an atmosphere of nitrogen, then added sodium hydride (60% by wt in mineral oil) (5.92 mg, 0.148 mmol) in one portion. Reaction mixture was continued to stir at 0 C for 10 minutes, then added iodomethane (8.54 µl, 0.137 mmol) and permitted to warm to room temperature. After 1 hour reaction mixture was diluted with MeOH & drops of water, then purified by reverse-phase chromatography (10-100% $CH_3CN$:0.1% TFA in $H_2O$) to yield tert-Butyl 4-{1-[(2,2-difluorocyclopropyl)methyl]-3-methyl-2,2-dioxido-1,3-dihydro[1,2,5]thiadiazole-[3,4-b]pyridin-5-yl}-3-methoxypiperidine-1-carboxylate (28-1). HRMS (M+H)$^+$: observed=489.1983, calculated=489.1978.

1-[(2,2-Difluorocyclopropypmethyl]-5-(3-methoxypiperidin-4-yl)-3-methyl-1,3-dihydro[1,2,5]thiadiazolo[3,4-b]pyridine 2,2-dioxide (28-2)

Procedure similar to that for 5-(4-Aminocyclohex-1-en-1-yl)-1-(2,2-dimethylpropyl)-3-methyl-1,3-dihydro-2H-imidazo[4,5-b]pyridin-2-one (17-2) gave 1-[(2,2-Difluorocyclopropyl)methyl]-5-(3-methoxypiperidin-4-yl)-3-methyl-1,3-dihydro[1,2,5]thiadiazolo[3,4-b]pyridine 2,2-dioxide (28-2). HRMS (M+H)$^+$: observed=389.1452, calculated=389.1453.

(4-{1-[(2,2-Difluorocyclopropyl)methyl]-3-methyl-2,2-dioxido-1,3-dihydro-[1,2,5]thiadiazole[3,4-b]pyridin-5-yl}-3-methoxypiperidin-1-yl)(isoxazol-3-yl)methanone (28-3)

Procedure similar to that for N-{4-[1-(2,2-Dimethylpropyl)-3-methyl-2-oxo-2,3-dihydro-1H-imidazo[4,5-b]pyridin-5-yl]cyclohex-3-en-1-yl}-1-methyl-1H-imidazole-2-carboxamide (17-3) gave (4-{1-[(2,2-Difluorocyclopropyl)methyl]-3-methyl-2,2-dioxido-1,3-dihydro-[1,2,5]thiadiazole[3,4-b]pyridin-5-yl}-3-methoxy-piperidin-1-yl)(isoxazol-3-yl)methanone (28-3). HRMS (M+H)$^+$: observed=484.1462, calculated=484.1461.

Scheme 29

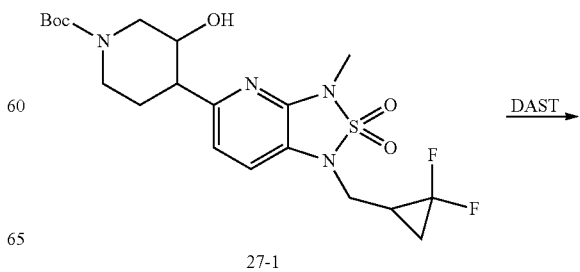

27-1

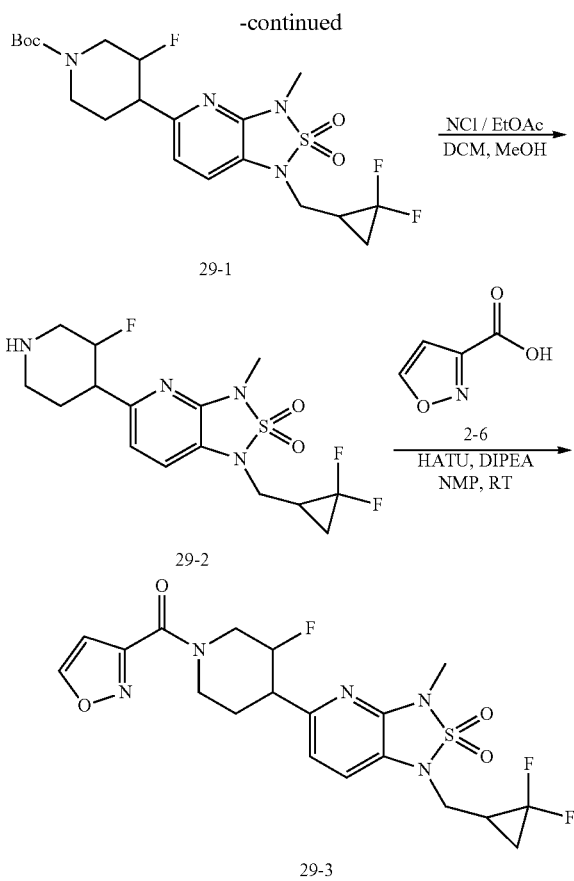

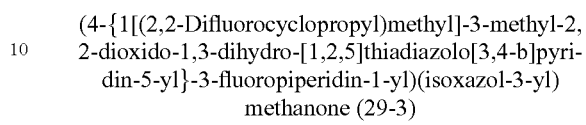

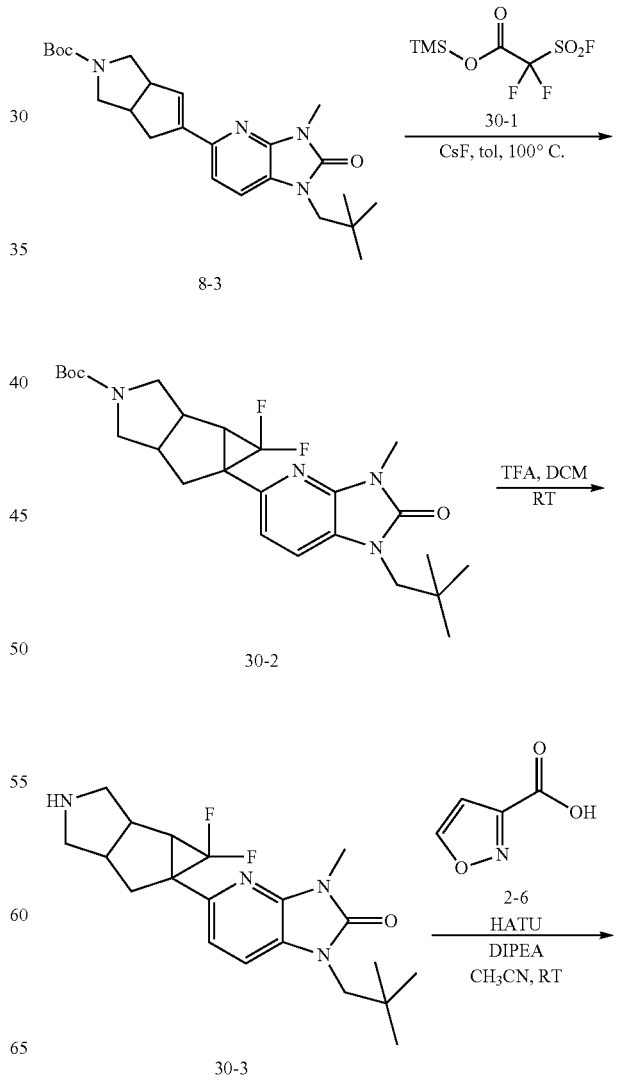

dazo[4,5-b]pyridin-2-one (17-2) gave 1-[(2,2-Difluorocyclopropyl)methyl]-5-(3-fluoropiperidin-4-yl)-3-methyl-1,3-dihydro[1,2,5]thiadiazolo[3,4-b]pyridine 2,2-dioxide (29-2). HRMS (M+H)$^+$: observed=377.1253, calculated=377.1254.

(4-{1[(2,2-Difluorocyclopropyl)methyl]-3-methyl-2,2-dioxido-1,3-dihydro-[1,2,5]thiadiazolo[3,4-b]pyridin-5-yl}-3-fluoropiperidin-1-yl)(isoxazol-3-yl)methanone (29-3)

Procedure similar to that for N-{4-[1-(2,2-Dimethylpropyl)-3-methyl-2-oxo-2,3-dihydro-1H-imidazo[4,5-b]pyridin-5-yl]cyclohex-3-en-1-yl}-1-methyl-1H-imidazole-2-carboxamide (17-3) gave (4-{1-[(2,2-Difluorocyclopropyl)methyl]-3-methyl-2,2-dioxido-1,3-dihydro-[1,2,5]thiadiazolo[3,4-b]pyridin-5-yl}-3-fluoropiperidin-1-yl)(isoxazol-3-yl)methanone (29-3). HRMS (M+H)$^+$: observed=472.1257, calculated=472.1261.

Scheme 30

(4-{1-[(2,2-Difluorocyclopropyl)methyl]-3-methyl-2,2-dioxido-1,3-dihydro-[1,2,5]thiadiazolo[3,4-b]pyridin-5-yl}-3-fluoropiperidin-1-yl)(isoxazol-3-yl)methanone (29-3)

tert-Butyl 4-{1-[(2,2-difluorocyclopropyl)methyl]-3-methyl-2,2-dioxido-1,3-dihydro[1,2, 5]thiadiazolo[3,4-b]pyridin-5-yl}-3-fluoropiperidine-1-carboxylate (29-1)

To a round bottom flask was added tert-butyl 4-{1-[(2,2-difluorocyclopropyl)methyl]-3-methyl-2,2-dioxido-1,3-dihydro[1,2,5]thiadiazolo[3,4-b]pyridin-5-yl}-3-hydroxypiperidine-1-carboxylate (27-1) (74 mg, 0.156 mmol), anhydrous DCM (1 mL), the reaction mixture was cooled to 0 C while stirring under an atmosphere of nitrogen, then added DAST (0.035 ml, 0.265 mmol) dropwise. Reaction mixture was continued to stir at 0 C for 10 minutes, then permitted to warm to room temperature. After 1 hour reaction mixture was diluted with MeOH & drops of water, then purified by reverse-phase chromatography (10-100% CH$_3$CN:0.1% TFA in H$_2$O) to yield tert-Butyl 4-{1-[(2,2-difluorocyclopropymethyl]-3-methyl-2,2-dioxido-1,3-dihydro[1,2,5]thiadiazolo[3,4-b]pyridin-5-yl}-3-fluoropiperidine-1-carboxylate (29-1). HRMS (M+H)$^+$: observed=477.1785, calculated=477.1778.

1-[(2,2-Difluorocyclopropyl)methyl]-5-(3-fluoropiperidin-4-yl)-3-methyl-1,3-dihydro[1,2,5]thiadiazolo[3,4-b]pyridine 2,2-dioxide (29-2)

Procedure similar to that for 5-(4-Aminocyclohex-1-en-1-yl)-1-(2,2-dimethylpropyl)-3-methyl-1,3-dihydro-2H-imi-

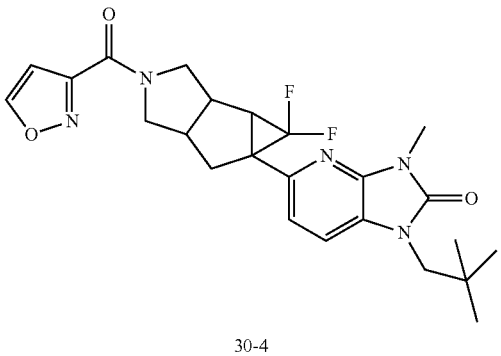

30-4

5-[4,4-Difluoro-2-(isoxazol-3-ylcarbonyl)octahydro-
4aH-cyclopropa[3,4]-cyclopenta[1,2-c]pyrrol-4a-yl]-
1-(2,2-dimethylpropyl)-3-methyl-1,3-dihydro-2H-
imidazo[4,5-b]pyridin-2-one (30-4)

tert-butyl 4a-[1-(2,2-dimethylpropyl)-3-methyl-2-oxo-2,3-dihydro-1H-imidazo-[4,5-b]pyridin-5-yl]-4,4-difluorooctahydro-2H-cyclopropa[3,4]cyclopenta[1,2-c]pyrrole-2-carboxylate (30-2)

tert-Butyl 5-[1-(2,2-dimethylpropyl)-3-methyl-2-oxo-2,3-dihydro-1H-imidazo[4,5-b]pyridin-5-yl]-3,3a,4,6a-tetrahydrocyclopenta[c]pyrrole-2(1H)-carboxylate (8-3, 73 mg, 0.17 mmol, 1.0 equiv) and cesium fluoride (2.6 mg, 0.02 mmol, 0.1 equiv) were added to anhydrous toluene (428 μL) and the resulting mixture was placed in a 100° C. bath. A solution of trimethylsilyl difluoro(fluorosulfonyl)acetate (30-1, 176 mg, 0.70 mmol, 4.1 equiv) in anhydrous toluene (1.3 mL) was then added dropwise via syringe pump over a period of 8 h. After stirring at 100° C. for an additional 6 h, the contents were filtered through Celite and purified by reverse-phase HPLC (40-100% 0.1% TFA in H₂O:CH₃CN) to give 30-2 as a colorless semi-solid. MS m/z (M+H): calculated=509.1276; observed=509.1278.

5-(4,4-Difluorooctahydro-4aH-cyclopropa[3,4]cyclopenta[1,2-c]pyrrol-4a-yl)-1-(2,2-dimethylpropyl)-3-methyl-1,3-dihydro-2H-imidazo[4,5-b]pyridin-2-one (30-3)

tert-butyl 4a-[1-(2,2-dimethylpropyl)-3-methyl-2-oxo-2,3-dihydro-1H-imidazo-[4,5-b]pyridin-5-yl]-4,4-difluorooctahydro-2H-cyclopropa[3,4]cyclopenta[1,2-c]pyrrole-2-carboxylate (30-2, 100 mg, 0.21 mmol) was added to a mixture of dichloromethane (2.0 mL) and trifluoroacetic acid (0.5 mL) at room temperature. After stirring for 18 h, the solvent was removed in vacuo. The resulting residue was then diluted with ethyl acetate (100 mL) and washed sequentially with saturated sodium bicarbonate (2×50 mL), water (1×50 mL) and brine (1×50 mL). The organics were dried over magnesium sulfate, filtered, and concentrated in vacuo to give 1-[(2,2-Difluorocyclopropyl)methyl]-5-(1,2,3,3a,4,6a-hexahydrocyclopenta-[c]pyrrol-5-yl)-3-methyl-1,3-dihydro-2H-imidazo[4,5-b]pyridin-2-one (30-3) as a white solid. This material was carried on without further purification.

5-[4,4-Difluoro-2-(isoxazol-3-ylcarbonyl)octahydro-
4aH-cyclopropa[3,4]-cyclopenta[1,2-c]pyrrol-4a-yl]-
1-(2,2-dimethylpropyl)-3-methyl-1,3-dihydro-2H-
imidazo[4,5-b]pyridin-2-one (30-4)

5-(4,4-Difluorooctahydro-4aH-cyclopropa[3,4]cyclopenta[1,2-c]pyrrol-4a-yl)-1-(2,2-dimethylpropyl)-3-methyl-1,3-dihydro-2H-imidazo[4,5-b]pyridin-2-one (30-3, 50 mg, 0.14 mmol, 1.0 equiv), isoxazole-3-carboxylic acid (2-6, 22.5 mg, 0.20 mmol, 1.5 equiv), DIPEA (0.070 mL, 0.40 mmol, 3.0 equiv) and HATU (76 mg, 0.20 mmol, 1.5 equiv) were added to anhydrous acetonitrile (1 mL). After stirring for 10 min at room temperature, LCMS showed consumption of starting material. Purification by reverse-phase HPLC (20-100% CH₃CN:0.1% TFA in H₂O) provided 30-4 as a white solid. MS m/z (M+H): calculated=472.2155; observed=472.2153.

The following compounds were prepared from the appropriate starting material (vide infra) by a reaction sequence analogous to that illustrated in Scheme 30:

TABLE 13

| # | Structure | Name | HRMS/LRMS |
|---|-----------|------|-----------|
| 30-5 | ![structure] | 5-{4,4-difluoro-2-(1,3-oxazol-2-ylcarbonyl)octahydro-4aH-cyclopropa[3,4]cyclopenta[1,2-c]pyrrol-4a-yl]-1-(2,2-dimethylpropyl)-3-methyl-1,3-dihydro-2H-imidazo[4,5-b]pyridin-2-one | C24H27F2N5O3 [M + H] calc 472.2155 obs 472.2153 |

TABLE 13-continued

| # | Structure | Name | HRMS/LRMS |
|---|---|---|---|
| 30-6 | 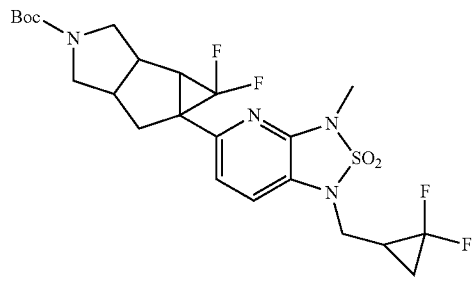 [SMILES: CN1c2nc(C34CC5CN(C(=O)OC(C)(C)C)CC5C3C4(F)F)ccc2N(CC2CC2(F)F)S1(=O)=O] | tert-butyl 4a-{1-[(2,2-difluorocyclopropyl)methyl]-3-methyl-2,2-dioxido-1,3-dihydro[1,2,5]thiadiazolo[3,4-b]pyridin-5-yl}-4,4-difluorooctahydro-2H-cyclopropa[3,4]cyclopenta[1,2-c]pyrrole-2-carboxylate | C23H28F4N4O4S [M − C4H9] calc 477.1 obs 477.0 |
| 30-7 | 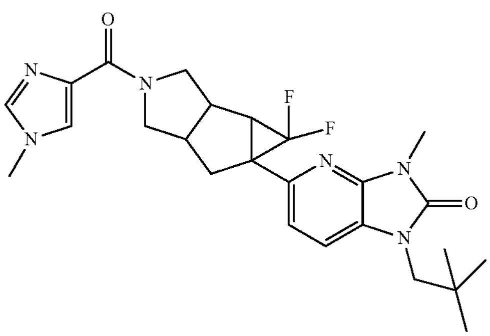 [SMILES: Cn1cnc(C(=O)N2CC3CC4(c5ccc6c(n5)n(C)c(=O)n6CC(C)(C)C)C(C3C2)C4(F)F)c1] | 5-{4,4-difluoro-2-[(1-methyl-1H-imidazol-4-yl)carbonyl]octahydro-4aH-cyclopropa[3,4]cyclopenta[1,2-c]pyrrol-4a-yl}-1-(2,2-dimethylpropyl)-3-methyl-1,3-dihydro-2H-imidazo[4,5-b]pyridin-2-one | C25H30F2N6O2 [M + H] calc 485.2471 obs 485.247 |
| 30-8 | 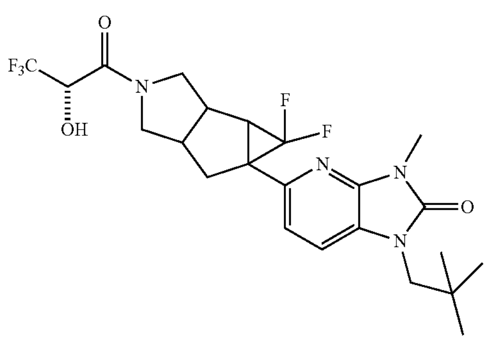 | 5-{4,4-difluoro-2-[(2S)-3,3,3-trifluoro-2-hydroxypropanoyl]octahydro-4aH-cyclopropa[3,4]cyclopenta[1,2-c]pyrrol-4a-yl}-1-(2,2-dimethylpropyl)-3-methyl-1,3-dihydro-2H-imidazo[4,5-b]pyridin-2-one | C23H27F5N4O3 [M + H] calc 503.2076 obs 503.2076 |
| 30-9 | 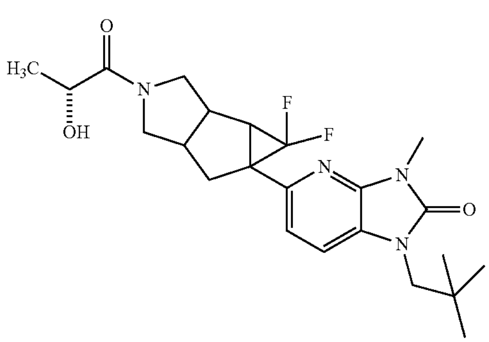 [SMILES: C[C@@H](O)C(=O)N1CC2CC3(c4ccc5c(n4)n(C)c(=O)n5CC(C)(C)C)C(C2C1)C3(F)F] | 5-{4,4-difluoro-2-[(2R)-2-hydroxypropanoyl]octahydro-4aH-cyclopropa[3,4]cyclopenta[1,2-c]pyrrol-4a-yl}-1-(2,2-dimethylpropyl)-3-methyl-1,3-dihydro-2H-imidazo[4,5-b]pyridin-2-one | C23H30F2N4O3 [M + H] calc 449.2359 obs 449.2362 |

TABLE 13-continued

| # | Structure | Name | HRMS/LRMS |
|---|---|---|---|
| 30-10 | 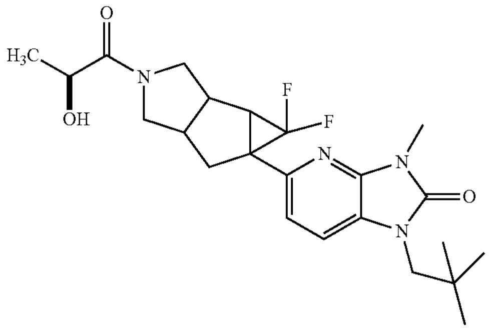 [SMILES: C[C@H](O)C(=O)N1CC2CC3(c4ccc5c(n4)n(C)c(=O)n5CC(C)(C)C)C(C2C1)C3(F)F] | 5-{4,4-difluoro-2-[(2S)-2-hydroxypropanoyl]octahydro-4aH-cyclopropa[3,4]cyclopenta[1,2-c]pyrrol-4a-yl}-1-(2,2-dimethylpropyl)-3-methyl-1,3-dihydro-2H-imidazo[4,5-b]pyridin-2-one | C23H30F2N4O3 [M + H] calc 449.2359 obs 449.2359 |
| 30-11 | 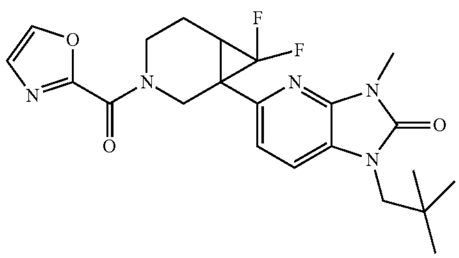 [SMILES: Cn1c(=O)n(CC(C)(C)C)c2ccc(C34CN(C(=O)c5ncco5)CCC3C4(F)F)nc21] | 5-[7,7-difluoro-3-(1,3-oxazol-2-ylcarbonyl)-3-azabicyclo[4.1.0]hept-1-yl]-1-(2,2-dimethylpropyl)-3-methyl-1,3-dihydro-2H-imidazo[4,5-b]pyridin-2-one | C22H25F2N5O3 [M + H] calc 446.1998 obs 446.1998 |
| 30-12 | 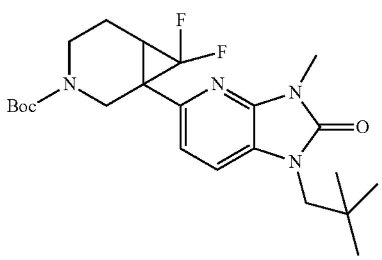 [SMILES: Cn1c(=O)n(CC(C)(C)C)c2ccc(C34CN(C(=O)OC(C)(C)C)CCC3C4(F)F)nc21] | tert-butyl 1-[1-(2,2-dimethylpropyl)-3-methyl-2-oxo-2,3-dihydro-1H-imidazo[4,5-b]pyridin-5-yl]-7,7-difluoro-3-azabicyclo[4.1.0]heptane-3-carboxylate | C23H32F2N4O3 [M + H] calc 451.2515 obs 451.2518 |
| 30-13 | 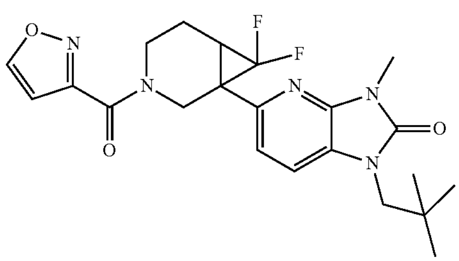 [SMILES: Cn1c(=O)n(CC(C)(C)C)c2ccc(C34CN(C(=O)c5ccon5)CCC3C4(F)F)nc21] | 5-[7,7-difluoro-3-(isoxazol-3-ylcarbonyl)-3-azabicyclo[4.1.0]hept-1-yl]-1-(2,2-dimethylpropyl)-3-methyl-1,3-dihydro-2H-imidazo[4,5-b]pyridin-2-one | C22H25F2N5O3 [M + H] calc 446.1998 obs 446.1999 |
| 30-14 | 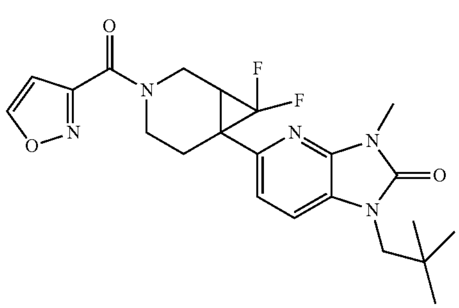 [SMILES: Cn1c(=O)n(CC(C)(C)C)c2ccc(C34CCN(C(=O)c5ccon5)CC3C4(F)F)nc21] | 5-[7,7-difluoro-3-(isoxazol-3-ylcarbonyl)-3-azabicyclo[4.1.0]hept-6-yl]-1-(2,2-dimethylpropyl)-3-methyl-1,3-dihydro-2H-imidazo[4,5-b]pyridin-2-one | C22H25F2N5O3 [M + H] calc 446.1998 obs 446.1988 |

TABLE 13-continued

| # | Structure | Name | HRMS/LRMS |
|---|---|---|---|
| 30-15 | 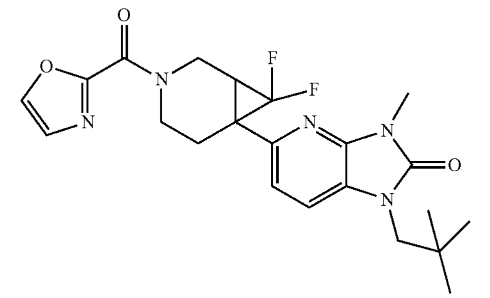 [SMILES: Cn1c(=O)n(CC(C)(C)C)c2ccc(C34CCN(C(=O)c5ncco5)CC3C4(F)F)nc21] | 5-[7,7-difluoro-3-(1,3-oxazol-2-ylcarbonyl)-3-azabicyclo[4.1.0]hept-6-yl]-1-(2,2-dimethylpropyl)-3-methyl-1,3-dihydro-2H-imidazo[4,5-b]pyridin-2-one | C22H25F2N5O3 [M + H] calc 446.1998 obs 446.1987 |
| 30-16 | 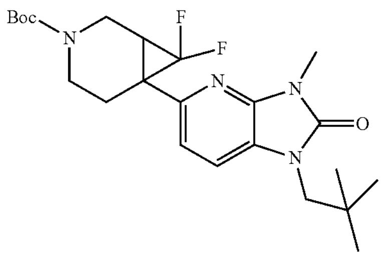 [SMILES: Cn1c(=O)n(CC(C)(C)C)c2ccc(C34CCN(C(=O)OC(C)(C)C)CC3C4(F)F)nc21] | tert-butyl 6-[1-(2,2-dimethylpropyl)-3-methyl-2-oxo-2,3-dihydro-1H-imidazo[4,5-b]pyridin-5-yl]-7,7-difluoro-3-azabicyclo[4.1.0]heptane-3-carboxylate | C23H32F2N4O3 [M + H] calc 451.2515 obs 451.2523 |
| 30-17 | 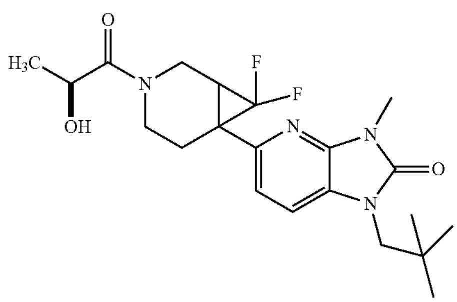 [SMILES: C[C@H](O)C(=O)N1CCC2(c3ccc4c(n3)n(C)c(=O)n4CC(C)(C)C)C(C1)C2(F)F] | 5-{7,7-difluoro-3-[(2S)-2-hydroxypropanoyl]-3-azabicyclo[4.1.0]hept-6-yl}-1-(2,2-dimethylpropyl)-3-methyl-1,3-dihydro-2H-imidazo[4,5-b]pyridin-2-one | C21H28F2N4O3 [M + H] calc 423.2202 obs 423.2198 |

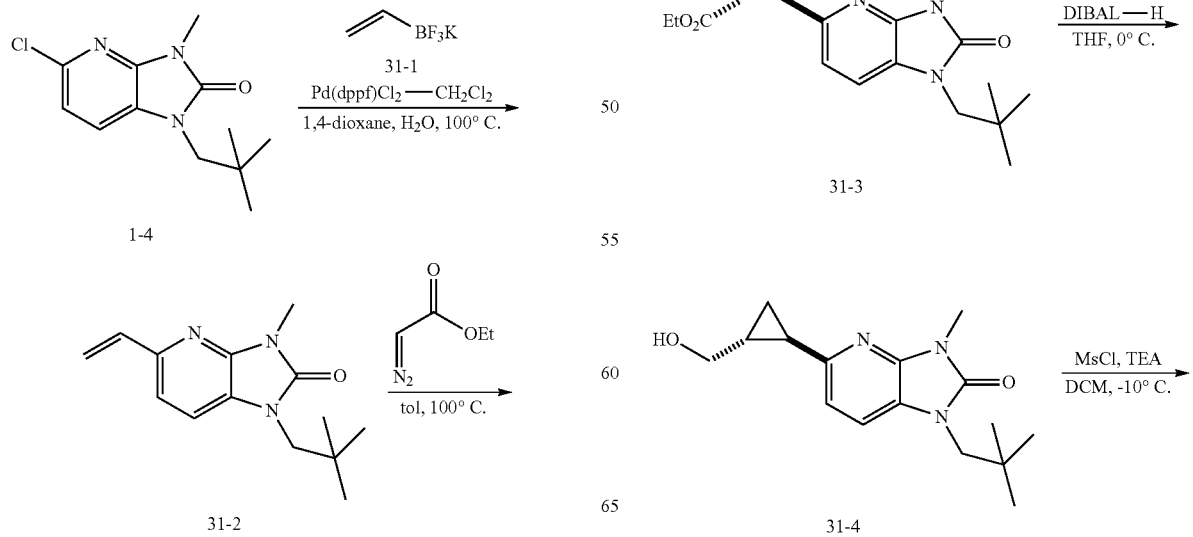

Scheme 31

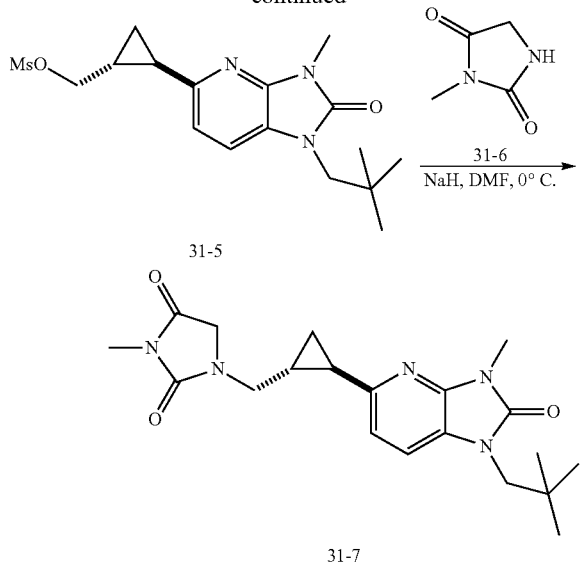

1-({(1R,2R)-2-[1-(2,2-Dimethylpropyl)-3-methyl-2-oxo-2,3-dihydro-1H-imidazo[4,5-b]pyridin-5-yl]cyclopropyl}methyl)-3-methylimidazolidine-2,4-dione (31-7)

1-(2,2-Dimethylpropyl)-5-ethenyl-3-methyl-1,3-dihydro-2H-imidazo[4,5-b]pyridin-2-one (31-2)

5-Chloro-1-(2,2-dimethylpropyl)-3-methyl-1,3-dihydro-2H-imidazo[4,5-b]pyridin-2-one (1-4, 3 g, 11.8 mmol, 1.0 equiv), potassium vinyltrifluoroborate (31-1, 3.2 g, 23.7 mmol, 2.0 equiv), $Cs_2CO_3$ (11.6 g, 35.5 mmol, 3.0 equiv) and 1,1'-bis(diphenylphosphino)-ferrocene-palladium(II)dichloride dichloromethane complex (0.97 g, 1.2 mmol, 0.10 equiv) were added to 1,4-dioxane (19.7 mL) and water (3.9 mL). The resulting reaction mixture was heated to 100° C. and stirred for 18 h. Following this duration, LCMS showed complete consumption of 1-4. The contents were filtered through Celite and washed with ethyl acetate (10 mL). The filtrate was diluted with saturated $NaHCO_3$ (50 mL) and the layers were separated. The aqueous layer was back-extracted with ethyl acetate (3×20 mL) and the combined organics were dried over $Na_2SO_4$, filtered and concentrated in vacuo to give a brown semi-solid. Purification by normal-phase HPLC (0-40% EtOAc:hexane) afforded 31-2 as a yellow solid. MS m/z (M+H): calculated=246.1601; observed=246.1608.

Ethyl (1R,2R)-2-[1-(2,2-dimethylpropyl)-3-methyl-2-oxo-2,3-dihydro-1H-imidazo[4,5-b]pyridin-5-yl]cyclopropanecarboxylate (31-3)

1-(2,2-Dimethylpropyl)-5-ethenyl-3-methyl-1,3-dihydro-2H-imidazo[4,5-b]pyridin-2-one (31-2, 636.4 mg, 2.6 mmol, 1.0 equiv) was added to anhydrous toluene (5.5 mL). Ethyl diazoacetate (807 µL, 7.8 mmol, 3.0 equiv) was added and the resulting solution was heated to 100° C. for 18 h. Following this duration, LCMS showed complete consumption of 31-2. The reaction mixture was diluted with ethyl acetate (50 mL) and saturated $NaHCO_3$ (25 mL). The layers were separated and the aqueous layer was extracted with ethyl acetate (3×10 mL). The combined organics were dried over $Na_2SO_4$, filtered and concentrated in vacuo to give an orange oil. Purification by normal-phase HPLC (0-40% EtOAc:hexanes) provided 31-3 as a white solid. MS m/z (M+H): calculated=332.1969; observed=332.1971.

1-(2,2-Dimethylpropyl)-5-[(1R,2R)-2-(hydroxymethyl)cyclopropyl]-3-methyl-1,3-dihydro-2H-imidazo[4,5-b]pyridin-2-one (31-4)

Ethyl (1R,2R)-2-[1-(2,2-dimethylpropyl)-3-methyl-2-oxo-2,3-dihydro-1H-imidazo[4,5-b]pyridin-5-yl]cyclopropanecarboxylate (31-3, 126 mg, 0.38 mmol, 1.0 equiv) was added to anhydrous THF (3.8 mL) and cooled to 0° C. DIBAL-H (1.9 mL, 1.90 mmol, 5.0 equiv, 1.0M in THF) was added dropwise and the resulting solution was stirred at 0° C. for 2 h. The reaction was then quenched by the addition of saturated Rochelle salts (20 mL), diluted with EtOAc (10 mL) and stirred at RT for 18 h. Following this duration, the layers were separated and the aqueous layer was extracted with ethyl acetate (3×10 mL). The combined organics were dried over $Na_2SO_4$, filtered and concentrated in vacuo to give a clear, yellow oil. Purification by reverse-phase HPLC (10-100% 0.1% TFA in 1-120:$CH_3CN$) provided 31-4 as a colorless oil.

{(1R,2R)-2-[1-(2,2-Dimethylpropyl)-3-methyl-2-oxo-2,3-dihydro-1H-imidazo[4,5-b]pyridin-5-yl]cyclopropyl}methyl methanesulfonate (31-5)

1-(2,2-Dimethylpropyl)-5-[(1R,2R)-2-(hydroxymethyl)cyclopropyl]-3-methyl-1,3-dihydro-2H-imidazo[4,5-b]pyridin-2-one (31-4, 53.2 mg, 0.18 mmol, 1.0 equiv) was added to anhydrous DCM (1.8 mL) and cooled to −10° C. Triethylamine (108 µL, 0.77 mmol, 4.2 equiv) and methanesulfonyl chloride (32 µL, 0.40 mmol, 2.2 equiv) were added sequentially and the resulting reaction mixture was stirred for 1 min. Following this duration, TLC showed complete consumption of 31-4. The reaction mixture was partitioned between ethyl acetate (5 mL) and saturated $NaHCO_3$ (5 mL). The layers were separated and the aqueous layer was extracted with ethyl acetate (3×5 mL). The combined organics were dried over $Na_2SO_4$, filtered and concentrated in vacuo to give a clear, yellow oil. The crude product was carried forward without further purification.

1-({(1R,2R)-2-[1-(2,2-Dimethylpropyl)-3-methyl-2-oxo-2,3-dihydro-1H-imidazo[4,5-b]pyridin-5-yl]cyclopropyl}methyl)-3-methylimidazolidine-2,4-dione (31-7)

{(1R,2R)-2-[1-(2,2-Dimethylpropyl)-3-methyl-2-oxo-2,3-dihydro-1H-imidazo[4,5-b]pyridin-5-yl]cyclopropyl}methyl methanesulfonate (31-5, 68 mg, 0.18 mmol, 1.0 equiv) was added to anhydrous DMF (0.92 mL) and cooled to 0° C. 3-Methylimidazolidine-2,4-dione (31-6, 105 mg, 0.92 mmol, 5.0 equiv) and NaH (37 mg, 0.92 mmol, 5.0 equiv, 60% dispersion in oil) were added sequentially and the resulting mixture was warmed to RT. After 18 h, LCMS showed complete consumption of 31-5. Purification by reverse-phase HPLC (10-100% 0.1% TFA in $H_2O$:$CH_3CN$) afforded 31-7 as a colorless oil. MS m/z (M+H): calculated=332.1969; observed=332.1971.

The following compounds were prepared from the 31-5 by a reaction sequence analogous to that illustrated in Scheme 29:

TABLE 14

| # | Structure | Name | HRMS/LRMS |
|---|---|---|---|
| 31-8 | 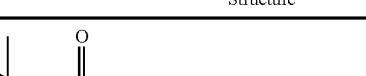 | tert-butyl 4-({(1S,2S)-2-[1-(2,2-dimethylpropyl)-3-methyl-2-oxo-2,3-dihydro-1H-imidazo[4,5-b]pyridin-5-yl]cyclopropyl}methyl)piperazine-1-carboxylate | C25H39N5O3 [M + H] calc 458.3126 obs 458.3124 |

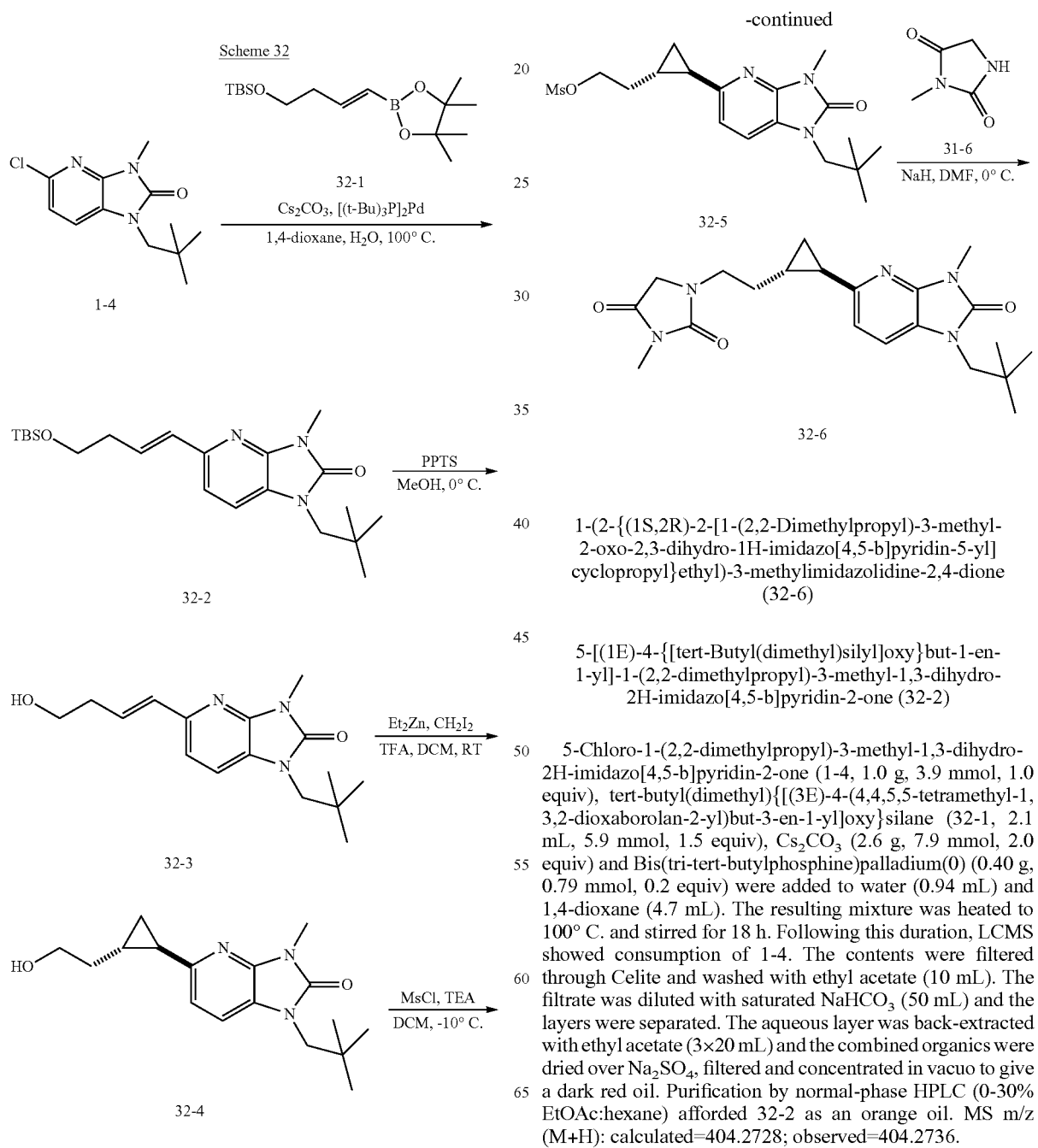

1-(2-{(1S,2R)-2-[1-(2,2-Dimethylpropyl)-3-methyl-2-oxo-2,3-dihydro-1H-imidazo[4,5-b]pyridin-5-yl]cyclopropyl}ethyl)-3-methylimidazolidine-2,4-dione (32-6)

5-[(1E)-4-{[tert-Butyl(dimethyl)silyl]oxy}but-1-en-1-yl]-1-(2,2-dimethylpropyl)-3-methyl-1,3-dihydro-2H-imidazo[4,5-b]pyridin-2-one (32-2)

5-Chloro-1-(2,2-dimethylpropyl)-3-methyl-1,3-dihydro-2H-imidazo[4,5-b]pyridin-2-one (1-4, 1.0 g, 3.9 mmol, 1.0 equiv), tert-butyl(dimethyl){[(3E)-4-(4,4,5,5-tetramethyl-1,3,2-dioxaborolan-2-yl)but-3-en-1-yl]oxy}silane (32-1, 2.1 mL, 5.9 mmol, 1.5 equiv), $Cs_2CO_3$ (2.6 g, 7.9 mmol, 2.0 equiv) and Bis(tri-tert-butylphosphine)palladium(0) (0.40 g, 0.79 mmol, 0.2 equiv) were added to water (0.94 mL) and 1,4-dioxane (4.7 mL). The resulting mixture was heated to 100° C. and stirred for 18 h. Following this duration, LCMS showed consumption of 1-4. The contents were filtered through Celite and washed with ethyl acetate (10 mL). The filtrate was diluted with saturated $NaHCO_3$ (50 mL) and the layers were separated. The aqueous layer was back-extracted with ethyl acetate (3×20 mL) and the combined organics were dried over $Na_2SO_4$, filtered and concentrated in vacuo to give a dark red oil. Purification by normal-phase HPLC (0-30% EtOAc:hexane) afforded 32-2 as an orange oil. MS m/z (M+H): calculated=404.2728; observed=404.2736.

1-(2,2-Dimethylpropyl)-5-[(1E)-4-hydroxybut-1-en-1-yl]-3-methyl-1,3-dihydro-2H-imidazo[4,5-b]pyridin-2-one (32-3)

5-[(1E)-4-{[tert-Butyl(dimethyl)silyl]oxy}but-1-en-1-yl]-1-(2,2-dimethylpropyl)-3-methyl-1,3-dihydro-2H-imidazo[4,5-b]pyridin-2-one (32-2, 207 mg, 0.51 mmol, 1.0 equiv) was added to anhydrous methanol (5.1 mL) and cooled to 0° C. p-Toluenesulfonic acid (9.7 mg, 0.05 mmol, 0.1 equiv) was added and the resulting solution was stirred at 0° C. for 18 h. Following this duration, LCMS showed complete consumption of 32-2. The contents were diluted ethyl acetate (15 mL) and saturated NaHCO$_3$ (15 mL) and the layers were separated. The aqueous layer was back-extracted with ethyl acetate (3×15 mL) and the combined organics were dried over Na$_2$SO$_4$, filtered and concentrated in vacuo to give a pale yellow oil. Purification by reverse-phase HPLC (10-100% 0.1% TFA in H$_2$O:CH$_3$CN) afforded 32-3 as a colorless oil. MS m/z (M+H): calculated=290.1863; observed=290.1864.

1-(2,2-Dimethylpropyl)-5-[(1R,2S)-2-(2-hydroxyethyl)cyclopropyl]-3-methyl-1,3-dihydro-2H-imidazo[4,5-b]pyridin-2-one (32-4)

Diethyl zinc (0.53 mL, 0.53 mmol, 2.0 equiv, 1M in hexanes) was added to anhydrous DCM (0.53 mL) and cooled to 0° C. To this solution was added TFA (41 µL, 0.53 mmol, 2.0 equiv) in anhydrous DCM (0.27 mL), and the resulting mixture was stirred at 0° C. for 15 min. Following this duration, iodomethane (43 µL, 0.53 mmol, 2.0 equiv) in anhydrous DCM (0.27 mL) as added and the resulting reaction mixture was stirred for and additional 20 min. 1-(2,2-Dimethylpropyl)-5-[(1E)-4-hydroxybut-1-en-1-yl]-3-methyl-1,3-dihydro-2H-imidazo[4,5-b]pyridin-2-one (32-3, 77 mg, 0.27 mmol, 1.0 equiv) in anhydrous DCM (0.27) as then added. After 1 h, the reaction vessel was removed from the 0° C. bath and allowed to gradually warm to RT. After 2.5 h, LCMS showed consumption of 32-3. The reaction was quenched with saturated NH$_4$Cl (5 mL) and extracted with ethyl acetate (3×5 ml). The combined organics were dried over Na$_2$SO$_4$, filtered and concentrated in vacuo to give 32-4 as a white solid. Since the material was determined to be of >95% purity by $^1$H NMR, further purification was deemed unnecessary. MS m/z (M+H): calculated=303.4; observed=304.1.

1-(2,2-Dimethylpropyl)-3-methyl-5-{(1R,2S)-2-[2-(methylsulfonyl)ethyl]-cyclopropyl}-1,3-dihydro-2H-imidazo[4,5-b]pyridin-2-one (32-5)

1-(2,2-Dimethylpropyl)-5-[(1R,2S)-2-(2-hydroxyethyl)cyclopropyl]-3-methyl-1,3-dihydro-2H-imidazo[4,5-b]pyridin-2-one (32-4, 46.4 mg, 0.15 mmol, 1.0 equiv) was added to anhydrous DCM (1.5 mL) and cooled to −10° C. Triethylamine (90 µL, 0.64 mmol, 4.2 equiv) and methanesulfonyl chloride (26 µL, 0.33 mmol, 2.2 equiv) were added sequentially and the resulting reaction mixture was stirred for 1 min. Following this duration, TLC showed complete consumption of 32-4. The reaction mixture was partitioned between ethyl acetate (5 mL) and saturated NaHCO$_3$ (5 mL). The layers were separated and the aqueous layer was extracted with ethyl acetate (3×5 mL). The combined organics were dried over Na$_2$SO$_4$, filtered and concentrated in vacuo to give 32-5 as a clear, yellow oil. The crude product was carried forward without further purification.

1-(2-{(1S,2R)-2-[1-(2,2-Dimethylpropyl)-3-methyl-2-oxo-2,3-dihydro-1H-imidazo[4,5-b]pyridin-5-yl]cyclopropyl}ethyl)-3-methylimidazolidine-2,4-dione (32-6)

1-(2,2-Dimethylpropyl)-3-methyl-5-{(1R,2S)-2-[2-(methylsulfonyl)ethyl]-cyclopropyl}-1,3-dihydro-2H-imidazo[4,5-b]pyridin-2-one (32-5, 39 mg, 0.10 mmol, 1.0 equiv) was added to anhydrous DMF (0.50 mL) and cooled to 0° C. 3-Methylimidazolidine-2,4-dione (31-6, 58 mg, 0.51 mmol, 5.0 equiv) and NaH (20 mg, 0.51 mmol, 5.0 equiv, 60% dispersion in oil) were added sequentially and the resulting mixture was warmed to RT. After 18 h, LCMS showed complete consumption of 32-5. Purification by reverse-phase HPLC (10-100% 0.1% TFA in H$_2$O:CH$_3$CN) afforded 32-6 as a colorless oil. MS m/z (M+H): calculated=400.2343; observed=400.2342.

Scheme 33

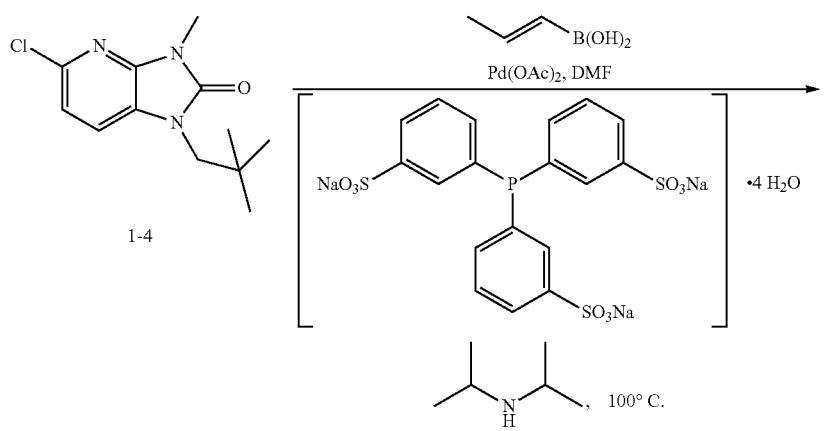

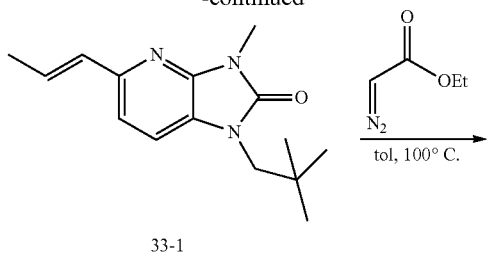

33-1

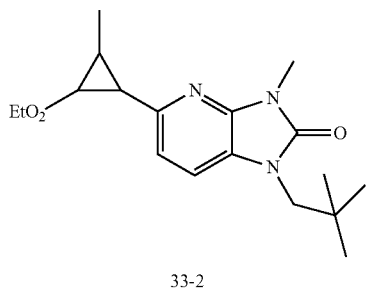

33-2

Ethyl 2-[1-(2,2-dimethylpropyl)-3-methyl-2-oxo-2,3-dihydro-1H-imidazo[4,5-b]pyridin-5-yl]-3-methylcyclopropanecarboxylate (33-2)

1-(2,2-Dimethylpropyl)-3-methyl-5-[(1E)-prop-1-en-1-yl]-1,3-dihydro-2H-imidazo[4,5-b]pyridin-2-one (33-1)

5-Chloro-1-(2,2-dimethylpropyl)-3-methyl-1,3-dihydro-2H-imidazo[4,5-b]pyridin-2-one (1-4, 1 g, 3.9 mmol, 1.0 equiv), (E)-prop-1-enylboronic acid (0.5 g, 5.9 mmol, 1.5 equiv), diisopropylamine (1.1 ml, 7.8 mmol, 2 equiv), triphenylphosphine-3,3',3''-trisulfonic acid trisodium salt hydrate (0.27 g, 0.43 mmol, 0.11 equiv), and Pd(OAc)$_2$ (44 mg, 0.197 mmol, 0.05 quiv) were dissolved in DMF (9.85 mL)/water (3.28 mL), placed in a sealed tube and heated to 100° C. for 18 h. Following this duration, LCMS showed complete consumption of 1-4. The contents were filtered through Celite and washed with ethyl acetate (10 mL). The filtrate was diluted with saturated NaHCO$_3$ (50 mL) and the layers were separated. The aqueous layer was back-extracted with ethyl acetate (3×20 mL) and the combined organics were dried over Na$_2$SO$_4$, filtered and concentrated in vacuo to give a brown semi-solid. Purification by normal-phase HPLC (0-40% EtOAc:hexane) afforded 33-1 as a yellow solid. MS m/z (M+H): observed=260.1.

Ethyl 2-[1-(2,2-dimethylpropyl)-3-methyl-2-oxo-2,3-dihydro-1H-imidazo[4,5-b]pyridin-5-yl]-3-methylcyclopropanecarboxylate (33-2)

1-(2,2-Dimethylpropyl)-3-methyl-5-[(1E)-prop-1-en-1-yl]-1,3-dihydro-2H-imidazo[4,5-b]pyridin-2-one (33-1, 600 mg, 2.3 mmol, 1.0 equiv) was added to anhydrous toluene (4.8 mL). Ethyl diazoacetate (720 µL, 6.9 mmol, 3.0 equiv) was added and the resulting solution was heated to 100° C. for 18 h. Following this duration, LCMS showed complete consumption of 33-1. The reaction mixture was diluted with ethyl acetate (50 mL) and saturated NaHCO$_3$ (25 mL). The layers were separated and the aqueous layer was extracted with ethyl acetate (3×10 mL). The combined organics were dried over Na$_2$SO$_4$, filtered and concentrated in vacuo to give an orange oil. Purification by normal-phase HPLC (0-40% EtOAc:hexanes) provided 33-2 as a white solid. MS m/z (M+H): calculated=346.2127; observed=346.2134.

The following compounds were prepared from the appropriate boronic acid and either 1-4 or 23-2 by a reaction sequence analogous to that illustrated in Scheme 33:

TABLE 15

| # | Structure | Name | HRMS/LRMS |
|---|---|---|---|
| 33-3 | 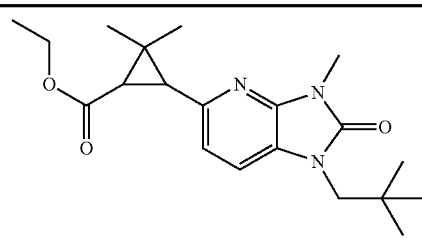 | ethyl 3-[1-(2,2-dimethylpropyl)-3-methyl-2-oxo-2,3-dihydro-1H-imidazo[4,5-b]pyridin-5-yl]-2,2-dimethylcyclopropanecarboxylate | C20H29N3O3 [M + H] calc 360.2283 obs 360.2294 |

TABLE 15-continued

| # | Structure | Name | HRMS/LRMS |
|---|---|---|---|
| 33-4 | 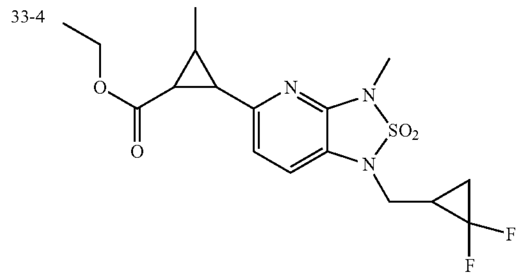 | ethyl 2-{1-[(2,2-difluorocyclopropyl)methyl]-3-methyl-2,2-dioxido-1,3-dihydro[1,2,5]thiadiazolo[3,4-b]pyridin-5-yl}-3-methylcyclopropanecarboxylate | C17H21F2N3O4S [M + H] calc 402.1296 obs 402.1305 |

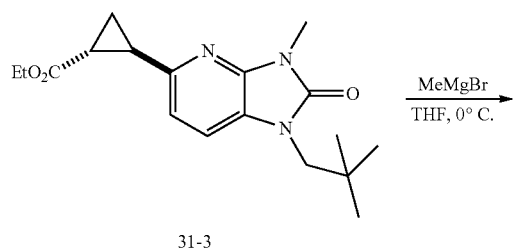

Scheme 34

31-3

34-1

1-(2,2-Dimethylpropyl)-5-[(1R,2R)-2-(2-hydroxypropan-2-yl)-cyclo-propyl]-3-methyl-1,3-dihydro-2H-imidazo[4,5-b]pyridin-2-one (34-1)

Ethyl (1R,2R)-2-[1-(2,2-dimethylpropyl)-3-methyl-2-oxo-2,3-dihydro-1H-imidazo[4,5-b]pyridin-5-yl]cyclopropanecarboxylate (31-3, 28.7 mg, 0.09 mmol, 1.0 equiv) was added to anhydrous THF (0.87 mL) and cooled to 0° C. To this solution was added methylmagnesium bromide (0.17 mL, 0.52 mmol, 6.0 equiv, 3M in ether) and the resulting solution was stirred at 0° C. for 3.5 h. Following this duration, LCMS showed complete consumption of 31-3. The reaction was quenched with saturated NH$_4$Cl (3 ml) and diluted with ethyl acetate (5 mL) and water (1 mL). The layers were separated and the aqueous layer was back-extracted with ethyl acetate (3×3 mL). The combined organics were dried over Na$_2$SO$_4$, filtered and concentrated to give a pale yellow semi-solid. Purification by reverse-phase chromatography (20-100% 0.1% TFA in H$_2$O:CH$_3$CN) afforded 34-1 as a pale yellow solid (15.7 mg). MS m/z (M+H): calculated=318.2176; observed=318.2175.

The following compounds were prepared from the appropriate ester by a reaction sequence analogous to that illustrated in Scheme 34:

TABLE 16

| # | Structure | Name | HRMS/LRMS |
|---|---|---|---|
| 34-2 | 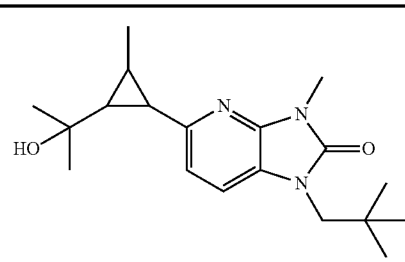 | 1-(2,2-dimethylpropyl)-5-[2-(1-hydroxy-1-methylethyl)-3-methylcyclopropyl]-3-methyl-1,3-dihydro-2H-imidazo[4,5-b]pyridin-2-one | C19H29N3O2 [M + H] calc 332.2334 obs 332.2341 |

TABLE 16-continued

| # | Structure | Name | HRMS/LRMS |
|---|---|---|---|
| 34-3 | 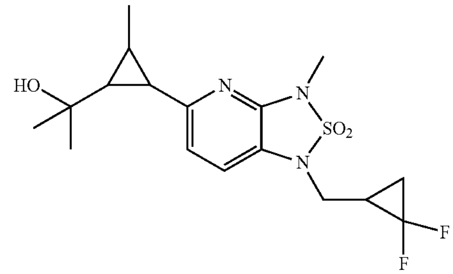 [SMILES: CC1C(c2ccc3c(n2)N(C)S(=O)(=O)N3CC2CC2(F)F)C1C(C)(C)O] | 2-(2-{1-[(2,2-difluorocyclopropyl)methyl]-3-methyl-2,2-dihydro[1,2,5]thiadiazolo[3,4-b]pyridin-5-yl}-3-methylcyclopropyl)propan-2-ol | C17H23F2N3O3S [M + H] calc 388.1503 obs 388.1513 |

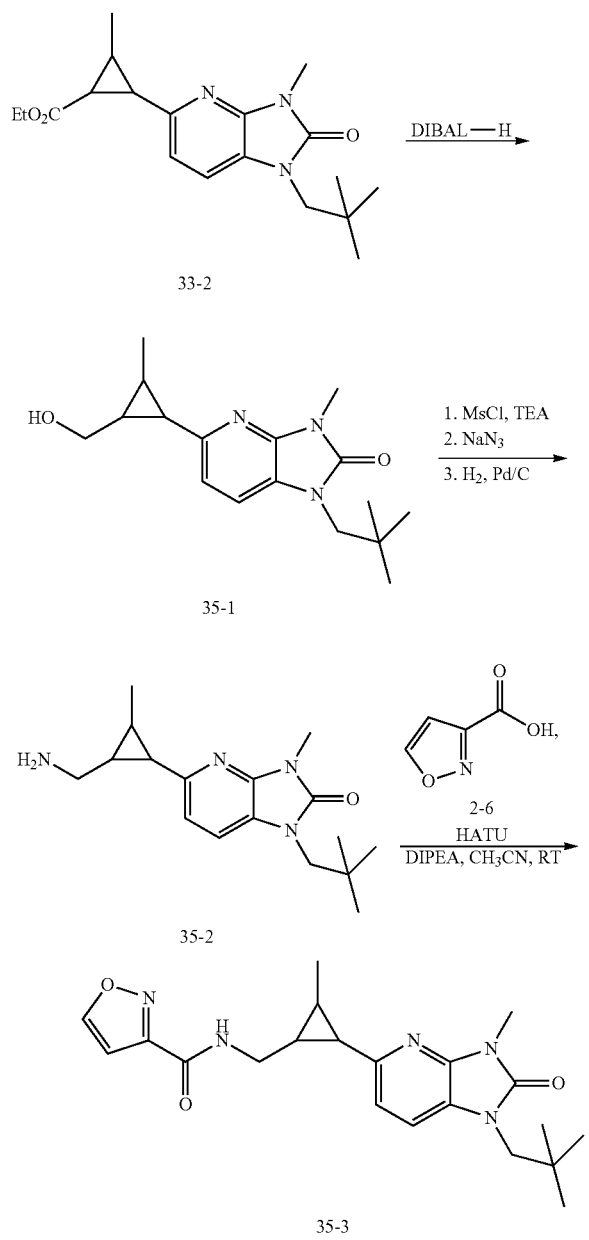

Scheme 35

N-({2-[1-(2,2-Dimethylpropyl)-3-methyl-2-oxo-2,3-dihydro-1H-imidazo[4,5-b]pyridin-5-yl]-3-methylcyclopropyl}methyl)isoxazole-3-carboxamide (35-3)

1-(2,2-Dimethylpropyl)-5-[2-(hydroxymethyl)-3-methylcyclopropyl]-3-methyl-1,3-dihydro-2H-imidazo[4,5-b]pyridin-2-one (35-1)

Ethyl 2-[1-(2,2-dimethylpropyl)-3-methyl-2-oxo-2,3-dihydro-1H-imidazo[4,5-b]pyridin-5-yl]-3-methylcyclopropanecarboxylate (33-2, 192 mg, 0.55 mmol, 1.0 equiv) was added to anhydrous THF (2.7 mL) and cooled to 0° C. DIBAL-H (2.78 mL, 2.78 mmol, 5.0 equiv, 1.0M in THF) was added dropwise and the resulting solution was stirred at 0° C. for 2 h. The reaction was then quenched by the addition of saturated Rochelle salts (20 mL), diluted with EtOAc (10 mL) and stirred at RT for 18 h. Following this duration, the layers were separated and the aqueous layer was extracted with ethyl acetate (3×10 mL). The combined organics were dried over $Na_2SO_4$, filtered and concentrated in vacuo to give a clear, yellow oil. Purification by reverse-phase HPLC (10-100% 0.1% TFA in $H_2O:CH_3CN$) provided 35-1 as a colorless oil. MS m/z (M+H): observed=304.1

5-[2-(Aminomethyl)-3-methylcyclopropyl]-1-(2,2-dimethylpropyl)-3-methyl-1,3-dihydro-2H-imidazo[4,5-b]pyridin-2-one (35-2)

1-(2,2-Dimethylpropyl)-5-[2-(hydroxymethyl)-3-methylcyclopropyl]-3-methyl-1,3-dihydro-2H-imidazo[4,5-b]pyridin-2-one (35-1, 61.6 mg, 0.20 mmol, 1.0 equiv) was added to anhydrous DCM (2.0 mL) and cooled to −10° C. Triethylamine (54.9 μL, 0.42 mmol, 2.1 equiv) and methanesulfonyl chloride (17.4 μL, 0.22 mmol, 1.1 equiv) were added sequentially and the resulting reaction mixture was stirred for 1 min. Following this duration, TLC showed complete consumption of 35-1. The reaction mixture was partitioned between ethyl acetate (5 mL) and saturated $NaHCO_3$ (5 mL). The layers were separated and the aqueous layer was extracted with ethyl acetate (3×5 mL). The combined organics were dried over $Na_2SO_4$, filtered and concentrated in vacuo to give a clear, yellow oil. The yellow oil (77 mg, 0.20 mmol, 1 equiv) and sodium azide (32.8 mg, 0.50 mmol, 2.5 equiv) were dissolved in DMF, cooled to 0° C. and added with sodium hydride (12.1 mg, 0.50 mmol, 2.5 equiv). The reaction mixture was stirred for 18 h. Following this duration, TLC showed complete consumption of the mesylate. Azide intermediate (5-(2-(azidomethyl)-3-methylcyclopropyl)-3-methyl-1-neopentyl-1H-imidazo[4,5-b]pyridin-2(3H)-one) was isolated by normal-phase HPLC (0-40% EtOAc:hexanes). 5-(2-

(azidomethyl)-3-methylcyclopropyl)-3-methyl-1-neopentyl-1H-imidazo[4,5-b]pyridin-2(3H)-one (65 mg, 0.19 mmol, 1 equiv), triphenylphosphine (156 mg, 0.59 mmol, 3 equiv) and water (35.1 μL, 1.9 mmol, 9.8 equiv) were added with THF. The reaction mixture was stirred at 55° C. for 1 h. Following this duration, UPLC showed trace of the azide intermediate. Purification by reverse-phase HPLC (20-100% CH₃CN:0.1% TFA in H₂O) provided 35-2.

N-({2-[1-(2,2-Dimethylpropyl)-3-methyl-2-oxo-2,3-dihydro-1H-imidazo-[4,5-b]pyridin-5-yl]-3-methylcyclopropyl}methyl)isoxazole-3-carboxamide (35-3)

5-[2-(Aminomethyl)-3-methylcyclopropyl]-1-(2,2-dimethylpropyl)-3-methyl-1,3-dihydro-2H-imidazo[4,5-b]pyridin-2-one (35-2, 35 mg, 0.11 mmol, 1.0 equiv), isoxazole-3-carboxylic acid (2-6, 14.3 mg, 0.12 mmol, 1.5 equiv), DIPEA (0.040 mL, 0.23 mmol, 2.0 equiv) and HATU (48.4 mg, 0.12 mmol, 1.1 equiv) were added to anhydrous acetonitrile (1 mL). After stirring for 10 min at room temperature, LCMS showed consumption of starting material. Purification by reverse-phase HPLC (20-100% CH₃CN:0.1% TFA in H₂O) provided 35-3 as a white solid. MS m/z (M+H): calculated=398.2188; observed=398.2195. $^1$H NMR δ (ppm) (CHCl₃-d): 8.47 (1H, d, J=1.68 Hz), 7.04 (1H, d, J=7.90 Hz), 6.96 (1H, s), 6.83 (1H, d, J=1.67 Hz), 6.81 (1H, d, J=7.90 Hz), 3.76-3.65 (1H, m), 3.61 (2H, s), 3.60-3.52 (1H, m), 3.43 (3H, s), 1.82 (1H, dd, J=7.68, 3.43 Hz), 1.70-1.65 (1H, m), 1.64 (1H, dd, J=7.82, 0.02 Hz), 1.30 (3H, d, J=6.23 Hz), 1.02 (9H, s).

N-{(3S)-3-[1-(2,2-Dimethylpropyl)-3-methyl-2-oxo-2,3-dihydro-1H-imidazo[4,5-b]pyridin-5-yl]butyl}isoxazole-3-carboxamide (36-5)

Methyl (3S)-3-[1-(2,2-dimethylpropyl)-3-methyl-2-oxo-2,3-dihydro-1H-imidazo[4,5-b]pyridin-5-yl]butanoate (36-1)

To a stirred solution of 1-4 (0.40 g, 1.58 mmol), Pd(OAc)₂ (0.02 g, 0.08 mmol), xphos (0.074 g, 0.16 mmol) in dioxane (12 mL) was added 3-methoxy-2-methyl-3-oxo-propylzincbromide 0.5M solution in THF (12.6 mL, 6.30 mmol) and the resulting mixture was microwave irradiated for 30 minutes at 100° C. The reaction was allowed to cool and partitioned between ethyl acetate and water. The organic phase was conc and flash column separation using a 0-30% ethyl acetate/hexane gradient gave 36-1. (0.47 g, 92%). LRMS (ES) (M+H)⁺: observed=320.1, calculated=320.4.

1-(2,2-Dimethylpropyl)-5-[(2S)-4-hydroxybutan-2-yl]-3-methyl-1,3-dihydro-2H-imidazo[4,5-b]pyridin-2-one (36-2)

To a stirred solution of 36-1 (0.46 g, 1.38 mmol) in THF (8 mL) chilled to −78° C. was added DIBAL 1.0M in THF heptane (4.22 mL, 4.22 mmol) dropwise. The resulting mixture was stirred at −78° C. for 3 hr, then quench with slow addition of Rochelle's salt solution (5 mL). The resulting mixture was allowed to warm to room temperature, diluted with water and extracted with ethyl acetate. The organic phase was concentrated and flash column separation using a 50-100% ethyl acetate/hexane gradient gave 36-2. (0.26 g, 64%). LRMS (ES) (M+H)⁺: observed=292.1, calculated=292.4.

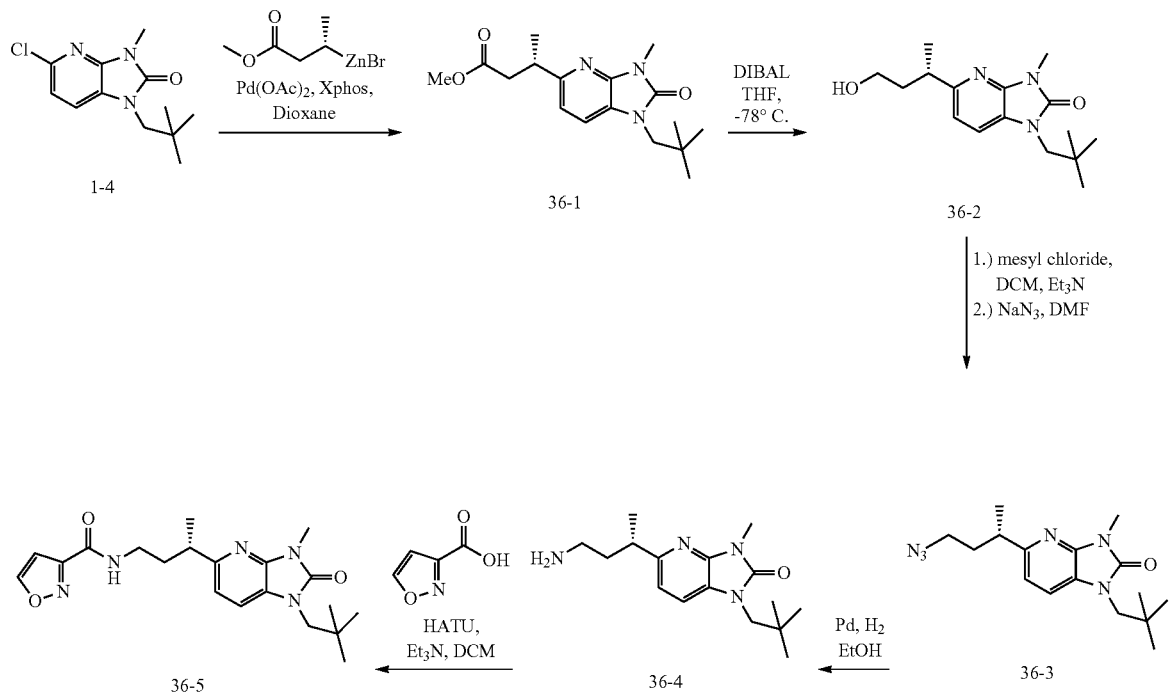

5-[(2S)-4-Azidobutan-2-yl]-1-(2,2-dimethylpropyl)-3-methyl-1,3-dihydro-2H-imidazo[4,5-b]pyridin-2-one (36-3)

To a stirred solution of 36-2 (0.15 g, 0.52 mmol) in dichloromethane (2 mL) was added triethylamine (0.15 mL, 1.08 mmol) and methanesulfonyl chloride (0.05 mL, 0.62 mmol). The resulting mixture was stirred at room temperature for 10 minutes and concentrated. The residue was dissolved in DMF (2 mL). To this solution was added sodium azide (0.20 g, 3.08 mmol) and the mixture was heated to 90° C. for 3 days. The reaction was allowed to cool and partitioned between ethyl acetate and water. The organic phase was concentrated to give 36-3. (0.13 g, 83%). LRMS (ES) (M+H)$^+$: observed=317.1, calculated=317.4.

5-[(2S)-4-Aminobutan-2-yl]-1-(2,2-dimethylpropyl)-3-methyl-1,3-dihydro-2H-imidazo[4,5-b]pyridin-2-one (36-4)

To a stirred solution of 36-3 (0.13 g, 0.43 mmol) in ethanol (7 mL) under N$_2$ was added 10% palladium on carbon (0.03 g, 0.03 mmol) in ethanol. The resulting mixture was flushed several times with H$_2$ gas. The resulting mixture was stirred overnight under a balloon of hydrogen. The mixture was flushed with nitrogen and filtered through celite. The filtrate was concentrated to give 36-4. (0.10 g, 84%). LRMS (ES) (M+H)$^+$: observed=291.2, calculated=291.4.

N-{(3R)-3-[1-(2,2-Dimethylpropyl)-3-methyl-2-oxo-2,3-dihydro-1H-imidazo[4,5-b]pyridin-5-yl]butyl}isoxazole-3-carboxamide (36-5)

To a stirred solution of 3-Isoxazolecarboxylic acid (0.015 g, 0.13 mmol), and triethylamine (0.1 mL, 0.72 mmol) in dichloromethane (2 mL) was added HATU (0.05 g, 0.13 mmol). The resulting mixture was stirred 20 minutes. To this mixture was added 36-4 (0.03 g, 0.10 mmol) and the resulting mixture was stirred room temperature overnight. The mixture was washed with water and concentrated. Flash column separation using a 0-60% ethyl acetate/hexane gradient, followed by 10-90% reverse phase gradient gave 36-5. (0.017 g, 43%). HRMS (M+H)$^+$: observed=386.2189, calculated=386.2187

The following compounds were prepared by a reaction sequence analogous to that illustrated in Scheme 36:

TABLE 17

| # | Structure | Name | HRMS/LRMS |
|---|---|---|---|
| 36-6 | 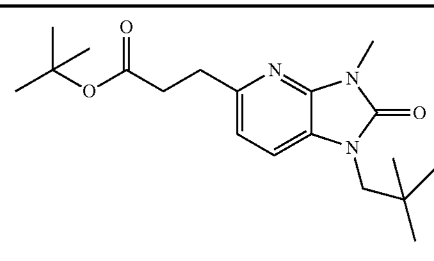 | tert-butyl 3-[1-(2,2-dimethylpropyl)-3-methyl-2-oxo-2,3-dihydro-1H-imidazo[4,5-b]pyridin-5-yl]propanoate | C19H29N3O3 [M + H] calc 348.2283 obs 348.2288 |
| 36-7 | 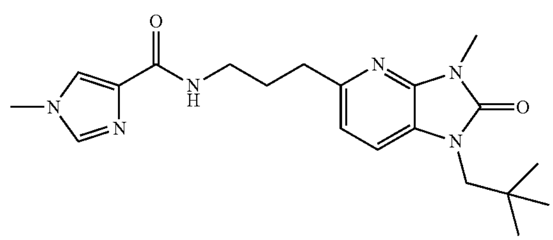 [SMILES: Cn1cnc(C(=O)NCCCc2ccc3c(n2)n(C)c(=O)n3CC(C)(C)C)c1] | N-{3-[1-(2,2-dimethylpropyl)-3-methyl-2-oxo-2,3-dihydro-1H-imidazo[4,5-b]pyridin-5-yl]propyl}-1-methyl-1H-imidazole-4-carboxamide | C20H28N6O2 [M + H] calc 385.2351 obs 385.2347 |
| 36-8 | 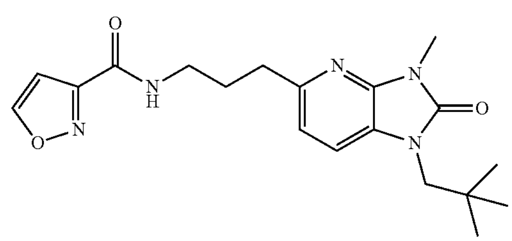 [SMILES: Cn1c(=O)n(CC(C)(C)C)c2ccc(CCCNC(=O)c3ccon3)nc21] | N-{3-[1-(2,2-dimethylpropyl)-3-methyl-2-oxo-2,3-dihydro-1H-imidazo[4,5-b]pyridin-5-yl]propyl}isoxazole-3-carboxamide | C19H25N5O3 [M + H] calc 372.2033 obs 372.2030 |
| 36-9 | 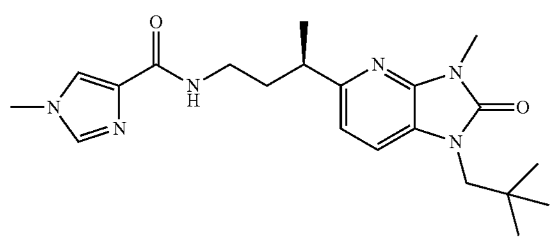 [SMILES: C[C@H](CCNC(=O)c1cn(C)cn1)c1ccc2c(n1)n(C)c(=O)n2CC(C)(C)C] | N-{(3R)-3-[1-(2,2-dimethylpropyl)-3-methyl-2-oxo-2,3-dihydro-1H-imidazo[4,5-b]pyridin-5-yl]butyl}-1-methyl-1H-imidazole-4-carboxamide | C21H30N6O2 [M + H] calc 399.2505 obs 399.2503 |

Scheme 37

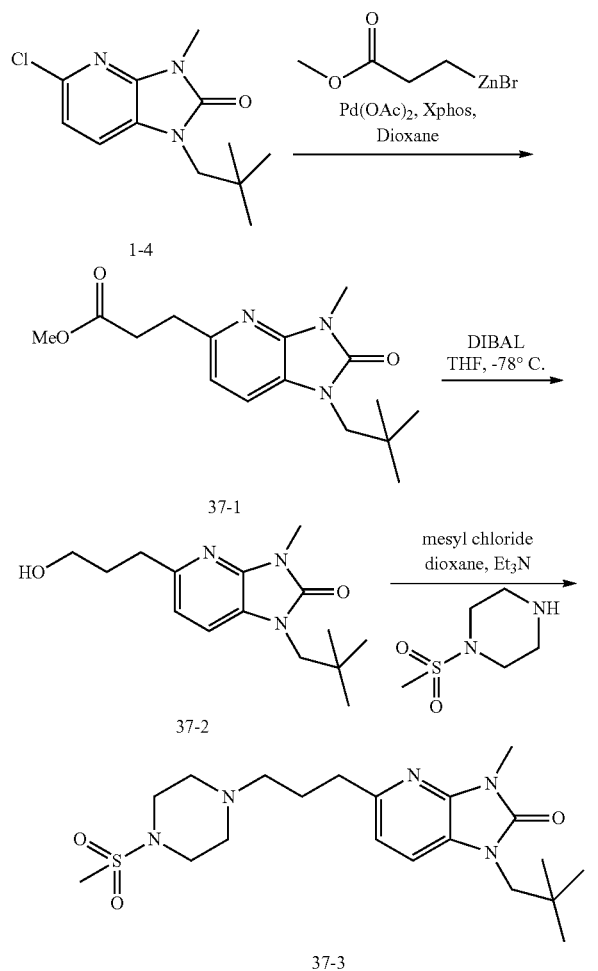

heptane (4.22 mL, 4.22 mmol) dropwise. The resulting mixture was stirred at −78° C. for 3 hr, then quench with slow addition of Rochelle's salt solution (3 mL). The resulting mixture was allowed to warm to room temperature, diluted with water and extracted with ethyl acetate. The organic phase was concentrated and flash column separation using a 20-100% ethyl acetate/hexane gradient gave 37-2. (0.22 g, 55%). LRMS (ES) (M+H)$^+$: observed=278.1, calculated=278.4.

1-(2,2-Dimethylpropyl)-3-methyl-5-{3-[4-(methylsulfonyl)piperazin-1-yl]propyl}-1,3-dihydro-2H-imidazo[4,5-b]pyridin-2-one (37-3)

To a stirred solution of 37-2 (0.05 g, 0.18 mmol) in dioxane (1 mL) was added triethylamine (0.10 mL, 0.72 mmol) and methanesulfonyl chloride (0.017 mL, 0.21 mmol). To this resulting mixture was added 1-methanesulfonyl-piperazine (0.09 g, 0.54 mmol) and the reaction was heated to 100° C. for 3 days. The reaction was concentrated and flash column separation using a 0-5% methanol/dichloromethane gradient gave 37-3. (0.025 g, 33%). HRMS (M+H)$^+$: observed=424.2378, calculated=424.2377

Scheme 38

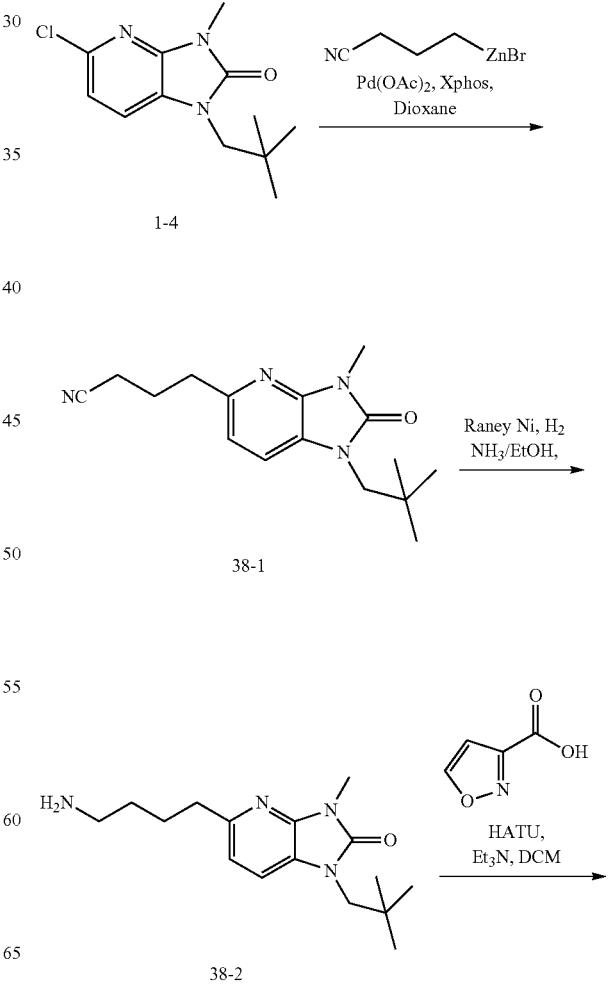

1-(2,2-Dimethylpropyl)-3-methyl-5-{3-[4-(methylsulfonyl)piperazin-1-yl]propyl}-1,3-dihydro-2H-imidazo[4,5-b]pyridin-2-one (37-3)

Methyl 3-[1-(2,2-dimethylpropyl)-3-methyl-2-oxo-2,3-dihydro-1H-imidazo[4,5-b]pyridin-5-yl]propanoate (37-1)

To a stirred solution of 1-4 (0.10 g, 0.39 mmol), Pd(OAc)$_2$ (0.004 g, 0.02 mmol), xphos (0.02 g, 0.039 mmol) in dioxane (3 mL) was added 3-ethoxy-3-oxopropylzinc bromide 0.5M solution in THF (3.15 mL, 1.57 mmol) and the resulting mixture was microwave irradiated for 30 minutes at 100° C. The reaction was allowed to cool and partitioned between ethyl acetate and water. The organic phase was concentrated and flash column separation using a 0-30% ethyl acetate/hexane gradient gave 37-1. (0.10 g, 86%). LRMS (ES) (M+H)$^+$: observed=320.1, calculated=320.4.

1-(2,2-Dimethylpropyl)-5-(3-hydroxypropyl)-3-methyl-1,3-dihydro-2H-imidazo[4,5-b]pyridin-2-one (37-2)

To a stirred solution of 37-1 (0.45 g, 1.40 mmol) in THF (8 mL) chilled to −78° C. was added DIBAL 1.0M in THF -continued

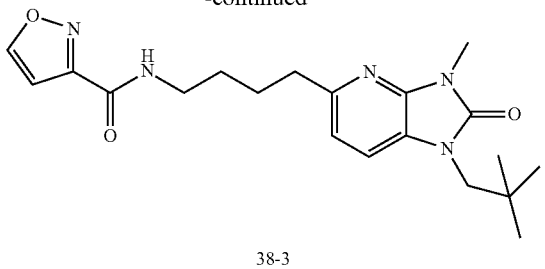

38-3

N-{4-[1-(2,2-Dimethylpropyl)-3-methyl-2-oxo-2,3-dihydro-1H-imidazo-[4,5-b]pyridin-5-yl]butyl}isoxazole-3-carboxamide (38-3)

4-[1-(2,2-Dimethylpropyl)-3-methyl-2-oxo-2,3-dihydro-1H-imidazo[4,5-b]pyridin-5-yl]butanenitrile (38-1)

To a stirred solution of 1-4 (0.40 g, 1.58 mmol), Pd(OAc)$_2$ (0.02 g, 0.08 mmol), xphos (0.074 g, 0.16 mmol) in dioxane (12 mL) was added 3-cyanopropylzinc bromide 0.5M solution in THF (12.6 mL, 6.3 mmol) and the resulting mixture was microwave irradiated for 30 minutes at 100° C. The reaction was allowed to cool and partitioned between ethyl acetate and water. The organic phase was concentrated and flash column separation using a 0-60% ethyl acetate/hexane gradient gave 38-1. (0.42 g, 94%). LRMS (ES) (M+H)$^+$: observed=287.2, calculated=287.4.

5-(4-Aminobutyl)-1-(2,2-dimethylpropyl)-3-methyl-1,3-dihydro-2H-imidazo[4,5-b]pyridin-2-one (38-2)

To a mixture of Raney nickel (1 mL) in ethanol 2M NH$_3$ solution (5 mL) under nitrogen was added 38-1 (0.40 g, 1.40 mmol) dissolved in ethanol (1 mL). The mixture was flushed with hydrogen and stirred overnight under a hydrogen filled balloon. The solution was filtered through a syringe and the filtrate was concentrated to give 38-2. (0.41 g, 100%). LRMS (ES) (M+H)$^+$: observed=291.2, calculated=291.4.

N-{4-[1-(2,2-Dimethylpropyl)-3-methyl-2-oxo-2,3-dihydro-1H-imidazo-[4,5-b]pyridin-5-yl]butyl}isoxazole-3-carboxamide (38-3)

To a stirred solution of 3-isoxazolecarboxylic acid (0.02 g, 0.18 mmol), and triethylamine (0.1 mL, 0.72 mmol) in dichloromethane (2 mL) was added HATU (0.07 g, 0.18 mmol). The resulting mixture was stirred 20 minutes. To this mixture was added 38-2 (0.04 g, 0.14 mmol) and the resulting mixture was stirred room temperature overnight. The mixture was washed with water and concentrated. Flash column separation using a 10-70% ethyl acetate/hexane gradient gave 38-3. (0.045 g, 85%). HRMS (M+H)$^+$: observed=386.2188, calculated=386.2187

The following compounds were prepared by a reaction sequence analogous to that illustrated in Scheme 38:

TABLE 18

| # | Structure | Name | HRMS/LRMS |
|---|---|---|---|
| 38-4 | 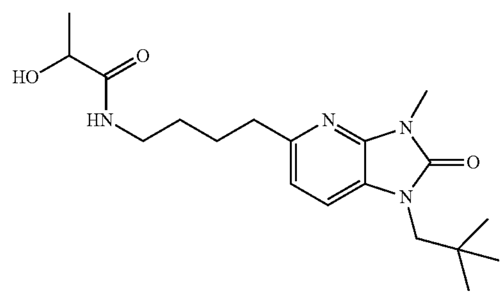 [SMILES: CC(O)C(=O)NCCCCc1ccc2c(n1)n(C)c(=O)n2CC(C)(C)C] | N-{4-[1-(2,2-dimethylpropyl)-3-methyl-2-oxo-2,3-dihydro-1H-imidazo[4,5-b]pyridin-5-yl]butyl}-2-hydroxypropanamide | C19H30N4O3 [M + H] calc 363.2391 obs 363.2394 |
| 38-5 | 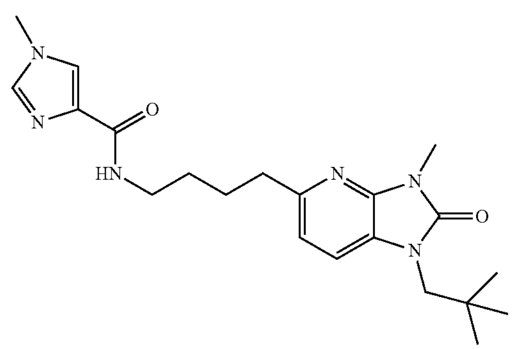 [SMILES: Cn1cnc(C(=O)NCCCCc2ccc3c(n2)n(C)c(=O)n3CC(C)(C)C)c1] | N-{4-[1-(2,2-dimethylpropyl)-3-methyl-2-oxo-2,3-dihydro-1H-imidazo[4,5-b]pyridin-5-yl]butyl}-1-methyl-1H-imidazole-4-carboxamide | C21H30N6O2 [M + H] calc 399.2503 obs 399.2503 |

What is claimed is:

1. A compound according to Formula Ia

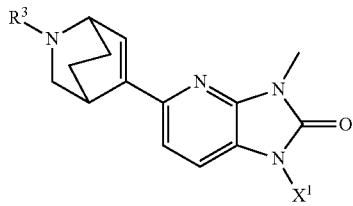

or a pharmaceutically acceptable salt thereof, wherein:

$X^1$ is selected from the group consisting of: $C_{1-8}$ alkyl, $C_{2-8}$ alkenyl, $C_{2-8}$ alkynyl, $C_{3-6}$ cycloalkyl and $C_{3-6}$cycloalkyl$C_{1-4}$alkyl, any of which may bear up to 5 halogen substituents;

$R^3$ is selected from the group consisting of: halogen, OH, oxo, CN, $CF_3$, $R^5$, $OR^4$, $SR^5$, $SO_2R^5$, $COCH_2SO_2R^5$, $SO_2N(R^4)_2$, $COR^5$, $CO_2R^4$, $CON(R^4)_2$, $N(R^4)_2$, $NR^4COR^5$, $NR^4CON(R^4)_2$, $NR^4CO_2R^4$, $NR^4SO_2R^5$, —$C_{1-4}$alkyl-$N(R^4)_2$, —$C_{1-4}$alkyl-$NR^4COR^5$ and —$C_{1-4}$alkyl-$NR^4CO^2R^4$;

each $R_4$ independently represents H, $C_{1-6}$alkyl, $C_{3-10}$cycloalkyl, $C_{3-10}$cycloalkyl$C_{1-4}$alkyl, $C_{3-10}$cycloalkenyl or $C_{3-10}$cycloalkenyl$C_{1-4}$alkyl, any of which except H optionally bear up to 3 halogen atoms or with OH, CN, $CF_3$, $OCF_3$, $C_{1-4}$alkoxy, $C_{1-4}$alkyl-C(O)—O—, $C_{1-4}$alkyl-C(O)—, amino, $C_{1-4}$alkylamino and di($C_{1-4}$alkyl)amino, or $R^4$ represents phenyl, benzyl, phenylethyl, 5- or 6-membered monocyclic heteroaryl optionally bridged with —(CH$_2$)$_p$—, or a 9- or 10-membered bicyclic heteroaryl optionally bridged with —(CH$_2$)$_p$—, any of which optionally bear up to 3 substituents independently selected from halogen, OH, CN, $CF_3$, $OCF_3$, $C_{1-4}$alkyl, $C_{3-6}$cycloalkyl, phenyl, $C_{1-4}$alkoxy, amino, $C_{1-4}$alkylamino, di($C_{1-4}$alkyl)amino, a 5- or 6-membered monocyclic heteroaryl optionally bridge with methylene and optionally substituted with one or two methyl groups, and Het, optionally substituted with 1 to 3 substituents selected from oxo and methyl, or $R^4$ represents Het, optionally bridged with —(CH$_2$)$_p$— and said Het optionally bearing up to 3 substituents independently selected from halogen, OH, oxo, CN, $CF_3$, $OCF_3$, $C_{1-4}$alkyl, $C_{3-6}$cycloalkyl, phenyl, benzyl, a 5- or 6-membered monocyclic heteroaryl optionally bridged with methylene and substituted with one or two methyl groups, $C_{1-4}$alkoxy, $C_{1-4}$alkyl-O—C(O)—, $C_{1-4}$alkyl-C(O)—, acetyl, amino, $C_{1-4}$alkylamino, di($C_{1-4}$alkyl)amino and Het, optionally substituted with 1 to 3 substituents selected from oxo and methyl;

each p is independently 1, 2, 3 or 4; and $R^5$ has the same definition as $R^4$ except that $R^5$ is not H.

2. The compound according to claim 1, or a pharmaceutically acceptable salt thereof, wherein $X^1$ is selected from 2,2-dimethylpropyl, [2,2-difluorocyclopropyl]methyl and [2,2-difluoro-1-methylcyclopropyl]methyl.

3. The compound according to claim 1, or a pharmaceutically acceptable salt thereof, wherein $R^3$ is $COR^5$, $CO_2R^5$, $NR^4COR^5$, $NR^4CO_2R^5$, $SO_2R^5$ or $NR^4SO_2R^5$.

4. The compound according to claim 3, or a pharmaceutically acceptable salt thereof, wherein $R^3$ is $COR^5$.

5. The compound according to claim 4, or a pharmaceutically acceptable salt thereof, wherein RS is a 5- or 6-membered monocyclic heteroaryl, which optionally bears up to 3 substituents independently selected from halogen, OH, CN, $CF_3$, $C_{1-4}$alkyl, $C_{3-6}$cycloalkyl, phenyl, $C_{1-4}$alkoxy, amino, $C_{1-4}$alkylamino and di($C_{1-4}$alkyl)amino.

6. The compound according to claim 5, or a pharmaceutically acceptable salt thereof, wherein $R^5$ is selected from the group consisting of: isoxazole, thiadiazole, pyridine, imidazole, pyrazole, oxazole, triazole, thiazole and isothiazole, any of which optionally bear up to 3 methyl substituents.

7. The compound according to claim 6, or a pharmaceutically acceptable salt thereof, wherein $R^5$ is isoxazole.

8. The compound, or a pharmaceutically acceptable salt thereof, selected from the group consisting of:

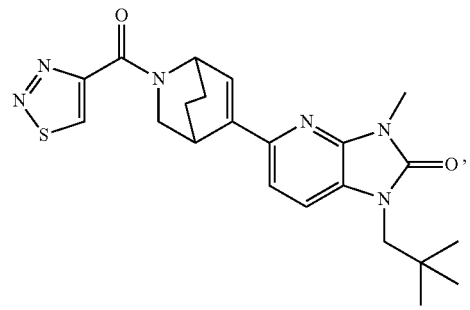

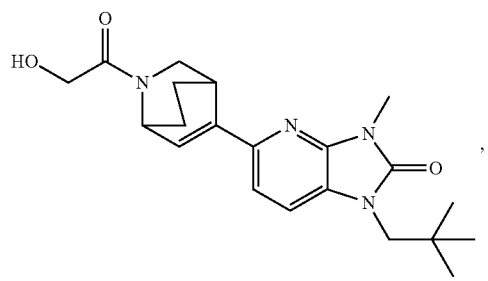

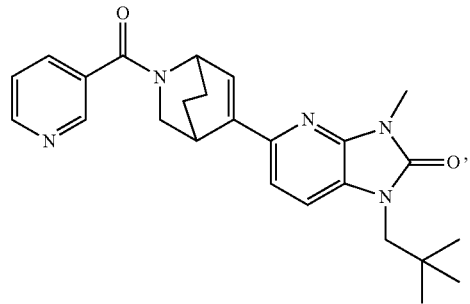

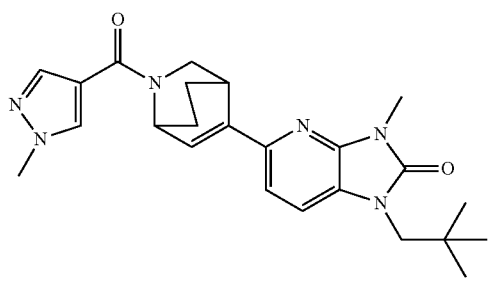

281
-continued
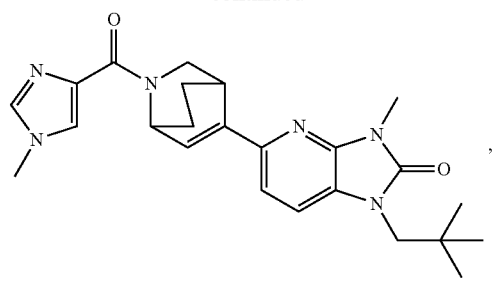,
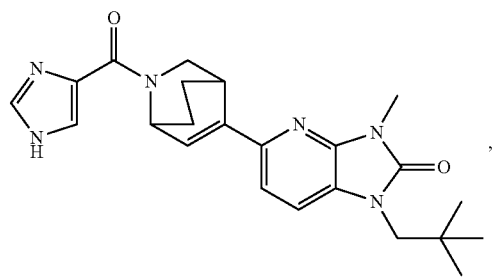,
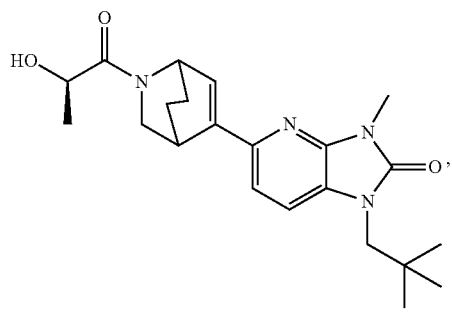,
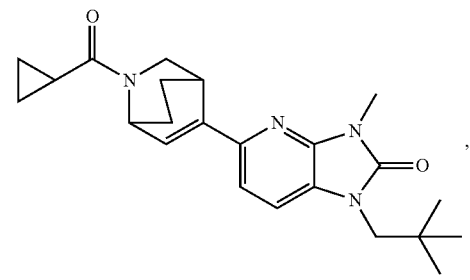,
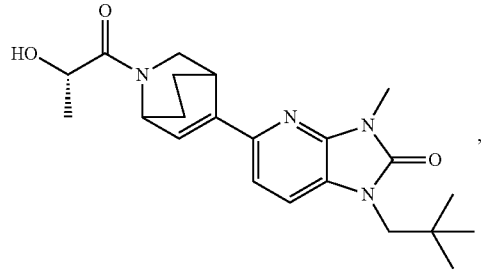,
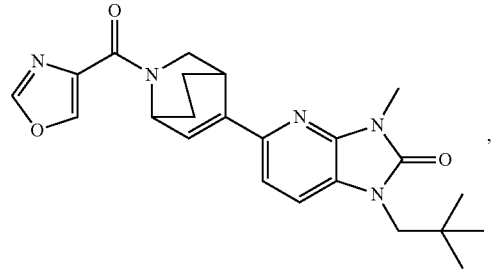,
282
-continued
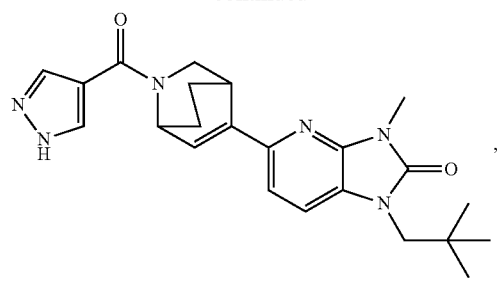,
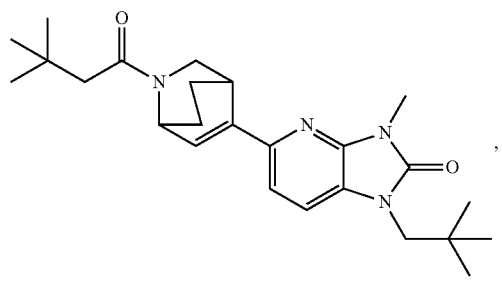,
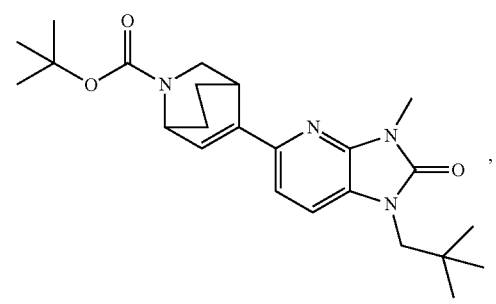,
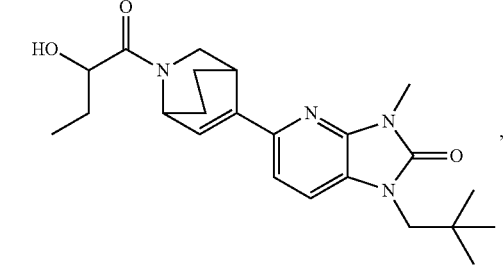,
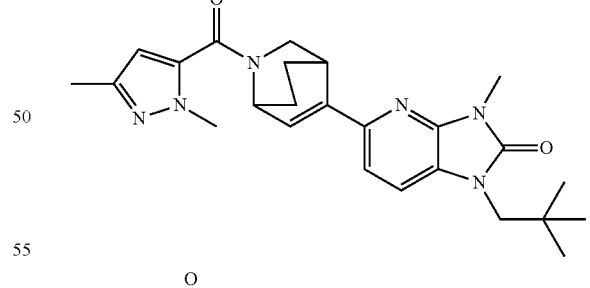,
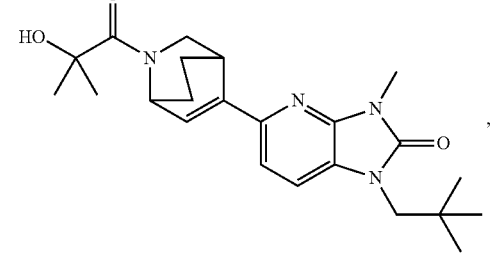, 283
-continued
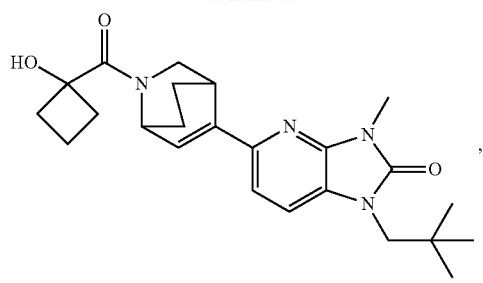,
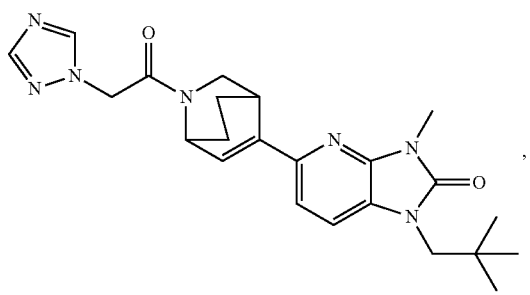,
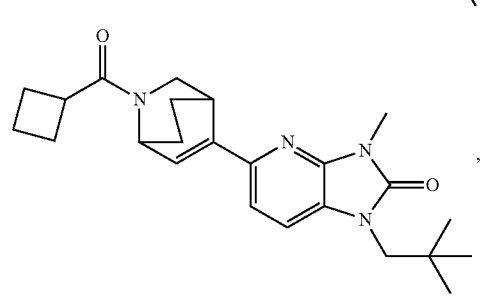,
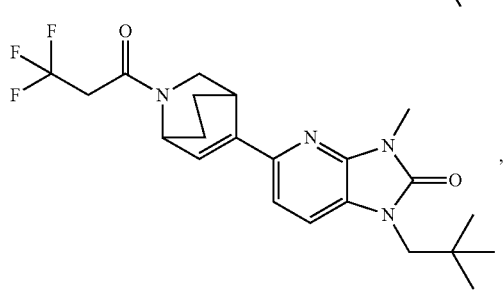,
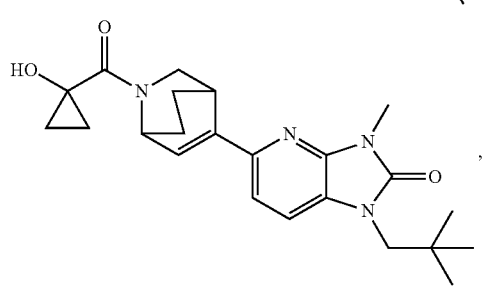,
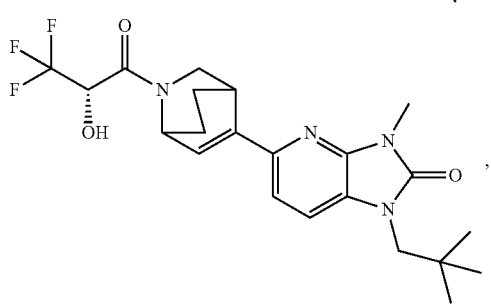,
284
-continued
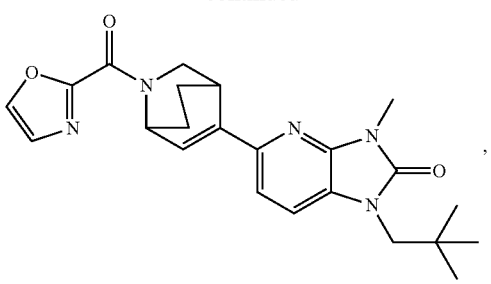,
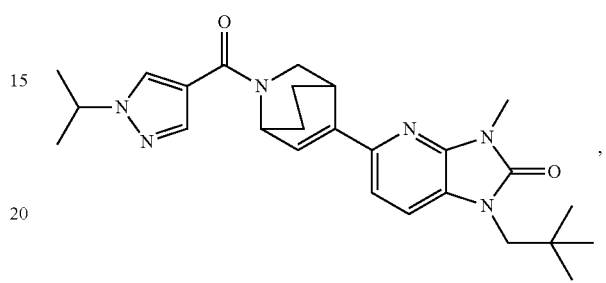,
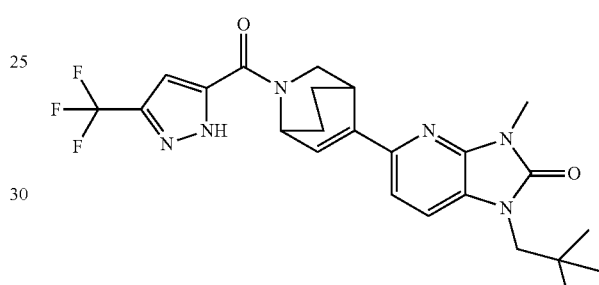,
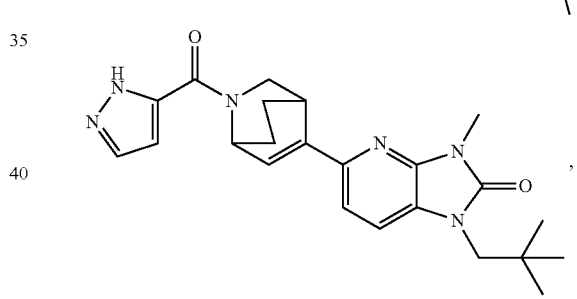,
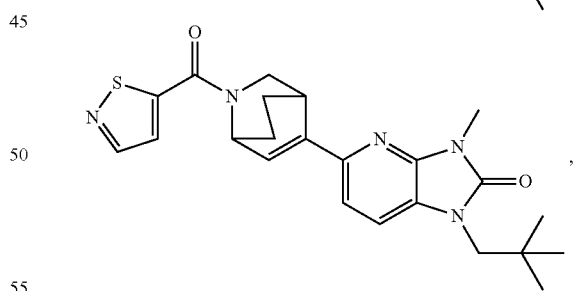,
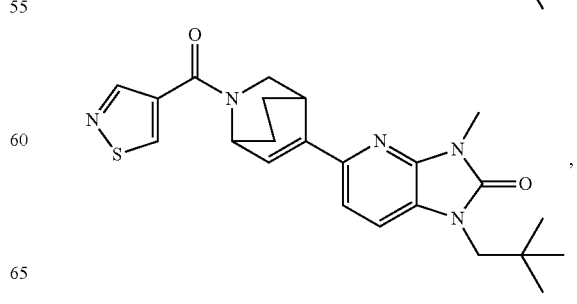,

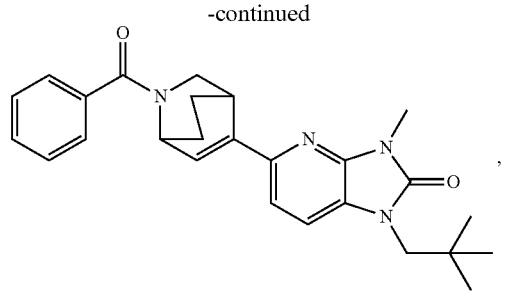
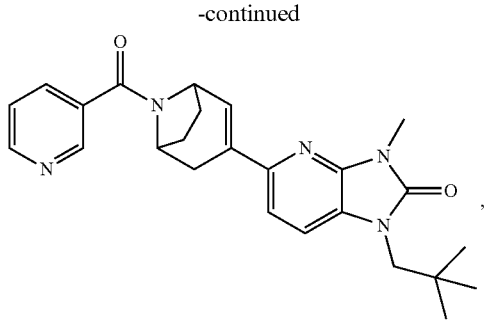
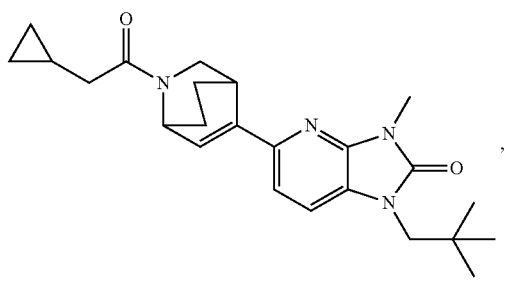
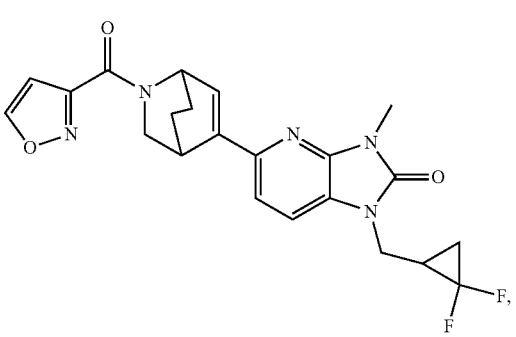
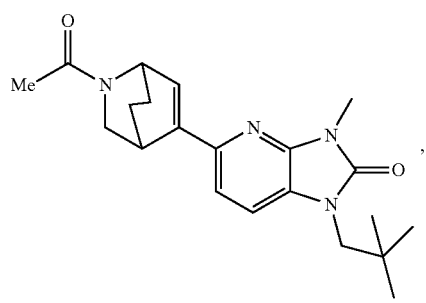
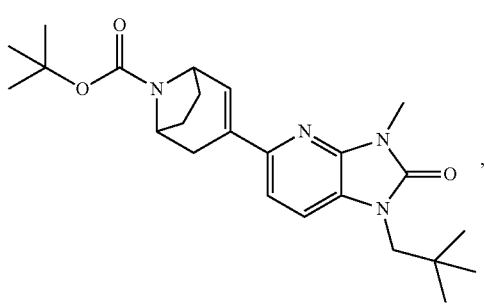
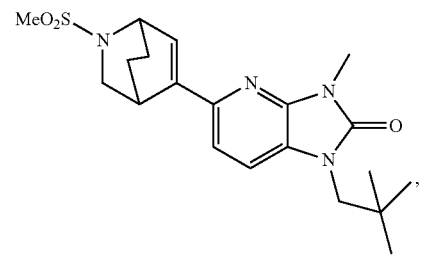
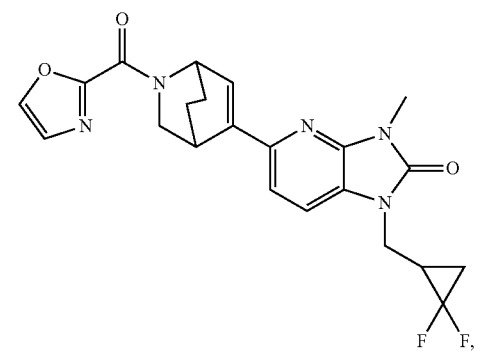
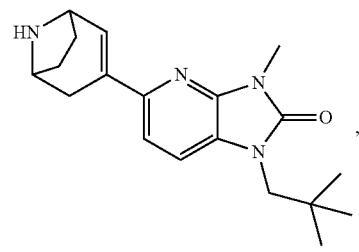
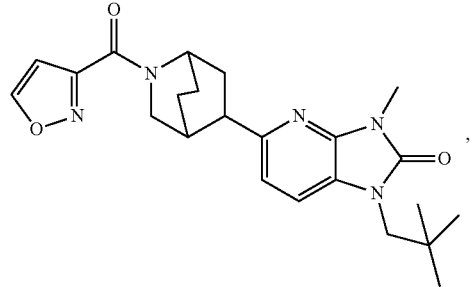
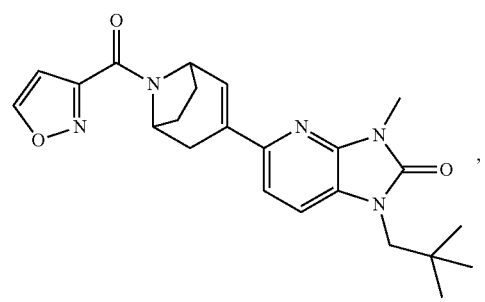

287
-continued
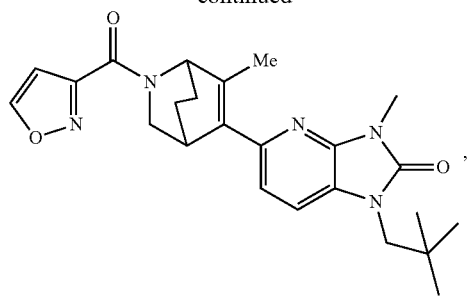
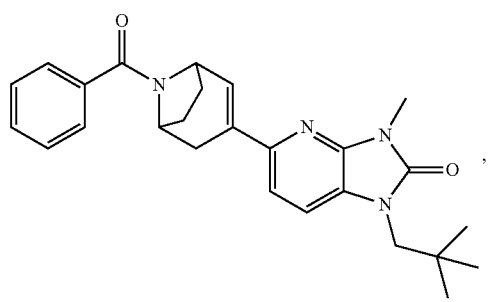
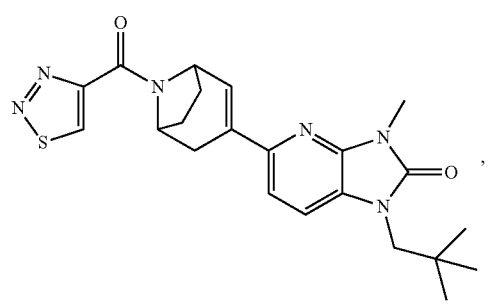
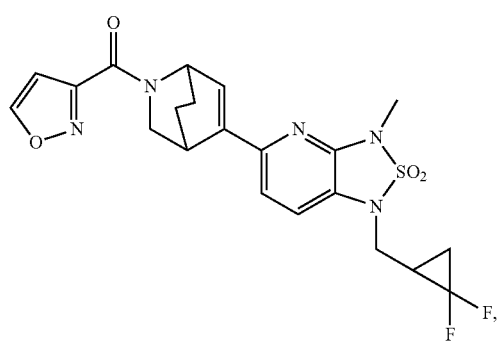
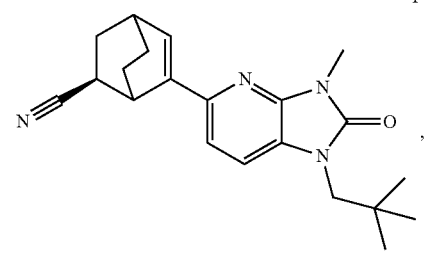
288
-continued
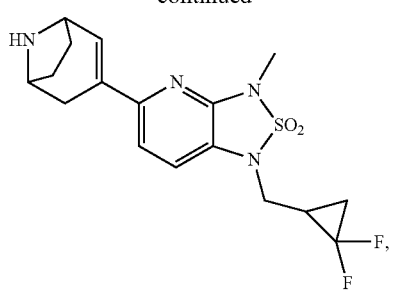
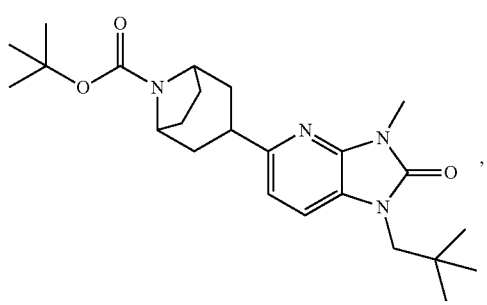
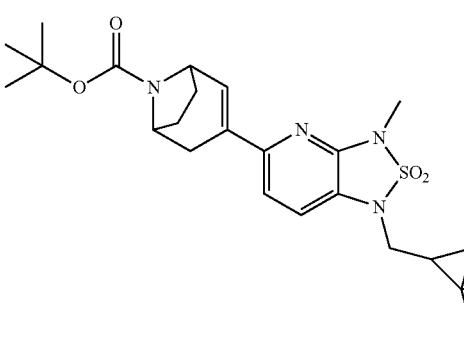
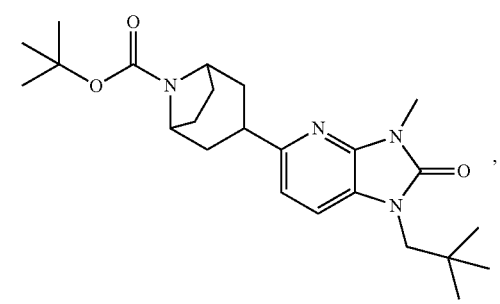
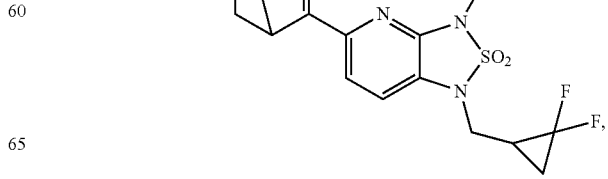

-continued
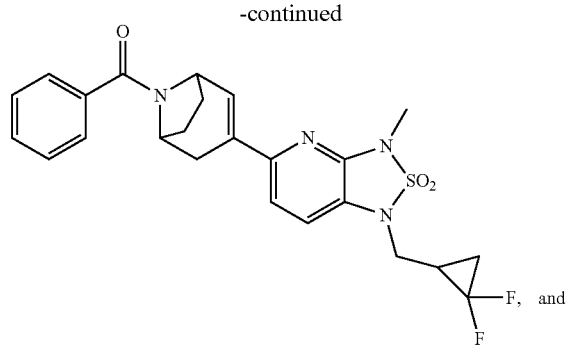
and
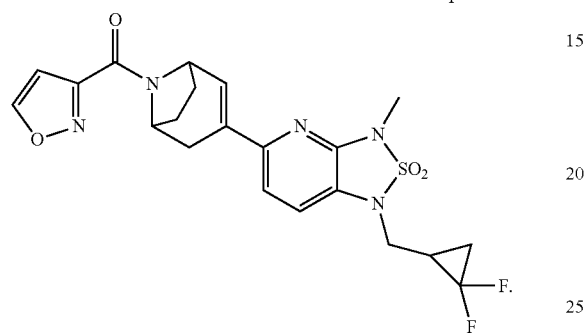
9. A pharmaceutical composition comprising a compound according to claim 1 in combination with a pharmaceutically acceptable carrier.
* * * * *